United States Patent
Hendrix et al.

(10) Patent No.: US 7,550,469 B2
(45) Date of Patent: Jun. 23, 2009

(54) HETEROCYCLIC AMIDE DERIVATIVES AND THEIR USE AS DOPAMINE D3 RECEPTOR LIGANDS

(75) Inventors: James A Hendrix, Hillsborough, NJ (US); Joseph T Strupczewski, Flemington, NJ (US); Kenneth Bordeau, Kintnersville, PA (US); Matthias Urmann, Eschborn (DE); Gregory Shutske, Pittstown, NJ (US); Horst Hemmerle, Indianapolis, IN (US); John G Jurcak, Bethlehem, PA (US); Harpal Gill, West Chester, OH (US); Franz J Weiberth, Ringoes, NJ (US); Thaddeus Nieduzak, Bridgewater, NJ (US); Sharon Anne Jackson, Whitehouse Station, NJ (US); Xu-Yang Zhao, Bridgewater, NJ (US); Paul Justin Mueller, Hoboken, NJ (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

(21) Appl. No.: 11/643,594

(22) Filed: Dec. 21, 2006

(65) Prior Publication Data
US 2007/0142351 A1 Jun. 21, 2007

Related U.S. Application Data

(63) Continuation of application No. 10/960,399, filed on Oct. 7, 2004, now abandoned, which is a continuation of application No. 10/078,206, filed on Feb. 19, 2002, now abandoned.

(60) Provisional application No. 60/269,253, filed on Feb. 16, 2001.

(30) Foreign Application Priority Data
Jul. 19, 2001 (GB) .................. 0117531.4

(51) Int. Cl.
| | |
|---|---|
| A61K 31/496 | (2006.01) |
| C07D 495/04 | (2006.01) |
| C07D 498/04 | (2006.01) |
| A61K 31/4525 | (2006.01) |
| A61K 31/4535 | (2006.01) |
| A61K 31/551 | (2006.01) |
| C07D 333/66 | (2006.01) |
| C07D 409/12 | (2006.01) |
| C07D 409/14 | (2006.01) |
| C07D 413/041 | (2006.01) |

(52) U.S. Cl. .................... 514/254.04; 514/254.06; 540/575; 544/355; 544/357; 544/362; 544/363; 544/364; 544/370; 544/373; 544/376; 546/126; 546/198; 546/199; 546/202

(58) Field of Classification Search ............... None
See application file for complete search history.

(56) References Cited

U.S. PATENT DOCUMENTS 7,186,724 B2 * 3/2007 Hendrix et al. ........ 514/252.13

* cited by examiner

*Primary Examiner*—Emily Bernhardt
(74) *Attorney, Agent, or Firm*—Barbara E. Kurys

(57) ABSTRACT

The invention relates to heterocyclic substituted amide derivatives that display selective binding to dopamine $D_3$ receptors. In another aspect, the invention relates to a method for treating central nervous system disorders associated with the dopamine $D_3$ receptor activity in a patient in need of such treatment comprising administering to the subject a therapeutically effective amount of said compounds for alleviation of such disorder. The central nervous system disorders that may be treated with these compounds include Psychotic Disorders, Substance Dependence, Substance Abuse, Dyskinetic Disorders (e.g. Parkinson's Disease, Parkinsonism, Neuroleptic-Induced Tardive Dyskinesia, Gilles de la Tourette Syndrome and Huntington's Disease), Dementia, Anxiety Disorders, Sleep Disorders, Circadian Rhythm Disorders and Mood Disorders. The subject invention is also directed towards processes for the preparation of the compounds described herein as well as methods for making and using the compounds as imaging agents for dopamine $D_3$ receptors.

5 Claims, No Drawings

HETEROCYCLIC AMIDE DERIVATIVES AND THEIR USE AS DOPAMINE D3 RECEPTOR LIGANDS

BACKGROUND OF THE INVENTION

The subject invention relates to novel heterocyclic derivatives that selectively bind to the dopamine $D_3$ receptor. The therapeutic effects of currently available antipsychotic agents (neuroleptics) are generally believed to be exerted via blockade of $D_2$ receptors; however this mechanism is also thought to be responsible for undesireable extrapyramidal side effects (eps) associated with many neuroleptic agents. Without wishing to be bound by theory, it has been suggested that blockade of the dopamine $D_3$ receptor may give rise to beneficial antipsychotic activity without significant eps. (see for example Sokoloff et al, Nature, 1990; 347:146-151; and Schwartz et al, Clinical Neuropharmacology, Vol 16, No. 4, 295-314, 1993). This receptor is found in high abundance in brain regions associated with emotional and cognitive functions. Compounds that selectively bind to the dopamine $D_3$ receptor are useful in treating certain central nervous system disorders. These central nervous system disorders include the following indications:

1) Psychoses (including schizophrenia)—See, for example, *Biochem Pharmacol*, 1992, 3(4), 659-66; *Clin Neuropharmacol*, 1993, 16(4), 295-314; *Neuropsychopharmacology*, 1997, 16(6), 375-84; Am J Psychiatry, 1999, 156(4), 610-61 6; *Psychopharmacology* (Berl), 1995, 120(1), 67-74.
2) Substance dependence and substance abuse—See, for example, *Neuroreport*, 1997, 8(9-10), 2373-2377; *J Pharmacol Exp Ther*, 1996, 278(3), 1128-37; *Brain Hes Mol Brain Res*, 1997, 45(2),335-9.
3) Mood Disorders (including mania, depressive disorders and bipolar disorders)—See, for example, *Clin Neuropharmacol*, 1998, 21 (3), 176-80; *Am J Med Genet*, 1998, 81 (2), 192-4; *J Clin Psychiatry*, 1995, 56(11), 514-518; *J Clin Psychiatry*, 1995, 56(9), 423-429; *Am J Med Genet*, 1995, 60(3), 234-237; *Pharmacopsychiatry*, 1999, 32(4), 127-135; *J Affect Disord*, 1999, 52(1-3), 275-290; *Am J Psychiatry*, 1999, 156(4), 610-616.
4) dyskinetic disorders (including Parkinson's Disease, Parkinsonism, Neuroleptic-Induced Tardive Dyskinesia and Gilles de la Tourette Syndrome)—See, for example, *Clin Neuropharmacol*, 2000, 23(1), 34-44; *Eur J Pharmacol*, 1999, 385(1), 39-46.
5) sleep disorders (including narcolepsy)—The $D_3$ agonist pramipexole causes narcolepsy. A $D_3$ antagonist would be useful for reversing this undesireable side effect. See *Aust Fam Physician*, 1999, 28(7), 737; *Neurology*, 1999, 52(9), 1908-1910.
6) anxiety disorders (including obsessive compulsive disorders)—See, for example, *Physiol Behav*, 1997, 63(1), 137-141; *J Clin Psychiatry*, 1995, 56(9), 423-429; *J Psychiatry Neurosci*, 2000, 25(2), 185; *J Affect Disord*, 1999, 56(2-3), 219-226.
7) nausea—Dopamine antagonists are used alone and in combination with 5HT3 antagonists. See, for example, Support Care Cancer, 1998, 6(1), 8-12; *Support Care Cancer*, 2000, 8(3), 233-237; *Eur J Anaesthesiol*, 1999, 16(5), 304-307.
8) dementia—See, for example, *Behav Brain Res*, 2000, 109 (1), 99-111; *Neuroscience*, 1999, 89(3), 743-749.

D3 receptor ligand compounds are also useful for the treatment of renal dysfunction. See WO 200067847.

Certain compounds within the scope of the present invention are generically disclosed and claimed in U.S. Pat. No. 5,801,176, the entire disclosure of which is herein incorporated by reference. For example, certain 6-trifluoromethyl benzo[b[thiophenes were disclosed therein to be useful as antipsychotics.

SUMMARY OF THE INVENTION

This invention relates to a class of compounds and pharmaceutically acceptable salts thereof which are selective modulators of dopamine $D_3$ receptors. The compounds may act as agonists, partial agonists, antagonists or allosteric modulators of dopamine $D_3$ receptors, and are useful for a variety of therapeutic applications.

In another aspect, the invention relates to a method for treating central nervous system disorders associated with the dopamine $D_3$ receptor activity in a patient in need of such treatment comprising administering to the subject a therapeutically effective amount of a compound described herein for alleviation of such disorder. The central nervous system conditions or disorders that may be treated with these compounds include Psychotic Disorders, Substance Dependence, Substance Abuse, Dyskinetic Disorders (e.g. Parkinson's Disease, Parkinsonism, Neuroleptic-Induced Tardive Dyskinesia, Gilles de la Tourette Syndrome and Huntington's Disease), Nausea, Dementia, Anxiety Disorders, Sleep Disorders, Circadian Rhythm Disorders and Mood Disorders. Renal Dysfunction may also be treated with these compounds.

In yet another aspect, the subject invention is directed toward a pharmaceutical composition comprising an effective amount of a compound described herein with a pharmaceutically-acceptable carrier or diluent optionally in conjunction with one or more dopamine $D_1$, $D_2$, $D_4$, $D_5$ or 5HT receptor antagonists.

In yet another aspect, the subject invention is directed towards processes for the preparation of the class of compounds described herein.

Also within the scope of this invention are methods for using these novel compounds as imaging agents for dopamine $D_3$ receptors. Methods of using these compounds as imaging agents are presented, as are intermediates and methods for making the imaging agents.

DETAILED DESCRIPTION OF THE INVENTION

In accordance with the present invention, there are provided compounds of formula I

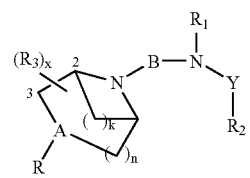

wherein
  Y is carbonyl, sulfonyl, or a bond;
  A is CH or N;
n is 1 or 2;
when n is 2, k is 0;
when n is 1, k is 0 or 2;
x is 0, 1 or 2;
each $R_3$ is independently hydrogen, $C_1$-$C_6$alkyl, or

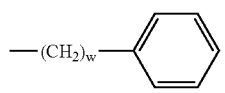

wherein w is 1, 2, or 3;
R is selected from the group consisting of (a)-(e):

a)

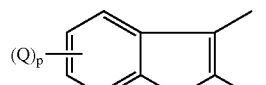

b)

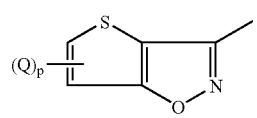

c)

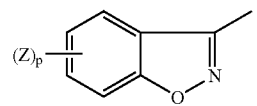

d)

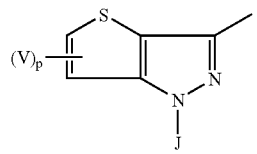

e)

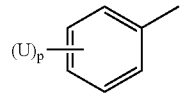

wherein
  each Q, Z, V and U is independently hydrogen, $C_1$-$C_6$alkyl,
  $C_1$-$C_6$alkoxy, halogen, trifluoromethyl or —$CH_2OC_1$-$C_6$alkyl;
  p is 0, 1 or 2;
  $R_4$ is hydrogen, $C_1$-$C_6$alkyl, halogen or phenyl;
  J is hydrogen,

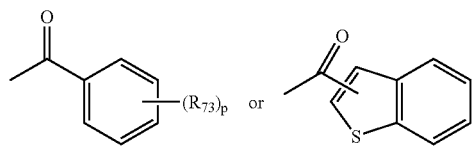

wherein each $R_{73}$ is independently hydrogen, $C_1$-$C_6$alkyl,
halogen or trifluoromethyl and p is as hereinbefore defined;
—B— represents a group selected from groups (a) through (m):

(a) —$(CH_2)_z$— wherein z is 2, 3, 4, 5, 6 or 7;

(b)

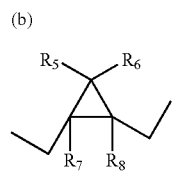

wherein
  $R_5$ and $R_6$ are each independently hydrogen or $C_1$-$C_3$ linear alkyl;
  $R_7$ and $R_8$ are each independently hydrogen or $C_1$-$C_3$ linear alkyl with the proviso that when $R_7$ is $C_1$-$C_3$ linear alkyl, $R_8$ cannot be $C_1$-$C_3$ linear alkyl;

(c)

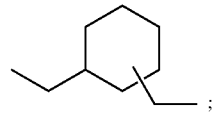

(d)

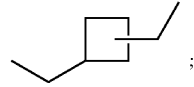

(e)

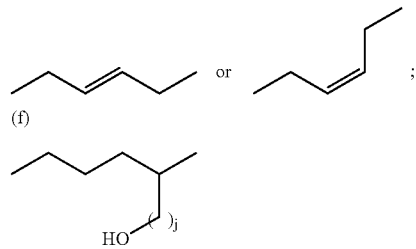

(f)

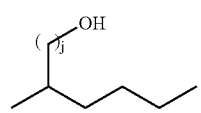

wherein j is 0 or 1;

(g)

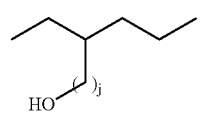

wherein j is defined as above;

(h)

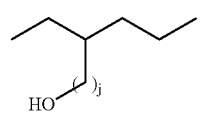

wherein j is defined as above;

(i)

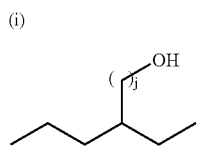

wherein j is defined as above;

(j)

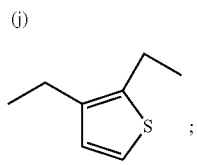

(k)

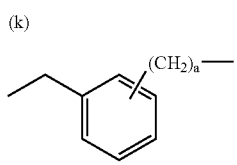

wherein a is 0 or 1;

(l)

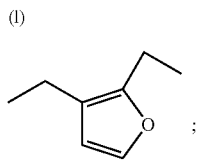

(m)

$R_1$ is a) hydrogen;
b) saturated or unsaturated $C_1$-$C_6$alkyl which is optionally mono- or di-substituted with hydroxy; or c)

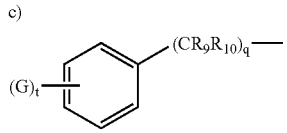

wherein
each G is independently hydrogen, $C_1$-$C_6$alkyl, halogen or trifluoromethyl;

each $R_9$ and $R_{10}$ is independently hydrogen or $C_1$-$C_3$alkyl;
t is 0 or 1; and
q is 0 or 1;

$R_2$ is a group selected from saturated or unsaturated $C_1$-$C_{10}$alkyl, trifluoromethyl or a group selected from (a)-(ss):

(a)

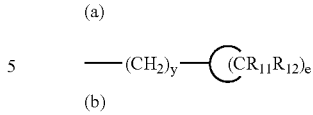

(b)

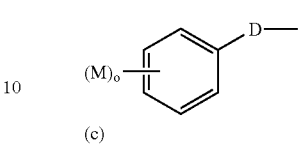

(c)

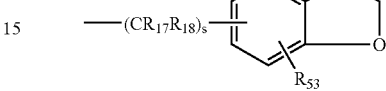

(d)

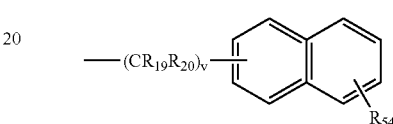

(e)

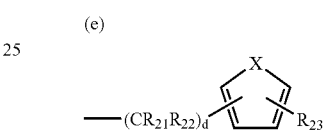

(f)

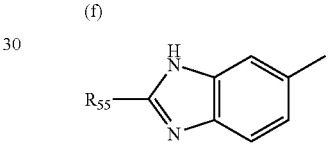

g)

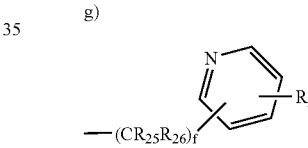

h)

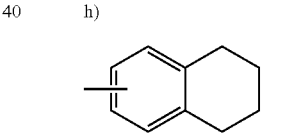

i)

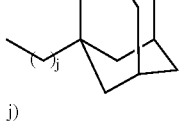

j)

k)

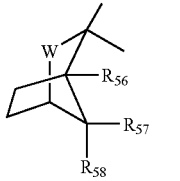

-continued
l) 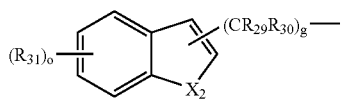
m) 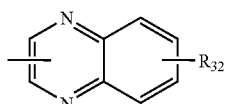
n) 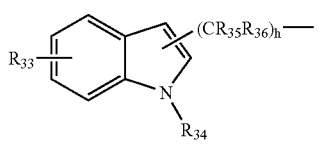
o) 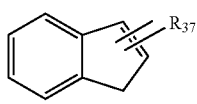
p) 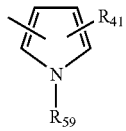
q) 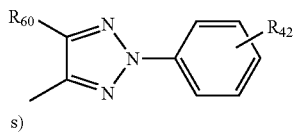
s) 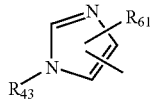
t) 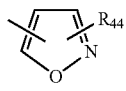
u) 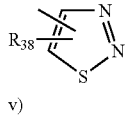
v) 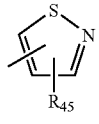
w) 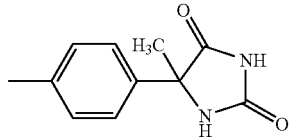
-continued
x) 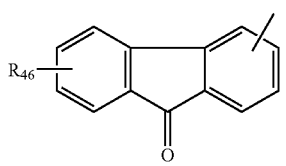
y) 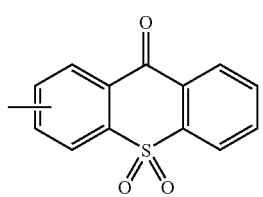
z) 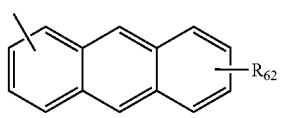
aa) 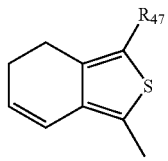
bb) 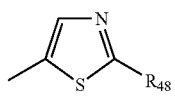
cc) 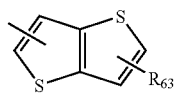
dd) 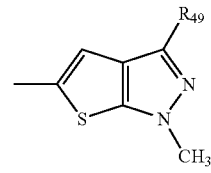
ee) 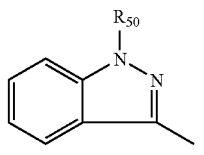
ff) 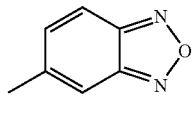

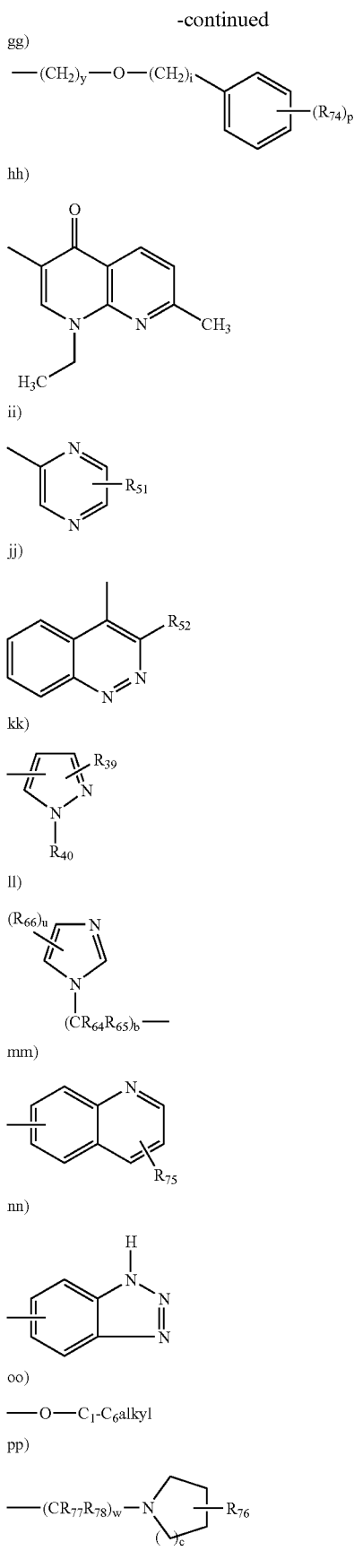
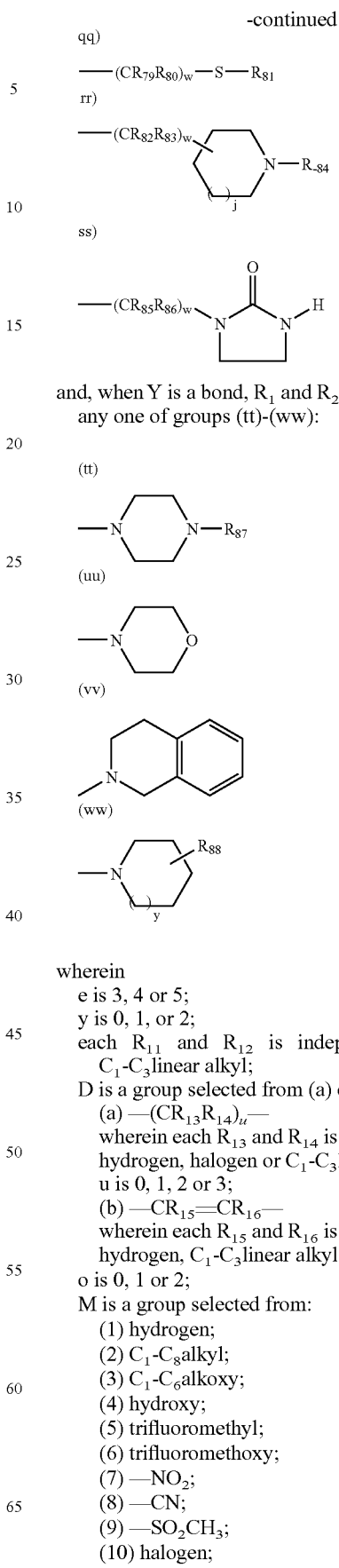

and, when Y is a bond, $R_1$ and $R_2$ taken together can form any one of groups (tt)-(ww):

wherein
e is 3, 4 or 5;
y is 0, 1, or 2;
each $R_{11}$ and $R_{12}$ is independently hydrogen or $C_1$-$C_3$ linear alkyl;
D is a group selected from (a) or (b):
  (a) —$(CR_{13}R_{14})_u$—
    wherein each $R_{13}$ and $R_{14}$ is independently hydrogen, halogen or $C_1$-$C_3$ linear alkyl; and
    u is 0, 1, 2 or 3;
  (b) —$CR_{15}$=$CR_{16}$—
    wherein each $R_{15}$ and $R_{16}$ is independently hydrogen, $C_1$-$C_3$ linear alkyl or amino;
o is 0, 1 or 2;
M is a group selected from:
  (1) hydrogen;
  (2) $C_1$-$C_8$ alkyl;
  (3) $C_1$-$C_6$ alkoxy;
  (4) hydroxy;
  (5) trifluoromethyl;
  (6) trifluoromethoxy;
  (7) —$NO_2$;
  (8) —CN;
  (9) —$SO_2CH_3$;
  (10) halogen;

(11)

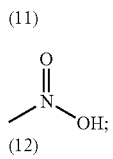

(12)

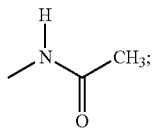

(13)

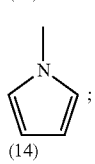

(14)

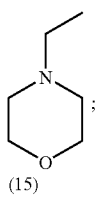

(15)

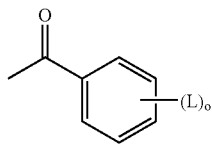

wherein each L is independently hydrogen or —NR$_{67}$R$_{68}$, wherein R$_{67}$ and R$_{68}$ are each independently hydrogen, C$_1$-C$_6$alkyl or C$_1$-C$_6$alkoxy and o is 0, 1 or 2 as hereinbefore defined;

(16)

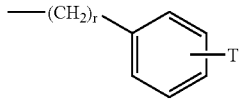

wherein T is hydrogen or halogen and r is 0, 1, or 2;

—NR$_{69}$R$_{70}$ (17)

wherein R$_{69}$ and R$_{70}$ are each independently hydrogen or C$_1$-C$_6$alkyl:

—SO$_2$NH$_2$; (18)

each R$_{17}$ and R$_{18}$ is independently hydrogen or C$_1$-C$_3$alkyl;
s is 0, 1 or 2;
R$_{53}$ is hydrogen, halogen, hydroxy, C$_1$-C$_6$alkyl, amino or C$_1$-C$_3$alkoxy;
R$_{54}$ is hydrogen, halogen, hydroxy, C$_1$-C$_6$alkyl, amino, —SO$_2$NH$_2$ or C$_1$-C$_3$alkoxy;
each R$_{19}$ and R$_{20}$ is independently hydrogen or C$_1$-C$_3$alkyl;
v is 0, 1 or 2;

X is O or S;
each R$_{21}$ and R$_{22}$ is independently hydrogen or C$_1$-C$_3$alkyl;
d is 0, 1 or 2;
R$_{23}$ is a group selected from (a)-(h):
 (a) hydrogen;
 (b) C$_1$-C$_6$alkyl;
 (c) halogen;
 (d) hydroxy;
 (e) C$_1$-C$_3$alkoxy; and (f)

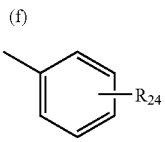

wherein R$_{24}$ is hydrogen or halogen;

(g)

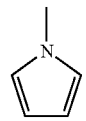

(h)

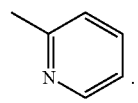

R$_{55}$ is hydrogen or C$_1$-C$_6$alkyl;
each R$_{25}$ and R$_{26}$ is independently hydrogen or C$_1$-C$_3$alkyl;
f is 0, 1 or 2;
R$_{27}$ is a group selected from (a)-(e):
 (a) hydrogen;
 (b) C$_1$-C$_6$alkyl;
 (c) halogen;
 (d) —SCH$_3$; and (e)

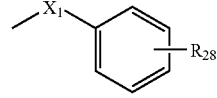

wherein X$_1$ is O or S and R$_{28}$ is hydrogen or C$_1$-C$_6$alkyl;
j is 0 or 1 as hereinbefore defined;
each R$_{56}$, R$_{57}$, R$_{58}$ is independently hydrogen or C$_1$-C$_6$alkyl;
W is CH$_2$, CH$_2$OH or C=O;
each R$_{29}$ and R$_{30}$ is independently hydrogen or C$_1$-C$_3$alkyl;
g is 0 or 1;
X$_2$ is O or S;
each R$_{31}$ is independently hydrogen, halogen, C$_1$-C$_6$alkyl, trifluoromethyl, trifluoromethoxy, C$_1$-C$_6$alkoxy or —NR$_{71}$R$_{72}$ wherein R$_{71}$ and R$_{72}$ are each independently hydrogen or C$_1$-C$_6$alkyl;
o is 0, 1 or 2 as hereinbefore defined;

$R_{32}$ is hydrogen, halogen or $C_1$-$C_6$alkyl;
$R_{33}$ is hydrogen, halogen, hydroxy, $C_1$-$C_6$alkyl or $C_1$-$C_3$alkoxy;
$R_{34}$ is hydrogen, $C_1$-$C_6$alkyl or —$CH_2CO_2C_1$-$C_6$alkyl;
each $R_{35}$ and $R_{36}$ is independently hydrogen or $C_1$-$C_3$ linear alkyl;
h is 0 or 1;
$R_{37}$ is hydrogen or $C_1$-$C_6$alkyl;
$R_{41}$ is hydrogen, $C_1$-$C_6$alkyl, benzyl, acyl, tosyl, pyridyl or phenyl wherein said phenyl is optionally mono- or di-substituted with substituents independently selected from halogen, hydroxy, $C_1$-$C_6$alkyl, $C_1$-$C_6$alkoxy and $C_1$-$C_6$acyl;
$R_{59}$ and $R_{60}$ are hydrogen, methyl or phenyl which is optionally mono- or di-substituted with substituents independently selected from halogen, hydroxy, $C_1$-$C_6$alkyl, $C_1$-$C_6$alkoxy and $C_1$-$C_6$acyl;
$R_{42}$ is hydrogen, $C_1$-$C_6$alkyl, $C_1$-$C_6$alkoxy, halogen, trifluoromethyl or phenoxy;
$R_{43}$ is hydrogen, $C_1$-$C_6$alkyl or benzyl;
$R_{61}$ is hydrogen or $C_1$-$C_6$alkyl;
$R_{44}$ is hydrogen, hydroxy, $C_1$-$C_6$alkyl, phenyl or acyl;
$R_{38}$ is hydrogen, methyl, phenyl which is optionally mono- or di-substituted with substituents independently selected from halogen, hydroxy, $C_1$-$C_6$alkyl, $C_1$-$C_6$alkoxy and $C_1$-$C_6$acyl;
$R_{45}$ is hydrogen, $C_1$ $C_6$alkyl, S-$C_1$-$C_6$alkyl, halogen or phenyl which is optionally mono- or di-substituted with substituents independently selected from halogen, hydroxy, $C_1$-$C_6$alkyl, $C_1$-$C_6$alkoxy and $C_1$-$C_6$acyl;
$R_{46}$ is hydrogen or halogen;
$R_{62}$ is hydrogen, halogen or $C_1$-$C_6$alkyl;
$R_{47}$ is SMe, SOMe or $SO_2Me$;
$R_{48}$ is hydrogen, $C_1$-$C_6$alkyl, trifluoromethyl, pyridyl, thiophenyl or phenyl which is optionally mono- or di-substituted with substituents independently selected from halogen, hydroxy, $C_1$-$C_6$alkyl,. $C_1$-$C_6$alkoxy and $C_1$-$C_6$acyl;
$R_{63}$ is hydrogen or $C_1$-$C_6$alkyl;
$R_{49}$ is methyl, trifluoromethyl, phenyl or —$CH_2SPh$;
$R_{50}$ is hydrogen, methyl, acyl or benzyl;
i is 0 or 1;
y is 0, 1 or 2 as hereinbefore defined;
p is 0, 1 or 2 as hereinbefore defined;
each $R_{74}$ is independently hydrogen, $C_1$-$C_6$alkyl, $C_1$-$C_6$alkoxy or halogen;
$R_{51}$ is hydrogen, hydroxy, methyl, methoxy, chlorine or —$SC_1$-$C_6$alkyl;
$R_{52}$ is hydrogen, phenyl or thiophene;
$R_{39}$ is hydrogen or $C_1$-$C_6$alkyl;
$R_{40}$ is hydrogen, $C_1$-$C_6$alkyl, phenyl or benzyl;
b is 1, 2, 3 or 4;
each $R_{64}$ and $R_{65}$ is independently hydrogen or $C_1$-$C_3$alkyl;
u is 0, 1, 2, or 3 as hereinbefore defined;
each $R_{66}$ is independently hydrogen, $C_1$-$C_6$alkyl, halogen or phenyl which is optionally mono- or di-substituted with halogen, $C_1$-$C_6$alkyl or trifluoromethyl;
$R_{75}$ is hydrogen, halogen, $C_1$-$C_6$alkyl or furanyl; cis 1 or 2;
w is 1, 2 or 3 as hereinbefore defined;
$R_{76}$ is hydrogen or $C_1$-$C_6$alkyl;
each $R_{77}$ and $R_{78}$ is independently hydrogen or $C_1$-$C_3$alkyl;
each $R_{79}$ and $R_{80}$ is independently hydrogen or $C_1$-$C_3$alkyl;

$R_{81}$ is $C_1$-$C_6$alkyl or phenyl optionally substituted with halogen;
each $R_{82}$ and $R_{83}$ is independently hydrogen or $C_1$-$C_3$alkyl;
$R_{84}$ is hydrogen or $C_1$-$C_6$alkyl;
j is 0 or 1 as hereinbefore defined;
each $R_{85}$ and $R_{86}$ is independently hydrogen or $C_1$-$C_3$alkyl;
$R_{87}$ is phenyl or benzyl each of which may be optionally mono- or disubstituted with $C_1$-$C_6$alkyl, $C_1$-$C_6$alkoxy or halogen;
$R_{88}$ is hydrogen, $C_1$-$C_6$alkyl, halogen or benzyl optionally mono- or disubstituted with $C_1$-$C_6$alkyl, halogen or one of the following groups (a)-(c):

(a)
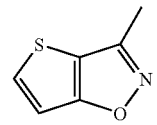

(b)
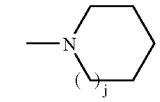

wherein j is 0 or 1 as hereinbefore defined (c)
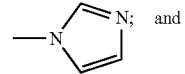
and y is 0, 1 or 2 as hereinbefore defined.

with the proviso that when R is (a); and Y is carbonyl; and n is 1; and k is 0, and Q is hydrogen, $C_1$-$C_6$alkyl, halogen or —$CH_2OC_1$-$C_6$alkyl; and $R_1$ is hydrogen or unsubstituted $C_1$-$C_6$alkyl; and $R_3$ is hydrogen or $C_1$-$C_6$alkyl;.and $R_4$ is hydrogen or $C_1$-$C_6$alkyl; and —B— is a group of formula (a) or (e); then $R_2$ cannot be saturated or unsaturated $C_1$-$C_{10}$alkyl or any of the following groups:
(a) wherein y is 0;
(b) wherein D is a group of formula (a) wherein u is 0 and M is hydrogen, $C_1$-$C_6$alkyl, $C_1$-$C_6$alkoxy, hydroxy, halogen, trifluoromethyl or

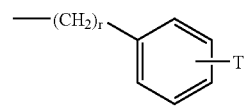

wherein r is 0;
(c) wherein s is 0;
(d) wherein v is 0;
(e) wherein d is 0;
(f);
(g) wherein f is 0;
(h);
(i);
(j);
(k);

(l) wherein g is 0;
(m);
(n) wherein h is 0;
(o);
(s);
(x);
(aa);
(cc);
(dd);
(ee);
(ff);
(ii); or
(jj).

The subject invention is directed toward compounds or pharmaceutically acceptable salts of Formula I as depicted above in either racemic or pure stereoisomeric forms.

Terms used herein have the following meanings:

a) "Pharmaceutically acceptable salts" means either an acid addition salt or a basic addition salt which is compatible with the treatment of patients for the intended use.

"Pharmaceutically acceptable acid addition salt" is any non-toxic organic or inorganic acid addition salt of the base compounds represented by Formula I or any of its intermediates. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tri-carboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxybenzoic, p-toluenesulfonic acid and sulfonic acids such as methanesulfonic acid and 2-hydroxyethanesulfonic acid. Either the mono- or di-acid salts can be formed, and such salts can exist in either a hydrated, solvated or substantially anhydrous form. In general, the acid addition salts of these compounds are more soluble in water and various hydrophilic organic solvents and which in comparison to their free base forms, generally demonstrate higher melting points.

"Pharmaceutically acceptable basic addition salts" means non-toxic organic or inorganic basic addition salts of the compounds of Formula (I) or any of its intermediates. Examples are alkali metal or alkaline-earth metal hydroxides such as sodium, potassium, calcium, magnesium or barium hydroxides; ammonia, and aliphatic, alicyclic, or aromatic organic amines such as methylamine, trimethylamine and picoline. The selection criteria for the appropriate salt will be known to one skilled in the art.

b) "Stereoisomers" is a general term for all isomers of the individual molecules that differ only in the orientation of their atoms in space. It includes mirror image isomers (enantiomers), geometric (cis/trans) isomers, and isomers of compounds with more than one chiral center that are not mirror images of one another (diastereoisomers).

c) "Alkyl" means a branched or straight chain alkyl or alkylene group, as is appropriate to the formula, specified by the amount of carbons in the alkyl, e.g., $C_1$-$C_6$ alkyl means a one, two, three, four, five or six carbon branched or straight chain alkyl or alkylene, as the case may be, or any ranges thereof, for example, but not limited to, C1-2, C1-3, C1-4, C1-5, C2-3, C2-4, C2-5, C2-C6, C3-C4, C3-5, C3-6, C4-5, C4-6, C5-6, etc.

d) "Patient" means a warm blooded animal, such as for example rat, mice, dogs, cats, guinea pigs, and primates such as humans.

e) "Treat" or "treating" means to alleviate symptoms, eliminate the causation of the symptoms either on a temporary or permanent basis, or to prevent or slow the appearance of symptoms of the named disorder or condition.

f) "Therapeutically effective amount" means a quantity of the compound which is effective in treating the named disorder or condition.

g) "Pharmaceutically acceptable carrier" is a non-toxic solvent, dispersant: excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

h) "Psychoses" or "Psychotic Disorders" means conditions wherein the patient experiences a major mental disorder of organic and/or emotional origin characterized by derangement of the personality and loss of contact with reality, often with delusions, hallucinations or illusions. Included under the term psychoses are the disorders schizophrenia, schizophreniform disorder, schizoaffective disorder, delusional disorder, brief psychotic disorder, shared psychotic disorder, psychotic disorder not otherwise specified, and substance-induced psychotic disorder, as defined by the Diagnostic and Statistical Manual of Mental Disorders, 4th ed., published 1994 by the American Psychiatric Association, Washington D.C. USA, incorporated herein by reference.

i) "Substance Dependence" means a condition wherein the patient exhibits a maladaptive pattern of substance use, leading to clinically significant impairment or distress. There is a pattern of repeated self-administration that usually results in tolerance, withdrawal, and compulsive drug-taking.

j) "Substance Abuse" means a condition wherein the patient exhibits a maladaptive pattern of substance use manifested by recurrent and significant adverse consequences related to the repeated use of substances. There may be repeated failure to fulfill major role obligations, repeated use in situations in which it is physically hazardous, multiple legal problems, and recurrent social and interpersonal problems. Unlike the criteria for Substance Dependence, the criteria for Substance Abuse do not include tolerance, withdrawal, or a pattern of compulsive use and instead only include the harmful consequences of repeated use.

k) "Parkinson's Disease" means a slowly progressive neurological condition, characterized by tremor, rigidity, bradykinesia, and postural instability. Other manifestations include depression and dementia.

l) "Parkinsonism" means a condition-where the patient exhibits Parkinsonian signs or symptoms (i.e. tremor, muscular rigidity, or akinesia) that develop in association with the use of neuroleptic medication.

m) "Neuroleptic-Induced Tardive Dyskinesia" means a disorder characterized by involuntary movements of the tongue, jaw, trunk, or extremities which have developed in association with the use of neuroleptic medication. The involuntary movements may be choreiform, athetoid or rhythmic.

n) "Gilles de la Tourette Syndrome" means a condition manifested by motor and vocal tics. (A tic is a sudden, rapid, recurrent, nonrhythmic, stereotyped motor movement or vocalization.) The disturbance causes marked distress or significant impairment in social, occupational, or other important areas of functioning. The onset is before age eighteen years and the disturbance is not due to the physiological effects of a substance or general medical condition.

o) "Dementia" means disorders characterized by the development of multiple cognitive deficits that include memory impairment and are due to the direct physiological effects of a general medical condition, to the persisting effects of a substance, or to multiple etiologies (e.g., the combined effects of cerebrovascular disease and Alzheimer's disease). Memory impairment is required to make the diagnosis of a dementia and is a prominent early symptom. Dementia disorders share a common symptom presentation but are differentiated 0based on etiology. See Diagnostic and Statistical Manual of Mental Disorders, 4th ed., American Psychiatric Association, for diagnostic criteria.

p) "Anxiety Disorders" means disorders that include Panic Disorder Without Agoraphobia, Panic Disorder with Agoraphobia, Agoraphobia Without History of Panic Disorder, Specific Phobia, Social Phobia, Obsessive-Compulsive Disorder, Post-traumatic Stress Disorder, Acute Stress Disorder, Generalized Anxiety Disorder, Anxiety Disorder Due to a General Medical Condition, Substance-Induced Anxiety Disorder, and Anxiety Disorder Not Otherwise Specified, as defined by the Diagnostic and Statistical Manual of Mental Disorders, 4th ed.

q) "Sleep Disorders" means disorders that include Primary Sleep Disorders, Sleep Disorder Related to Another Mental Disorder, Sleep Disorder Due to a General Medical Condition, and Substance-Induced Sleep Disorder as defined by the Diagnostic and Statistical Manual of Mental Disorders, 4th ed. Primary Sleep Disorders are those in which none of the etiologies listed below (i.e., another mental disorder, a general medical condition, or a substance) is responsible. Primary Sleep Disorders are presumed to arise from endogenous abnormalities in sleep-wake generating or timing mechanisms, often complicated by conditioning factors. Primary Sleep Disorders in turn are subdivided into Dyssomnias (characterized by abnormalities in the amount, quality, or timing of sleep) and Parasomnias (characterized by abnormal behavioral or physiological events occurring in association with sleep, specific sleep stages, or sleep-wake transitions). A representative example of a Primary Sleep Disorder is Narcolepsy. Narcolepsy is characterized by repeated irresistible attacks of refreshing sleep, cataplexy, and recurrent intrusions of elements of rapid eye movement (REM) sleep into the transition period between sleep and wakefulness.

r) "Mood Disorders" are disorders that have a disturbance in mood as the predominant feature. As defined by the Diagnostic and Statistical Manual of Mental Disorders, 4th ed., Mood Disorders are divided into the Depressive Disorders ("unipolar depression"), the Bipolar Disorders, and two disorders based on etiology—Mood Disorder Due to a General Medical Condition and Substance-Induced Mood Disorder. The Depressive Disorders (i.e., Major Depressive Disorder, Dysthymic Disorder, and Depressive Disorder Not Otherwise Specified) are distinguished from the Bipolar Disorders by the fact that there is no history of ever having had a Manic, Mixed, or Hypomanic Episode. The Bipolar Disorders (i.e., Bipolar I Disorder, Bipolar II Disorder, Cyclothymic Disorder, and Bipolar Disorder Not Otherwise Specified) involve the presence (or history) of Manic Episodes, Mixed Episodes, or Hypomanic Episodes, usually accompanied by the presence (or history) of Major Depressive Episodes.

s) "Circadian Rhythm Disorder" means a persistent or recurrent pattern of sleep disruption leading to excessive sleepiness or insomnia that is due to a mismatch between the sleep-wake schedule required by a person's environment and his or her circadian sleep-wake pattern. The sleep disturbance causes clinically significant distress or impairment in social, occupational, or other important areas of functioning. The disturbance does not occur exclusively during the course of another Sleep Disorder or other mental disorder. The disturbance is not due to the direct physiological effects of a substance (e.g., a drug of abuse, a medication) or a general medical condition.

Presently preferred compounds of the invention include those compounds of formula I wherein R is group (a), $R_4$ is hydrogen, and Q is $CF_3$. Also preferred are compounds wherein R is group (b), and Q is hydrogen, $C_1$-$C_6$alkyl, or —$CH_2OC_1$-$C_6$alkyl.

Y is preferably carbonyl.

—B— is preferably selected from group (a) or (b). When B is group (a), z is further preferred to be 4 When —B— is-group (b), $R_5$, $R_6$, $R_7$ and $R_8$ are further preferred to be hydrogen.

$R_2$ is preferably selected from group (a), (b), (I), (n), (s) or (II).

When $R_2$ is group (a), y is further preferred to be 0 or 1 and e is further preferred to 5.

When $R_2$ is group (b), M is further preferred to be hydrogen, $C_1$-$C_6$alkoxy, $C_1$-$C_6$alkyl or group (16); and D is further preferred to be:

group (a) wherein each $R_{13}$ and $R_{14}$ is independently hydrogen, halogen or $C_1$-$C_3$ linear alkyl; and u is 0 or 1; or group (b) wherein $R_{15}$ and $R_{16}$ are hydrogen.

When $R_2$ is (I), g is further preferred to be 0 or 1 and $R_{31}$ is further preferred to be hydrogen.

When $R_2$ is (s), $R_{61}$ is further preferred to be hydrogen, $C_1$-$C_6$alkyl or halogen.

When $R_2$ is (n), $R_{33}$ is further preferred to be hydrogen, $C_1$-$C_6$alkyl, or $C_1$-$C_6$alkoxy and $R_{34}$ is hydrogen or $C_1$-$C_6$alkyl.

When $R_2$ is (II), $R_{66}$ is further preferred to be hydrogen, $C_1$-$C_6$alkyl or halogen.

Specific embodiments of the invention include the compounds set forth in the various tables herein.

Preferred embodiments of the invention are those compounds of Formula I set forth in the tables herein that exhibit enhanced D3 potency. Particularly preferred compounds include the following:

benzo[b]thiophene-2-carboxylic acid {4-[4-(6-trifluoromethyl-benzo[b]thiophen-3-yl)-piperazin-1-yl]-butyl}-amide 4-ethoxy-N-{4-[4-(6-trifluoromethyl-benzo[b]thiophen-3-yl)-piperazin-1-yl]-butyl}-benzamide biphenyl-4-carboxylic acid {4-[4-(6-trifluoromethyl-benzo[b]thiophen-3-yl)-piperazin-1-yl]-butyl}-amide N-{4-[4-(fluoro-trifluoromethyl-benzo[b]thiophen-3-yl)-piperazin-1-yl]-butyl}-trifluoromethyl-benzamide thiophene-2-carboxylic acid {6-[4-(6-trifluoromethyl-benzo[b]thiophen-3-yl)-piperazin-1-yl]-hexyl}-amide biphenyl-4-carboxylic acid [4-(4-thieno[2,3-d]isoxazol-3-yl-piperazin-1-yl)-butyl]-amide benzo[b]thiophene-2-carboxylic acid {4-[4-(6-fluoro-benzo[b]thiophen-3-yl)-[1,4]diazepan-1-yl]-butyl}-amide 1H-indole-2-carboxylic acid {4-[4-(6-fluoro-benzo[b]thiophen-3-yl)-[1,4]diazepan-1-yl]-butyl}-amide naphthalene-2-carboxylic acid {4-[4-(6-fluoro-benzo[b]thiophen-3-yl)-[1,4]diazepan-1-yl]-butyl}-amide 2-methyl-5-phenyl-furan-3-arboxylic acid {4-[4-(6-fluoro-benzo[b]thiophen-3-yl)-[1,4]diazepan-1-yl]-butyl}-amide (E)-N-{4-[4-(6-fluoro-benzo[b]thiophen-3-yl)-[1,4]diazepan-1-yl]-butyl})-3-phenyl-acrylamide 5-hydroxy-1H-indole-2-carboxylic acid {4-[4-(6-fluoro-benzo[b]thiophen-3-yl)-[1,4]diazepan-1-yl]-butyl}-amide 4-Fluoro-N-{2R-[4-(6-trifluoromethyl-benzo[b]thiophen-3-yl)-piperazin-1-ylmenthyl]-1R-cyclopropylmethyl}-benzenesulfonamide (MDL 831495)

(3-imidazol-1-yl-propyl)-{(1R,2R)-2-[4-(6-trifluoromethyl-benzo[b]thiophen-3-yl)-piperazin-1-ylmethyl]-cyclopropylmethyl}-amine (MDL-833257)

The compounds of the present invention may be prepared by various methods. Schemes I through VI show the different ways of preparing the compounds of Formula I.

The compounds of formula (I) can be synthesized by following or combining one or more of the steps described below, not necessarily in the order presented. Throughout the description of the synthetic steps, the definitions of R, $R_1$, $R_2$, $R_3$, n, B and A are as given above unless otherwise stated or indicated, and other nomenclatures appearing below shall have the same meanings defined in their respective first appearances unless otherwise stated or Indicated.

Compounds of formula I wherein Y is carbonyl may be prepared according to a process which comprises reacting a compound of formula (II):

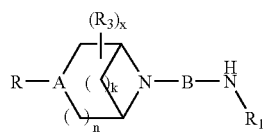

(II)

wherein R, $R_3$, x, k, n, B, and $R_1$ are as defined in formula I with a compound of formula (III)

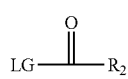

(III)

wherein $R_2$ is as defined in formula I and "LG" is a suitable leaving group selected from chlorine, bromine or iodine or, mixed anhydride if the reaction is carried out in the presence of a suitable coupling reagent, "LG" can also be hydroxy.

A suitable coupling reagent is, for example, DCC (1,3-dicyclohexylcarbodiimide), EEDQ (2-ethoxy-1-ethoxycarbonyl-1,2 dihydroquinoline) or TOTU {O-[(ethoxycarbonyl)cyanomethyleneamino]-N,N,N',N'-tetramethyluronium tetrafluoroborate}.

Typically, this reaction is carried out in an organic solvent such as, for example, chloroform or tetrahydrofuran in the presence of a weak base such as, for example, Amberlite IRA-67 or triethylamine, at a temperature of about 20° C. to about 25° C. for about 6 to 18 hours.

Alternatively, compounds of formula I may be prepared according to a process which comprises reacting a compound of formula (IV):

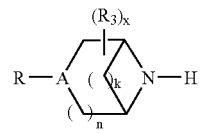

(IV)

wherein R, $R_3$, x, k, n, and B is as defined in formula I with a compound of formula V

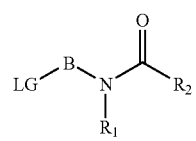

(V)

wherein $R_1$ and $R_2$ are as defined in formula I and "LG" is a suitable leaving group selected from chlorine, bromine, iodine, mesyl, tosyl, brosyl, triflyl, nosyl, nonaflyl or tresyl.

Typically, this reaction is carried out in an aqueous miscible solvent such as, for example, tetrahydrofuran or acetonitrile, in the presence of water and a base such as, for example, potassium carbonate, cesium carbonate, or triethylamine, at a temperature of about 50° C. to about 75° C. for about 12 to 24 hours.

If the intermediate compound of formula (IV) is specifically the compound of formula (VI), the compound may be prepared via a process that comprises 1) reacting a compound of formula (VII) with one-half equivalent of piperazine until de-esterification/decarboxylation is substantially complete thereby providing the compound of formula (VIII) and 2) reacting the compound of formula (VIII) with additional piperazine to effect the displacement of the amino group thereby providing the compound of formula (VI). If an excess of piperazine is used to effect both the de-esteriication and the displacement of the amino-group, de-esterification/decarboxylation proceeds by attack of an excess of piperazine on the methyl group of (VI) to give (VII) together with N-methylpiperazine. It was discovered that, in the subsequent displacement reaction, the N-methylpiperazine by-product competes with piperazine for reaction with (VII) resulting in compound of formula (VIII) that is contaminated with the N-methyl analog of (VIII). This side reaction can be avoided by employing only ca. 0.5 eq rather than an excess of piperazine for the de-esterification. In this way, the by-product that is generated during the de-esterification process is N,N'-dimethylpiperazine, which does not compete with piperazine during the displacement reaction.

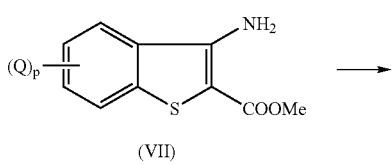

(VII)

-continued

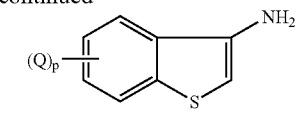

(VIII)

↓

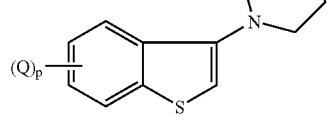

(VI)

The compound of formula (II) may be prepared via synthetic methods well known in the art. The starting materials are either commercially available or readily synthesized via methods known from the literature. For example, Scheme I describes the coupling of an amino-substituted benzthiophene with a commercially-available substituted piperazine. The synthesis is analogous for the un-substituted piperazine analogs. The less sterically hindered piperazine nitrogen is more reactive and cleanly gives a single product in the benzo[b]thiophene coupling. The more sterically hindered nitrogen can then be alkylated with the appropriate alkylating agent.

SCHEME I

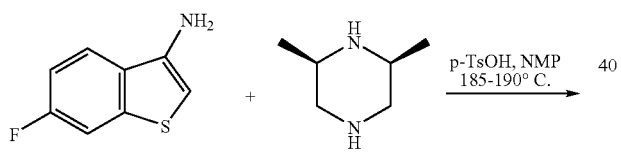

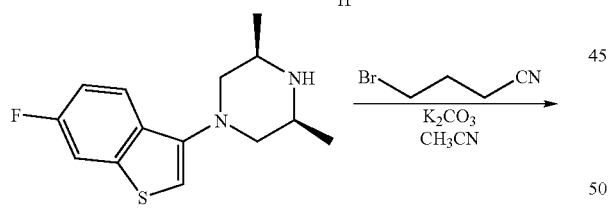

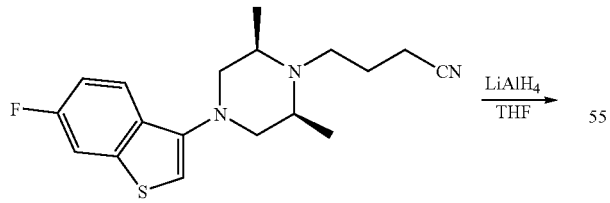

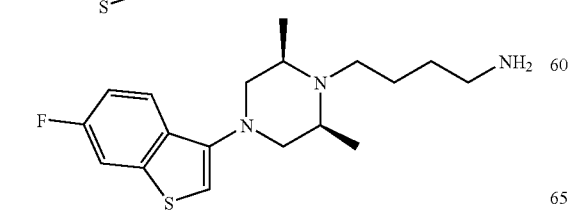

Piperidine-substituted compounds may be prepared via syntheses analogous to those shown in the following reaction schemes II and III.

SCHEME II

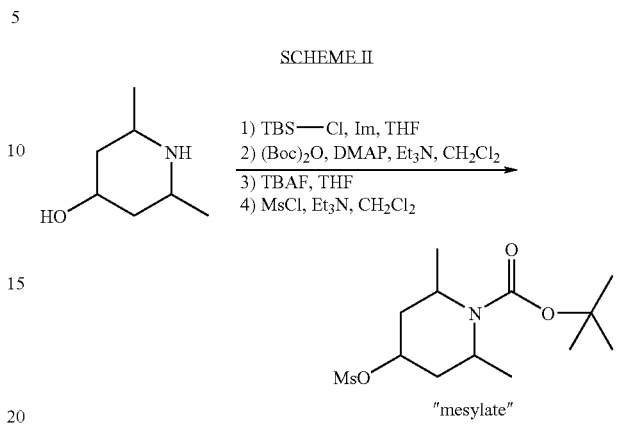

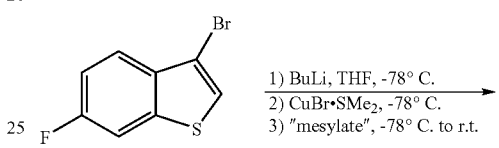

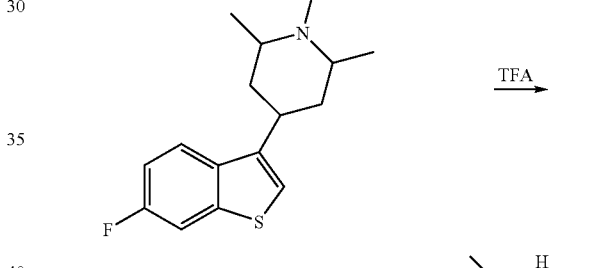

SCHEME III

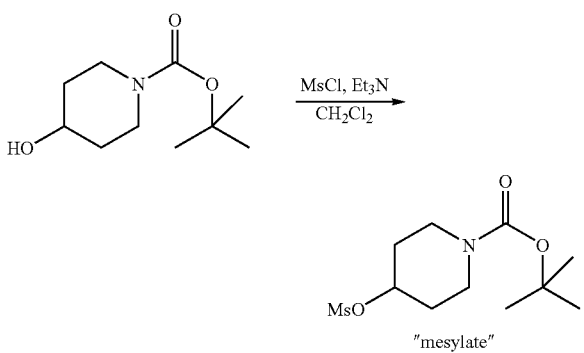

-continued

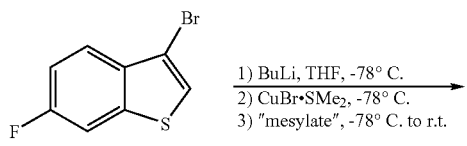

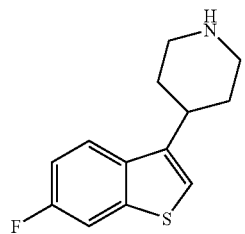

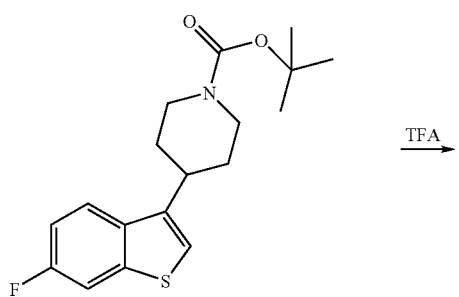

The preparation of various substituted aza- and diazacycloheptanes is described by Treiber et al. in WO 9725324.

The synthesis of compounds of formula (I) wherein the variable designated as B contains a carbocycle is shown in general reaction Scheme IV. It will be apparent that compounds which do not contain a carbocyclic group can be prepared by utilizing these synthetic schemes and making necessary modifications.

Scheme IV

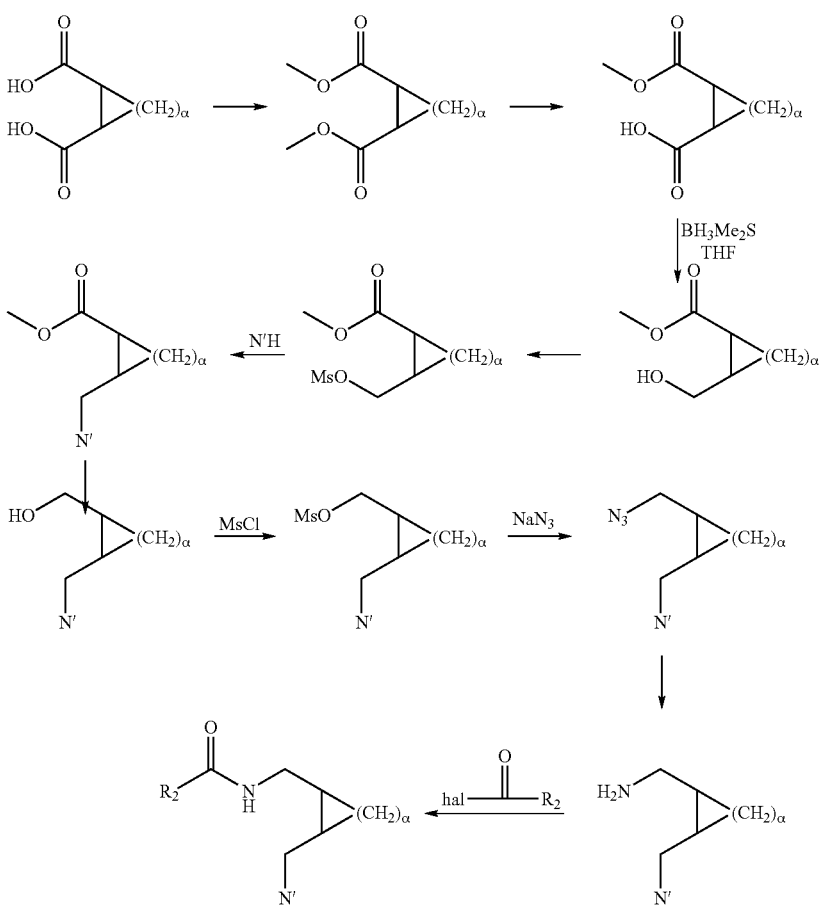

wherein $R_2$ is as hereinbefore defined; α is 1, 2, 3 or 4; and N'— is

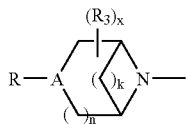

wherein R, A, k, $R_3$, x, and n are as hereinbefore defined.

Many of the dicarboxylates or more advanced intermediates that are generically described in Scheme IV are commercially available. Several of these are shown in Table 1. This table is used for illustrative purposes only and is not intended to limit the scope of the present invention in any way.

TABLE 1

| Starting Materials: | | | |
|---|---|---|---|
| Structure | Name | CAS # | Supplier |
| | Dimethyl cis-1,2-cyclopropane dicarboxylate | 826-34-6 | Acros |
| | Dimethyl trans-1,2-cyclopropane dicarboxylate | 826-35-7 | Acros |
| | Dimethyl 1-methyl-trans-1,2-cyclopropane dicarboxylate | 702-92-1 | Acros |
| | Dimethyl 3-methyl-trans-1,2-cyclopropane dicarboxylate | 28363-79-3 | Acros |
| | trans-Cyclobutane-1,2-dicarboxylic acid dimethylester | | Syntec |
| | trans-1,2-Cyclohexane dicarboxylic acid | 2305-32-0 | Aldrich Acros |
| | trans-2-Carbomethoxy cyclohexane-1-carboxylic acid | | Rieke |
| | cis-1,2-Cyclohexane dicarboxylic acid | 610-09-3 | Acros |

TABLE 1-continued

Starting Materials:

| Structure | Name | CAS # | Supplier |
|---|---|---|---|
| (structure of cis-2-carbomethoxy cyclohexane-1-carboxylic acid) | cis-2-Carbomethoxy cyclohexane-1-carboxylic acid | | Rieke |

When not commercially available, the appropriate starting material may be obtained via standard synthetic methods.

Compounds of formula (I) wherein Y is sulfonyl or a bond may be synthesized via methods analogous to those examples described later herein.

When a compound of formula (I) is obtained as a mixture of enantiomers these may be separated by conventional methods such as crystallization in the presence of a resolving agent, or chromatography, for example using a chiral HPLC column.

Compounds of formula (I) have been found to exhibit affinity for dopamine receptors, in particular $D_3$ receptors, and are expected to be useful in the treatment of disease states which require modulation of such receptors, such as psychotic conditions. Preferred compounds of the present invention are those which have higher affinity for dopamine $D_3$ than dopamine $D_2$ receptors.

As stated earlier herein, certain compounds within the scope of the present invention are generically disclosed in U.S. Pat. No. 5,801,176. For example, certain 6-trifluoromethyl benzo[b[thiophenes were disclosed therein to be useful as antipsychotics.

A major challenge in antipsychotic research is to produce agents with reduced side effects. Orthostatic hypotension is a common side effect in antipsychotics that is associated with the high potency that these agents have at the alpha-1 receptor (hereinafter referred to as "α-1"). A major goal of this work was to find agents with reduced α-1 potency.

The 6-trifluoromethyl benzo[b]thiophenes described herein have a clear and somewhat surprising advantage over the 6-fluoro benzo[b[thiophenes as shown in the following table. The 6-fluoro benzo[b]thiophenes are clearly more potent at the α-1 receptor than are the 6-trifluoromethyl benzo[b]thiophenes. This is shown by comparing pairs of analogs that only differ in substitution at the 6-position of the benzo[b]thiophene. In every case, as can be seen in the table that follows, the 6-fluoro benzo[b]thiophene is more potent than the corresponding 6-trifluoromethyl analog. In some cases this small structural difference in substitution at the 6-position produces a dramatic change in α-1 potency.

| CMPD NUMBER | MOLSTRUCTURE | halpha 1 Ki (nM) h = human | halpha 1% I h= human | rat alpha 1 Ki (nM) | rat alpha 1% I |
|---|---|---|---|---|---|
| 811614 | (structure) | | | 5 | |
| 814238A | (structure) | 78.3 | | | 50% @ 10 uM |

| CMPD NUMBER | MOLSTRUCTURE | halpha 1 Ki (nM) h = human | halpha 1% I h= human | rat alpha 1 Ki (nM) | rat alpha 1% I |
|---|---|---|---|---|---|
| 813377 | | | | 15.4 | |
| 815546 | | | | 59 | |
| 813914 | | | | 3 | |
| 815541 | | 1110 | 48% Inh @ 10 uM | | |
| 813376 | | | | 10.9 | |
| 815545 | | | | 25% Inh @ 10 uM | |

-continued

| CMPD NUMBER | MOLSTRUCTURE | halpha 1 Ki (nM) h = human | halpha 1% I h= human | rat alpha 1 Ki (nM) | rat alpha 1% I |
| --- | --- | --- | --- | --- | --- |
| 813585A | | 5.67 | | | |
| 815547A | | 18.7% @ 10 uM | | | |
| 813754 | | | | 7 | |
| 815548 | | 27% Inh @ 1 uM | | | |
| 813368 | | | | 4.1 | |

-continued

| CMPD NUMBER | MOLSTRUCTURE | halpha 1 Ki (nM) h = human | halpha 1% I h= human | rat alpha 1 Ki (nM) | rat alpha 1% I |
| --- | --- | --- | --- | --- | --- |
| 815554 | | | 40% Inh @ 1 uM | | |
| 813374 | | | | 32.4 | |
| 815555 | | | 24% Inh @ 1 uM | | |
| 813371 | | | | 1.1 | |
| 815556 | | | | 12 | |
| 813375 | | | | 2.6 | |

-continued

| CMPD NUMBER | MOLSTRUCTURE | halpha 1 Ki (nM) h = human | halpha 1% I h= human | rat alpha 1 Ki (nM) | rat alpha 1% I |
|---|---|---|---|---|---|
| 815544 | | 62 | | | |
| 813381 | | 32.3 | | | |
| 815551 | | 80 | | | |
| 813918 | | 4 | | | |
| 815557 | | 72 | | | |

-continued

| CMPD NUMBER | MOLSTRUCTURE | halpha 1 Ki (nM) h = human | halpha 1% I h= human | rat alpha 1 Ki (nM) | rat alpha 1% I |
|---|---|---|---|---|---|
| 813920 | | | | | 2 |
| 815542 | | | | | 68 |

Another example of the surprising effect on α-1 potency that can result from small structural changes is shown in the table that follows. The benzo[b[thiophene piperazines (n is 1) are more potent at the α-1 receptor than are the benzo[b[thiophene homopiperazines (n is 2, hereinafter referred to as "homopiperazines"). Despite the fact that these compounds are merely homologs of one another, a significant decrease in α-1 receptor binding affinity is shown for the homopiperazines.

TABLE II

Piperazines (n = 1) vs. Homopiperazines (n = 2)

r = rat h = human

| R | n | CMPD # | r-α1 Ki (nM) | h-α1 Ki (nM) |
|---|---|---|---|---|
| 2-benzo[b]thiophene | 1 | 811614 | 5 | |
| 2-benzo[b]thiophene | 2 | 822224G | | 82.5 |
| 2-Methoxy phenyl | 1 | 813368 | 4.1 | |
| 2-Methoxy phenyl | 2 | 822157 | 41% Inh @ 1 μM | 27.4 |
| 2-Furyl | 1 | 813371 | 1.1 | |
| 2-Furyl | 2 | S981843 | | 5.6 |
| 2-Naphthyl | 1 | 813372 | 40.6 | |
| 2-Naphthyl | 2 | 822223G | | 123 |
| 2-Indol | 1 | 813373 | 25.2 | |
| 2-Indol | 2 | 822225 | 0% Inh @ 1 μM | 598 |
| 4-Trifluoromethyl phenyl | 1 | 813374 | 32.4 | |
| 4-Trifluoromethyl phenyl | 2 | 826705 | | 136 |
| m-Methoxy benzyl | 1 | 813380 | 21.9 | |

TABLE II-continued

Piperazines (n = 1) vs. Homopiperazines (n = 2)

[Structure: 6-fluorobenzothiophene linked to piperazine/homopiperazine with N-acyl side chain, R-C(=O)-N-(CH2)-]

r = rat  h = human

| R | n | CMPD # | r-α1 Ki (nM) | h-α1 Ki (nM) |
|---|---|---|---|---|
| m-Methoxy benzyl | 2 | 826733 | | 35 |
| 4-t-Butyl phenyl | 1 | 813383 | 70.7 | |
| 4-t-Butyl phenyl | 2 | 822198 | 0% inh. @ 1 μM | 209 |
| 5-Isoxazolyl | 1 | 813589 | 48% 0.1 nM | |
| 5-Isoxazolyl | 2 | 826695 | | 35% Inh @ 1 μM |
| 3-Fluoro phenyl | 1 | 813761 | 4 | |
| 3-Fluoro phenyl | 2 | 822154 | 0% Inh @ 1 μM | 41.8 |
| 4-Trifluoro methoxy phenyl | 1 | 813912 | 17 | |
| 4-Trifluoro methoxy phenyl | 2 | 822152 | 14% Inh @ 1 μM | 122 |
| 3,5-Difluoro phenyl | 1 | 813921 | 5 | |
| 3,5-Difluoro phenyl | 2 | 815542 | | 45.4 |
| 5-Indolyl | 1 | 814018 | 5 | |
| 5-Indolyl | 2 | 822229 | 47% Inh @ 1 μM | 53.4 |
| 3-Indolyl | 1 | 814026 | 12 | |
| 3-Indolyl | 2 | 825658 | 34% Inh @ | 111 |

Especially preferred compounds of the instant invention are those with a reduced liability for α-1 receptor binding while at the same time having a higher affinity for dopamine $D_3$ than dopamine $D_2$ receptors.

Receptor affinity can be measured using standard methodology (Protocols1-5) such as is described below.

Protocol 1

[N-Methyl-$^3$H]Spiroperidol Binding to Cloned Human Dopamine $D_3$ Receptors

Purpose

This assay measures the in vitro activity of compounds on cloned human dopamine ($D_3$) receptors and predicts the direct dopamine-blocking properties of putative neuropsychiatric agents at human dopamine $D_3$ receptors.

Methods

A. Cloning

The $D_3$ gene was isolated from a human striatal cDNA library (Stratagene). The gene was sequenced and sub-cloned into the expression vector RC/RSV (Invitrogen). CHO (Chinese Hamster Ovary) cells were stably transfected with 10 μg of the $D_3$/RSV plasmid using the DOTAP method from Boehringer Mannheim and 72 clones that were G418 resistant were isolated. Using mRNA and binding displacement data a single high expressing clone was identified. This clone was then grown in large batches for the purpose of developing a 96 well format assay.

B. Cell Culture

1. One plate (10 cm) with approximately 2-3 million $D_3$ cells per plate is incubated with 1 ml of Trypsin-EDTA at room temperature for ~2 min or until cells have lifted off plates. Four ml of Ham's F12+10% Fetal Bovine Serum+1% Penicillin/Streptomycin+G418 (400 μg/ml) medium are added to resuspend cells and 1 ml of this is added to each large plate (15 cm) containing 19 ml of the same medium as mentioned above.
2. The 5 large plates are incubated at 37° C.+5% $CO_2$ for ~3 days or until the cells are confluent.
3. After these plates are confluent, they are split into 10 large plates. Medium is aspirated off, 2 ml of Trypsin-EDTA are added to each plate and plates are incubated at RT for 2 min or until cells have lifted off the plate. Eight ml of the F12 medium (same medium as #1 above) are added to each plate (10 ml total) to resuspend the cells and 5 ml are transferred to the 2 new plates containing 15 ml of the F12 media.
4. The 10 large plates are incubated at 37° C.+5% $CO_2$ for ~2 days or until the cells are confluent.
5. The 10 large plates are split into 60 large plates (using Trypsin-EDTA as #3 except 4 ml of F12 medium are added to resuspend cells and 1 ml is aliquoted to 6 new plates containing 19 ml of F12 medium each).
6. Plates are incubated at 370° C.+5% $CO_2$ for ~3 days or until cell are confluent.
7. The 60 large plates are then split into 60 roller bottles (100-150 million cells/bottle). Medium is aspirated off, 2 ml of Trypsin-EDTA are added to each plate and incubated at RT for ~2 minutes or until cells have lifted off plates. Eight ml of F12 medium are added to each plate to resuspend cells and the entire 10 ml are added to 1 roller bottle containing 90 ml of the F12 medium.
8. The 60 roller bottles are immediately placed on their sides and transferred to the roller bottle incubator. They are incubated at 37° C.+5% $CO_2$ for ~3-5 days. Cells are spun at 30-40% motor speed in the Forma incubator.
9. Medium is poured off and cells are washed 2× in PBS.
10. Cells are then scraped off in 20 ml of PBS and the bottles are rinsed again with 5 ml of PBS to remove any remaining cells. Cells are stored on ice before membrane preparation.
11. The yield for 60 $D_3$ roller bottles has varied from ~260-500 mg.

Note: All tissue culture reagents are from Gibco-BRL.

C. Membrane Preparation

The cells are harvested into 250 ml centrifuge tubes with 100 volumes of cold phosphate buffered saline (PBS) and spun down (1200×G for 10 min at 4° C.). The medium is removed and 100 ml PBS are added to each centrifuge tube, cells are resuspend and spun down again. The PBS is removed and the final pellet is homogenized in an appropriate volume of 10% DMSO with a polytron on ice at a medium setting.

D. Lowry Protein Assay

A 200 µl sample membrane homogenate is added to 200 µl of 1% SDS, vortexed and allowed to stand for 5 min. Aliquots (25, 50 and 100 µl) of this mixture are assayed in duplicate following the standard Bio-Rad DC protein assay protocol (kit catalog number 500-0112) and using reagent S. Absorbance readings are made at 750 nm (note: the most accurate protein OD readings are between 0.1-0.5 units). The protein concentration is calculated using a standard curve generated concurrently with bovine serum albumin as standard.

E. Storage/Freezing Conditions

Following the determination of the protein concentration and Scatchard analysis, the protein is diluted into distilled water with 10% DMSO to the appropriate volume based on expression levels (Bmax). The concentrated protein is then aliquoted into 1.5 ml screw top cap Eppendorf tubes and placed into a −800° C. freezer.

F. Binding Assay Reagents
1. 0.5M Tris Buffer, pH 7.7
   a) 44.4 g Tris HCl 26.5 g Tris Base q.s. to 1 Liter (0.5 M Tris buffer, pH 7.7 at 37° C.)
   b) make a 1:10 dilution in distilled $H_2O$ (0.05 M. Tris buffer, pH 7.7)
2. Tris Buffer Containing Physiological Salts
   a) Stock buffer
      NaCl 7.014 g
      KCl 0.372 g
      $CaCl_2$ 0.222 g
      $MgCl_2$ 0.204 g
      q.s. To 100 ml with 0.5 M. Tris Buffer
   b) Dilute 1:10 in distilled $H_2O$
   This yields 0.05 M. Tris HCl, pH 7.7, containing NaCl (120 mM), KCl (5 mM), $CaCl_2$ (2 mM) and $MgCl_2$ (1 mM)
      Optional: add 0.1% ascorbic acid and check pH (in assays with compounds that may oxidize.
3. a) 1.0% polyethyleneimine stock in 0.5M Tris (reagent 1.a)
   b) Dilute 1:10 in distilled $H_2O$
4. [N-methyl-$^3$H]-Spiroperidol (60-90 Ci/mmol) is obtained from New England Nuclear; catalog #NET-856.
   For $K_i$ determinations: [$^3$H]NMSP is made up to a concentration of 2.7 nM in buffer 2b, such that when 150 µl is added to each tube a final concentration of 0.4 nM is attained in the 1 ml assay. Samples of total CPM added are taken for each experiment to calculate the total ligand concentration.
5. S(−)-Eticlopride is obtained from Research Biochemicals International (RBI catalog number E-101). A refrigerated stock (good for up to a month) solution of S(−)-eticlopride is made at a concentration of 30 µM in buffer 2b. One hundred microliters are added to 3 wells for the determination of nonspecific binding (this yields a final concentration of 3 µM in the 1 ml assay).
6. Test Compounds
   For most assays, a 100 µM stock solution of the test compound is made up in a suitable solvent (usually <0.1% acetic acid) and serially diluted with buffer 2b, such that when 100 µl of drug is combined with the total 1 ml assay, final concentrations ranging from $10^{-5}$-$10^{-8}$ M are attained. Characteristically eight concentrations are studied for each assay; however, higher or lower concentrations may be used, depending on the potency of the drug.

G. Binding Assay
   750 µl Tissue
   150 µl [$^3$H]NMSP
   100 µl vehicle (for total binding) or 30 µM (−)eticlopride (for nonspecific binding) or appropriate drug concentration.

The 96-Well Packard Unifilters GF/B are incubated for >1 h at 25° C. in 0.1% polyethylamine (from 3,b). The cold tissue is added last and mixed on a orbital shaker for a few seconds and is then incubated at 37° C. for 30 min in a shaking water bath. The assay is stopped by rapid filtration through Packard Unifilter plates. The filter membranes are then washed with 15 ml of ice-cold 0.05 M Tris buffer. The filters are then dried (~15 min under a heat lamp or incubated for 15 min in a 60° C. oven) and a bottom seal is applied. Then 40 µl of Packard Microscint 20 scintillation cocktail is added and a permanent topseal (Type P) is applied and heat sealed. The plates are then shaken on an orbital shaker for 1 h and placed in the Packard Topcount and counted for at least 5 minutes for each point.

Specific binding is defined as the difference between total binding and the binding in the presence of 3 µM S-(−)-eticlopride. Total binding is approximately 10% of the total added ligand. Cheng-Prusoff determination ($K_i$'s) are performed using Prism software using a one-site competition curve analysis where the top and the bottom of the non-linear regression are held constant at 0% and 100% percent inhibition. The percent inhibition at each drug concentration is the mean of duplicate determinations.

Protocol 2

[N-Methyl-$^3$H]Spiroperidol Binding to Cloned Human Dopamine $D_2$Long Receptors Purpose:

This assay measures the in vitro activity of drugs on cloned human dopamine $D_2$Long ($D_2$L) receptors and predicts the direct dopamine-displacing properties of neuropsychiatric, cardiovascular and renal agents at human dopamine $D_2$ receptors.

Methods:

A. Cloning

The $D_2$L gene was isolated from a human striatal (caudate/putamen) cDNA library. The gene was sequenced and subcloned into the expression vector pRC/RSV (Invitrogen). CHO (Chinese Hamster Ovary) cells were stably transfected and 72 clones that were geneticin (G418) resistant were isolated. Using mRNA and binding data a single high expressing cell line was identified (#44). This cell line was then grown in suspension culture for the purpose of developing a 96 well format assay.

B. Cell Culture Conditions
1. Medium for adherent CHO cultures:
   Ham's F12+10% fetal bovine serum (FBS)+400 µg/ml geneticin
   (G418)+10 ml/L penicillin-streptomycin (pen-strep)
2. Cells are transferred to suspension culture when at least 1.5 million cells are available (this allows for 300,000 cells/ml in a 50 ml spinner flask; this is the ideal suspension density). Cell are removed from flasks with trypsin, spun down (1000×G) and resuspended in fresh medium:
   50% CHO-SFM II+50% Ham's F12 w/10% FBS (final FBS conc. 5%)
   +400 µg/ml G418+pen-strep (10 ml/L)
3. After the transfer to suspension culture, growth is monitored and cell viability is assessed using trypan blue exclusion. Total and viable cell count on 5 sectors of the hemocytometer are recorded. When the viable cell density reaches 600,000 cell/ml, the volume is doubled.

4. After 1 week of growth in the 50/50 medium, the cells are spun down and transferred to a new spinner flask and replaced with 75% CHO-SFM II/25% Ham's F12+10% FBS plus the pen-strep and G418. Thereafter every 3 days, the medium is replaced with new medium containing a decreasing amount of FBS as follows:

| ml of CHO SFM: ml of Ham'S F12 | Final % FBS conc. |
|---|---|
| 87.50:12.5 | 1.25 |
| 93.75:6.25 | 0.625 |
| 99.00:1.00 | 0.1 |

5. The final maintenance culturing medium is made up as follows:

A stock mixture of 10 ml of pen-strep, 0.5 ml of 400 mg/ml (active; final concentration: 200 mg/ml) G418 and 1 ml of FBS are mixed and filtered and refrigerated. A volume (11.5 ml) of this mixture is added to a freshly opened 1 L bottle of CHO-SFM II.

C. Membrane Preparation

The cells are harvested into 250 ml centrifuge tubes with 100 volumes of cold phosphate buffered saline (PBS) and spun down (1200×G for 10 min at 4° C.). The medium is removed and 100 ml PBS are added to each centrifuge tube, cells are resuspened and spun down again. The PBS is removed and the final pellet is homogenized in an appropriate volume of PBS with a polytron on ice at a medium setting.

D. Lowry Protein Assay

A 200 µl sample membrane homogenate is added to 200 µl of 1% SDS, vortexed and allowed to stand for 5 min. Aliquots (25, 50 and 100 µl) of this mixture are assayed in duplicate following the standard Bio-Rad DC protein assay protocol (kit catalog number 500-0112) and using reagent S. Absorbance readings are made at 750 nm (note: the most accurate protein OD readings are between 0.1-0.5 units). The protein concentration is calculated using a standard curve generated concurrently with bovine serum albumin as standard.

E. Storage/Freezing Conditions

Following the determination of the protein concentration, the protein is diluted into distilled water with 10% DMSO to the appropriate volume based on expression levels (Bmax). The concentrated protein is aliquoted into 1.5 ml screw top eppendorf tubes and placed into a −80° C. freezer.

F. Binding Assay Reagents
1. 0.5M Tris Buffer, pH 7.7
   a) 44.4 g Tris HCl
      26.5 g Tris Base
      q.s. to 1 Liter (0.5 M Tris buffer, pH 7.7 at 37° C.)
   b) make a 1:10 dilution in distilled $H_2O$ (0.05 M. Tris buffer, pH 7.7)
2. Tris Buffer Containing Physiological Salts
   a) Stock buffer
      NaCl 7.014 g
      KCl 0.372 g
      $CaCl_2$ 0.222 g
      $MgCl_2$ 0.204 g
      q.s. To 100 ml with 0.5 M. Tris Buffer
   b) Dilute 1:10 in distilled $H_2O$
   This yields 0.05 M. Tris HCl, pH 7.7, containing NaCl (120 mM), KCl (5 mM), $CaCl_2$ (2 mM) and $MgCl_2$ (1 mM) Optional: add 0.1% ascorbic acid and check pH (in assays with compounds that may oxidize.
3. a) 1.0% polyethyleneimine stock in 0.5M Tris (reagent 1.a)
   b) Dilute 1:10 in distilled $H_2O$
4. [N-methyl-$^3$H]-Spiroperidol (60-90 Ci/mmol) is obtained from New England Nuclear; catalog #NET-856.

For $K_i$ determinations: [$^3$H]NMSP is made up to a concentration of 2.7 nM in buffer 2b, such that when 150 µl is added to each tube a final concentration of 0.4 nM is attained in the 1 ml assay. Samples of total CPM added are taken for each experiment to calculate the total ligand concentration.

5. S(−)-Eticlopride is obtained from Research Biochemicals International (RBI catalog number E-101). A refrigerated stock (good for up to a month) solution of S(−)-eticlopride is made at a concentration of 30 µM in buffer 2b. One hundred microliters are added to 3 wells for the determination of nonspecific binding (this yields a final concentration of 3 µM in the 1 ml assay).

6. Test Compounds

For most assays, a 100 µM stock solution of the test compound is made up in a suitable solvent (usually <0.1% acetic acid) and serially diluted with buffer 2b, such that when 100 µl of drug is combined with the total 1 ml assay, final concentrations ranging from $10^{31\ 5}$-$10^{31\ 8}$ M are attained. Characteristically eight concentrations are studied for each assay; however, higher or lower concentrations may be used, depending on the potency of the drug.

G. Binding Assay
   750 µl Tissue
   150 µl [$^3$H]NMSP
   100 µl vehicle (for total binding) or 30 µM (−)eticlopride (for nonspecific binding) or appropriate drug concentration.

The 96-Well Packard Unifilters GF/B are incubated for >1 h at 25° C. in 0.1% polyethylamine (from 3,b). The cold tissue is added last and mixed on a orbital shaker for a few seconds and is then incubated at 37° C. for 30 min in a shaking water bath. The assay is stopped by rapid filtration through Packard Unifilter plates. The filter membranes are then washed with 15 ml of ice-cold 0.05 M Tris buffer. The filters are then dried (~15 min under a heat lamp or incubated for 15 min in a 60° C. oven) and a bottom seal is applied. Then 40 µl of Packard Microscint 20 scintillation cocktail is added and a permanent topseal (Type P) is applied and heat sealed. The plates are then shaken on an orbital shaker for 1 h and placed in the Packard Topcount and counted for at least 5 minutes for each point.

Specific binding is defined as the difference between total binding and the binding in the presence of 3 µM S-(−)-eticlopride. Total binding is approximately 10% of the total added ligand. Cheng-Prusoff determination ($K_i$'s) are performed using Prism software using a one-site competition curve analysis where the top and the bottom of the non-linear regression are held constant at 0% and 100% percent inhibition. The percent inhibition at each drug concentration is the mean of duplicate determinations.

Protocol 3

[$^3$H]Prazosin: $\alpha_1$-Adrenergic Receptor Binding in Rat Brain

Purpose:

The [$^3$H]Prazosin binding assay quantitates the $\alpha_1$-adrenergic receptor binding properties of psychoactive agents and can be used to assess a compounds' potential to cause orthostatic hypotension and sedation as side effects.

Procedure:

This assay method is adapted from the modifications of the original α-adrenergic receptor binding assay described by Morrow and Creese(1986).

A. Reagents
1. 0.5 M Tris buffer, pH 7.7
   57.2 g Tris HCl
   16.2 g Tris base
   q.s. to 1 liter (0.5 M Tris buffer, pH 7.7)
   Make a 1:10 dilution in distilled $H_2O$ (0.05 M Tris buffer, pH 7.7 at 25° C.)
2. [7-Methoxy-$^3$H]-Prazosin, (71.8 Ci/mmol; New England Nuclear). For $IC_{50}$ determinations: [$^3$H]Prazosin is made up to a concentration of 2 nM and 0.150 ml is added to each tube (yields a final concentration of 0.13 nM in the 1 ml assay volume).
3. Phentolamine is used to determine non-specific binding (Sigma Chemical). A 1 mM stock solution of phentolamine is made up in 0.01 N Glacial Acetic Acid and serially diluted to 100 μM to determine nonspecific binding. This yields a final concentration of 10 μM in the assay tube.
4. Test compounds. For most assays, a 1 mM stock solution is made up in a suitable solvent and serially diluted such that the final concentration in the assay ranges from $10^{-5}$ to $10^{-9}$M. Nine concentrations are usually used for each assay. Higher or lower concentrations may be used depending on the potency of the drug.

B. Tissue Preparation

Rat brain tissue can be obtained from either fresh (male Wistar rats; 200-250 g) or frozen (male Sprague Dawley 200-250 g from Harlan, Indianapolis, Ind.; Cat. BT-403 or Cortices Cat. BT-451). Cortices are homogenized in 50 volumes times the wet weight in ice-cold 50 mM Tris buffer (pH 7.7 at 25° C.) using a Tekmar homogenizer (setting 8) for 10-15 seconds. The homogenate is centrifuged at 48,000 g for 10 min (approximately 21,000 rpm using the Sorvall RC-5 centrifuge with head SS-34), the supernatant discarded and the pellet resuspended in fresh 50 mM Tris. buffer and recentrifuged at 48,000× g for 10 min. The pellet is resuspended in a final tissue concentration of 1 g wet weight tissue per 149 ml fresh 50 mM Tris buffer, pH 7.7. The final protein concentration in the assay is 0.2-0.5 mg/ml.

C. Binding Assay
   0.100 ml Vehicle (for total binding), or 10 μM
      Phentolamine (for nonspecific binding) or appropriate drug concentrations
   0.150 ml $^3$HPrazosin stock solution
   0.750 ml Tissue suspension Sample tubes are kept on ice for additions, then vortexed and incubated for 30 minutes at 30° C. The binding is terminated by rapid vacuum filtration through Whatman GF/B filters, followed by three 5-ml washes with ice-cold 0.05 M Tris buffer. The filters are counted in 5 ml of liquid scintillation cocktail. Specific Prazosin binding is defined as the difference between the total binding and that displayed by 10 μM Phentolamine. $IC_{50}$ calculations are performed using nonlinear regression to a one or two site model. (GRAPHPAD-INPLOT).

Protocol 4

[$^3$H]Prazosin Binding to Alpha-1 Adrenergic Receptors from Rat Brain Cortex

Objective: This in vitro assay is designed as a screen to identify compounds displaying a affinity for the a, adrenoceptor subtype in membranes from rat cortex. It measures the ability of the test compounds to displace [$^3$H]prazosin from the $α_1$ sites.

Membrane Preparation: Rat brain tissue can be obtained from either fresh (male Wistar rats; 200-250 g) or frozen (male Sprague-Dawley 200-250 g from Harlan; cat. #BT-403) stocks. The cortex is dissected, homogenized in 50 vol (wet weight) ice-cold 50 mM Tris buffer (pH 7.7 at 25° C.). The homogenate is centrifuged at 48,000 g for 10 min, the pellet is resuspended in 50 mM Tris buffer and centrifuged a second time. The second pellet ($P_2$) is resuspended to yield a concentration of 115 mg wet weight per 10 ml. This results in a protein concentration of ~120 μg/well in the final assay. Membranes should be mixed just before addition to ensure an even suspension.

Assay Requirement: 1 cryovial per 96 well plate

[$^3$H]-Ligand: [$^3$H]prazosin: 0.8 nM (NEN, NET-823)
   $K_D$=0.25 nM (200 μl assay)

Materials: Phentolamine mesylate (Research Biochemicals Int. #P-131)
   96 well flat bottom plates (Beckman)
   Unifilter GF/B Plate (Packard)
   Polyethylenimine (Sigma #P-3134)
   TomTec or Packard Filtermate 196 Cell Harvesters
   Packard TopCount Scintillation Counter Buffers: A: 50 mM Tris HCl; 0.1% ascorbate, pH 7.7-(incubation buffer)
   B: 50 mM Tris HCl; pH 7.7 (wash buffer)

Procedure: Assay additions are as follows (in the order indicated):
   Total Binding=50 μl bufferA+50 μl [$^3$H]prazosin+100 μl membrane
   Nonspecific Binding=50 μl phentolamine (10 μM final)+50 μl [$^3$H]prazosin+100 μl membrane
   Test Cpd=50 μl compound+50 μl [$^3$H]prazosin+100 μl membrane
   Compounds to be evaluated are weighed out to yield a 10 mM stock solution in DMSO in a 24 well polystyrene plate. This is diluted to a 0.5 mM stock in $dH_2O$. Serial dilutions in Buffer A are made from which 50 μl additions to the plate are made in duplicate in order to achieve the final concentrations desired. Typically, one 96 well plate is used to evaluate 11 compounds at 4 concentrations ($10^{-6}$-$10^{-9}$ M) in duplicate. Total binding and nonspecific binding are determined in quadruplicate. Usually one standard is run with each assay.
   [$^3$H]Prazosin is made up in Buffer A such that when 50 μl are added per well the final concentration is 0.8 nM in a final assay volume of 200 μl. The final concentration should be verified by running a sample in a scintillation counter prior to adding the [$^3$H]prazosin to the 96 well plate. Note: The radioactivity should be prepared just before the additions are made so that it is not allowed to sit on the bench for very long.

Packard GF/B Plate Pretreatment: The filter plates are presoaked for at least 30 min in ice cold Buffer B containing 0.05% polyethyleneimine (200 µl/200 ml) to maximize filtration efficiency and minimize filter blank binding.

Incubation & Filtration: Once buffer, compounds, [$^3$H] prazosin and membrane have been added (and mixed), the 96 well plates are incubated for 40 min at 37° C. and spaced 3-5 min apart. At 40 min, the plates are filtered using a Tomtec Automated Cell Harvester. Filtration is immediately followed by washes of ice cold Buffer B (total vol. ~7 ml).

Drying and Counting: Each filter plate is dried under a heat lamp for 15 min. The back of the plate is sealed and 40 µl of Packard microscint fluid are added per well. Using Packard film, each plate is heat sealed prior to being counted in a Packard Topcount Scintillation counter. A program has been written that counts each plate twice sending DPM, CPM and TSIS data to disk and printer.

Analysis of Results: Raw DPM and CPM data are captured on disk and are imported into one of several software packages (Graphpad Prism Ver 2.0, Excel) residing on the LAN. Specific binding is defined as the difference between total binding and the binding in the presence of 10 µM phentolamine. Total binding is less than 10% of the total added ligand. Software using one-site competition curve analysis is employed in the calculation of $IC_{50}$ and $K_I$ (Cheng-Prusoff equation, 1973). The top and bottom of the non-linear regression are held constant at 0% and 100% inhibition. The percent inhibition at each drug concentration is the mean of duplicate determinations.

[$^3$H]PRAZOSIN BINDING TO CLONED HUMAN ALPHA-1A ADRENERGIC RECEPTORS ($\alpha_{1a}$) EXPRESSED IN CHINESE HAMSTER OVARY CELLS (CHO)

Purpose: This in vitro assay is designed as a screen to identify compounds displaying a affinity for the human $\alpha_{1a}$ adrenoceptor subtype expressed in the membrane fragments of CHO cells. The assay measures the ability of the test compounds to displace [$^3$H] prazosin from $\alpha_{1a}$ sites.

The identification of multiple vascular $\alpha_1$-addrenoceptors ($\alpha_{1a}$, $\alpha_{1b}$, $\alpha_{1d}$) in vitro has provided impetus to define the role(s) of these subtypes in cardiovascular regulation in vivo (Vargas and Gorman, 1995). Hemodynamic studies in the unanesthetized rat suggest that vascular $\alpha_{1a}$ receptors are the major subtype involved in the sympathetic regulation of peripheral resistance and systemic arterial pressure (Piascik et al., 1989). Additional evidence for an involvement of peripheral $\alpha_{1a}$ receptors in the maintenance of arterial pressure was demonstrated by the findings that the selective $\alpha_{1a}$ antagonist 5-MU dose dependently lowered resting arterial pressure in awake conscious dogs (Piascik et al., 1989). A demonstrated inability of the irreversible antagonist, chloroethylclonidine, to reduce arterial pressure in rats when administered intravenously, is strong evidence against the role of 60 $_{1b}$ and $\alpha_{1d}$ receptors in the acute regulation of arterial pressure (Vargas et al., 1993).

Therefore, the binding of compounds to $\alpha_{1a}$ adrenergic receptors is believed to be a good measure of a compound's potential to cause orthostatic hypotension and sedation as side effects. Prazosin is a potent antagonist of the human $\alpha_{1a}$-adrenoceptor subtype, which has been cloned and is expressed in the membrane fragments of CHO cells.

h$\alpha_{1a}$ Receptor: The cloning of the human $\alpha_{1a}$ cDNA was accomplished first by screening a human prostate cDNA library (Clontech), from which a portion of the coding region was obtained. This DNA fragment was then used to screen a human leukocyte genomic library (Clontech), and the rest of the coding sequence was obtained. Later these two fragments were spliced together. The entire coding sequence was then fully sequenced including matching PCR sequence with original genomic coding sequence, thus ensuring splice sites were joined correctly (Schwinn et al., 1995). Once sequenced, the gene was subcloned into the expression vector pcDNA3 (Invitrogen). Plasmid DNA was then used for transfection into CHO cells and G418 resistant clones were isolated. A clone expressing high levels of the h$\alpha_{1a}$ receptor (as determined by mRNA and receptor binding data) was chosen and pharmacologically characterized.

Culture Media: Media Ingredients for Adherent $\alpha_{1a}$ expressing CHO Culture:
A. HAM's F-12 (Cellgro)
B. 10% 0.2 micron filtered Fetal Bovine Serum (FBS) (Cellgro)
C. 1% 0.2 micron filtered Penicillin-Streptomycin (Celigro)
D. G418 0.2 micron filtered (Geneticin 400 µg/ml)(Cellgro)
Cells are cultured using established methods and procedures in either 150×25 mm culture plates (scale up to 100 plates) or a combination of these plates and 70 roller bottles. One culturing/harvest cycle typically requires 2 weeks and yields between 100-400 mg protein. Plates or bottles are incubated at 37° C.+5% $CO_2$.

Storage: Cells are harvested by mechanical scraping, washed using PBS, collected in 250 ml Corning polypropylene centrifuge tubes, spun down (1500RPM) and resuspended in $dH_2O$ 10% DMSO (final volume per harvest is approximately 50 ml). Protein determination is made using the Biorad DC Assay Kit. Finally, the appropriate volume is aliquoted into a 2 ml Corning Cryovial (10 mg/1-1.5 ml) which is stored at −80° C.

Current Lot Data:

| | |
|---|---|
| $\alpha_{1a}$ (clone #7) | |
| Batch 1/14/98 | |
| Receptor Concentration | 2418 fmoles/mg protein |
| $K_d$ | O.18 nM |
| Volume | 1.5 ml/cryovial |
| Protein Concentration | approx. 10 mg/1.5 ml |

Assay Requirement: 0.5 cryovials per 96 well plate (assay volume=200 µl/well)

[$^3$H]-Ligand: [7-methoxy-$^3$H]-Prazosin: 1.0 nM (NEN, NET-823)
70-87 Ci/mmol

Materials: Phentolamine mesylate (Research Biochemicals Int. #P-131)
96 well flat bottom plates (Beckman)
Unifilter GF/B Plate (Packard)
Polyethylenimine (Sigma #P-3134)
TomTec or Packard Filtermate 196 Cell Harvesters Packard TopCount Scintillation Counter Buffers: A: 50 mM Tris HCl; 0.1% ascorbate, pH 7.7 (incubation buffer)
B: 50 mM Tris HCl; pH 7.7 (wash buffer)

Procedure: Assay additions are as follows (in the order indicated):
Total Binding=50 µl buffer A+50 µl [$^3$H]prazosin+100 µl membrane
Nonsp. Bd.=50 µl 10 µM phentolamine+50 µl [$^3$H]prazosin+100 µl membrane
Test Cpd.=50 µl compound+50 µl [$^3$H]prazosin+100 µl membrane
Compounds to be evaluated are weighed out to yield a 10 mM stock solution in DMSO in a 24 well polystyrene plate. This is diluted to a 0.5 mM stock in dH$_2$O. Serial dilutions in Buffer A are made from which 50 µl additions to the plate are made in duplicate in order to achieve the final concentrations desired. Typically, one 96 well plate is used to evaluate 11 compounds at 4 concentrations ($10^{-6}$-$10^{-9}$ M) in duplicate. Total binding and nonspecific binding are determined in quadruplicate. Usually one standard is run with each assay.
[$^3$H]Prazosin is made up in Buffer A such that when 50 µl are added per well the final concentration is 1.0 nM in a final assay volume of 200 µl. The final concentration should be verified by running a sample in a scintillation counter prior to adding the [$^3$H]prazosin to the 96 well plate. Note: The radioactivity should be prepared just before the additions are made so that it is not allowed to sit on the bench for very long.
Packard GF/B Plate Pretreatment: The filter plates are pre-soaked for at least 30 min in ice cold Buffer B containing 0.05% polyethyleneimine (200 µl/200 ml). to maximize filtration efficiency and minimize filter blank binding.
Incubation & Filtration: Once buffer, compounds, [$^3$H] prazosin and membrane have been added (and mixed), the 96 well plates are incubated for 40 min at 37° C. and spaced 3-5 min apart. At 40 min, the plates are filtered using a Tomtec Automated Cell Harvester. Filtration is immediately followed by washes of ice cold Buffer B (total vol. ~7 ml).
Drying and Counting: Each filter plate is dried under a heat lamp for 15 min. The back of the plate is sealed and 40 µl of Packard microscint fluid are added per well. Using Packard film, each plate is heat sealed prior to being counted in a Packard Topcount Scintillation counter. A program has been written that counts each plate twice sending DPM, CPM and TSIS data to disk and printer.
Analysis of Results: Raw DPM and CPM data are captured on disk and are imported into one of several software packages (Graphpad Prism Ver 2.0, Excel) residing on the LAN. Specific binding is defined as the difference between total binding and the binding in the presence of 10 µM phentolamine. Total binding is less than 10% of the total added ligand. Software using one-site competition curve analysis is employed in the calculation of $IC_{50}$ and $K_I$ (Cheng-Prusoff equation, 1973). The top and bottom of the non-linear regression are held constant at 0% and 100% inhibition. The percent inhibition at each drug concentration is the mean of duplicate determinations.

References: Vargas, H. M. and A. J. Gorman. *Life Sciences*. Vol. 57, No. 25, pp. 2291-2308, 1995.
Morrow, A. L. and 1. Creese. *Mol. Pharmacol.* 29: 321-330, 1986.
Piascik, M. T., J. W. Kusiak, and K. W. Barron. *Eur. J. Pharmacol* 11:101-107, 1989.
Vargas, H. M., D. Cunningham, L. Zhou, H. B. Hartman and A. J. Gorman. *J. Pharmacol. Exp. Ther.* 267:264-272, 1993.

The functional activity of compounds of the invention (i.e. whether they are antagonists, agonists or partial agonists) can readily be determined using the microphysiometer test method that follows:

Chinese Hamster Ovary (CHO) cells, expressing the human dopamine $D_3$ receptor, were grown on the surface of a capsule cup. Cups are assembled and placed on the microphysiometer, and buffer (Dulbecco's Modified Eagle's Medium without sodium bicarbonate and without serum) is perfused through the cup assembly until a stable baseline is achieved (4 hours). Buffer perfusion rate and solution changes are controlled by a computer. Intracellular acidification rate is measured in each of the 8 cup assemblies and recorded by the computer. Buffer containing test compound (10 nM, 100 nM, and 1 uM) is perfused through the cup assembly for 20 min. Buffer containing quinpirole (10 nM) (a $D_3$ agonist) and test compound (same concentrations) is perfused for an additional 1 min. This is followed by a recovery period of 10-60 min where buffer alone was perfused through the cups. Quinpirole increases the rate of acidification. If the test compound is a $D_3$ antagonist, this increase will be inhibited in a concentration dependent manner. Testing of compound numbers 815541 and 813782 showed these compounds to be $D_3$ antagonists.

$D_3$ antagonists are of potential use as antipsychotic agents for example in the treatment of schizophrenia, schizo-affective disorders, psychotic depression and mania. Conditions which may be treated by $D_3$ agonists include dyskinetic disorders such as Parkinson's disease, neuroleptic-induced parkinsonism and tardive dyskinesias; depression; anxiety; dementia; circadian rhythm disorders, and drug (e.g. cocaine) dependency.

In accordance with yet another embodiment of the present invention, there is provided a method of modulating the activity of dopamine $D_3$ receptors, said method comprising: contacting cell-associated dopamine $D_3$ receptors with a concentration of a compound of formula IA, or a physiologically acceptable salt thereof, sufficient to modulate the activity of said dopamine $D_3$ receptor. As employed herein, a "compound of formula IA" shall refer to the compound of formula I except that the proviso therein i.e. "Proviso A" is deleted therefrom and inserted therefor is the following proviso (hereinafter referred to as "Proviso B"):

"with the proviso that when R is (a); and Y is carbonyl; and n is 1; and k is 0; and Q is hydrogen, $C_1$-$C_6$alkyl, halogen or —$CH_2OC_1$-$C_6$alkyl; and $R_1$ is hydrogen or unsubstituted $C_1$-$C_6$alkyl; and $R_3$ is hydrogen or $C_1$-$C_6$alkyl; and $R_4$ is hydrogen or $C_1$-$C_6$alkyl; and —B— is a group of formula (a) or (e); then $R_2$ cannot be a group of formula (x)".

As employed herein, the phrase "modulating the activity of dopamine $D_3$ receptors"refers to a variety of therapeutic applications. Said therapeutic applications refer to the treatment of conditions or disorders which include dyskinetic disorders, psychoses, anxiety disorders, mood disorders, dementia, sleep disorders, circadian rhythm disorders, substance dependence, substance abuse and nausea.

The instant invention also provides a method of treating conditions or disorders of the central nervous system comprising administering to a patient in need thereof a therapeutically effective amount of a compound of formula I, IA, or IB, or a pharmaceutically acceptable salt thereof. The compounds of formula IB are preferred for this method. As employed herein, a "compound of formula IB" shall refer to the compound of formula I except that the proviso therein i.e. "Proviso A" is deleted therefrom and inserted therefor is the following proviso (hereinafter referred to as "Proviso C"):

"with the proviso that when R is (a); and Y is carbonyl; and n is 1; and k is 0; and Q is hydrogen, $C_1$-$C_6$alkyl, halogen or —$CH_2OC_1$-$C_6$alkyl; and $R_1$ is hydrogen or unsubstituted $C_1$-$C_6$alkyl; and $R_3$ is hydrogen br $C_1$-$C_6$alkyl; and $R_4$ is hydrogen or $C_1$-$C_6$alkyl; and —B— is a group of formula (a) or (e); then $R_2$ cannot be saturated or unsaturated $C_1$-$C_{10}$alkyl or any of the following groups:

(a) wherein y is 0;
(b) wherein D is a group of formula (a) wherein u is 0 and M is hydrogen, $C_1$-$C_6$alkyl, $C_1$-$C_6$alkoxy, hydroxy, halogen, trifluoromethyl or

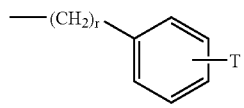

wherein r is 0;
(d) wherein v is 0;
(e) wherein d is 0;
(f);
(g) wherein f is 0;
(i);
(j);
(k);
(l) wherein g is 0;
(n) wherein h is 0;
(o);
(s);
(x);
(ee);
(ff);
(ii); or
(jj)".

The instant invention further provides a method of treating conditions or disorders of the central nervous system comprising administering to a patient in need thereof a therapeutically effective amount of a compound of formula I, IA or IB, or a pharmaceutically acceptable salt thereof, in conjunction with one or more $D_1$, $D_2$, D4, D5 or 5HT receptor antagonists. Compounds of formula IB are preferred for this method.

In treating a patient afflicted with a condition or disorder described above, a compound of formula I, IA, or IB can be administered in any form or mode which makes the compound bioavailable in therapeutically effective amounts, including orally, sublingually, buccally, subcutaneously, intramuscularly, intravenously, transdermally, intranasally, rectally, topically, and the like. One skilled in the art of preparing formulations can determine the proper form and mode of administration depending upon the particular characteristics of the compound selected for the condition or disease to be treated, the stage of the disease, the condition of the patient and other relevant circumstances. For example, see Remington's Pharmaceutical Sciences, 18th Edition, Mack Publishing Co. (1990), incorporated herein by reference.

The compounds of Formula I, IA or IB can be administered alone or in the form of a pharmaceutical composition in combination with pharmaceutically acceptable carriers, the proportion and nature of which are determined by the solubility and chemical properties of the compound selected, the chosen route of administration, standard pharmaceutical practice and other relevant criteria.

The compounds of formula I, IA or IB may be administered orally, for example, in the form of tablets, troches, capsules, elixirs, suspensions, solutions, syrups, wafers, chewing gums and the like and may contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors.

The compounds of Formula I, IA, or IB may also be administered topically, and when done so the carrier may suitably comprise a solution, ointment or gel base. The base, for example, may comprise one or more of petrolatum, lanolin, polyethylene glycols, bee wax, mineral oil, diluents such as water and alcohol, and emulsifiers and stabilizers.

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials.

The highly lipophilic esters, amides and carbamates of compounds I, IA or IB are capable of sustained release in mammals for a period of several days or from about one to four weeks when formulated and administered as depot preparations, as for example, when injected in a properly selected pharmaceutically acceptable oil. The preferred oils are of vegetable origin such as sesame oil, cottonseed oil, corn oil, coconut oil, soybean oil, olive oil and the like, or they are synthetic esters of fatty acids and polyfunctional alcohols such as glycerol or propyleneglycol.

The depot compositions of formula I, IA, or IB are prepared by dissolving a highly lipophilic ester, amide or carbamate of the instant invention in a pharmaceutically acceptable oil under sterile conditions. The oil is selected so as to obtain a release of the active ingredient over a desired period of time. The appropriate oil may easily be determined by consulting the prior art, or without undue experimentation by one skilled in the art.

The dosage range at which the compounds of formula I, IA or IB exhibit their ability to act therapeutically can vary depending upon the particular disease or condition being treated and its severity, the patient, the formulation, other underlying disease states that the patient is suffering from, and other medications that may be concurrently administered to the patient. Generally, the compounds of formula I, IA, or IB will exhibit their therapeutic activities at dosages of between about 0.001 mg/kg of patient body weight/day to about 100 mg/kg of patient body weight/day.

In a further aspect, the present invention provides novel radiolabeled imaging agents of formula I, IA or IB, useful, inter alia, for imaging dopamine $D_3$ receptors in the CNS to diagnose CNS abnormalities.

The radiolabeled (tritiated and $^{14}C$ labeled) forms compounds of formula I, IA or IB are useful as radioligands to determine the binding of compounds to the dopamine $D_3$ receptor. They are also useful as labeled parent compounds to determine the metabolism of the compound in animals. Preferred for this purpose are compounds of formula I, IA, or IB wherein R is group (a), Q is trifluromethyl, p is 1, $R_3$ is hydrogen, $R_4$ is hydrogen, n is 1, k is 0, Y is carbonyl, A is N, and the carbon atom of R that is bonded to A is the radionuclide $^{14}C$. Particularly preferred for this purpose are compounds of formula IC. As employed herein, a "compound of formula IC" shall refer to the compound of formula I wherein R is group (a) wherein Q is trifluoromethyl substituted in the 6-position of the benzthiophene ring system; p is 1; Y is carbonyl, $R_4$ is hydrogen, A is N, n is 1; k is 0, Y is carbonyl, k is o, $R_3$ is hydrogen and the carbon atom of R that is bonded to A is the radionuclide $^{14}C$. Compounds of formula IC may be prepared in a manner analogous to that set forth in Example 35.

Imbalances in dopamine production have been implicated in a variety of mental and physical disorders, such as Parkinson's disease (PD). It is thus desirable to diagnose and monitor such imbalances and to monitor the effectiveness of drugs and substances that affect brain chemistry. New and powerful imaging methods that enable one to assess the living brain in vivo and thereby monitor brain chemistry and the effectiveness of drugs and substances that affect brain chemistry have been developed. Methods such as positron emission tomography (PET) and single photon emission computed tomography (SPECT) involve administering to a patient a radioactive tracer substance comprising a ligand that binds to the presynaptic or postsynaptic neuroreceptors in the patient's brain. Emissions (primarily gamma rays are emitted from the positrons or photons from the radioactive tracer) are measured. These emissions are indicative of the number and degree of occupancy of blocking of the neuroreceptors. The number of neuroreceptors and the degree of occupancy or blocking is calculated utilizing a mathematical model, and compared with an intra-person or inter-person control to determine the degree of drug response. Further treatment of the patient with drugs is based on the comparisons made. For these methods to be useful, however, a ligand that has a high specificity and affinity for the desired receptor is required.

It is believed that certain radioactive ligands may be selective for dopamine transporters and are thus potentially useful in evaluating changes in dopamine function in vivo and in vitro, especially for patients with Parkinson's disease (PD), which is characterized by a selective loss of dopamine neurons in the basal ganglia and substantia nigra.

Another aspect of this invention relates to methods for utilizing the compounds of the invention as CNS imaging agents. Imaging techniques are non-invasive diagnostic techniques that generally involve administering a compound with marker atoms that can be detected externally to the mammal. Generally, these methods comprise administering to a mammal a compound of the invention, dissolved or dispersed in a suitable pharmaceutical carrier or diluent. The compound of the invention selectively binds to dopamine $D_3$, thus permitting the imaging of CNS receptors and the ability to, inter alia, evaluate brain chemistry, the effectiveness of drugs, and neuronal functions. Imaging techniques suitable for practicing the present invention include, but are not limited to, single photon emission computed tomography (SPECT) and positron emission tomography (PET). Radionuclides that are widely used in diagnostic nuclear medicine include technetium [$^{99}Tc$], iodine [$^{123}I$], carbon [$^{11}C$], and fluorine [$^{18}F$].

The invention is further illustrated by the following non-limiting examples and tabulated information. These examples are understood to be illustrative only and are not intended to limit the scope of the present invention in any way. As used herein, the following terms have the indicated meanings: "g" refers to grams; "mmol" refers to millimoles; "ml" refers to milliliters; "° C." refers to degrees Celsius; "TLC" refers to thin layer chromatography; "LC/MS" refers to liquid chromatography mass spectrometry; "APCI" refers to atmospheric pressure chemical ionization; "mp" refers to melting point.

EXAMPLES

Example 1

Synthesis of Intermediate Substituted Piperazines

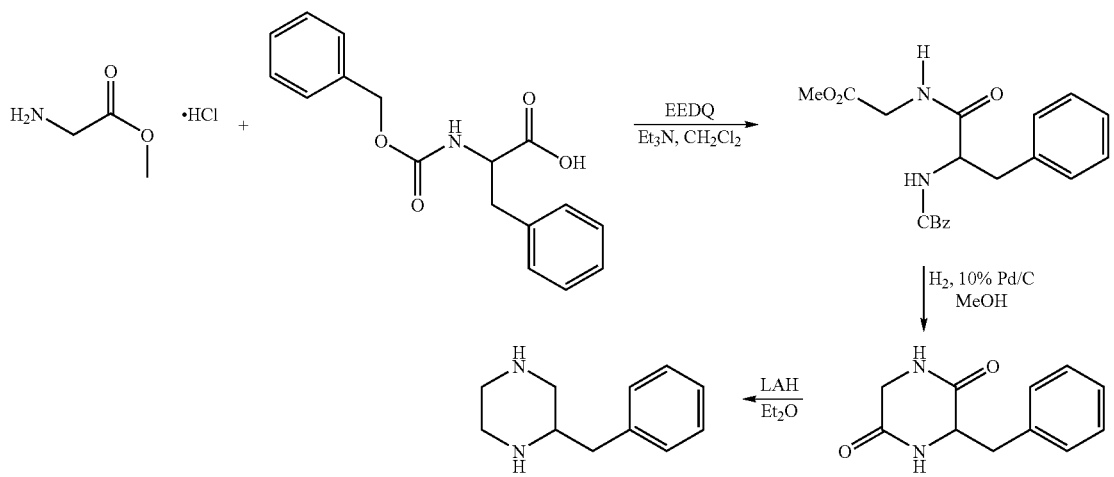

Example 1(a)

Preparation of intermediate 3-benzyl-piperazine

To a suspension of 3-benzyl-piperazine-2,5-dione (14.98 g, 73 mmol, prepared following generally the procedure of Halpern and Westley, J. Org. Chem. 1968, 33, 864) in dry diethyl ether (500 mL) is added dropwise to a solution of lithium aluminum hydride (400 mL of a 1 M solution in diethyl ether, 400 mmol, 5.4 eq). The suspension is heated at reflux for 23 hours and then cooled to 0° C. Water (70 mL) is then cautiously added and the resulting suspension is warmed to room temperature. After 3 hours the suspension is filtered and the solid washed with diethyl ether (1 L).

The filtrate is concentrated under vacuum to provide crude title compound (11.40 g, 88%) as a yellow, crystalline solid. A sample (2 g) is recrystallized from cyclohexane and then from toluene to provide the purified title compound (0.83 g) as a fine, white crystals: mp 80-81° C.
Anal. Calcd. For $C_{11}H_{16}N_2$: C, 74.96; H, 9.15; N, 15.89; Found: C, 74.84; H, 9.01; N, 16.15.

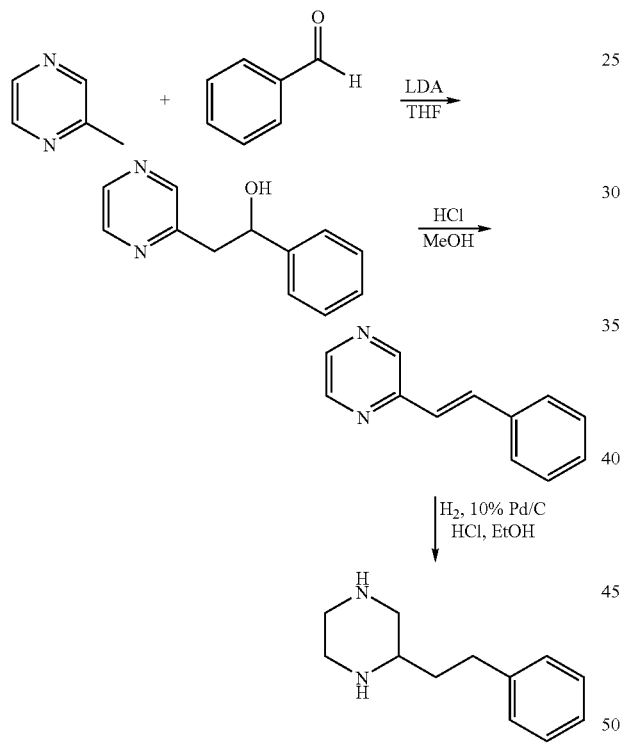

Example 1(b)

To a solution of LDA (295 mL, 0.59 mol, 2 M in heptane/THF/ethylbenzene) in anhydrous THF (300 mL) cooled to −40° C. was added 2-methylpyrazine (48.5 mL, 0.531 mol) dropwise via an addition funnel. The reaction was allowed to warm to −20° C. and was stirred for 90 minutes when a solution of benzaldehyde (54 mL, 0.531 mol) in anhydrous THF (200 mL) was added dropwise via an addition funnel. After complete addition, the reaction was allowed to warm to room temperature and was stirred for 20 hours. The reaction was then cooled in an ice bath and saturated NH₄Cl (500 mL) was added. The resulting mixture was extracted with EtOAc (500 mL, 250 mL). The combined extracts were dried (Na₂SO₄), filtered and concentrated to a damp, beige solid. The product was triturated with Et₂O and collected then dried overnight to yield 56.0 g (53%) of a light brown solid, mp 81-84° C.

A solution of the above-obtained solid (56.0 g, 0.28 mol) in MeOH (1.1 L) and conc. HCl (290 mL) was stirred at reflux for 24 hours. The reaction was cooled to room temperature and concentrated to a dark liquid. The dark liquid was cooled in an ice bath and water (1 L) was added. The resulting solution was neutralized with a saturated solution of Na₂CO₃ and the product was extracted with EtOAc (1 L, 2×500 mL). The combined extracts were dried (Na₂SO₄), filtered and concentrated to yield 46 g of a dark brown solid. The solid was purified via flash column chromatography (40% EtOAc in heptane) yielding 22.7 g of the olefin as a brown foam.

A 1 L Parr shaker bottle was flushed with nitrogen and charged with 10% Pd/C (4.5 g, Degussa type) and the above-obtained olefin (20.0 g, 0.110 mol) in EtOH (450 mL). The reaction was hydrogenated at 50 psi for 3.5 hours when the reaction was filtered through a celite plug and rinsed with ethanol. The bottle was recharged with fresh 10% Pd/C (4.5 g, Degussa type), the filtrate and conc. HCl (15 mL). The reaction was hydrogenated at 50 psi for 18 hours when the reaction was diluted with warm MeOH and filtered through a plug of celite. The solid was thoroughly washed with hot MeOH and the filtrate was concentrated to yield 11.2 g (39%) of the final product as the di-HCl salt, mp 297-300. See: Tetrahedron, 30, 1974 pp 667-673 and Tet. Lett. 1979, pp 4483-4486

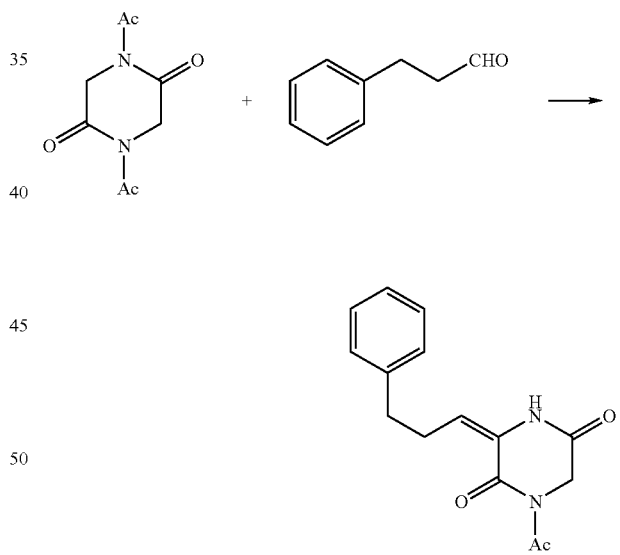

Example 1(c)

DBU (14.0 g, 92 mmol) was added to a solution of the piperazine diacetate (18.2 g, 92 mmol) and aldehyde (12.3 g, 92 mmol) in 92 mL of DMF at ambient temperature. The resulting mixture was stirred at room temperature for 5 h. The precipitated product was collected by filtration, providing 17.1 g of product.

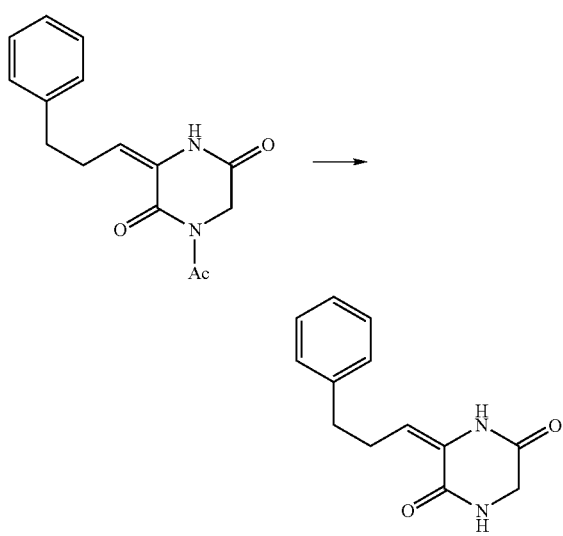
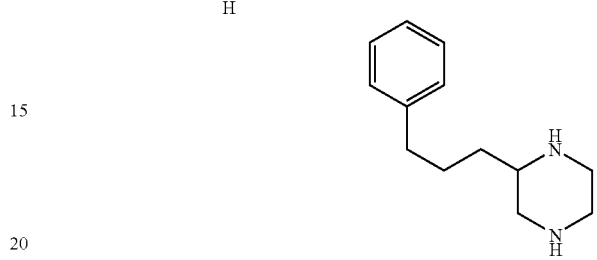

The monoacetate (17.0 g, 62.8 mmol) and hydrazine hydrate (9.4 g, 188.6 mmol) in 125 mL of DMF were stirred at room temperature for 20 h. The precipitated solid was collected by filtration, and washed with water and ethanol, leaving 13.7 g of product.

A solution of LAH (156 mL, 156 mmol, 1M in THF) was added dropwise to a 0° C. solution of the piperazine dione (12.1 g, 52.1 mmol) in 100 ml of THF. The mixture was heated to reflux and stirred overnight. The mixture was cooled to 0° C. and 38 mL of water in 200 mL of THF was carefully added. The resulting mixture stirred for 1 h, then it was filtered, the filter cake was washed with THF, and the filtrate was concentrated in vacuo to give 7.4 g of product.

Example 2

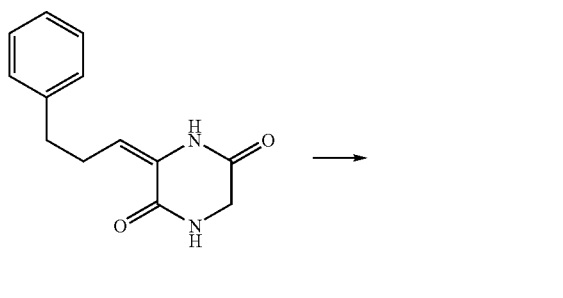
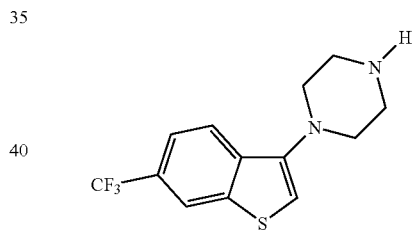

1-(6-(trifluoromethyl)-benzo[b]thien-3-yl)-piperazine hydrochloride

2a: 2-Carbomethoxy-3-amino-6-trifluoromethylbenzo[b]thiophene:

Equip a 22-L, 3-necked, round-bottom flask with a mechanical stirrer, nitrogen bubbler, and a thermocouple probe, charge with 1.20 kg (5.55 mole) of 2-nitro-4-trifluoromethylbenzonitrile, 589.3 g (496 mL, 5.55 mole) of methyl thioglycolate, and 4.3 L of NMP. Cool the resulting yellow solution to 2° C., and add slowly, over a period of 78 min a solution prepared from 466.0 g (11.11 mole, 2.0 eq) of lithium hydroxide monohydrate in 3.36 L of water while maintaining the temperature between 2-20° C. Allow the brown slurry to warm to 21° C. over a 2 h period, and then dilute with 8.0 L of water (observe exotherm->27° C.). Stir for 40 min and cool to 18° C., collect the product by filtration, rinsing with 10 L of water, then air-drying at ambient temperature to give 1.295 kg (84.7% yield) of 2-carbomethoxy-3-amino-6-trifluoromethylbenzo[b]thiophene, as a light-yellow solid, 99.8% pure by HPLC assay.

The olefin (13.6 g, 59.1 mmol) and palladium on carbon (2.7 g, 10% Pd/C, Degussa type, 50% H₂O) in 1.2 l of methanol were shaken on a Parr hydrogenation apparatus at 40 psi of hydrogen, until hydrogen uptake ceased. The mixture was diluted with dichloromethane and filtered through celite. Concentration of the filtrate provided 12.1 g of product.

2b: 1-(6-(trifluoromethyl)-benzo[b]thien-3-yl)-piperazine hydrochloride

Equip a 12-L, 3-necked, round-bottom flask with a mechanical stirrer, nitrogen bubbler, and a thermocouple probe, and charge with 1.14 kg (4.14 mole) of 2-carbomethoxy-3-amino-6-trifluoromethylbenzo-[b]thiophene (Example 2a), 196.0 g (2.28 mole, 0.55 eq) of piperazine, 4.0 L of NMP, and 570 mL of xylene. Heat the solution, and hold at 170-180° C. for 4 h, at which time the reaction is ca. 98% complete as determined by HPLC assay. Cool the brown solution to 168° C., and then add 1.605 kg (18.63 mole, 4.5 eq) of piperazine (temp->109° C.) following with 1.575 kg (28.28 mole, 2.0 eq) of p-toluenesulfonic acid monohydrate (observe exotherm, 109->130° C.). Connect a Dean-Stark trap to the condenser, and heat the reaction to collect an azeotrope. Remove a total of 410 mL of an aqueous distillate, while allowing the pot temperature to increase from 145 to 165° C. Monitor the progress of the reaction by GC/MS and HPLC assays. After 14 h at ca. 165° C. (>99% conversion by HPLC and GC/MS assay), cool the reaction to 30-35° C., and then quench into an extractor that contains 5 kg of ice, 12 L of water, and 8.5 L of toluene. Separate the phases, wash the organic extract with 11 L of 0.5 N NaOH, 2 L of saturated aq. NaCl., and then extract with 8 L of 1 N HCl. Dilute the acidic aqueous extract with 1 kg of ice, and basify to pH 11.2 by adding 624 g of 50% NaOH. Extract the resulting mixture with 9.5 L of toluene. Wash the toluene extract with 2 L of saturated aqueous NaCl, dry (Na$_2$SO$_4$), and filter. Charge the filtrate into a 22 L 3-necked, round-bottomed flask (N$_2$, mechanical stirring, temperature control probe), and add a total of 3.7 L of 1N ethereal HCl at 20-27° C. so that the mixture is positive to Congo Red indicator paper. During the HCl addition, add a total of 2.5 L of toluene to improve the stirring of the thick slurry that results. Stir at ambient temperature for 40 min, filter the slurry and wash with 4.5 L of toluene. After air drying, obtain 1.165 kg (87% yield) of 3-piperazinyl-6-trifluoromethyl-benzo[b]thiophene hydrochloride as a light pink-beige solid, 99.1% pure by GC/MS assay.

Example 3

3-Piperidinyl-4-yl-thieno[2.3-d]isoxazole hydrochloride

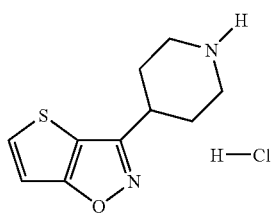

3a: 4-(3-Bromo-thiophene-2-carbonyl)-piperidine-1-carboxylic acid tert-butyl ester Stir a solution, under nitrogen, of 3-bromothiophene (21.0 mL, 0.224 mol) in tetrahydrofuran (1.0 L) at −78° C., and add a 2.0M solution of lithium diisopropylamide in heptane/tetrahydrofuran/ethylbenzene (112 mL, 0.224 mol) for 45 min. Add, dropwise, over 2 h, a solution of 4-(N-methoxy-N-methylcarboxamido)-1-piperidinecarboxylic acid 1,1-dimethylethyl ester (prepared according to U.S. Pat. No. 5,134,139) (79.4 g, 0.291 mol) in tetrahydrofuran (800 mL). Stir for 2 h, add a saturated ammonium chloride solution, and stir for an additional 0.5 h. Filter the resulting solid, and pour the filtrate into water (800 mL). Extract the aqueous mixture with ether and concentrate to obtain a dark liquid. Pour the liquid into water (400 mL), add NaCl and extract the aqueous mixture with ether. Wash the extract with water, brine, and dry over Na$_2$SO$_4$. Filter and concentrate to obtain the crude product.

Chromatograph the product over silica gel (pet.ether/ether, 4:1) to obtain 41.5 g (50%) of white solid.

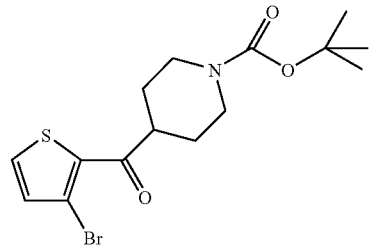

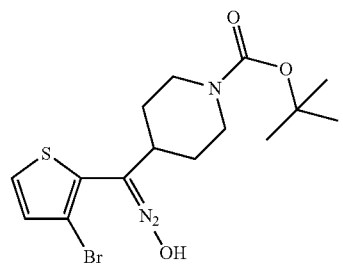

3b: 4-[(3-Bromo-thiophen-2-yl)-hydroxyimino-methyl]-piperidine-1-carboxylic acid tert-butyl ester Stir a mixture of 4-(3-bromo-thiophene-2-carbonyl)-piperidine-1-carboxylic acid tert-butyl ester (Example 3a) (41.5 g, 0.11 mol), hydroxylamine hydrochloride (15.4 g, 0.23 mol) and pyridine (190 mL) at ambient temperature overnight. Pour the reaction into water (500 mL) and extract with dichloromethane (3×). Wash the combined extracts with saturated CuSO$_4$ solution (2×), dry (MgSO$_4$) and concentrate to a green solid. Dissolve the solid in toluene (175 mL) and let stand at ambient temperature for 3 h. Collect the resulting crystals that form and wash with toluene (60 mL). Concentrate the filtrate and again dissolve the residue in toluene and proceed to collect additional crystals to obtain a total yield of 25 g (58%) of the title compound as a light, green solid.

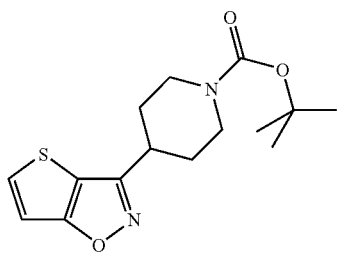

3c: 4-Thieno[2,3-d]isoxazol-3-yl-piperidine-1-carboxylic acid tert-butyl ester

Add to a stirring solution of 4-[(3-bromo-thiophen-2-yl)-hydroxyimino-methyl]piperidine-1-carboxylic acid tert-butyl ester (Example 3b) (25 g., 64.2 mmol) in 2-methoxyethanol (200 mL), a solution of potassium hydroxide (7.2 g,128.4 mmol) in water (20 mL). Heat the reaction to 60° C. and then add copper powder (1.25 g). Stir at 60-70° C. for 6 h and then at ambient temperature overnight. Pour the reaction mixture into water (500 mL) and extract with EtOAc (3×). Concentrate to a dark residue and purify by column chromatography over silica gel (heptane/EtOAc, 4:1) to provide 9.8 g (50%) of a white solid.

3d: 3-Piperidinyl-4-yl-thieno[2,3-d]isoxazole hydrochloride

Add ethereal HCl (10 mL) to 4-thieno[2,3-d]isoxazol-3-yl-piperidine-1-carboxylic acid tert-butyl ester (Example 3c) (1.0 g, 3.2 mmol) and then methanol (1 mL) to effect solution. Permit to stand at ambient temperature for 1 h and then collect 0.34 g of white solid, mp 240-241° C. From the filtrate collect 0.25 g of additional white solid, mp 263-265° C. Both samples: MS, m/z=209 (M+H)$^+$.

Analysis (Sample mp 263-265° C.):

| | | | |
|---|---|---|---|
| Calc. For: $C_{10}H_{12}N_2OS \cdot HCl$: | 49.08% C | 5.35% H | 11.45% N |
| Found: | 49.03% C | 5.29% H | 11.25% N |

Example 4

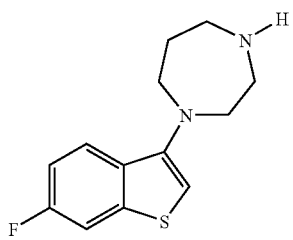

1-(6-Fluoro-benzo[b]thiophen-3-yl)-[1,4]diazepane 4a. 3-Amino-6-fluoro-benzo[b]thiophene-2-carboxylic acid At 50° C., add to a stirring solution of 2-carbomethoxy-3-amino-6-fluoro-benzo[b]thiophene (prepared according to U.S. Pat. No. 5,143,923), (90.1 g, 0.4 mol) in H$_2$O (450 mL), a 50% aqueous solution of NaOH (64 g, 0.8 mol) over 2-3 min. Heat the reaction to 70-73° C. and continue to stir for 3 h. Add 10% aqueous isopropanol (45 mL) and bring to reflux. Remove the isopropanol under N$_2$ and add H$_2$O (300 mL). Cool the reaction mixture to between 7-10° C. and add concentrated HCl (80 mL). Add H$_2$O (650 mL), cool to 5-7° C., filter the resulting solid, and wash the filter cake with H$_2$O (2×150 mL). Dry the solid under vacuum at 35° C. to obtain 80.6 g (94.7%) of solid mp 160-163° C., TLC on silica gel (dichloromethane/methanol, 3:1), R$_f$=0.69.

4b. 1-(6-Fluoro-benzo[b]thiophen-3-yl)-[1,4]diazepane

Heat a solution of 3-amino-6-fluoro-benzo[b]thiophene-2-carboxylic acid (5.0 g, 24 mmol) in 1-methyl-2-pyrrolidinone (5 ml) to 100° C. for 2 h., and then, introduce a stream of nitrogen, to cool the solution to room temperature. Add homopiperazine (9.5 g, 95 mmol) and p-toluene sulfonic acid monohydrate (9.0 g, 47 mmol) and heat the mixture to 145° C. for 4 h. After that time, cool the reaction mixture to room temperature, dilute with ethyl acetate (30 mL) and wash with brine (3×15 mL). Separate the organic layer and dry over MgSO$_4$. Evaporate the solvent and purify the crude product by column chromatography (SiO$_2$, 100 g CH$_2$Cl$_2$/MeOH 9:2, then CH$_2$Cl$_2$/MeOH/NH$_4$OH 9:2:0.15) to give 3.9 g (65%) of yellowish oil LC/MS (LiChrospher 5μ, RP-18, 250 mm CH$_3$CN/Water-gradient 20%→100% (25 min), Flow: 1.5 mL/min)

t$_R$=10.74 min, m/z=250.3.

Example 5

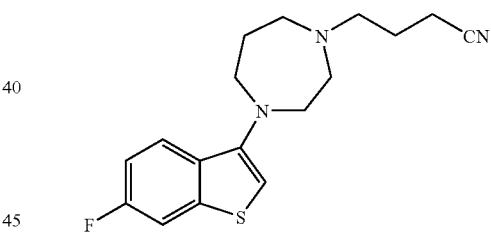

4-[4-(6-Fluorobenzo[b]thiophen-3-yl)-[1,4]diazapan-1-yl]butyronitrile

Add potassium carbonate (39.3 g, 284 mmol) to a solution of 1-(6-fluoro-benzo[b]thiophen-3-yl)-[1,4]diazepane (Example 4) (23.7 g, 95 mmol) and 4-bromobutyronitrile (21.0 g, 142 mmol) in acetonitrile (400 mL) and stir the mixture under reflux for 10 h. Filter the mixture, evaporate the solvent, and dissolve the residue in ethyl acetate (EtOAc). Wash with water and saturated sodium chloride solution, and dry the organic phase over MgSO$_4$. Evaporate the solvent under vacuum, and purify the crude product by column chromatography (EtOAc/MeOH 9:1) to give 12.9 g of a yellow oil LC/MS, (LiChrospher 5μ, RP-18, 250 mm CH$_3$CN/Water(0.05% TFA)-gradient 2%→98% (20 min), Flow: 0.75 mL/min)

t$_R$=9.46 min, m/z=317.3.

Example 6

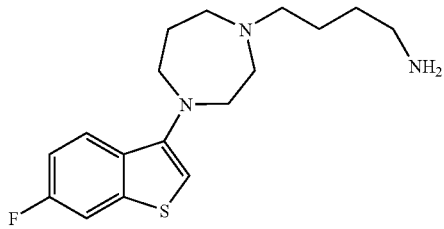

4-[4-(6-Fluoro-benzo[b]thiophen-3-yl)-[1,4]diazapan-1-yl]butylamine

Add over 30 min, at room temperature, a solution of LiAlH$_4$ in diethyl ether (1M, 72.5 mL) to a solution of 4-[4-(6-fluoro-benzo[b]thiophen-3-yl)-[1,4]diazapan-1-yl]butyronitrile (Example 5) (11.5 g, 36.2 mmol) in dry diethyl ether (200 mL). Heat the solution to reflux for 5 h. After that time, allow the solution to cool to room temperature and carefully quench the reaction with water and aqueous sodium hydroxide solution. Separate the phases, and re-extract the aqueous phase with EtOAc. Dry the combined organic phases over MgSO$_4$ and remove the solvent under vacuum. Purify the crude product by column chromatography (CH$_2$Cl$_2$/MeOH/NH$_4$OH 9:2:0.25) to obtain 8.9 g of a colorless oil LC/MS, (LiChrospher 5µ, RP-18, 250 mm CH$_3$CN/Water(0.05% TFA)-gradient 2%→98% (20 min), Flow: 0.75 mL/min), t$_R$=7.79 min, m/z=321.3.

Example 7

4-[4-(6-Fluoro-benzo[b]thiophen-3-yl)-[1,4]diazapan-1-yl]pentano-nitrile

Follow the procedure of Example 5, and substitute pentanonitrile for butyronitrile therein to obtain the title compound. (LiChrospher 5µ, RP-18, 250 mm CH$_3$CN/Water (0.05% TFA)-gradient 2%→98% (20 min), Flow: 0.75 mL/min) t$_R$=10.4 min, m/z=331.5

Example 8

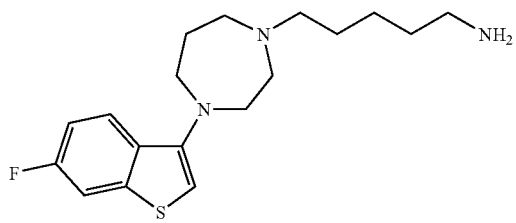

4-[4-(6-Fluoro-benzo[b]thiophen-3-yl)-[1,4]diazapan-1-yl]pentylamine

Follow the procedure of Example 6, and substitute 4-[4-(6-Fluoro-benzo[b]thiophen-3-yl)-[1,4]diazapan-1-yl]pentanonitrile (Example 7) therein to obtain the title compound. LC/MS, (LiChrospher 5µ, RP-18, 250 mm CH$_3$CN/Water (0.05% TFA)-gradient 2%→98% (20 min), Flow: 0.75 mL/min), t$_R$=8.31 min, m/z=335.5.

Example 9

1H-Indole-2-carboxylic acid {4-[4-(6-fluoro-benzo[b]thiophen-3-yl)-[1,4]diazepan-1-yl]-butyl}-amide Add indole-2-carboxylic acid (507 mg, 3.15 mmol) to a solution of 4-[4-(6-fluoro-benzo[b]thiophen-3-yl)-[1,4]diazapan-1-yl]butylamine (Example 6) (920 mg, 2.86 mmol), diisopropylethylamine (2.5 mL, 14.3 mmol), 1-hydroxy-1H-benzotriazole (503 mg, 3.72 mmol) and morpholinocarbodiimide (1.39 g, 3.29 mmol) in DMF (10 mL), and stir the solution overnight at room temperature. Remove the solvent under vacuum and dissolve the residue in EtOAc. Wash the organic phase with ether and saturated sodium chloride solution, and dry over MgSO$_4$. Evaporate the solvent under vacuum and purify the crude product by column chromatography (EtOAc/MeOH 7:3) to obtain 716 mg of a colorless solid LC/MS, (LiChrospher 5μ, RP-18, 250 mm CH$_3$CN/Water-gradient 20%→100% (25 min), Flow: 1.5 mL/min) t$_R$=19.89 min, m/z=464.3.

Example 10

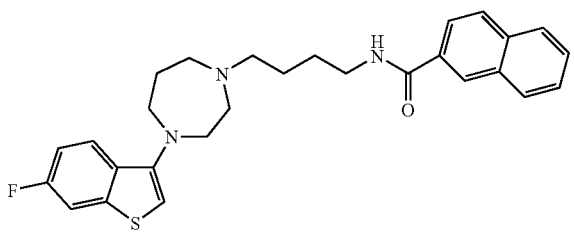

Naphthalene-2-carboxylic acid {4-[4-(6-fluoro-benzo[b]thiophen-3-yl)-[1,4]diazepan-1-yl]-butyl}-amide Add slowly a solution of 2-naphthoyl chloride (600 mg, 3.15 mmol) to a solution of 4-[4-(6-fluoro-benzo[b]thiophen-3-yl)-[1,4]diazapan-1-yl]butylamine (Example 6) (920 mg, 2.86 mmol), in pyridine-methylene chloride (10 mL,1:1), and stir the solution at room temperature overnight. Evaporate the solvent under vacuum, dissolve the residue in EtOAc and wash the organic layer with water and saturated sodium chloride solution. Combine the organic phases, dry over MgSO$_4$ and evaporate the solvent under vacuum. Purify the crude product by column chromatography (EtOAc/MeOH 7:3) to obtain 1.25 g of a solid LC/MS (LiChrospher 5μ, RP-18, 250 mm CH$_3$CN/Water-gradient 20%→100% (25 min), Flow: 1.5 mL/min) t$_R$=21.11 min, m/z=475.3.

Example 11

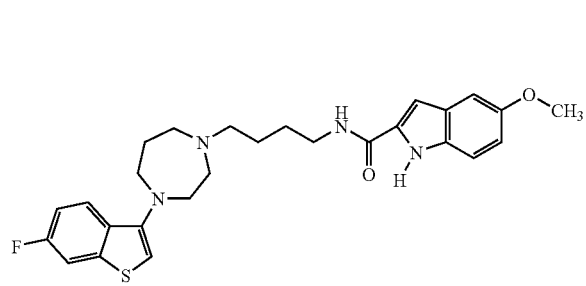

5-Methoxy-1H-indole-2-carboxylic acid {4-[4-(6-fluoro-benzo[b]thiophen-3-yl)-[1,4]diazepan-1-yl]-butyl}-amide Follow the procedure of Example 9, and substitute 5-methoxy-indole-2-carboxylic acid for the indole-2-carboxylic acid therein to obtain the title compound, LC/MS (LiChrospher 5μ, RP-18, 250 mm CH$_3$CN/Water-gradient 20%→100% (25 min), Flow: 1.5 mL/min) t$_R$=19.75 min, m/z=494.6

Example 12

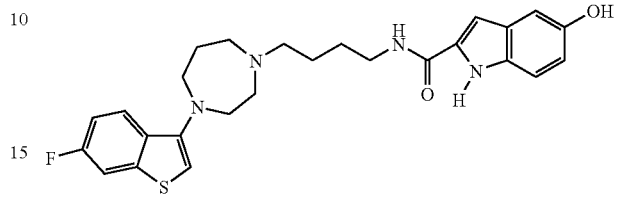

5-Hydroxy-1H-indole-2-carboxylic acid {4-[4-(6-fluoro-benzo[b]thiophen-3-yl)-[1,4]diazepan-1-yl]-butyl}-amide Follow the procedure of Example 9, and substitute 5-hydroxy-indole-2-carboxylic acid for the indole-2-carboxylic acid therein to obtain the title compound, LC/MS (LiChrospher 5μ, RP-18, 250 mm CH$_3$CN/Water-gradient 20%→100% (25 min), Flow: 1.5 mL/min) t$_R$=19.73 min, m/z=480.2 m/z.

Example 13

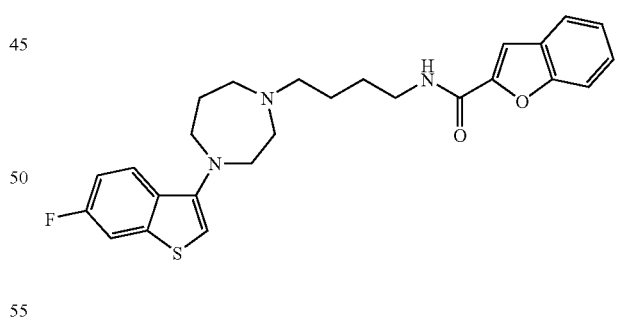

Benzofuran-2-carboxylic acid {4-[4-(6-fluorobenzo[b]thiophen-3-yl)-[1,4]diazepan-1-yl]-butyl)-amide Follow the procedure of Example 9, and substitute benzofuran-2-carboxylic acid for the indole-2-carboxylic acid therein to obtain the title compound, LC/MS, (LiChrospher 5μ, RP-18, 250 mmCH₃CN/Water-gradient 20%→100% (25 min), Flow: 1.5 mL/min) t_R=20.80 min, m/z=465.3.

Example 14

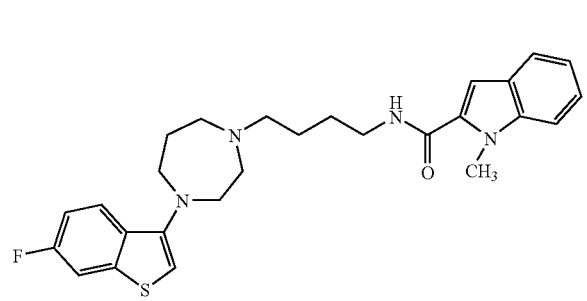

1-Methyl-1H-indole-2-carboxylic acid {4-[4-(6-fluoro-benzo[b]thiophen-3-yl)-[1,4]diazepan-1-yl]-butyl}-amide Follow the procedure of Example 9, and substitute 1-methyl-indole-2-carboxylic acid for the indole-2-carboxylic acid therein to obtain the title compound, LC/MS (LiChrospher 5μ, RP-18, 250 mm CH₃CN/Water-gradient 20%→100% (25 min), Flow: 1.5 mL/in) t_R=21.35 min, m/z=478.6.

Example 15

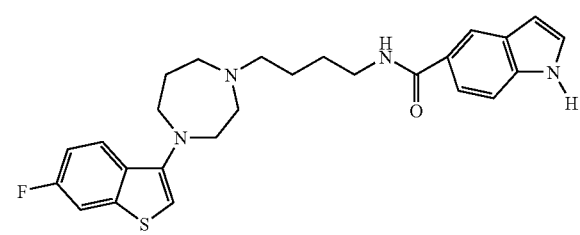

1H-indole-5-carboxylic acid {4-[4-(6-fluoro-benzo[b]thiophen-3-yl)-[1,4]diazepan-1-yl]-butyl}-amide Follow the procedure of Example 9, and substitute indole-5-carboxylic acid for the indole-2-carboxylic acid, therein to obtain the title compound LC/MS, (LiChrospher 5μ, RP-18, 250 mm CH₃CN/Water-gradient 20% →100% (25 min), Flow: 1.5 mL/min) t_R=18.35 min, m/z=464.6.

Example 16

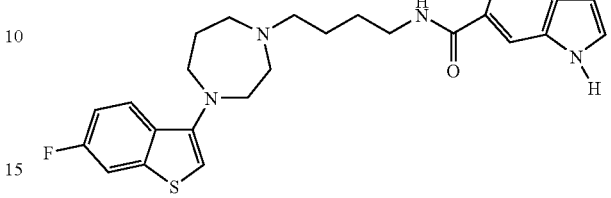

1H-indole-6-carboxylic acid {4-[4-(6-fluoro-benzo[b]thiophen-3-yl)-[1,4]diazepan-1-yl]-butyl}-amide Follow the procedure of Example 9, and substitute indole-6-carboxylic acid for the indole-2-carboxylic acid therein to obtain the title compound LC/MS (LiChrospher 5μ, RP-18, 250 mm CH₃CN/Water-gradient 20%→100% (25 min), Flow: 1.5, mL/min) t_R=19.25 min, m/z=464.6.

Example 17

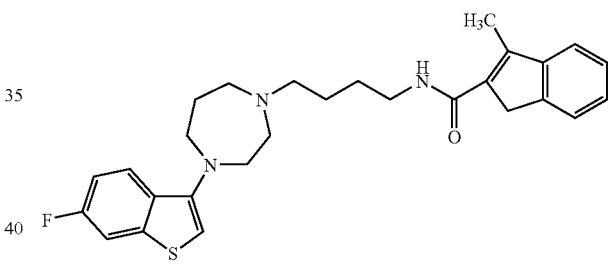

3-Methyl-1H-indene-2-carboxylic acid {4-[4-(6-fluoro-benzo[b]thiophen-3-yl)-[1,4]diazepan-1-yl]-butyl}-amide Follow the procedure of Example 9, and substitute 3-methylindene-2-carboxylic acid for the indole-2-carboxylic acid therein to obtain the title compound LC/MS (LiChrospher 5μ, RP-18, 250 mm CH₃CN/Water-gradient 20%→100% (25 min), Flow: 1.5 mL/min) t_R=21.86 min, m/z=477.6.

Example 18

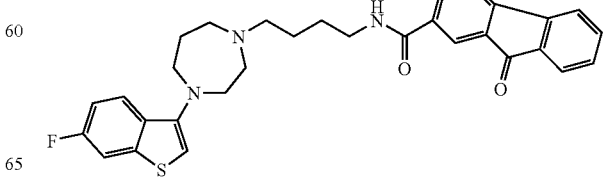

9-Oxo-9H-fluorene-2-carboxylic acid {4-[4-(6-fluoro-benzo[b]thiophen-3-yl)-[1,4]diazepan-1-yl]-butyl}-amide Follow the procedure of Example 9, and substitute 9-fluorenone-2-carboxylic acid for the indole-2-carboxylic acid therein to obtain the title compound, LC/MS (LiChrospher 5μ, RP-18, 250 mm CH$_3$CN/Water-gradient 20%→100% (25 min), Flow: 1.5 mL/min) $t_R$=21.57 min, m/z=527.3 m/z.

Example 19

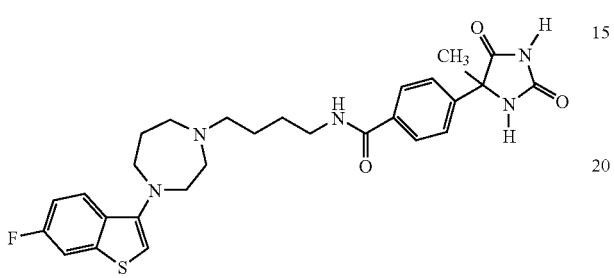

N-{4-[4-(6-fluoro-benzo[b]thiophen-3-yl)-[1,4]diazepan-1-yl]-butyl}4-(4-methyl-2,5-dioxo-imidazolidin-4-yl)-benzamide Follow the procedure of Example 9, and substitute 4-(4-methyl-2,5-dioxo-imidazolidin-4-yl)-benzoic acid for the indole-2-carboxylic acid therein to obtain the title compound, LC/MS (LiChrospher 5μ, RP-18, 250 mm CH$_3$CN/Water-gradient 20%→100% (25 min), Flow: 1.5 mL/min) $t_R$=19.52 min, m/z=537.4.

Example 20

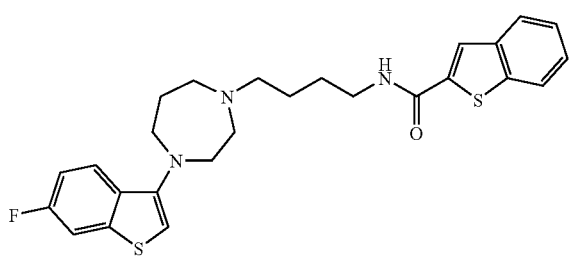

Benzo[b]thiophene-2-carboxylic acid {4-[4-(6-fluorobenzo[b]thiophen-3-yl)-[1,4]diazepan-1-yl]-butyl)-amide Follow the procedure of Example 10, and substitute benzo[b]thiophene-2-carbonyl chloride for the 2-naphthoyl chloride therein to obtain the title compound, LC/MS, (LiChrospher 5μ, RP-18, 250 mmCH$_3$CN/Water-gradient 20%→100% (25 min), Flow: 1.5 mL/min) $t_R$=21.23 min, m/z=481.3.

Example 21

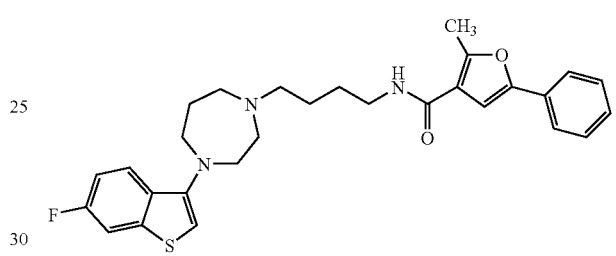

2-Methyl-5-phenyl-furan-3-carboxylic acid {4-[4-(6-fluorobenzo[b]thiophen-3-yl)-[1,4]diazepan-1-yl]-butyl)-amide Follow the procedure of Example 10, and substitute 2-methyl-5-phenyl-furan-3-carbonyl chloride for the 2-naphthoyl chloride therein to obtain the title compound, LC/MS (LiChrospher 5μ, RP-18, 250 mm CH$_3$CN/Water-gradient 20%→100% (25 min), Flow: 1.5 mL/min) $t_R$=22.07 min, m/z=505.3 m/z

Example 22

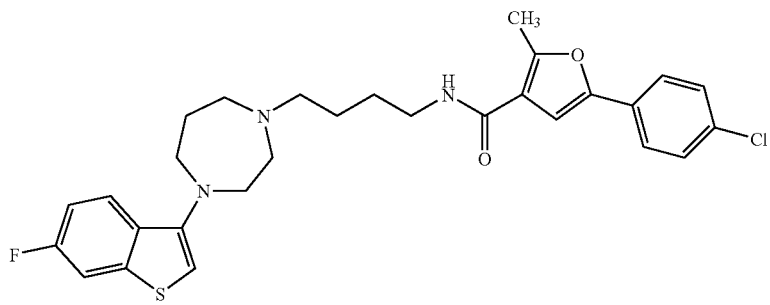

5-(4-Chlorophenyl)-2-methyl-furan-3-carboxylic acid {4-[4-(6-fluorobenzo[b]thiophen-3-yl)-[1,4]diazepan-1-yl]-butyl)-amide Follow the procedure of Example 10, and substitute 2-methyl-5-(4-clorophenyl)-furan-3-carbonyl chloride for the 2-naphthoyl chloride therein to obtain the title compound, LC/MS (LiChrospher 5μ, RP-18, 250 mm CH₃CN/Water-gradient 20%→100% (25 min), Flow: 1.5 mL/min) $t_R$=22.81 min, m/z=539.3.

Example 23

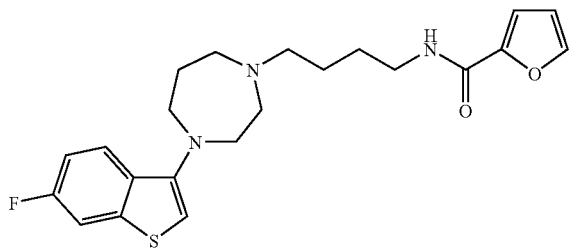

Furan-2-carboxylic acid {4-[4-(6-fluorobenzo[b]thiophen-3-yl)-[1,4]diazepan-1-yl]-butyl)-amide Follow the procedure of Example 10, and substitute furan-2-carbonyl chloride for the 2-naphthoyl chloride therein to obtain the title compound, LC/MS (LiChrospher 5μ, RP-18, 250 mm CH₃CN/Water-gradient 20%→100% (25 min), Flow: 1.5 mL/min) $t_R$=18.86 min, m/z=415.3 m/z.

Example 24

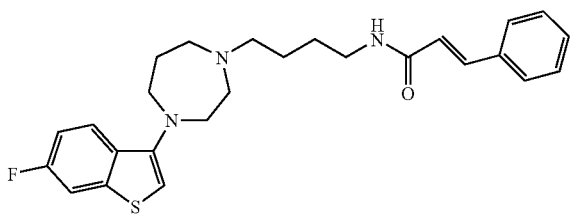

N-{4-[4-(6-fluorobenzo[b]thiophen-3-yl)-[1,4]diazepan-1-yl]-butyl)-3-phenyl-acrylamide Follow the procedure of Example 10, and substitute cinnamoyl chloride for the 2-naphthoyl chloride therein to obtain the title compound, LC/MS (LiChrospher 5μ, RP-18, 250 mm CH₃CN/Water-gradient 20%→100% (25 min), Flow: 1.5 mL/min) $t_R$=20.34 min, m/z=451.3 m/z.

Example 25

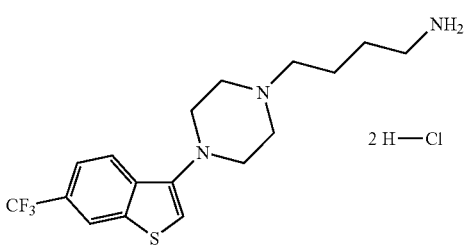

4-[6-(Trifluoromethyl)-benzo[b]thien-1-piperazinebutanamine dihydrochloride

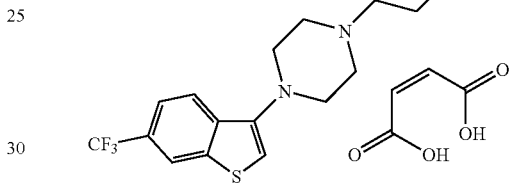

25a: 4-(6-Trifluoromethyl)-benzo[b]thien-3-yl)-1-piperazinebutyl-nitrile (Z)-2-butenedioate Reflux a mixture of 1-(6-(trifluoromethyl)-benzo[b]thien-3-yl)-piperazine (Example 1b) (10.1 g, 35.3 mmol), 4-bromobutyronitrile (6.25 g, 42.3 mmol), anhydrous potassium carbonate (8.00 g, 57.9 mmol), and anhydrous acetonitrile (80 mL) for 18 h. Filter the slurry, wash the insolubles with dichloromethane (2×150 mL), and concentrate the filtrate under vacuum. Take up the residue in dichloromethane (125 mL), wash with 5% aqueous NaOH (75 mL), water (75 mL) and dry ($K_2CO_3$). Concentrate under vacuum and chromatograph the crude product over silica gel (EtOAc) to obtain 10.3 g (82%) of amber oil. Add to an ethanolic solution of the oil (1.2 g, 3.40 mmoL), maleic acid (400 mg, 3.45 mmol) and concentrate the solution under vacuum to receive a gum. Triturate the gum with EtOAc to afford a solid. Recrystallize the solid from methanol/EtOAc to obtain 1.01 g of white crystals, mp 158-159° C.

Analysis

| | | | |
|---|---|---|---|
| Calc. for: $C_{21}H_{22}F_3N_3O_4S$: | 53.73% C | 4.72% H | 8.95% N |
| Found: | 53.57% C | 4.65% H | 8.86% N |

25b: 4-[6-(Trifluoromethyl)-benzo[b]thien-1-piperazinebutanamine dihydrochloride Under $N_2$. add, dropwise ,a solution of 4-(6-trifluoromethyl)-benzo[b]thien-3-yl)-1-pierazinebutyl-nitrile (free base of Example 25a) (9.00 g, 25.5 mmol) in anhydrous tetrahydrofuran (THF, 70 mL) to a stirred, cooled (3° C.) suspension, of LiAlH₄ (1.06 g, 27.9 mmol) in anhydrous THF (120 mL). Maintain the temperature at 3° C. for 5 min and then stir at ambient temperature for 21 h. Cool the mixture to 0° C. and treat sequentially with H$_2$O (1 mL), 15% aqueous NaOH (1 mL), and H$_2$O (3 mL). After 20 min at room temperature, filter the mixture, wash the insolubles with dichloromethane (2×50 mL), and concentrate the filtrate under vacuum. Take the residue up in dichloromethane (150 mL), wash sequentially with 5% aqueous NaOH (75 mL), H$_2$O (75 mL) and then dry (K$_2$CO$_3$). Remove the solvent under vacuum and purify the residue by chromatography over silica gel (ethano/NH$_4$OH, 95:5) to obtain 5.32 g (58%) of the free base of the title compound. To a solution of the free base (689 mg) in ethanol, add ethanolic HCl until the solution is acidic (pH 2-3). Concentrate under vacuum to a gum, and triturate the gum with ethanol to obtain an off-white solid. Recrystallize the solid from MeOH/CHCl$_3$ to obtain 485 mg of white powder, mp 256-258° C.

Analysis

| | | | |
|---|---|---|---|
| Calculated for C$_{17}$H$_{22}$F$_3$N$_3$S · 2HCl: | 47.45% C | 5.62% H | 9.76% N |
| Found: | 47.10% | 5.67% H | 9.62% N |

Example 26

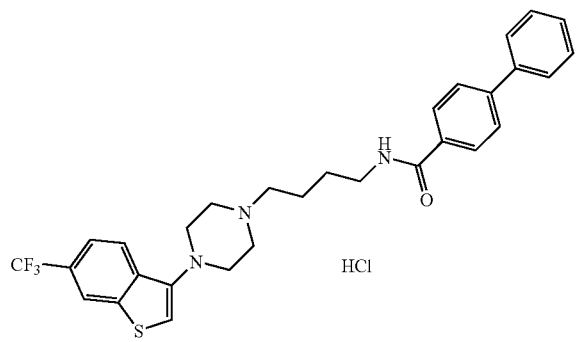

HCl

Biphenyl-4-carboxylic acid {4-[4-(6-trifluoromethyl-benzo[b]thiophen-3-yl)-piperazin-1-yl]-butyl}-amide hydrochloride Charge a 250 mL round bottom flask with dry Amberlite IRA-68 (5.0 g) and purge the flask with argon. Add a solution of 4-[6-(trifluoromethyl)-benzo[b]thien-1-piperazinebutanamine (free base of Example 25b) (1.0 g, 2.8 mmol) in CHCl$_3$ (30 mL), and then a suspension of 4-biphenylcarbonyl chloride (849 mg, 3.9 mmol) in CHCl$_3$ (15 mL). Add additional CHCl$_3$ (20 mL), and shake under argon for 2.0 h. Add polymer supported tris(2-aminoethyl)amine(500 mg), shake for 1.5 h and then add H$_2$O (4 mL) and shake an additional 1 h. Filter off the resins and wash the filter cake with CHCl$_3$. Concentrate the filtrate to obtain 1.5 g of an off-white solid. Chromatograph the solid over 40 g of silica gel (CH$_2$Cl$_2$/MeOH, 97:3). Concentration the appropriate fractions and obtain 860 mg of the product as a white solid. Dissolve the compound in hot, absolute ethanol, filter and add 1.0M ethereal HCl until the solution is acidic. Concentrate the solution to a volume of about 20 mL, add a few seed crystals and allow the solution to stand at ambient temperature for 18 h. Collect the resulting precipitate and obtain 725 mg (45%) of the desired product as a white solid, mp 258-261° C.

Analysis

| | | | |
|---|---|---|---|
| Calculated for C$_{30}$H$_{30}$F$_3$N$_3$OS · HCl: | 62.76% C | 5.44% H | 7.32% N |
| Found: | | 62.69% C | 5.54% H | 7.28% N |

Example 27

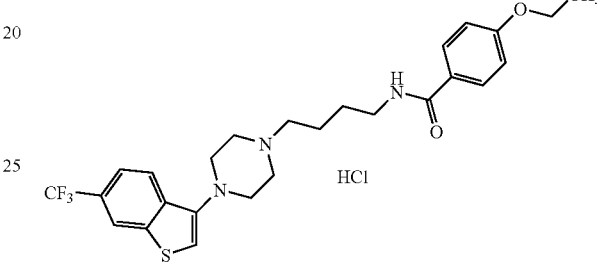

4-Ethoxy-N-{4-[-(6-trifluoromethyl-benzo[b]thiophen-3-yl]-butyl}-benzamide hydrochloride Add a solution of 4-ethoxybenzoyl chloride (0.723 g, 3.9 mmol) in CHCl$_3$ (15 mL) to a mixture of 4-[6-(trifluoromethyl)-benzo[b]thien-1-piperazine -butanamine (free base of Example 25b) (1.0 g, 2.8 mmol) and anhydrous Amberlite IRA-68 (5.0 g) in CHCl$_3$. Add an additional amount of CHCl$_3$ (15 mL) and shake, under argon, at ambient temperature for 2 h. Add polymer supported tris(2-aminoethyl)amine (500 mg), shake for 1.5 h, add H$_2$O (1 mL), shake for 1 h and then filter. Wash the filter cake thoroughly with CHCl$_3$, and concentrate to 1.4 g of white solid, LC/MS, m/z=506 (M+H)$^+$. Chromatograph the solid over silica gel (CH$_2$Cl$_2$/MeOH, 24:1) and obtain 0.84 g of the free base of the title compound.

Dissolve the above solid in warm absolute ethanol (50 mL), filter and add 1M HCl in ether to the filtrate until acidic. Heat the solution at reflux to remove ca. 15 mL of the ethanol and allow the solution to cool. After 18 h, collect and dry the product and obtain 0.595 g of hydrochloride salt as white solid, mp 228-230° C.

Analysis

| | | | |
|---|---|---|---|
| Calculated for C$_{26}$H$_{30}$F$_3$N$_3$O$_2$S · HCl: | 57.61% C | 5.76% H | 7.75% N |
| Found: | 57.81% C | 5.87% H | 7.66% N |

Example 28

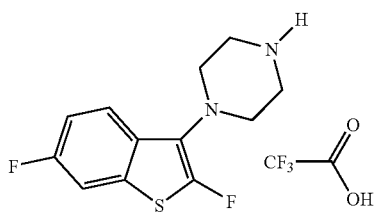

1-(2,6-Difluoro-benzo[b]thien-3-yl)-piperazine trifluoroacetate

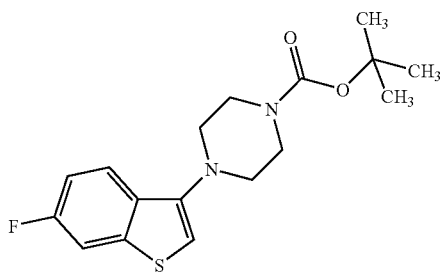

28a: 4-(6-Fluoro-benzo[b]thiophen-3-yl)-piperazine-1-carboxylic acid tert-butyl ester Add a solution of di-tert-butyl dicarbonate (5.15 g,.23.6 mmol) in CHCl$_3$ (15 mL), dropwise, over 45 min to a solution at −65° C. of 1-(6-fluorobenzo[b]thiophen-3-yl)-piperazine (prepared according to U.S. Pat. No. 5,143,923), (2.8 g, 11.8 mmol), 4-(dimethyl-amino)pyridine (0.16,1.3 mmol), and diisopropylethylamine (4.3 mL, 3.2 g, 24.8 mmol) in CHCl$_3$ (50 mL). Following complete addition, stir the reaction at ambient temperature for 20 h, and then pour the reaction into a mixture of cold (5° C.).5% aqueous NaOH/EtOAc (150/150 mL). Extract the product into EtOAc, wash the extract with H$_2$O, brine and concentrate to a red oil. Purify the crude oil over silica gel (EtOAc), to obtain 3.6 g, of red oil, LC/MS m/z=337 (M+H)$^+$.

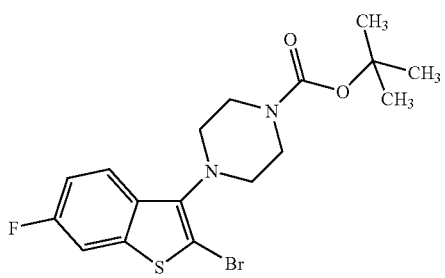

28b: 4-(2-Bromo-6-fluoro-benzo[b]thiophen-3-yl)-piperazine-1-carboxylic acid tert-butyl ester Add N-bromosuccinimide (0.59 g, 3.3 mmol) to a stirring solution of 4-(6-fluoro-benzo[b]thiophen-3-yl)-piperazine-1-carboxylic acid tert-butyl ester (Example 28a) (1.00 g, 2.97 mmol) in CHCl$_3$ (32.8 mL) and reflux for 30 min. Allow cooling to room temperature and filter. Evaporate the solvent and purify the residue by chromatography over silica gel (EtOAc/heptane, 9:1) to obtain 0.53 g (43%) of oil, MS, m/z=416 (M+H)$^+$.

In an alternative procedure, add N-bromosuccinimide (1.319 g, 6.62 mmol) to a stirring solution of 4-(6-fluoro-benzo[b]thiophen-3-yl)-piperazine-1-carboxylic acid tert-butyl ester (Example 28a) (2.226 g, 6.62 mmol) in CCl$_4$ and reflux for 2 h. Allow cooling to room temperature and filter. Evaporate the solvent and purify the residue by chromatography over silica gel (EtOAc/heptane, 9:1) to obtain 2.34 g (94%) of oil.

28c: 4-(2-Fluoro -6-fluoro-benzo[b]thiophen-3-yl)-piperazine-1-carboxylic acid tert-butyl ester At a temperature of −65° C. stir, under nitrogen, a solution of the 4-(2-bromo-6-fluoro-benzo[b]thiophen-3-yl)-piperazine-1-carboxylic acid tert-butyl ester (Example 28b) (15.59 g, 37.55 mmol) in anhydrous THF (247 mL) and add, dropwise, n-butyllithium in hexane (2.5M, 19.53 mL, 48.82 mmol). Stir for 30 min and then add, dropwise, N-fluorobenzenesulfonimide (17.76 g, 56.33 mmol) dissolved in anhydrous THF. Stir overnight at ambient temperature, cool the reaction to 0° C., add saturated NaCl solution and then water. Extract the mixture with EtOAc (3x's), combine the extracts and wash with water and brine. Dry the extract (MgSO$_4$), and concentrate to obtain 11.0 g of oil. Chromatograph the oil over silica gel (ether/pet. ether, 9:1) and obtain is 6.28 g (52%) of red oil, MS, m/z, 354 (M+H)$^+$.

28d: 1-(2,6-Difluoro-benzo[b]thien-3-yl)-piperazine trifluoroacetate

Stir a solution of 4-(2-fluoro -6-fluoro-benzo[b]thiophen-3-yl)-piperazine-1-carboxylic acid tert-butyl ester Example 28c (250 mg, 0.70 mmol) in trifluoroacetic acid (2.2 mL) at ambient temperature for 30 min. Evaporate the trifluoroacetic acid and treat the residue with ether. Stir the suspension at ambient temperature for 2 h, and filter the resulting white solid to obtain 191 mg (56%) of the trifluoroacetate salt. MS, m/z=255 (M+H)$^+$.

Example 29

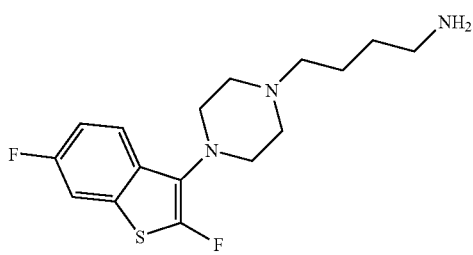

4-[6-(2,6Difluoro-benzo[b]thien-1-piperazinebutan-amine

29a: 2-[4-[4-(6-Fluorobenzo[b]thiophen-3-yl)piperazin-1-yl]butylisoindole-1,3-dione Stir and reflux under argon a mixture of 1-(2,6-difluoro-benzo[b]thien-3-yl)-piperazine (free base of Example 28d) (1.48 g, 5.8 mmol), bromobutylphthalimide (1.65 g, 5.8 mmol), triethylamine (1.2 mL) and acetonitrile (25 mL) for 4 h. Allow the reaction to cool and then dilute with dichloromethane. Wash the organic solution with water, saturated $K_2CO_3$ solution and dry ($K_2CO_3$). Concentrate the solvent and obtain 2.55 g of solid. Chromatograph the solid over silica gel ($CH_2Cl_2$/MeOH, 49:1) to obtain 2.1 g of solid, mp 123-125° C.; MS, m/z=456 $(M+H)^+$.

29b: 4-[6-(2,6-Difluoro-benzo[b]thien-1-piperazinebutanamine

Stir a suspension, under argon, of 2-[4-[4-(6-fluorobenzo[b]thiophen-3-yl)piperazin-1-yl]butylisoindole-1,3-dione (Example 29a) (2.05 9, 4.5 mmol) in anhydrous MeOH (30 mL) and add hydrazine (0.5 mL,15.9 mmol). Reflux for 2.5 h and allow cooling to ambient temperature. Cool the reaction in an ice bath and add 1M HCl to a pH ~1. Filter the mixture, cool the filtrate in an ice bath, and add 50% aqueous NaOH to basify. Extract the aqueous mixture with dichloro -methane, wash the extract with $H_2O$, dry with $K_2CO_3$ and concentrate to obtain 1.4 g of oil, which crystallizes upon standing, LC/MS, m/z=326 $(M+H)^+$.

Example 30

4-Trifluoromethyl-N-{4-[-(2,6-difluoro-benzo[b]thiophen-3-yi]-butyl}-benzamide hydrochloride Add a solution of 4-(trifluoromethyl)benzoyl choride (90.5 mg, 0.43 mmol) in $CHCl_3$ (1-2 mL) to a mixture of anhydrous Amberlite IRA-68 (0.5 g) and 4-[6-(2,6-difluoro-benzo[b]thien-1-piperazinebutanamine (Example 29b) (100 mg, 0.31 mmol) in $CHCl_3$ (3.5 mL). Shake the reaction mixture for 5.0 h and then add polymer supported tris(2-aminoethyl)amine (120 mg). Continue shaking the reaction for 18 h and then filter. Rinse the filter cake well with $CHCl_3$ and concentrate the filtrate to obtain 135 mg of solid, LC/MS (Ymc005-AQ, 4×50 mm; water/$CH_3CN$/acetic acid, 94.5:5.0:0.5 100% for 0.1 min then water/$CH_3CN$/acetic acid, 5.0:94.5:0.5 linear gradient→100% (2 min, hold 4 min), Flow: 1.0 mL/min) $t_R$=min, m/z=498 $(M+H)^+$.

The following HPLC conditions are referred to in Examples 31-33:

HPLC Condition I

A) 95/5/0.1% Water/Acetonitrile/Formic Acid,
B) 5/95/0.1% Water/Acetonitrile/Formic Acid.
Column: YMC ODS-A 4×50 mm, Flow rate: 2 mL/minute.

The initial HPLC conditions consisted of 100% (A) flowing at 2 mL/minute. After the initial injection a linear gradient was performed so that at 2 minutes the HPLC conditions were 100% B. These conditions were then held for 3.4 minutes at which time the system switched back to initial conditions and equilibrated for the next analysis.

HPLC Condition II

A) 95/5/0.1% Water/Acetonitrile/Formic Acid,
B) 5/95/0.1% Water/Acetonitrile/Formic Acid.
Column: YMC ODS-A 2×50 mm, Flow rate=1 mL/minute.

The initial HPLC conditions consisted of 100% (A) flowing at 0.1 mL/minute. After the initial injection a linear gradient was performed so that at 2 minutes the HPLC conditions were 100% B. These conditions were then held for 3.5 minutes at which time the system switched back to initial conditions and equilibrated for the next analysis.

Example 31

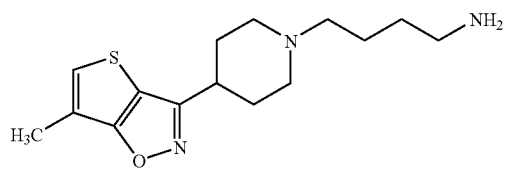

4-[4-(6-methyl-thieno[2,3-d]isoxazol-3-yl)-piperidin-1-yl]-butylamine

31a: Preparation of 4-[1-(3-bromo-4-methyl-thiophen-2-yl)-methanoyl]-piperidine-1-carboxylic acid tert-butyl ester

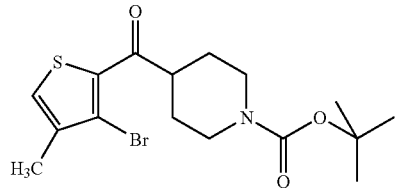

Under inert conditions, add a 2.0 M solution (in tetrahydrofuran/n-heptane) of lithium diisopropylamide (29.65 mmol, 14.83 mL, 1.05 equivalents) to a cold (−78° C.) solution of 3-bromo-4-methylthiophene (28.24 mmol, 5.00 g, 1.00 equivalents) in dry tetrahydrofuran (27.33 mL). Stir at −78° C. for 1 hour and add a solution of 4-(methoxy-methyl-carbamoyl)-piperidine-1-carboxylic acid tert-butyl ester (28.24 mmol, 7.69 g, 1.00 equivalents), dropwise. Continue stirring at −78 ° C. for 3 hours. Quench the reaction mixture with saturated ammonium chloride (aqueous, 55 mL) and allow to warm to room temperature. Extract the reaction mixture with a mixture of ethyl acetate : diethyl ether (1:1, 3×40 mL). Combine the extracts and dry over magnesium sulfate, filter and evaporate. Purify the residue via flash column chromatography using a mixture of n-heptane:ethyl acetate (4:1) to yield a yellow, crystalline solid (9.84 g).

MS (CI, methane) m/e 388 (MH+), LC/MS (APCl), m/e 288 (M-100), retention time 2 min. 43 sec. Condition I.

31b: Preparation of 4-[1-(3-bromo-4-methyl-thiophen-2-yl)-1-hydroxyimino-methyl]-piperidine-1-carboxylic acid tert-butyl ester

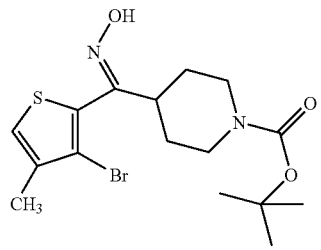

Add ammonium hydroxide hydrochloride (50.68 mmol, 3.52 g, 2.00 equivalents) to a stirred solution of 4-[1-(3-bromo-4-methyl-thiophen-2-yl)-methanoyl]-piperidine-1-carboxylic acid tert-butyl ester (25.54 mol, 9.84 9, 1.00 equivalents) in pyridine (47.5 mL). Stir at room temperature overnight and at 70° C. for 4 hours. Cool the reaction mixture and add hydrochloric acid (3 M solution, 115 mL). Extract the reaction mixture with dichloromethane (115 mL), filter the organic layer, wash with water (100 mL), dry over magnesium sulfate, filter and evaporate. Recrystallize the resulting residue from toluene to yield a white solid (4.84 9). LC/MS (APCl), m/e 403 (MH+), retention time 2 min. 32 sec. Condition I.

31c: Preparation of 4-(6-methyl-thieno[2,3-d]isoxazol-3-yl)-piperidine-1-carboxylic acid tert-butyl ester

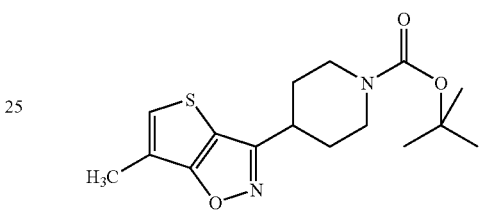

Add cesium carbonate (3.72 mmol, 1.21 g, 1.50 equivalents) and copper iodide (0.25 mmol, 47 mg, 0.10 equivalents) to a stirred solution of 4-[1-(3-bromo-4-methyl-thiophen-2-yl)-1-hydroxyimino-methyl]-piperidine-1-carboxylic acid tert-butyl ester (2.48 mmol, 1.00 g, 1.00 equivalents) in 2-methoxy ethanol (25 mL). Stir the resulting mixture at room temperature overnight and filter to remove the inorganic material. Concentrate the filtrate and partition the resulting oil between ethyl acetate (75 mL) and water (25 mL). Extract the aqueous layer with ethyl acetate (2×75 mL) and wash the combined organic layers with saturated sodium chloride (aqueous, 25 mL), dry over magnesium sulfate, filter and evaporate. Purify the residue via flash column chromatography eluting with n-heptane:ethyl acetate (4:1) to yield a white solid (588 mg). MS (Cl, methane) m/e 323 (MH+), LC/MS (ESI), m/e 345 (MNa+), retention time 2.05 minutes. Condition II.

31d: Preparation of 6-methyl-3-piperidin-4-yl-thieno[2,3-d]isoxazole hydrochloride

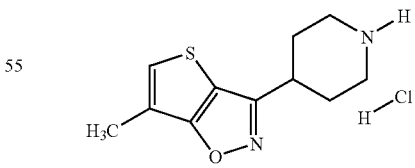

Stir a solution of 4-(6-methyl-thieno[2,3-d]isoxazol-3-yl)-piperidine-1-carboxylic acid tert-butyl ester (8.84 mmol, 2.85 g, 1.00 equivalents) in hydrochloric acid (48.75 mL, 1 M solution in diethyl ether) and methanol (2.00 mL) at room temperature for 3.5 hours. Filter the suspension, collect the white solid and dry to yield the desired product (659 mg). Allow the mother liquor to age overnight, filter, collect the white solid and dry to yield additional desired product (1.252 g). LC/MS (ESI), m/e 223 (MH+), retention time 1.14 minutes. Condition II.

31e: Preparation of 4-[4-(6-methyl-thieno[2,3-d]isoxazol-3-yl)-piperidin-1-yl]-butyronitrile

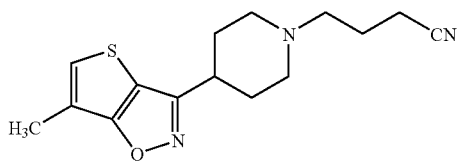

Add potassium carbonate (17.72 mmol, 2.45 g, 2.40 equivalents), potassium iodide (0.73 mmol, 123 mg, 0.10 equivalents), and 4-bromobutyronitrile (8.86 mmol, 0.88 mL, 1.20 equivalents) to a stirred solution of 6-methyl-3-piperidin-4-yl-thieno[2,3-d]isoxazole hydrochloride (7.38 mmol, 1.91 g, 1.00 equivalents) in acetonitrile (10.84 mL) and water (3.60 mL). Stir the resulting mixture at reflux overnight. Cool to room temperature, filter the reaction mixture and wash the solid material collected with dichloromethane and evaporate the filtrate. Take the residue up in dichloromethane (45 mL), wash with sodium hydroxide (aqueous, 18 mL, 2 M), water (18 mL), saturated sodium hydroxide (aqueous, 18 mL), dry over magnesium sulfate, filter and evaporate. Purify the residue via flash column chromatography using a gradient and eluting with a mixture of n-heptane : ethyl acetate (0.5:9.5) to ethyl acetate (100%) to yield the desired product as a brown oil (663 mg). LC/MS (ESI), m/e 290 (MH+), retention time 1.19 minutes. Condition II.

31f: Preparation of 4-[4-(6-methyl-thieno[2,3-d]isoxazol-3-yl)-piperidin-1-yl]-butylamine

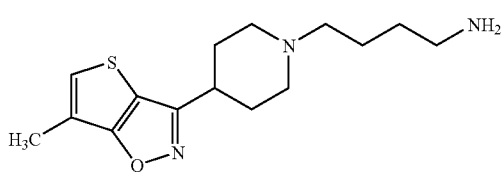

Under inert conditions, add lithium aluminum hydride (3.42 mmol, 3.42 mL, 1.50 equivalents, 1.0 M solution in tetrahydrofuran) to a stirred solution of 4-[4-(6-methyl-thieno[2,3-d]isoxazol-3-yl)-piperidin-1-yl]-butyronitrile (2.28 mmol, 660 mg, 1.00 equivalents) in tetrahydrofuran (dry, 12.86 mL). Stir the resulting solution at room temperature for 2.5 hours. Quench the reaction mixture by adding water (0.16 mL), then sodium hydroxide (aqueous, 0.16 mL, 2 M solution), and then water (0.5 mL). Dilute the resulting suspension with dichloromethane (16 mL) and vigorously stir for 30 minutes. Filter the resulting mixture through a bed of celite®, dry over magnesium sulfate, filter and evaporate to yield the desired product (457 mg) as a brown oil. LC/MS (ESI), m/e 294 (MH+), retention time 0.56 minutes. Condition II.

Example 32

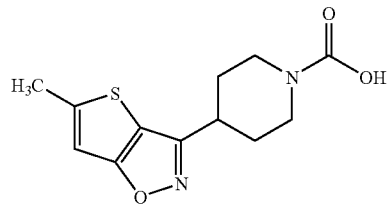

4-(5-methyl-thieno[2,3-d]isoxazol-3-yl)-piperidine-1-carboxylic acid

32a: Preparation of 4-[1-(3-bromo-5-methyl-thiophen-2-yl)-methanoyl]-piperidine-1-carboxylic acid tert-butyl ester

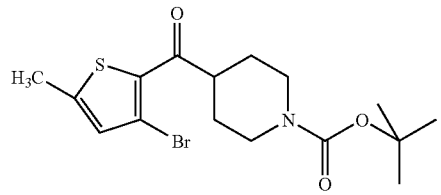

Prepared essentially as 2211-195 except that 2-bromo-5-methyl thiophene is used as the starting material. In addition, 1.20 equivalents of lithium diisopropylamide and 1.24 equivalents of 4-(methoxy-methyl-carbamoyl)-piperidine-1-carboxylic acid tert-butyl ester are used for the reaction. Accordingly, stirring time of the reaction mixture may vary. Purification of the residue via flash column chromatography uses a gradient with a mixture of ethyl acetate: n-heptane (1:9) to ethyl acetate:n-heptane (2:8) to yield a yellow oil. LC/MS (ESI), m/e 332 (M-56) and 388 (MH+), retention time 2.15 minutes. Condition II.

32b: Preparation of 4-[1-(3-bromo-5-methyl-thiophen-2-yl)-1-hydroxyimino-methyl]-piperidine-1-carboxylic acid tert-butyl ester

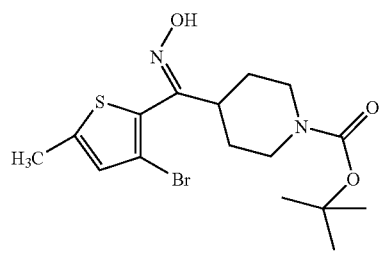

Prepared essentially as 2211-196 except that 4-[1-(3-Bromo-5-methyl-thiophen-2-yl)-methanoyl]-piperidine-1-carboxylic acid tert-butyl ester is used as the starting material and the reaction mixture was stirred at 70° C. for 6 hours. LC/MS (ESI), m/e 347 (M-56) and 403 (MH+), retention time 2.03 minutes. Condition II.

32c: Preparation of 4-(5-methyl-thieno[2,3-d]isoxazol-3-yl)-piperidine-1-carboxylic acid

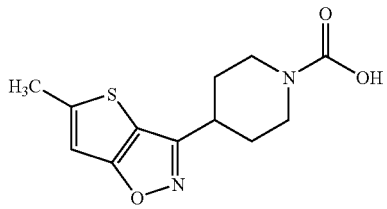

Prepared essentially as 2211-198 except that 4-[1-(3-bromo-5-methyl-thiophen-2-yl)-1-hydroxyimino-methyl]-piperidine-1-carboxylic acid tert-butyl ester is used as the starting material. Two other differences are: 1) 0.05 equivalents of copper iodide is used, and 2) no partition between ethyl acetate and water accompanied by subsequent extraction with ethyl acetate is required. Purification of the residue via flash column chromatography uses a mixture of ethyl acetate: n-heptane (1:4) to yield a white solid. LC/MS (ESI), m/e 345 (MNa+), retention time 2.12 minutes. Condition II.

Example 33

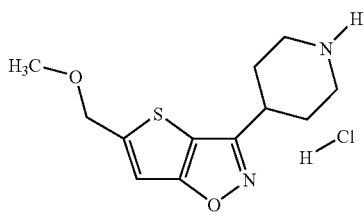

5-methoxymethyl-3-piperidin-4-yl-thieno[2,3-d]isoxazole hydrochloride

33a: Preparation of (4-bromo-thiophen-2-yl)-methanol

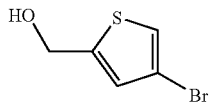

Under inert conditions, add sodium borohydride (13.82 mmol, 0.523 g, 2.08 equivalents) in absolute ethanol (16 mL) dropwise over a period of 15 minutes to a stirred mixture of 4-bromothiophene-2-carboxaldehyde (26.58 mmol, 5.08 g, 1.00 equivalents) in cold (0° C.) absolute ethanol (32 mL). Stir the resulting mixture at room temperature for 2.5 hours and add glacial acetic acid dropwise until the effervescence ceases. Evaporate the resulting solution, take the residue up in diethyl ether (75 mL), wash with water (15 mL) and brine (15 mL) and dry over magnesium sulfate. Filter and evaporate to yield the product as a colorless oil (5.13 g).

33b: Preparation of 4-bromo-2-methoxymethyl-thiophene

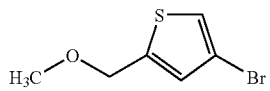

Add sodium hydride (737 mg, 29.23 mmol, 1.10 equivalents, 95%) to a solution containing methyl iodide (1.65 mL, 26.57 mmol, 1.00 equivalents) and (4-bromo-thiophen-2-yl)-methanol (5.13 g, 26.57 mmol, 1.00 equivalents) in tetrahydrofuran (dry, 25 mL). Stir the resulting mixture at room temperature overnight and evaporate. Partition the residue between water (100 mL) and dichloromethane (100 mL). Extract the aqueous layer with dichloromethane (100 mL), combine the organic layers, dry over magnesium sulfate, filter and evaporate to yield the desired product as a yellow oil.

33c: Preparation of 4-[1-(3-bromo-5-methoxymethyl-thiophen-2-yl)-methanoyl]-piperidine-1-carboxylic acid tert-butyl ester

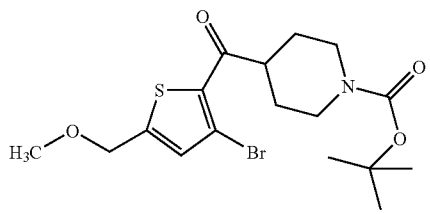

Add lithium diisopropyl amide (13.20 mL, 26.37 mmol, 1.05 equivalents) to a stirred, cold (−78° C.) solution of 4-bromo-2-methoxymethyl-thiophene (5.20 g, 25.11 mmol, 1.00 equivalents) in tetrahydrofuran (dry, 24.30 mL). Stir at −78° C. for 1 hour and add a solution of 4-(methoxy-methyl-carbamoyl)-piperidine-1-carboxylic acid tert-butyl ester (6.84 g, 25.11 mmol, 1.00 equivalents) in tetrahydrofuran (dry, 16.40 mL), dropwise. Stir the resulting solution at −78° C. for 3 hours. Quench the reaction mixture with saturated sodium chloride (aqueous, 50 mL). Allow the resulting mixture to warm to room temperature and extract with a mixture of ethyl acetate: diethyl ether (1:1, 3×35 mL). Combine the extracts, dry over magnesium sulfate, filter and evaporate. Purify the residue via flash column chromatography eluting with a mixture of n-heptane:ethyl acetate (4:1) to yield the desired product as a yellow oil (9.47 g). LC/MS (ESI), m/e 362 (M-56) and 418 (MH+), retention time 2.08 minutes. Condition II.

33d: Preparation of 4-[1-(3-bromo-5-methoxymethyl-thiophen-2-yl)-1-hydroxyimino-methyl]-piperidine-1-carboxylic acid tert-butyl ester

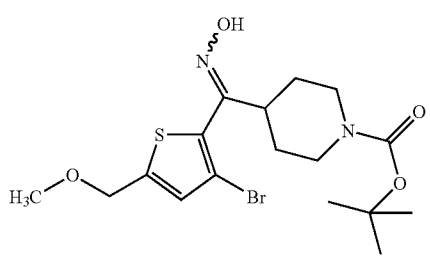

Add hydroxylamine hydrochloride (2.29 g, 45.27 mmol, 2.00 equivalents) to a stirred solution of 4-[1-(3-bromo-5-methoxymethyl-thiophen-2-yl)-methanoyl]-piperidine-1-carboxylic acid tert-butyl ester (9.47 g, 22.64 mmol, 1.00 equivalents) in pyridine (42.40 mL). Stir the resulting solution at room temperature overnight and then at 70° C. for 4 hours. Cool the reaction mixture slightly, add hydrochloric acid (3N, 100 mL) and extract the resulting mixture with dichloromethane (100 mL). Wash the extract with water (100 mL), dry over magnesium sulfate, filter and evaporate to yield the desired product as a yellow oil (9.48 g).

33e: Preparation of 4-(5-methoxymethyl-thieno[2,3-d]isoxazol-3-yl)-piperidine-1-carboxylic acid tert-butyl ester

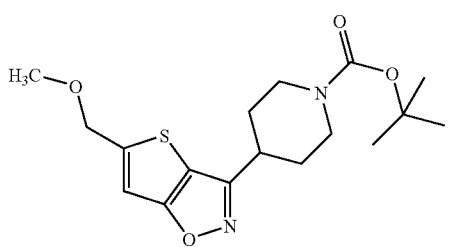

Add cesium carbonate (1.13 g, 3.46 mmol, 1.50 equivalents) and copper iodide (44 mg, 0.23 mmol, 0.10 equivalents) to a stirred solution of 4-[1-(3-bromo-5-methoxymethyl-thiophen-2-yl)-1-hydroxyimino-methyl]-piperidine-1-carboxylic acid tert-butyl ester (1.00 g, 2.31 mmol, 1.00 equivalents) in 2-methoxy ethanol (23.30 mL). Stir the resulting mixture at room temperature overnight or up to 3 days and filter through celite. Evaporate the filtrate, partition the residue between ethyl acetate (70 mL) and water (23 mL) and separate. Extract the aqueous layer with ethyl acetate (3×70 mL), combine the organic layers, dry over magnesium sulfate, filter and evaporate. Purify the residue via flash column chromatography eluting with a mixture of hexane:ethyl acetate (4:1) to yield the desired product as a yellow oil. LC/MS (ESI), m/e 375 (MNa$^+$), retention time 1.98 minutes. Condition II.

33f: Preparation of 5-methoxymethyl-3-piperidin-4-yl-thieno[2,3-d]isoxazole hydrochloride

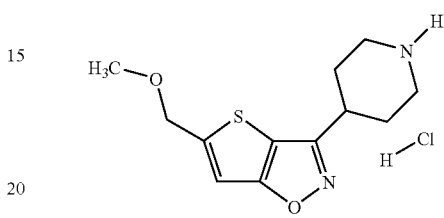

Stir a solution of 4-(5-methoxymethyl-thieno[2,3-d]isoxazol-3-yl)-piperidine-1-carboxylic acid tert-butyl ester (2.21 g, 6.68 mmol, 1.00 equivalents) and hydrochloric acid (1.0 M in diethyl ether, 35 mL) overnight to form a suspension. Add additional hydrochloric acid (1.0 M in diethyl ether, 10 mL). Stir the suspension overnight, filter and wash the solid with ether. Collect the solid and dry to yield the desired product as a dark blue solid. LC/MS (ESI), m/e 253 (MH$^+$), retention time 1.17 minutes. Condition II.

Example 34

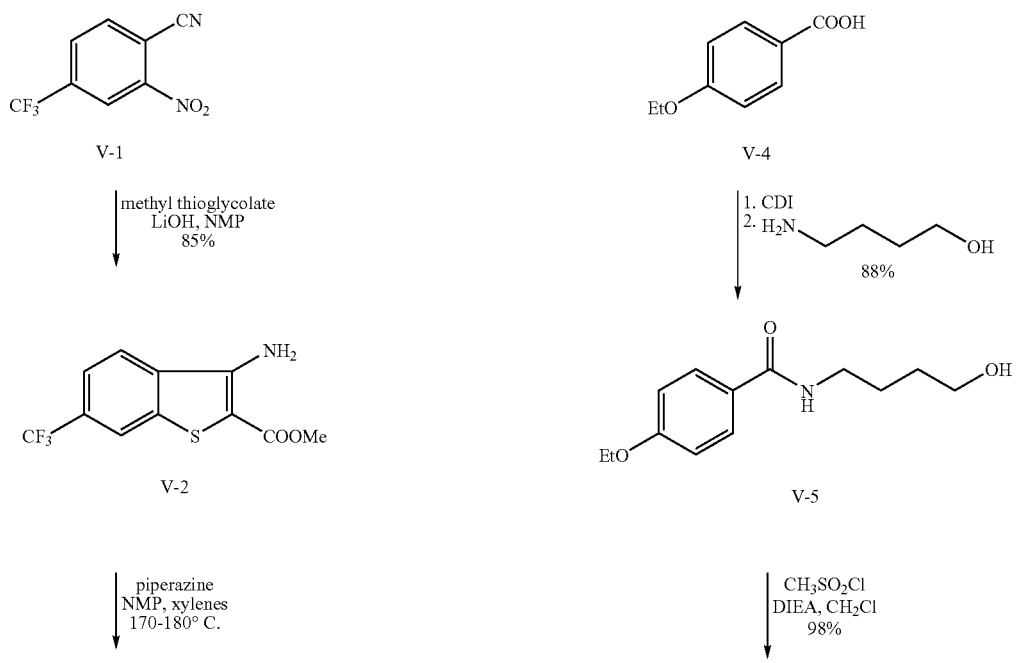

SCHEME V

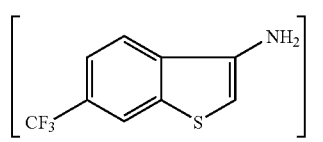

V-3

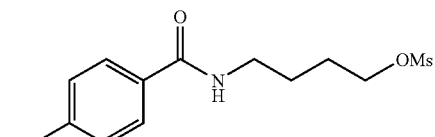

V-6

1. piperazine, p-TsOH, NMP, 160-167° C.
2. HCl/Et₂O 87%

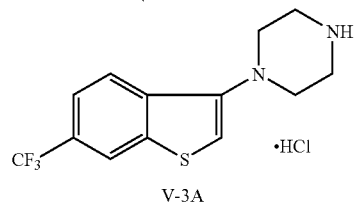

V-3A

1. K₂CO₃, THF
2. n-BuOAc recryst.
3. CH₃SO₂OH, THF 85%

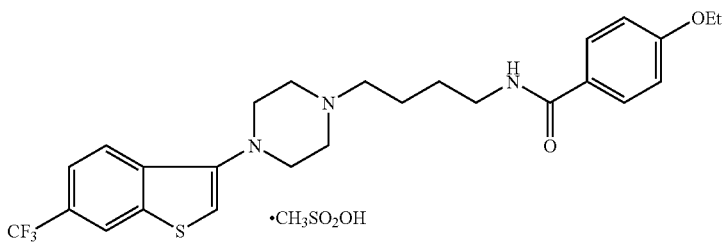

V-7

General: Gas chromatography/mass spectroscopy was accomplished using a HP Model 5972 system with the following conditions: 0.25 mm×30 m, HP 5MS column, cross-linked 5% Ph Me silicone, 0.25μ film thickness; injector at 250° C.; detecttor at 280° C.; 50° C. for 1 min. ramp at 20° C./min to 300° C. for 5 min to 10 min. Mass spectra were obtained on a Finnigan TSQ 700 spectrometer.

2-Carbomethoxy-3-amino-6-trifluoromethylbenzo[b]thiophene (V-2): A 22-L, 3-necked, round-bottom flask equipped with a mechanical stirrer, nitrogen bubbler, and a thermocouple probe, was charged with 1.20 kg (5.55 mole) of 2-nitro-4-trifluoromethylbenzonitrile, 589.3 g (496 mL, 5.55 mole) of methyl thioglycolate, and 4.3 L of NMP. After the resulting yellow solution was cooled to 2° C., a solution prepared from 466.0 g (11.11 mole, 2.0 eq) of lithium hydroxide monohydrate in 3.36 L of water was slowly added over a period of 78 min while maintaining a temperature of 2-20° C. The brown slurry was allowed to warm to 21° C. over a 2 h period, then was diluted with 8.0 L of water ($T_{exo}$->27° C.). After stirring for 40 min and cooling to 18° C., product was collected by filtration, rinsing with 10 L of water, then air-drying at ambient temperature to give 1.295 kg (84.7% yield) of 2-carbomethoxy-3-amino-6-trifluoromethylbenzo[b]thiophene, as a light-yellow solid.

3-Piperazinyl-6-trifluoromethylbenzo[b]thiophene hydrochloride (V-3a): A 12-L, 3-necked, round-bottom flask equipped with a mechanical stirrer, nitrogen bubbler, and a thermocouple probe, was charged with 1.14 kg (4.14 mole) of 2-carbomethoxy-3-amino-6-trifluoromethyl-[b]thiophene (V-2), 196.0 g (2.28 mole, 0.55 eq) of piperazine, 4.0 L of NMP, and 570 mL of xylene. The solution was heated to and held at 170-180° C. for 4 h. The brown solution was cooled to 168° C., and then 1.605 kg (18.63 mole, 4.5 eq) of piperazine (T->109° C.) and 1.575 kg (28.28 mole, 2.0 eq) of p-toluenesulfonic acid monohydrate (exotherm observed, 109->130° C.) were added. A Dean-Stark trap was connected to the condenser, and the reaction was heated to collect an azeotrope. A total of 410 mL of an aqueous distillate was removed, allowing the pot temperature to increase from 145 to 165° C. After 14 h at ca. 165° C., the reaction was cooled to 30-35° C., then quenched into an extractor that contained 5 kg of ice, 12 L of water, and 8.5 L of toluene. The phases were separated. The organic extract was washed with 11 L of 0.5 N NaOH followed by 2 L of saturated aq. NaCl., then was extracted with 8 L of 1 N HCl. The acidic aqueous extract was diluted with 1 kg of ice, then was basified to pH 11.2 by adding 624 g of 50% NaOH. The resulting mixture was extracted with 9.5 L of toluene. The toluene extract was washed with 2 L of saturated aq. NaCl, dried (Na₂SO₄), and filtered. The filtrate was charged into a 22 L 3-necked, round-bottomed flask (N₂, mechanical stirring, TC probe). A total of 3.7 L of 1 N ethereal HCl was added at 20-27° C.until the mixture was positive to Congo Red indicator paper. A total of 2.5 L of toluene was also added during the HCl addition to improve the stirring of the thick slurry that resulted. After stirring at ambient temperature for 40 min, the slurry was filtered and washed with 4.5 L of toluene. After air drying, 1.165 kg (87.1% yield) of 3-piperazinyl-6-trifluoromethylbenzo[b]thiophene hydrochloride (V-3a) was obtained as a light pink-beige solid.

N-(4-Hydroxybutyl)-4-ethoxybenzamide (V-5). A 22-L, 3-necked, round-bottom flask equipped with a mechanical stirrer, nitrogen bubbler, and a thermocouple probe, was charged with 1.16 kg of 4-ethoxybenzoic acid and 11 L of THF. A total of 1.403 kg (8.65 mole, 1.24 eq) of 1,1'-carbonyldiimidazole was added at ambient temperature in 4 portions (to control $CO_2$ evolution) to attain a conversion of 98% to the activated acid. After the yellow solution was cooled to −5° C., a solution prepared from 684.5 g (7.68 mole, 1.10 eq) of 4-amino-1-butanol in 0.5 L of THF was added over a period of 50 min while maintaining a temperature of −7 to −3° C. The gummy mixture was allowed to warm to room temperature and stir overnight. The light-yellow solution was concentrated (45° C., 50 mbar) to 3.22 kg of an orange oil that was charged to an extractor along with 5.7 kg of 10% HCl and 6 L DCM. The aqueous phase was extracted with 3 L DCM. The DCM extracts were combined, washed with 5 L of 0.5 N HCl, washed with 5 L of saturated aq. $NaHCO_3$, dried ($MgSO_4$), filtered, concentrated (45° C., 25 mbar), and air dried to give 1.52 kg (91.9%) of crude product as a white solid. Impurities were removed by saponification. A 12-L, 3-necked, round-bottom flask equipped with a mechanical stirrer, nitrogen bubbler, and a thermocouple probe, was charged with 1.52 kg of crude product, 5.5 L of IPA and 156.5 g of 50% NaOH. The mixture was heated for 30 min at 55-78° C. After cooling to 37° C., the hazy solution was charged into an extractor along with 7.8 L of water and 17 L of DCM. After the phases were separated, the aqueous layer was is extracted with 6 L of DCM. The organic extracts were combined, washed with 7.8 L of water, dried ($MgSO_4$), filtered, concentrated (50° C., 25 mbar) and air dried to give 1.453 kg (87.7%) of N-(4-hydroxybutyl)-4-ethoxybenzamide (V-5) as a white lumpy solid.

N-(4-Hydroxybutyl)-4-ethoxybenzamide methanesulfonate (V-6). A 22-L, 3-necked, round-bottom flask equipped with a mechanical stirrer, nitrogen bubbler, and a thermocouple probe, was charged with 2.00 kg (8.43 mole) of N-(4-hydroxybutyl)-4-ethoxybenzamide (V-5), 2.94 L (2.18 kg, 16.85 mole, 2.00 eq) of diisopropylethylamine, and 11 L of DCM. The white slurry was cooled to 6° C., and 718 mL (1.062 kg, 9.27 mole, 1.10 eq) of methanesulfonyl chloride was added over a period of 1.5 h while maintaining a pot temperature of 5-12° C. with cooling. After stirring for 10 min at 5-10° C. the pale-brown solution was quenched into an extractor that contained 14 L of 1 N HCl. The phases were separated. The organic extract was washed with 14 L of 1 N HCl, washed with 9 L of saturated aq. $NaHCO_3$, dried ($MgSO_4$), filtered and concentrated (30° C., 50 mbar), to give, after air drying, 2.65 kg (99.7%) of N-(4-hydroxybutyl)-4-ethoxybenzamide methanesulfonate (V-6) as a pale-beige solid.

N-[4-[4-(6-Trifluoromethylbenzo[b]thieny-3-yl)-1-piperazinyl]butyl]-4-ethoxybenzamide (V-7, free base): A 22-L, 3-necked, round-bottom flask equipped with a mechanical stirrer, nitrogen bubbler, and a thermocouple probe, was charged with 1.500 kg (4.65 mole) of V-3a, 1.502 kg (4.76 mole, 1.025 eq) of N-(4-hydroxybutyl)-4-ethoxybenzamide methanesulfonate (V-6), 9 L of THF, 3.18 L of water, and 1.285 kg (9.29 mole, 2.00 eq) of $K_2CO_3$. The biphasic solution was heated at reflux (64° C.) for 18 h, then cooled to room temperature. The resulting thick slurry was concentrated (40° C., 50-75 mbar) to remove THF, then diluted with 14 L of water, stirred at ambient temperature for 4 h, filtered, rinsed with water, and air dried to give 2.33 kg (99.3%) of crude product. This crude product was recrystallized from 12 parts (v/wt) of n-BuOAc (dissolution at ca. 115° C., heated to 122° C., crystallization at 100° C., aging at 0-5° C. for ca. 30 min) to give, after air drying, 2.09 kg (89.7%) of N-[4-[4-(6-trifluoromethylbenzo[b]thieny-3-yl)-1-piperazinyl]butyl]-4-ethoxybenzamide (V-7, free base) as a white, fluffy solid.

N[4-[4-(6-Trifluoromethylbenzo[b]thieny-3-yl)-1-piperazinyl]butyl]-4-ethoxybenzamide monomethanesulfonic acid (V-7): A 22-L, 3-necked, round-bottom flask equipped with a mechanical stirrer, nitrogen bubbler, and a thermocouple probe, was charged with 1.903 kg (3.764 mole) of free base of V-7 and 12.2 L of THF. The white slurry was warmed to 32° C. A solution of 365.3 g (3.707, 0.985 eq) of methanesulfonic acid in 1.8 L of THF was added in one portion. An exotherm was observed (T->40° C.), and the mixture became homogeneous at the end of the addition. After 2 min, precipitation commenced. After cooling 20° C. and stirring for 30 min, product was collected by filtering, rinsing with 2 L of THF, and air drying to give 2.16 kg (95.6%) of/[4-[4-(6-trifluoromethylbenzo[b]thieny-3-yl)-1-piperazinyl]butyl]-4-ethoxybenzamide monomethanesulfonic acid (V-7), as a white, fluffy powder.

Example 35

SCHEME VI

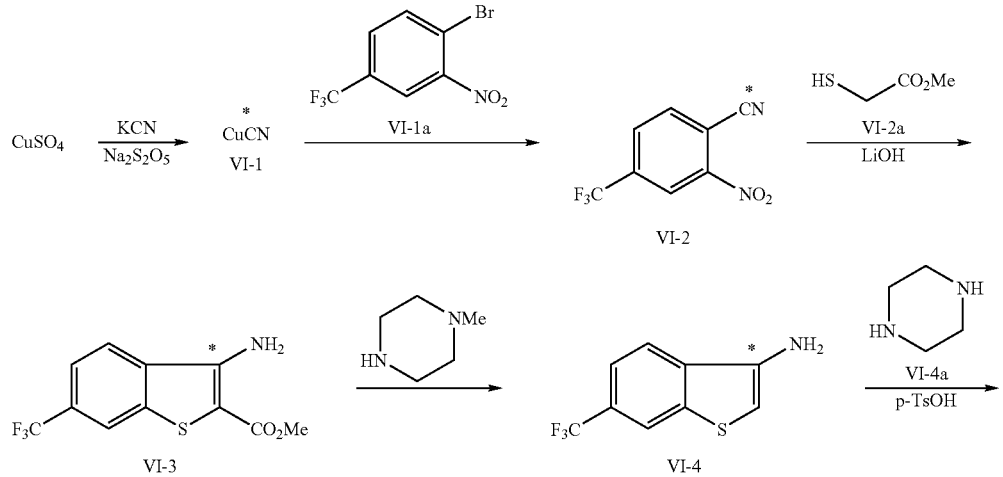

-continued

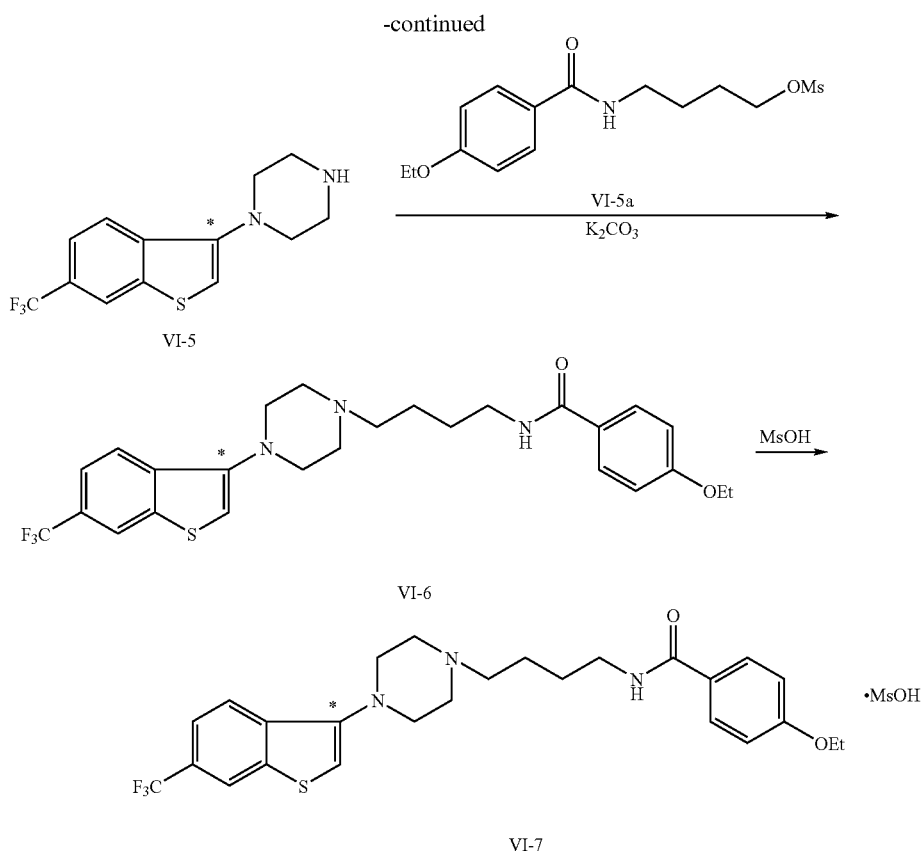

General: Analytical thin layer chromatography (TLC) was performed on E. Merck TLC plates with silica gel 60 $F_{254}$ (0.25 mm). TLC plates used in the analysis of radioactive samples were scanned on a BIOSCAN system 2000 Imaging Scanner using P-10 gas (10% methane, 90% argon). Identity of the intermediates was established by co-migration in radio-TLC and/or radio-HPLC with the standard samples of unlabeled analogues. Flash chromatography was performed using silica gel with a particle size of 40-63 μm. Specific activity was determined on a Packard Minaxi Tri-Carb Liquid Scintillation Analyzer (Model 1600 TR) using Bio-Safe II as scintillation cocktail.

Purification of compounds VI-2, VI-3, VI-4, VI-5, and VI-6 was monitored by HPLC (conditions: A) which was carried out on Waters 600 Controller, Waters 996 Photodiode Array Detector, Millennium Chromatography Manager and Beta-Ram Radioactive Flow Through Monitor System, Model 2 (IN/US Systems Inc.). Final purity determination of VI-7 by HPLC (conditions: B) was performed on Waters Model 510 Pumps, Waters 680 Gradient Controller, Waters 715 Ultra Wisp Autosampler, Waters 484 Tunable Absorbance Detector and Beta-Ram Radioactive Flow-Through Monitor System, Model 2 (IN/US Systems Inc.).

Conditions A: YMC Basic 5 μm, C18, 4.6×250 mm, mobile phase A: (v/v) 50/50 acetonitrile/0.1N ammonium formate, mobile phase B: (v/v) 75/25 acetonitrile/0.1N ammonium formate, flow rate 1.0 mL/min, uv detection at 254 nm.

| Gradient: | Time (minutes) | % MP:A | % MP:B |
|---|---|---|---|
| | 0 | 100 | 0 |
| | 15 | 100 | 0 |
| | 25 | 0 | 100 |
| | 30 | 0 | 100 |
| | 35 | 100 | 0 |

Conditions B: Ultremex 5 μm, C8, 4.6×150 mm, mobile phase (v/v/v) 50/50/0.25 acetonitrile/0.05 M potassium phosphate buffer, pH 3.0/triethylamine, flow rate 1.0 mL/min, uv detection at 210 nm.

[$^{14}$C] Copper (I) Cyanide (VI-1): A solution of copper (II) sulfate pentahydrate (4.16 g, 16.67 mmol) in water (13.3 mL) was heated to 70º C. and a solution of sodium metabisulfite (1.94 g, 6.28 mmol) in water (3.3 mL) at 70° C. was added in one minute. Immediately a solution of [$^{14}$C] potassium cyanide (245.5 mg, 200 mCi, 3.77 mmol, S.A. 53.0 mCi/mmol) and unlabeled potassium cyanide (0.84 g, 12.9 mmol) in water (3.3 mL) at 70° C. was added in one minute. A white solid precipitated out of solution and blue color of the solution was discharged. After stirring for 10 min at 70° C., the mixture was filtered hot and the solid was washed with hot water (15 mL) and ethanol (15 mL). The white solid was dried under vacuum (0.1 mm Hg) for 27 h 45 min to prove VI-1 (1.393 g, 186.6 mCi) in 93.3% yield.

2-Nitro-4-(trifluoromethyl)-[7-$^{14}$C]benzonitrile (VI-2): To a suspension of [$^{14}$C]copper (I) cyanide (VI-1) (1.393 g, 15.55 mmol, 186.6 mCi) in 1-methyl-2-pyrrolidinone (NMP, 10 mL) was added 4-bromo-3-nitrobenzotrifluoride (6.33 g, 23.45 mmol) and the mixture was heated at 190-195° C. for 1 h. Ethyl acetate (25 mL) and water (20 mL) were added at room temperature and the mixture was filtered through celite. To the filtrate more water (20 mL) and ethyl acetate (25 mL) were added and the aqueous layer was extracted with ethyl acetate (90 mL). The organic extract was washed with iron (III) chloride solution (50 mL) prepared by dissolving iron (III) chloride (7.468 g, 46.04 mmol) in water (50 mL). The organic extract was further washed with water (30 mL), sat. sodium chloride (15 mL), dried (Na$_2$SO$_4$) and the solvent was removed in vacuo.

The residue was purified by flash chromatography on silica gel (hexane/ethyl acetate, 9/1-7/3) to provide an oil which was dissolved in hexane (70 mL). The solvent was removed under reduced pressure and residue was dried under vacuum for 15 h 40 min to provide VI-2 (3.01 g, 167.13 mCi, 89.6% yield) as a yellow solid. Radio-TLC (hexane/ethyl acetate, 9/1), R$_f$=0.21; HPLC (System A), RCP 99.86% (ret. time, 9.2 min).

[3-$^{14}$C]-3-Amino-2-carbomethoxy-6-trifluoromethyl-benzo[b]thiophene (VI-3): Nitrile (VI-2) (3.01 g, 13.9 mmol, 167.13 mCi) was dissolved in DMF (14 mL) and methyl thioglycolate (1.78 g, 15.94 mmol, 95%) was added in one minute. The mixture was cooled to 0-5° C. and a solution of lithium hydroxide (0.689 g, 28.77 mmol) in water (9.2 mL) was added dropwise in 12 minutes. After the addition, cooling bath was removed and the mixture was stirred at room temperature for 4 hours. Water (70 mL) was added at 0-5° C. and the mixture was stirred for 15 min at 0-5° C. the solid was collected on a filter, washed with water (20 mL) and dried under vacuum (0.1 mm Hg) for 40 h 15 min to provide VI-3 (3.469 g, 151.24 mCi, 90.49% yield). Radio-TLC (CH$_2$Cl$_2$), R$_f$=0.372; HPLC (system A), RCP 99.92% (ret. time, 16.722 min).

[3-$^{14}$C]-3-Amino-6-trifluoromethylbenzo[b]thiophene (VI-4): To a solution of benzo[b] thiophene (VI-3) (3.469 g, 12.6 mmol, 151.2 mCi) in NMP (14 mL) was added 1-methylpiperazine (6.69 g, 66.79 mmol) and the mixture was heated at 140-145° C. for 5 h. The mixture was allowed to cool to room temperature, poured into water (60 mL) and extracted with ethyl acetate (140 mL). The organic extract was washed with water (30 mL), sat. sodium chloride (10 mL), dried (Na$_2$So$_4$) and the solvent was removed in vacuo. The residue was purified by flash chromatography on silica gel (hexane/ethyl acetate, 1/1) to yield a greenish solid which was dried under vacuum (0.1 mm HG) for 14 h to provide VI-4 (w.66 g, 146.95 mCi, 97.16% yield). ). Radio-TLC (hexane/ethyl acetate, 1/5), R$_f$=0.407; HPLC (system A), RCP 99.44% (ret. time, 10.552 min).

1-[6(trifluoromethyl)benzo[b]thien-3-yl-[3-$^{14}$C]piperazine (VI-5): To a solution of benzo[b]thiophene (VI4) (2.66 g, 12.24 mmol, 146.95 mCi) in NMP (17 mL)was added piperazine (4.309 g, 50.02 mmol) and p-toluenesulfonic acid (4.76 g, 25.02 mmol) at room temperature. The mixture was heated at 170° C. for 20 m h 24 min, allowed to cool to room temperature and poured into a solution of sodium carbonate (4.70 g, 44.3 mmol) in water (6 mL). The mixture was extracted with ethyl acetate (20 mL), dried (Na$_2$SO$_4$) and the solvent was removed in vacuo. The residue was purified by flash chromatography on silica gel (CH$_2$Cl$_2$/MeOH/NH$_4$OH, 9/1/0.2) and product was dried under vacuum (0.1 mm Hg) for 11 h 50 min. Ethanol (absolute, 30 mL) was added to the product and solvent was removed under reduced pressure. The residue was dried under vacuum (0.1 mm Hg) for 24 h 55 min to provide VI-5 (3.44 g, 144.18 mCi, 98.1% yield) as an oil. Radio-TLC (CH$_2$Cl$_2$/MeOH/NH$_4$OH, 9/1/0.2), R$_f$=0.46; HPLC (system A), RCP 99.88% (ret. time, 5.807 min).

N-[4-[4-(6-Trifluoromethylbenzo[b]thien-3-yl-[3-$^{14}$C]-1-piperazinyl]butyl]-4-ethoxybenzamide (VI-6): Water (10.5 mL) and powdered potassium carbonate (4.07 g, 29.45 mmol) were added to a solution of benzo[b] thiophene (VI-5) (3.44 g, 12.01 mmol, 144.18 mCi) in THF (35 mL). The mixture was stirred until all potassium carbonate dissolved and mesylate (VI-5a) (4.7 g, 14.9 mmol) was added in 10 min. The mixture was heated under reflux for 21 h 50 min, allowed to cool to room temperature and poured into dichloromethane (300 mL) and water (35 mL). Aqueous layer was extracted with dichloromethane (60 mL). Organic extract was washed with water (60 mL), sat. sodium chloride (20 mL), dried (Na$_2$SO$_4$) and concentrated to (350 mL) under reduced pressure. Silica gel (32 g) was added, solvent removed in vacuo and residue was purified by flash chromatography on silica gel (CH$_2$Cl$_2$/MeOH/NH$_4$OH, 10/0.5/0.2) to provide a solid to which ethanol (abs., 125 ML) was added and solvent was removed under reduced pressure. The white solid (4.98 g) was dried under vacuum (0.1 mm Hg) for 13 h 35 min and dissolved in ethyl acetate (225 mL) at reflux. The solution was allowed to cool to room temperature and kept at 0-5° C. for 3 hours. The crystalline solid was collected on a filter, washed with ethyl acetate (70 mL), dried under vacuum (0.1 mm Hg) for 33 h to provide VI-6 (4.5 g, 106.8 mCi, 74.1% yield). Radio-(TLC CH$_2$Cl$_2$/MeOH/NH$_4$OH, 10/0.5/0.2), R$_f$=0.593; HPLC (system A), RCP 100.0% (ret. time, 16.324 min), HPLC (System B), RCP 98.92% (ret. time, 27.838 min).

N-[4-[4-(6-Trifluoromethylbenzo[b]thien-3-yl[3-[$^{14}$C]-1-piperazinyl]butyl]-4-ethoxybenzamide methanesulfonate (VI-7): To a suspension of free base (VI-6) (4.50 g, 8.90 mmol, 106.8 mCi) in THF (70 mL) was added methanesulfonic acid (0.844 g, 8.78 mmol) in 2 min. All solid dissolved to give a clear colorless solution. After 5 min of stirring, a solid came out of solution. The mixture was stirred for 40 min at room temperature and concentrated to a volume of 24 mL. Ether (120 mL) was added to the thick paste and the mixture was stirred for 35 min at room temperature. The solid was collected on a filter, washed with THF/ether (8/2, 15 mL), dried under vacuum (0.1 mm Hg) for 19 h 20 min to provide product (5.35 g) which was crystallized twice from ethanol (absolute) to provide (VI-7) (4.223 g, 77.281 mCi, 72.4% yield) as a white solid. Radio-TLC (CH$_2$Cl$_2$/MeOH/NH$_4$OH, 10/0.5/0.2), displayed a single peak (R$_f$=0.602) corresponding to R$_f$ of the non-radiolabeled VI-7. $^1$H, $^{19}$F NMR (DMSO-d$_6$) spectra of VI-7 and non-radiolabeled VI-7 match in all essential details and are consistent with the structure.

HPLC (Ultremex 5 μm, C8, 4.6×150 mm, mobile phase (v/v/v) 50/50/0.25 acetonitrile/0.05 M potassium phosphate buffer, pH 3.0/triethylamine, flow rate 1.0 mL/min, uv detection at 210 nm) analysis of VI-7 provided radiochemical purity of 100.0% and chemical purity of 99.96% and retention time of 8.96 minutes.

Specific Activity

A single 12.61 mg sample of VI-7 was weighed into a vial, dissolved in methanol, quantitatively transferred to a 50-mL volumetric flask and diluted to volume with methanol. Six 100-μL alliquots of the solution were counted in Bio Safe II™ liquid scintillation cocktail. The average of six dpm values Example 36

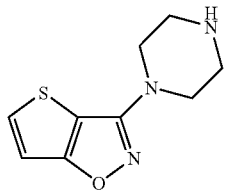

Synthesis of BOC protected piperazine-thienylisoxazole

3-Bromothiophene-2-carbaldehyde oxime

3-Bromothiophene-2-carbaldehyde (maybridge) (28.7 gm, 0.15 mol) in ethanol (50 ml) was added in one portion to a solution of hydroxylamine hydrochloride (13.8 gm, 0.2 mole), sodium hydroxide (8 gm, 0.2 mol) in water (30 ml) and ethanol (100 ml). The mixture was stirred at 0° C. for 2 hours and was kept at 0° C. overnight. The reaction mixture was diluted with cold water (600 ml), and the precipitated solids were collected by filtration to provide 20.5 gm, (67%) of product. The aqueous layer was further extracted with ethyl acetate and, the combined organic layers were washed with brine, dried with magnesium sulfate filtered and concentrated in vacuo to leave an additional 6.9 g of product.

3-bromothiophene-2-hydroximidoyl chloride

To a solution of 3-bromothiophene-2-carbaldehyde oxime (1 0.8 gm, 52.4 mmol), hydrogen chloride (14.5 ml, 4M in dioxane) in DMF (100 ml) was added oxone (16.9 gm, 1.05 eqiv) in one portion at room temperature. The mixture was stirred at ambient temperature overnight. At the end of the reaction, DMF solution was poured into water and product was extracted into ethyl acetate. The organic solution was washed with brine, dried over magnesium sulfate, filtered and concentrated in vacuo to 12.68 gm of product which was used in the next reaction without further purification.

(4-t-Butoxycarbonylpiperazinyl)-3-bromo-2-thienyl methanone oxime 3-bromothiophene-2-hydroximidoyl chloride (16.4 gm, 68 mmol) in tetrahydrofuran (THF, 70 ml) was added dropwise to a solution of N-(t-butoxycarbonyl)piperazine (14 gm, 1.1 equiv.), DABCO (9.5 gm, 1.25 eqiv.) in DMF (100 ml) at 0° C. over 25 minutes. The mixture was stirred for 3.5 hrs. At the end, the mixture was poured into water and was extracted with ethyl acetate. The organic was washed with brine and dried over magnesium sulfate. The solvent was removed on a rotary evaporator. The crude product (30.5 gm) was purified by chromatography on a Biotage cartridge (400 gm of silica gel), eluting with methanol in dichloromethane (0-5% of MeOH). The product thus obtained weighed 24.6 gm (85%).

(t-BOC-piperazine)-3-thienylbenzisoxazole

A mixture of (4-t-Butoxycarbonylpiperazinyl)-3-bromo-2-thienyl methanone oxime (10.3 gm, 26.4 mmol), cesium carbonate (10.7 gm, 32.7 mmol), and copper iodide (500 mg) in methoxyethanol (200 ml) was stirred at room temperature overnight. The reaction mixture was diluted with ethyl acetate, the washed with water. The aqueous solution was extracted three times with ethyl acetate. The organic solution (total 600 ml) was washed with brine and was dried over magnesium sulfate then concentrated to an oil (~10 gm). This material was purified by chromatography using a Biotage carridge (120 gm of silica gel, eluting with 0-8% Methanol in dichloromethane). The product thus obtained as light oil (5.1 gm, 62%).

Example 37

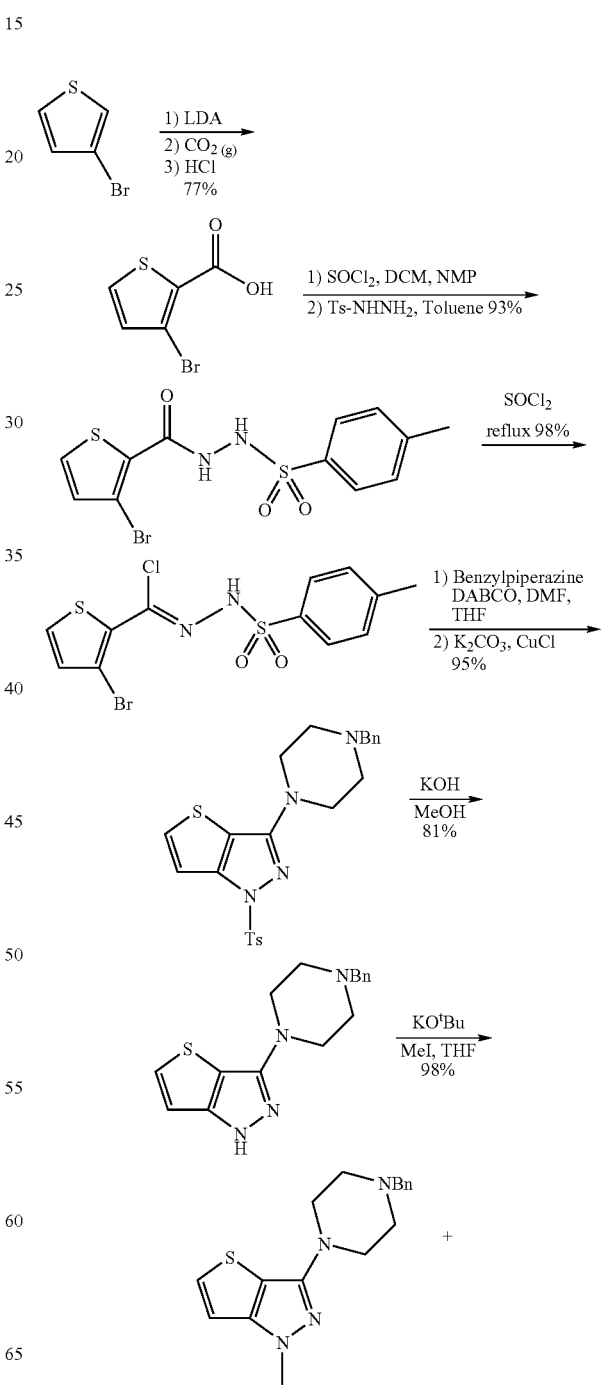

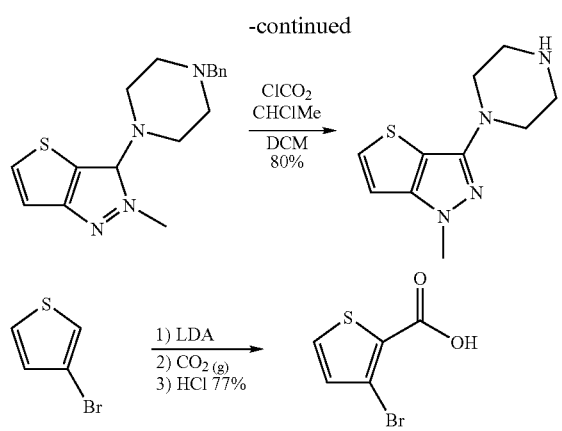

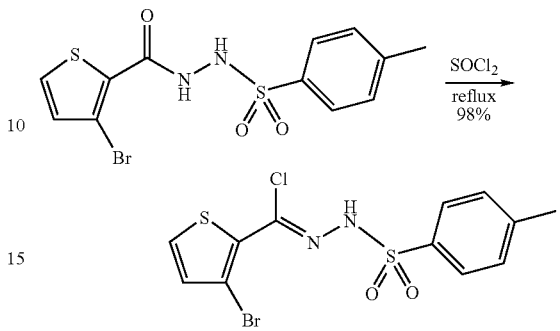

water. The solid were dried under vacuum at 40° C. then recrystallized from toluene/isoproyl alcohol yielding 484.28 g (93%) of the desired product.

3-Bromo-thiophene-2-carboxylic acid. To a solution of 3-bromothiophene (600.0 g, 3.68 mol) in THF (3 L) cooled to −72° C. was added LDA (1.93 L, 3.86 mol, 2 N) slowly over 2 hours. The rate of LDA addition is such that the reaction temperature never exceeded −68° C. After complete addition, the solution is stirred for an additional 40 minutes. Diethyl ether (3 L) is then added via an addition funnel such that the temperature is maintained below −65° C. The addition funnel is then replaced with a dispersion tube and $CO_2$ gas is bubbled through the solution for 3 hours. Dry ice (500 g) is then added and the mixture is stirred overnight. The reaction flask is then placed in an ice bath and 6 N HCl is added slowly to prevent excessive bubbling until the pH of the solution is adjusted to 1-2. The resulting mixture is then extracted with EtOAc. The extract is washed with brine then dried over $MgSO_4$, filtered and evaporated. The product is dried under vacuum at room temperature yielding 585.15 g (77%) as an off-white solid.

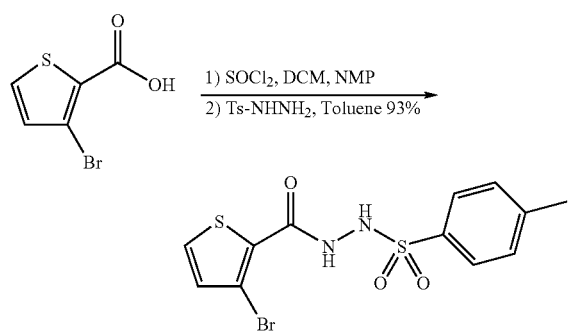

1-(3-Bromo-thiophene-2-carboxylic acid)-2-(4-toluenesulfonyl)-hydrazine. To a stirred suspension of the acid (285.53 g, 1.38 mol) in DCM (1.5 L) was added a catalytic amount of NMP (2 mL). Thionyl chloride (105.8 mL, 1.45 mol) is then added and the solution is refluxed until the solids have completely dissolved. The solution is further refluxed for 1 hour, cooled to room temperature and evaporated to afford a light, brown solid. The crude material is dried under vacuum overnight. The brown solid is taken up in toluene (3.5 L) and ptoluenesulfonhydrazine (402.25 g, 2.16 mol) is added. The mixture is stirred at 100° C. for 8 hours then at room temperature overnight. The resulting mixture was cooled with an ice bath and the resulting solids were collected by filtration and washed with toluene. The solids were then stirred as a slurry in 1 N HCl for 1 hour. The solids were collected by filtration and washed with copious amounts of N-((4-Methylphenyl)-sulfonyl)-3-bromo-thiophene-2-carbohydrazonyl chloride. 1-(3-Bromo-thiophene-2-carboxylic acid)-2-(4-toluenesulfonyl)-hydrazine (60.80 g, 0.161 mol) was added to thionyl chloride (70.5 mL, 0.966 mol). The resulting mixture was stirred at 80° C. until the mixture becomes homogenous. The solution is then stirred at 70° C. for 30 minutes and heptane (300 mL) is added over a period of 20 minutes. The solution was cooled slowly to room temperature then cooled further to 5° C. The solids are collected by filtration, washed with heptane (3×100 mL) and dried under vacuum yielding 62.1 g (98%) of the desired product as an off-white solid.

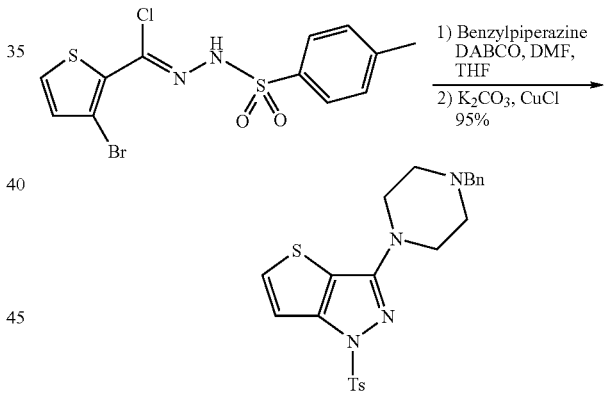

3-(4-Benzyl-piperazin-1-yl)-1-(toluene-4-sulfonyl)-1H-thieno[3,2-c]pyrazole. To a stirred solution of DABCO (14.18 g, 112.18 mol) and benzylpiperazine (35.35 g, 0.200 mol) in DMF (200 mL) cooled to −30° C. was added via cannula a solution of N-((4-Methylphenyl)-sulfonyl)-3-bromo-thiophene-2-carbohydrazonyl chloride (62.1 g, 0.158 mol) in THF (100 mL). The addition is controlled to prevent the reaction temperature from exceeding −30° C. After complete addition precipitation occurs and the mixture is then allowed to stir at room temperature overnight when $K_2CO_3$ (65.41 g, 0.473 mol) and CuCl (1.0 g, 0.010 mol) was added. The resulting mixture is heated to 110° C. and the THF is removed by distillation at this point. The temperature is then increased to 140° C. and the mixture is stirred for 6 hours, cooled to room temperature and stirred overnight. The mixture was then poured over water (100 mL) and EtOAc (100 mL). The EtOAC layer is then separated and the aqueous layer is extracted with EtOAC (3×500 mL). The combined EtOAC layers were washed with water (500 mL) and then filtered through celite and concentrated. The solids were collected by filtration and washed with cold water then EtOAc/heptane (1:4) and dried under vacuum yielding 66.05 g (95%) of the desired product as an off-white solid.

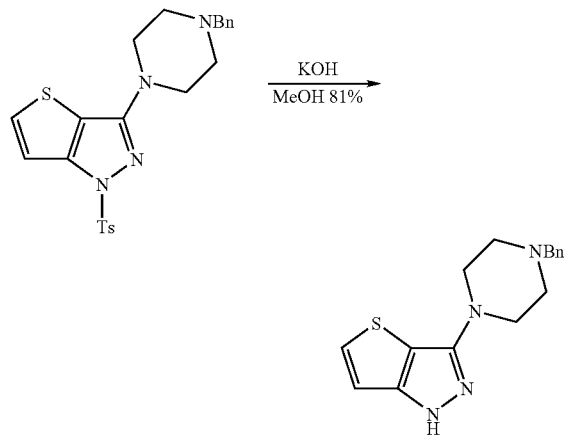

3-(4-Benzyl-piperazin-1-yl)-1H-thieno[3,2-c]pyrazole. To a stirred mixture of KOH$_{(s)}$ (56.09 g, 2.66 mol) in methly alcohol (1.33 L) is added 3-(4-benzyl-piperazin-1-yl)-1-(toluene-4-sulfonyl)-1H-thieno[3,2-c]pyrazole (241 g, 0.532 mol). The mixture is heated at reflux for 1.25 hours, cooled to room temperature and evaporated. The is residue is taked up in EtOAc (1 L) washed with water (2 L), dried (MgSO$_4$) filtered and evaporated. The residue was recrystallized from EtOAc/Heptane yielding 129 g (81%).

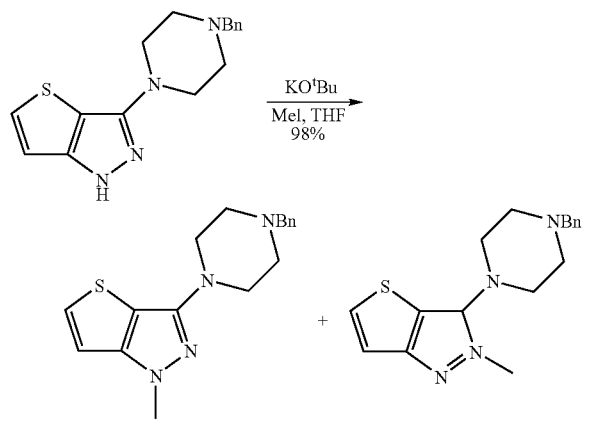

3-(4-Benzyl-piperazin-1-yl)-1-methyl-1H-thieno[3,2-c] pyrazole. To a stirred solution of 3-(4-benzyl-piperazin-1-yl)-1H-thieno[3,2-c]pyrazole (318.0 g, 1.07 mol) in THF (2.5 L) was added a mixture of potassium t-butoxide (134.4 g, 1.2 mol) in THF (1.5 L) dropwise over a period of 1 hour while keeping the reaction temperature below 25° C. After complete addition, the mixture was cooled to −30° C. and MeI (65.4 mL, 1.05 mol) was added dropwise over a period of 30 minutes. The mixture is then slowly warmed to room temperature overnight. To the reaction mixture is slowly added saturated NaHCO$_3$ (1 L). The solution is then evaporated to remove the THF and the resulting aqueous mixture is taken up in EtOAc and washed with water and brine. The EtOAc extract is dried (Na$_2$SO$_4$), filtered and evaporated. The viscous concentrate is filtered through a silica gel plug with 1:1 EtOAc/heptane and evaporated yielding a viscous oil that is then dried under vacuum where it solidifies and yields 326.03 g (98%) as a 12:1 ratio of regioisomers in favor of the desired product.

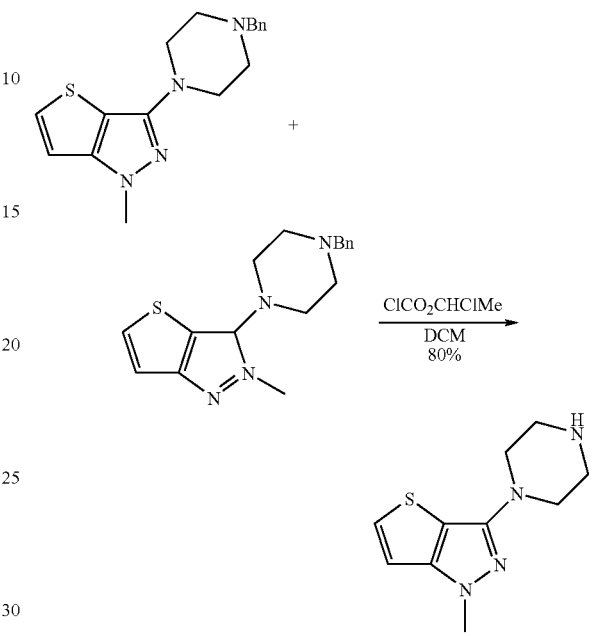

1-Methyl-3-piperazin-1-yl-1H-thieno[3,2-c]pyrazole. To a solution of a mixture of 3-(4-Benzyl-piperazin-1-yl)-1-methyl-1H-thieno[3,2-c]pyrazole and the 2-methyl analog (189.0 g, 0.60 mol) is dissolved in DCM (1.25 L) is added 1-chloroethylchloroformate (78.6 mL, 0.72 mol). The solution is heated at reflux for 1 hour when the mixture is cooled and the solvent is removed by evaporation. The residue is taken up in methanol (1 L) and heated at reflux for 30 minutes. After cooling, the solution is treated with 1 N HCl in ether (200 mL) and an additional 1 L of ether to afford the precipitation of the product. The solid is collected via filtration and washed with cold ether. The solid is recrystallized from methanol (1 L) and the HCl salt is collected by filtration, washed with ether and dried under vacuum yielding 123.04 g (80%) of the desired product as an 80:1 mixture of regioisomers in favor of the desired regioisomer as seen by NMR.

Example 38

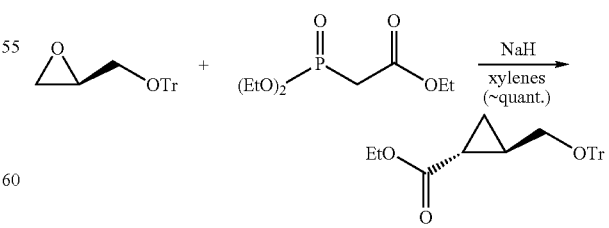

Trityloxymethyl-(1R, 2R)-cyclopropanecarboxylic acid ethyl ester. To a suspension of sodium hydride (15.20 g, 380 mmol, 60% oil dispersion) in xylenes (300 mL) was added triethylphosphonoacetate (85.07 g, 379 mmol) in a controlled manner to avoid the excessive evolution of gas and to maintain the internal temperature less than 55° C. After the complete addition, the mixture was stirred for 20 minutes when the yellow solution was added via cannula to a solution of (R)-trityl glycidyl ether (100.0 g, 316 mmol) in xylenes (300 mL). The resulting solution was heated to 125° C. for 2 hours. The resulting solution was cooled to room temperature, acidified with the addition of 10% HCl (320 mL) and extracted with EtOAc (2×300 mL). The combined extracts were washed with brine (100 mL), dried (MgSO$_4$), filtered and evaporated yielding a 175 g of a crude product as an oil. The material was carried on crude.

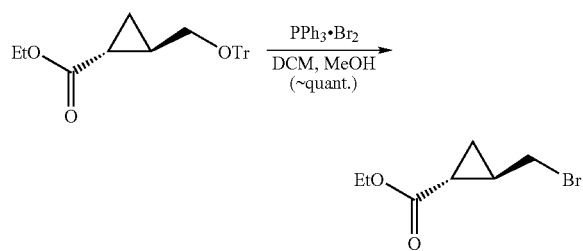

2R-bromomethyl-cyclopropane-1 R-carboxylic acid methyl ester. A solution of triphenylphosphine (124.7 g, 1.34 mol) in CH$_2$Cl$_2$ (260 mL) was cooled to 5° C. when a solution of bromine (24.4 mL, 1.34 mol) in CH$_2$Cl$_2$ (65 mL) was added over 20 minutes while the temperature was maintained below 12° C. The mixture was stirred at 5° C. for 1 hour when 2 M HCl/Et$_2$O (16 mL, 32 mmol) was added followed by the addition of crude trityloxymethyl-(1R , 2R)-cyclopropane carboxylic acid ethyl ester (124 g, 0.32 mol). The resulting mixture was stirred at room temperature overnight when saturated NaHCO$_3$ (600 mL) was added. The mixture was separated and the aqueous layer was extracted with CH$_2$Cl$_2$ (200 mL). The combined organic layers were washed with water (400 mL), dried (MgSO$_4$), filtered and evaporated. The residue was diluted with heptane (200 mL) and evaporated two times to remove excess CH$_2$Cl$_2$. The residue was allowed to stand for 30 minutes when the solid impurities were removed by filtration. The filter cake was washed with heptane (2×400 mL). The combined organic layers were evaporated to provide 92.68 g of a crude yellow liquid. The crude liquid was distilled (BP=80-85° C./1.5 torr) to provide 55.19 g (84% yield for the two steps) of a colorless liquid.

Example 39

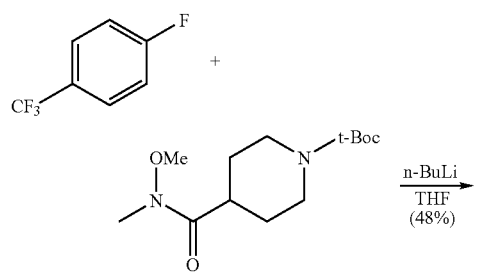

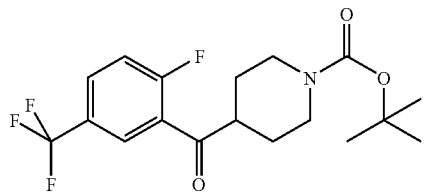

4-(2-Fluoro-5-trifluromethyl-benzoyl)-piperidine-1-carboxylic acid tert-butyl ester. A solution of 4-fluorobenzotrifluoride (25 g, 0.152M) in anhydrous THF (300 ml) was cooled to −60° C. (IPA/CO2 bath) and treated with n-butyl lithium (84 mL of a 2.0M solution in Hexane, 0.168M -1.1 eq) with a maximum rate so not to exceed −60 ° C. The reaction was stirred for 3 hours (temperature maintained) and then treated with a solution of 4-(methoxy-methyl-carbamoyl)-piperidine-1-carboxylic acid tert-butyl ester (51.86 g, 0.190M -1.25 eq, in 130 mL of anhydrous THF) with a maximum rate so as not to exceed −55° C. The mixture was stirred for a further two hours before allowing to warm to room temperature and stirred for 0.5 hours. The reaction was quenched with saturated ammonium chloride solution (75 mL) and the THF removed under reduced pressure. The residue was dissolved in ethylacetate (800 mL), washed with 1 N Hydrochloric acid (400 ml), 5%aq NaHCO$_3$ (400 mL), water (400 mL) and brine (400 mL) successively. The organics were dried over MgSO$_4$, filtered and concentrated to give a brown oil, which on triturating in ethyl acetate gave a white solid 27.6 g (48%).

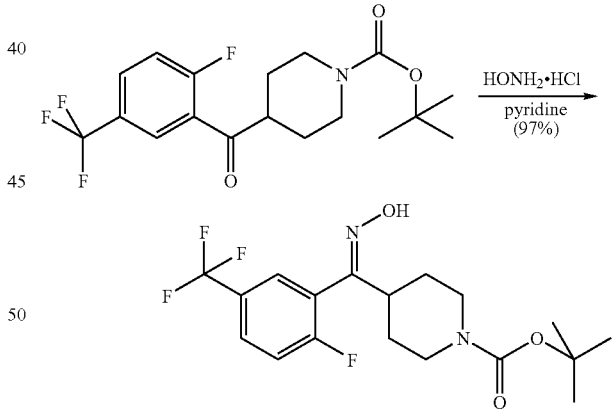

4-[(2-Fluoro-5-trifluoromethyl-phenyl)-hydroxyimino-methyl]-piperidine-1-carboxylic acid tert-butyl ester. A solution of 4-(2-fluoro-5-trifluromethyl-benzoyl)-piperidine-1-carboxylic acid tert-butyl ester (5 g, 0.013M) in pyridine (25 mL) was treated with hydroxylamine hydrochloride (1.11 g, 0.015 M -1.2 eq). The reaction was stirred under N$_2$ at room temperature for 14 hours and then poured onto ice water (250 mL). The mixture was stirred at 0° C. for 1 hour, the product was then filtered off, washed with cold water (3×15 mL) and dried in a vacuum oven at 50° C. A white solid was obtained (5.03 g, 97%).

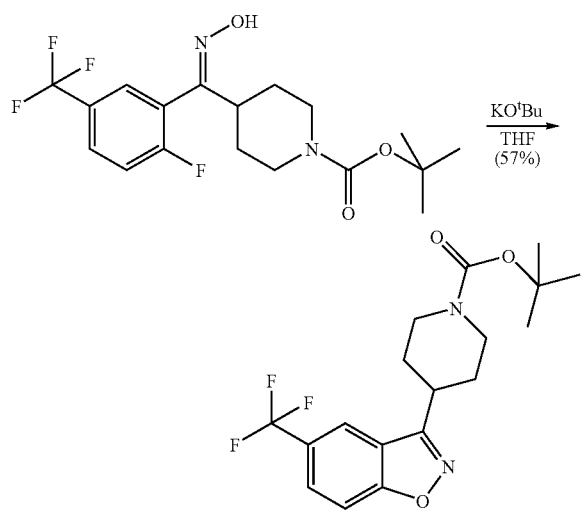

4-(5-Trifluoromethyl-benzo[d]isoxazol-3-yl)-piperidine-1-carboxylic acid tert-butyl ester. A solution of 4-[(2-Fluoro-5-trifluoromethyl-phenyl)-hydroxyimino-methyl]-piperidine-1-carboxylic acid tert-butyl ester (4.969 g, 0.013 M) in anhydrous THF (59 mL) was treated with Potassium tert-butoxide (13.4 mL of a 1M solution in THF, 0.0133 M -1.05 eq). The mixture was stirred at ambient temperature for 1 hour and then heated to 65° C. for 2 hours. The THF was removed under reduced pressure. The residue was dissolved in ethyl acetate (100 mL), washed with H$_2$O (50 mL) and brine (50 mL) respectively. It was then dried over MgSO$_4$, filtered and concentrated to give a solid (5 g) which was purified on silica ~120 g, (eluting with ethylacetate/heptane (30:70) to give the product as a white solid (2.69 g, 57%).

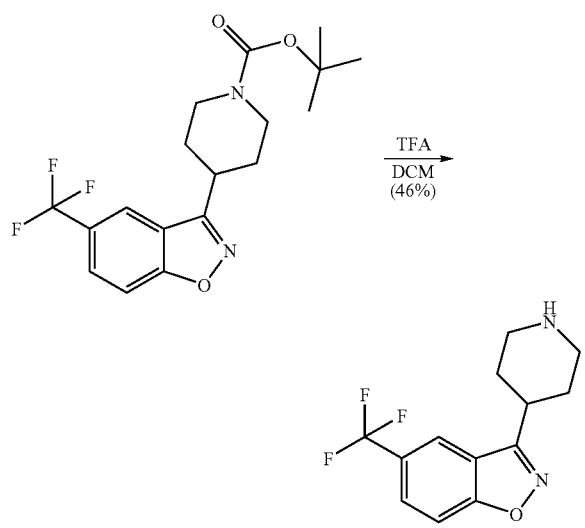

3-Piperidin-4-yl-5-trifluoromethyl-benzo[d]isoxazole. 4-(5-Trifluoromethyl-benzo[d]isoxazol-3-yl)-piperidine-1-carboxylic acid tert-butyl ester (2.69 g, 0.007M) was suspended in a 50:50 mixture of DCM/Trifluoroacetic acid (4 mL). The mixture was heated for 30 minutes at 50° C. and then concentrated to give the product as the TFA salt. This was dissolved in dichloromethane (10 mL), washed with saturated Na$_2$CO$_3$ solution (3×3 mL), dried over MgSO$_4$, filtered and concentrated to give the product as an oil (0.91 g, 46%)

Example 40

7-Methoxy benzisoxazolyl piperidine

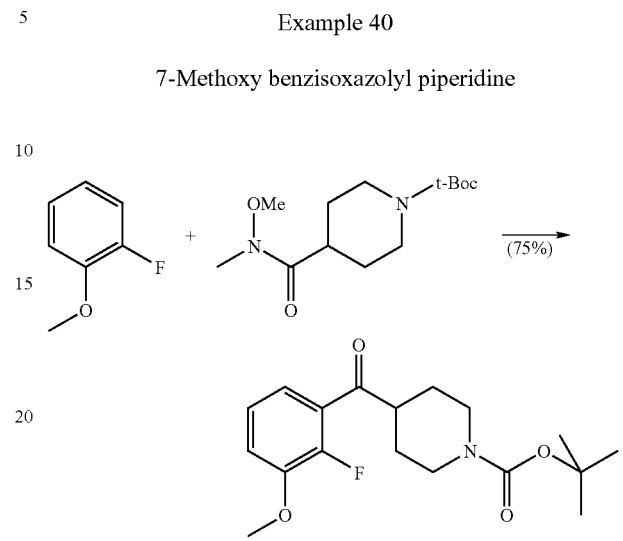

4-(2-Fluoro-3-methoxy-benzoyl)-piperidine-1-carboxylic acid tert-butyl ester. To a stirred solution of 2-fluoroanisole (6.00 g, 47.6 mmol) and anhydrous THF (125 mL) at –78 ° C. under nitrogen was added butyllithium (35 mL of a 1.6 M solution in hexanes, 56.0 mmol). After stirring for 13 min, N,N,N',N',N"-Pentamethyldiethylenetriamine (12.9 mL, 61.8 mmol) was added dropwise and the reaction stirred at –78° C. After 168 min, a solution of 4-(methoxy-methyl-carbamoyl)-piperidine-1-carboxylic acid tedt-butyl ester (16.8 g, 61.7 mmol) in anhydrous THF (40 mL) was added dropwise over 25 min. The reaction was stirred at –78° C. for 35 min and at room temperature for 65 min. The reaction was diluted with ethyl acetate (400 mL) and washed with cold 0.5 N aqueous HCl (2×200 mL), 5% aqueous potassium carbonate (200 mL), water (200 mL), and brine (200 mL) successively. The organic phase was dried over magnesium sulfate, filtered, and the solvent removed to give 20.1 g of a yellow oil. The product was chromatographed on silica gel (350 g), using a step gradient elution of 20% ethyl acetate/heptane to 30% ethyl acetate/heptane, to afford 12.0 g (75%) of the desired product as a white solid.

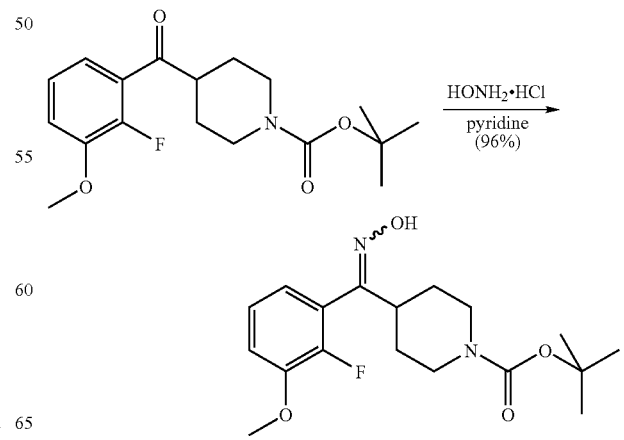

4-[(2-Fluoro-3-methoxy-phenyl)-hydroxyimino-methyl]-piperidine-1-carboxylic acid tert-butyl ester. A mixture of 4-(2-Fluoro-3-methoxy-benzoyl)-piperidine-1-carboxylic acid tert-butyl ester (11.6 g, 34.4 mmol), hydroxylamine hydrochloride (2.87 g, 41.3 mmol) and pyridine (50 mL) was stirred at room temperature under nitrogen overnight. The yellow reaction solution was poured into cold water (500 mL) and the mixture aged at 0° C. for 15 min. The product was collected by filtration, washed with water, and dried under vacuum at 50° C. to afford 11.6 g (96%) of the desired product as a white powder. Proton NMR showed product to be a 2:1 mixture of Z- to E-isomers.

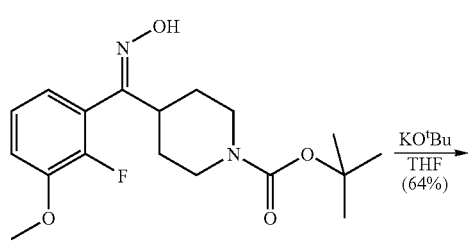

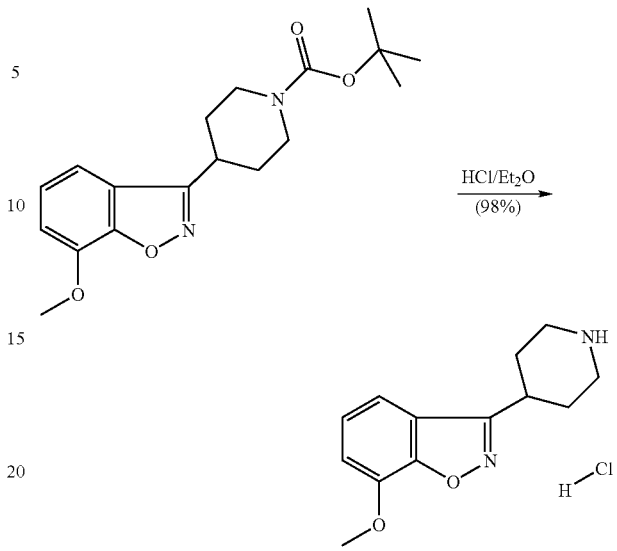

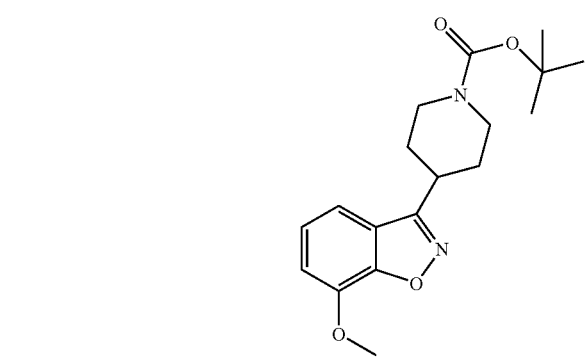

4-(7-Methoxy-benzo[d]isoxazol-3-yl)-piperidine-1-carboxylic acid tert-butyl ester (MDL 831478). To a room temperature mixture of 4-[(2-Fluoro-3-methoxy-phenyl)-hydroxyimino-methyl]-piperidine-1-carboxylic acid tert-butyl ester (5.00 g, 14.2 mmol) in THF (50 mL) under nitrogen was added potassium tert-butoxide (15.0 mL of a 1M THF solution, 15.0 mmol) rapidly and the reaction refluxed for 4 h. After cooling to room temperature, the reaction was diluted with ethyl acetate (250 mL) and washed with water (100 mL) and brine (100 mL) successively. The organics were dried over magnesium sulfate, filtered, and concentrated to give a waxy solid. Recrystallization of the solid did not remove impurities so the crude product was chromatographed on silica using a step gradient elution of 10% ethyl acetate/dichloromethane to 40% ethyl acetate/dichloromethane to afford 3.04 g (64%) of the desired product as a white powder, mp: 130-132° C.

7-Methoxy-3-piperidin-4-yl-benzo[d]isoxazole hydrochloride (MDL 831587A). A mixture of 4-(7-Methoxy-benzo[d]isoxazol-3-yl)-piperidine-1-carboxylic acid tert-butyl ester (3.00 g, 9.03 mmol), HCl (35 mL of a 1 M ether solution, 35.0 mmol), and methanol (25 mL) was stirred at room temperature under nitrogen for 18 h. Ether (75 mL) was added, the mixture stirred at room temperature for 15 min, and the product collected by filtration to afford 2.37 g (98%) of the desired product as a white powder, mp: >250° C.

Example 41

7-trifluoromethyl benzisoxazol piperidine

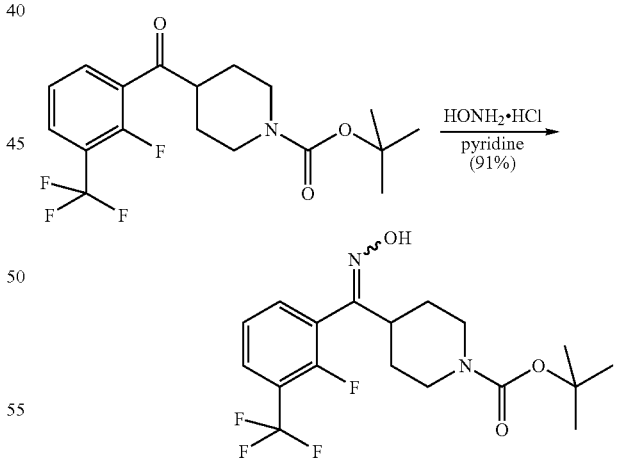

[(2-Fluoro-3-trifluoromethyl-phenyl)-hydroxyimino-methyl]-piperidine-1-carboxylic acid tert-butyl ester (MDL 832163). A mixture of 4-(2-Fluoro-3-trifluromethyl-benzoyl)-piperidine-1-carboxylic acid tert-butyl ester (9.00 g, 24.0 mmol), hydroxylamine hydrochloride (2.00 g, 28.8 mmol) and pyridine (50 mL) was stirred at room temperature under nitrogen overnight. The yellow reaction solution was poured into cold water (500 mL) and the mixture aged at 0° C. for 1 h. The product was collected by filtration, washed with water, and dried under vacuum at 50° C. to afford 9.54 g of a white solid. Trituration of the solid with hot 25% ethyl acetate/heptane afforded 8.50 g (91%) of the desired product as a white solid. Proton NMR showed product to be a 3.8 to 1 mixture of isomers.

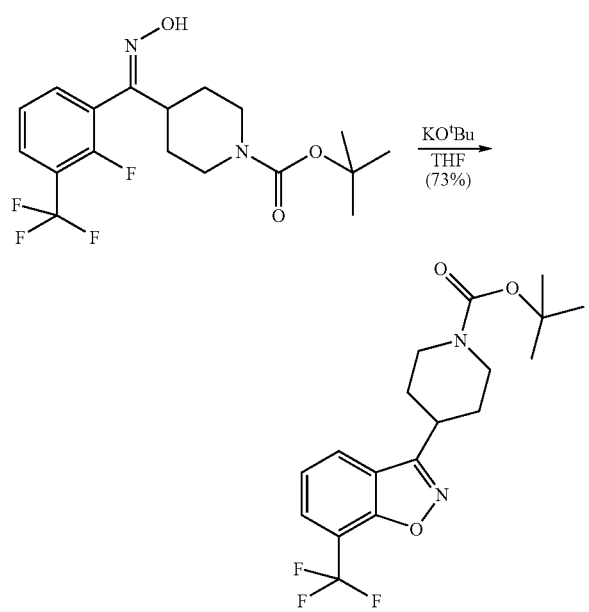

4-(7-Trifluoromethyl-benzo[d]isoxazol-3-yl)-piperidine-1-carboxylic acid tert-butyl ester (MDL 832159). To a room temperature mixture of 4-[(2-fluoro-3-trifluoromethyl-phenyl)-hydroxyimino-methyl]-piperidine-1-carboxylic acid tert-butyl ester (1.40 g, -3.59 mmol) in THF (20 mL) under nitrogen was added potassium tert-butoxide (3.60 mL of a 1 M THF solution, 3.60 mmol) in one portion and the reaction heated at 60° C. for 1.5 h. After standing at room temperature overnight, the solvent was removed and the residue diluted with ethyl acetate (60 mL). The organics were washed with water (30 mL) and brine (30 mL) successively, dried over magnesium sulfate, filtered, and concentrated to give an amber solid. The crude product was chromatographed on silica using 40% ethyl acetate/heptane as eluent to afford 0.97 g (73%) of the desired product as a white solid, mp: 111-113° C.

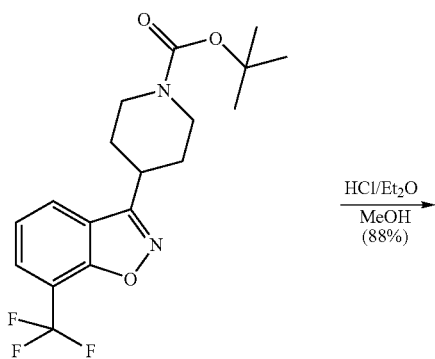

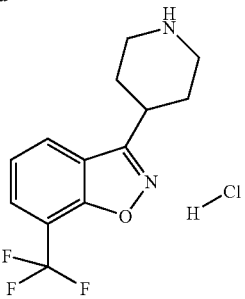

3-Piperidin-4-yl-7-trifluoromethyl-benzo[d]isoxazole (MDL 832106A). A mixture of 4-(7-trifluoromethyl-benzo[d]isoxazol-3-yl)-piperidine-1-carboxylic acid tert-butyl ester (8.00 g, 21.6 mmol), HCl (100 mL of a 1 M ether solution, 100 mmol), and methanol (50 mL) was stirred at room temperature under nitrogen overnight. The reaction was concentrated and the solid triturated with methanol/ether to afford 5.84 g (88%) of the desired product as a white powder, mp: 242-243° C.

Example 42

7-Trifluoromethyl benzo[b]thienyl piperidine

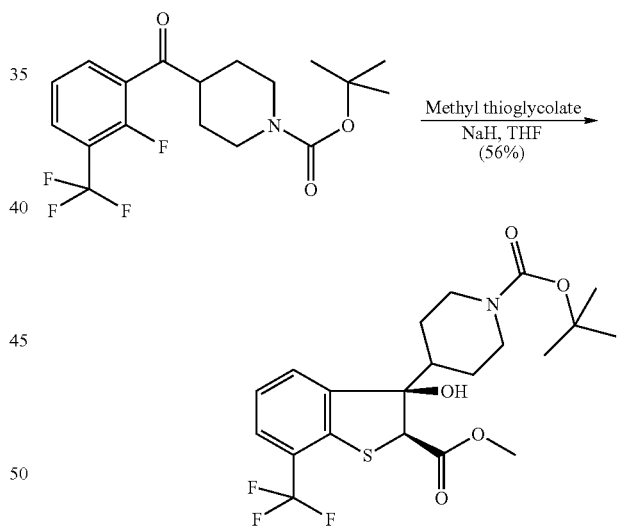

4-(3-Hydroxy-2-methoxycarbonyl-7-trifluoromethyl-2,3-dihydro-benzo[b]thiophen-3-yl)-piperidine-1-carboxylic acid tert-butyl ester (MDL 832712). To a room temperature solution of 4-(2-fluoro-3-trifluromethyl-benzoyl)-piperidine-1-carboxylic acid tert-butyl ester (9.00 g, 24.0 mmol), methyl thioglycolate (2.40 mL, 26.8 mmol), and anhydrous THF (200 mL) under nitrogen was added NaH (1.15 g of a 60% oil dispersion, 28.7 mmol) in one portion. After the gas evolution ceased, the reaction was stirred at 55° C. After 100 min, the reaction was cooled to room temperature and diluted with ethyl acetate (500 mL). The mixture was washed with water (300 mL) and brine (300 mL) successively, dried over magnesium sulfate, filtered, and the solvent removed to

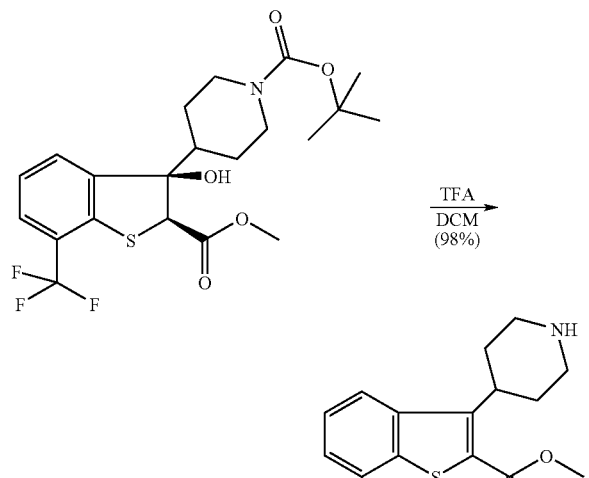

3-Piperidin-4-yl-7-trifluoromethyl-benzo[b]thiophene-2-carboxylic acid methyl ester. To a room temperature solution of 4-(3-hydroxy-2-methoxycarbonyl-7-trifluoromethyl-2,3-dihydro-benzo[b]thiophen-3-yl)-piperidine-1-carboxylic acid tert-butyl ester (6.00 g, 13.0 mmol) in DCM (30 mL) was added TFA (30 mL) causing-rapid gas evolution. After 5 min, the reaction was stirred at 40° C. for 5.5 h. After cooling to room temperature, the reaction was poured into 20% aqueous potassium carbonate (400 mL) and extracted with DCM (2×200 mL). The combined extracts were dried over magnesium sulfate, filtered, and the solvent removed to give a thick oil. After drying under high vacuum 4.37 g (98%) of the desired product was obtained as a white foam.

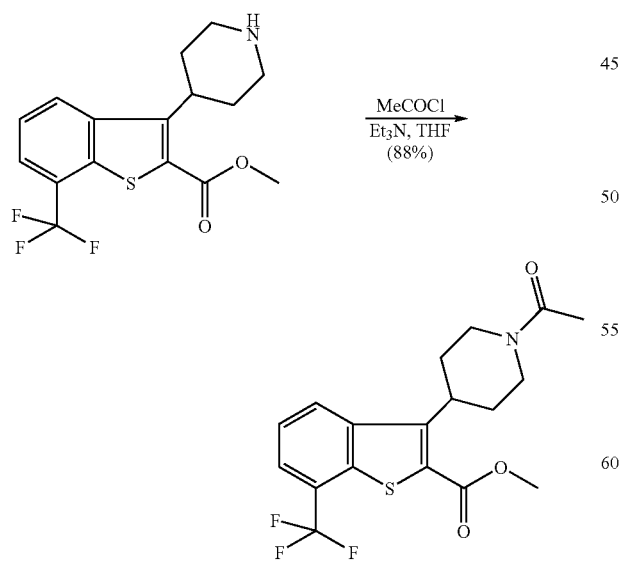

3-(1-Acetyl-piperidin-4-yl)-7-trifluoromethyl-benzo[b]thiophene-2-carboxylic acid methyl ester. To a room temperature solution of 3-piperidin-4-yl-7-trifluoromethyl-benzo[b]thiophene-2-carboxylic acid methyl ester (4.37 g, 12.7 mmol), triethylamine (2.70 mL.19.4 mmol), and anhydrous THF (80 mL) under nitrogen was added acetyl chloride (1.10 mL, 15.5 mmol) in one portion and the reaction stirred at room temperature overnight. The reaction was diluted with ethyl acetate (300 mL) and washed with water (150 mL) and brine (150 mL) successively. The organic layer was dried over magnesium sulfate, filtered, and the solvent removed. The residue was chromatographed on silica, eluting with 10% methanol/ethyl acetate, to afford 4.28 g (88%) of the desired product as a white solid, mp: 155.2° C.

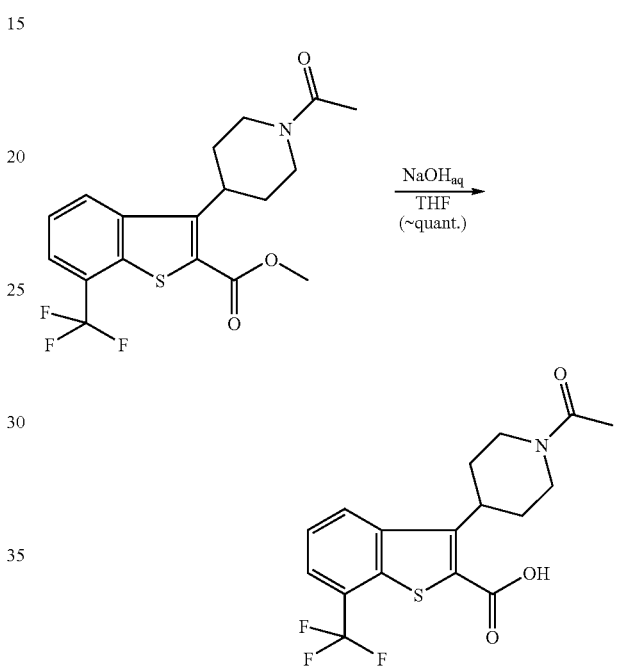

3-(1-Acetyl-piperidin-4-yl)-7-trifluoromethyl-benzo[b]thiophene-2-carboxylic acid. To a solution of 3-(1-acetyl-piperidin-4-yl)-7-trifluoromethyl-benzo[b]thiophene-2-carboxylic acid methyl ester (4.10 g, 10.6 mmol) in THF (25 mL) was added 0.5 N aqueous sodium hydroxide (23.4 mL, 11.7 mmol) and the reaction stirred at room temperature. After 18 h, the reaction was acidified with 1 N HCl (200 mL) and the mixture extracted with DCM (2×100 mL). The organics were washed with water (100 mL), dried over magnesium sulfate, filtered and concentrated to give 4.13 g of the desired product as a white foam.

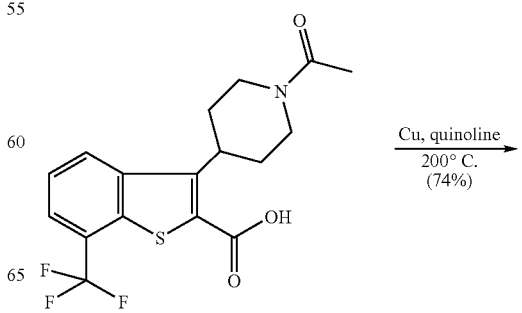

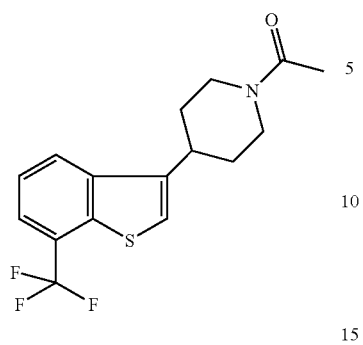

1-[4-(7-Trifluoromethyl-benzo[b]thiophen-3-yl)-piperidin-1-yl]-ethanone (MDL 832823). A mixture of 3-(1-acetyl-piperidin-4-yl)-7-trifluoromethyl-benzo[b]thiophene-2-carboxylic acid (4.13 g, 11.1 mmol), Cu powder (0.706 g, 11.1 mmol), and quinoline (20 mL) was heated to 200° C. under nitrogen. After 10 min, no gas evolution was observed and the reaction cooled at room temperature. The mixture was diluted with ethyl acetate (100 mL), filtered through a Celite bed and the filtrate washed with 1 N HCl (2×100 mL), 5% aqueous potassium carbonate (100 mL), water (100 mL), and brine (100 mL) successively. The organics were dried over magnesium sulfate, filtered, and concentrated to give an amber oil. The oil was chromatographed on silica, eluting with 10% methanovethyl acetate to afford 2.69 g (74%) of the desired product as a tan solid.

4-(7-Trifluoromethyl-benzo[b]thiophen-3-yl)-piperidine. A mixture of 1-[4-(7-trifluoromethyl-benzo[b]thiophen-3-yl)-piperidin-1-yl]-ethanone (2.95 g, 9.01 mmol), concentrated HCl (30 mL), and ethanol was heated at 80° C. for 18 h. After cooling to room temperature, the reaction was basified with 20% aqueous potassium carbonate (150 mL) and the mixture extracted with DCM (2×100 mL). The organics were washed with water (100 mL), dried over potassium carbonate, filtered, and concentrated to give 2.42 g (94%) the desired product as an amber waxy solid.

Example 43

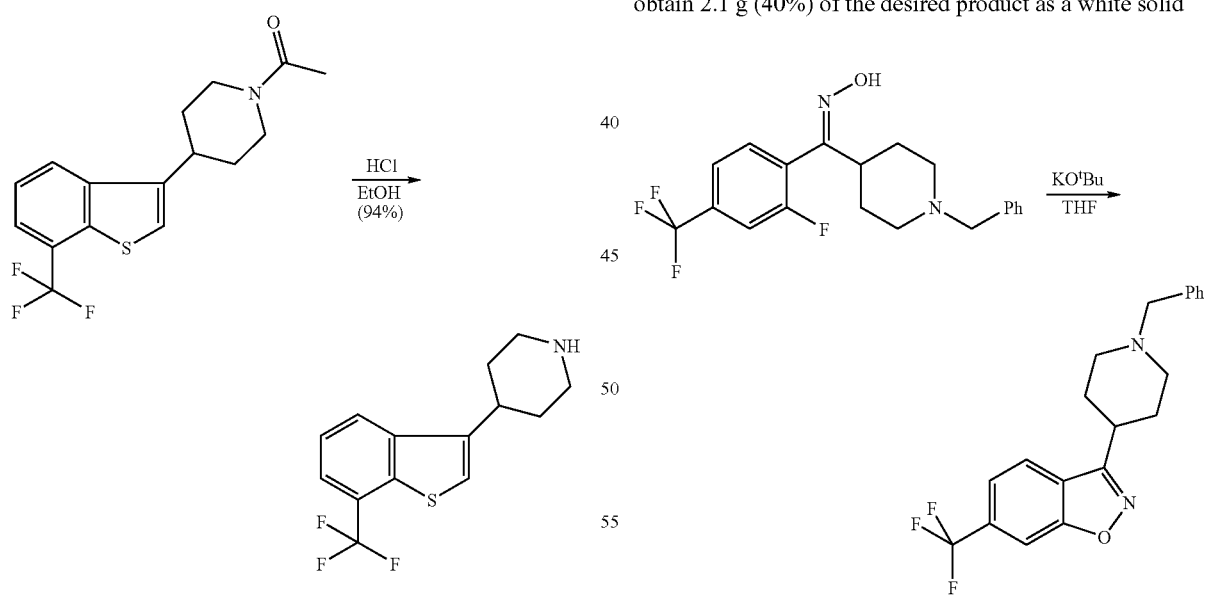

(1-Benzyl-piperidin-4-yl)-(2-fluoro-4-trifluoromethyl-phenyl)-methanone oxime. A mixture of (1-benzyl-piperidin-4-yl)-(2-fluoro-4-trifluoromethyl-phenyl)-methanone (5.0 g, 13.66 mmol), hydroxylamine hydrochloride (1.1 g, 16.39 mmol) and pyridine (50 mL) was stirred at room temperature overnight when the mixture was distilled to remove pyridine (35 mL). The solid residue was washed with heptane then ether. The resulting solid was partitioned between a saturated solution of NaHCO₃ and EtOAc. The organic layer was dried (MgSO₄), filtered and evaporated. The solid residue was washed with 3:1 heptane/EtOAc and dried under vacuum to obtain 2.1 g (40%) of the desired product as a white solid 3-(1-Benzyl-piperidin-4-yl)-64-trifluoromethyl-benzo[b]isoxazole. To a room temperature mixture of (1-benzyl-piperidin-4-yl)-(2-fluoro-4-trifluoromethyl-phenyl)-methanone oxime (2.1 g, 5.51 mmol) in THF (20 mL) under nitrogen was added potassium tert-butoxide (5.78 mL of a 1 M THF solution, 5.78 mmol) in one portion. The resulting solution was stirred at room temperature for 6 hours when the -mixture was partitioned between water (60 mL) and ethyl acetate (60 mL).

The aqueous layer was extracted with EtOAc (60 mL). The combined organic layers were washed with water (30 mL) and brine (30 mL), dried over magnesium sulfate, filtered, and concentrated to give 1.9 g (96%) as the desired product.

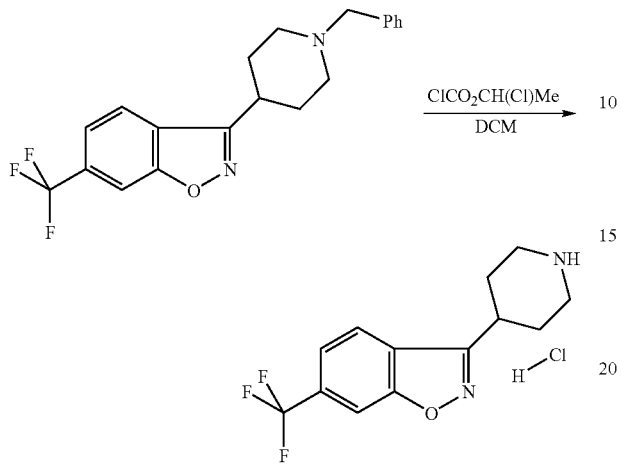

3-Piperidin-4-yl-6-trifluoromethyl-benzo[d]isoxazole hydrochloride. To the 3-(1-Benzyl-piperidin-4-yl)-6-trifluoromethyl-benzo[b]isoxazole (1.9 g, 5.27 mmol) in DCM (26 mL) was added 1-chloroethyl chloroformate (0.69 mL, 6.33 mmol). The resulting solution was stirred at room temperature overnight when the volatiles were removed in vacuo. The residue was taken un in methanol (25 mL) and the resulting solution was heated at reflux for 1 hour. The mixture was cooled to room temperature and the solution was evaporated. The residue was taken up in EtOAc and the solid product was collected by filtration yielding 1.2 g (74%) of the HCl salt as a white solid.

Example 44

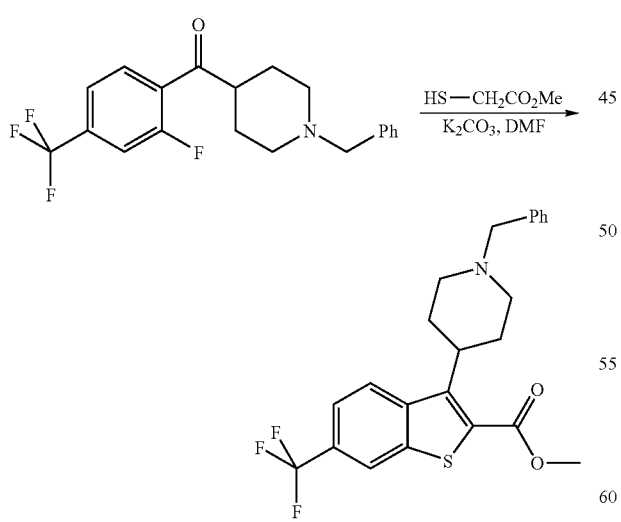

3-(1-Benzyl-piperidin-4-yl)-6-trifluoromethyl-benzo[b]thiophene-2-carboxylic acid methyl ester (MDL 833803). To a room temperature solution of (1-benzyl-piperidin-4-yl)-(2-fluoro-4-trifluoromethyl-phenyl)-methanone (7.5 g, 20.5 mmol), methyl thioglycolate (2.0 mL, 22.5 mmol), and DMF (100 mL) was added $K_2CO_3$ (5.65 g, 41.0 mmol). The reaction was stirred at 60° C. for 24 hours, cooled to room temperature and diluted with ethyl acetate (500 mL). The mixture was washed with water (2×300 mL) and brine (300 mL) successively, dried over magnesium sulfate, filtered, and the solvent removed to afford an oil. The oil was purified via chromatography (30% EtOAc in heptane) yielding 5.91 g (67%) as a solid.

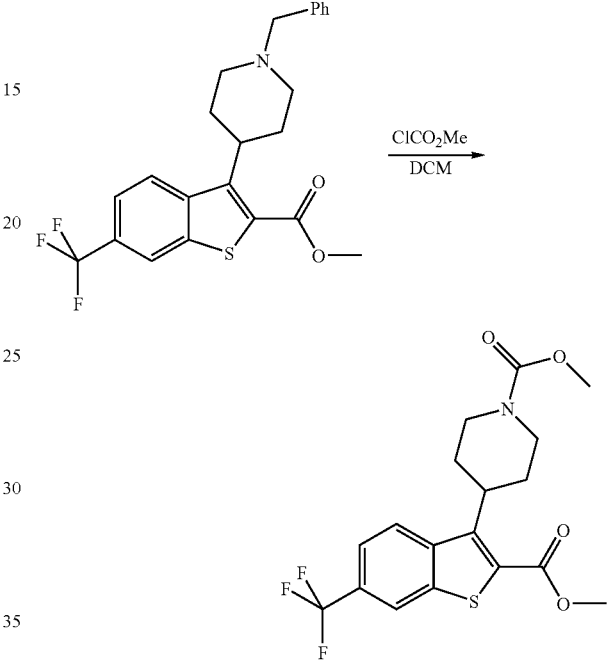

4-(2-Methoxycarbonyl-6-trifluoromethyl-benzo[b]thiophen-3-yl)-piperidine-1-carboxylic acid methyl ester. To a solution of 3-(1-benzyl-piperidin-4-yl)-6-trifluoromethyl-benzo[b]thiophene-2-carboxylic acid methyl ester (5.9 g, 13.6 mmol) in DCM (50 mL) was added methyl chloroformate (1.26 mL, 16.3 mmol) drop-wise. The resulting solution was stirred overnight when the volatiles were removed in vacuo. The residue was washed with heptane to yield 4.2 g (77%) of the desired product as a white solid.

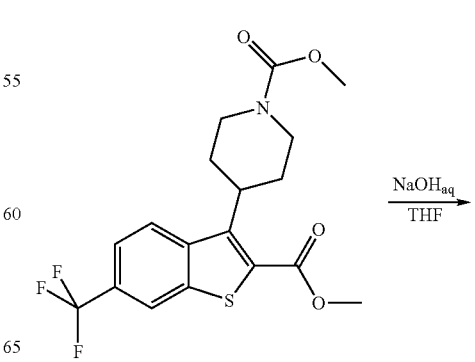

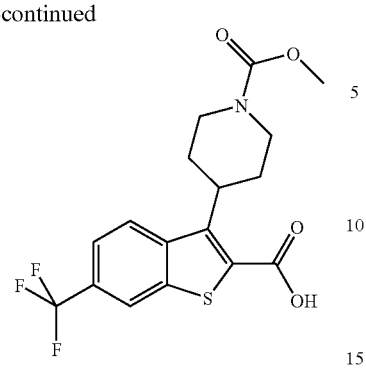

4-(2-Carboxy-6-trifluoromethyl-benzo[b]thiophen-3-yl)-piperidine-1-carboxylic acid methyl ester. To a stirred solution of 4-(2-Methoxycarbonyl-6-trifluoromethyl-benzo[b]thiophen-3-yl)-piperidine-1-carboxylic acid methyl ester (1.1 g, 2.7 mmol) in THF (7.0 mL) was added 1 N NaOH (2.97 mL). The resulting mixture was stirred at room temperature overnight when the mixture was diluted with water (50 mL) and washed with ether (100 mL). The aqueous layer was acidified with the addition of 3 N HCl and the product was extracted with EtOAc (2×150 mL). The combined organic layers were washed with brine (50 mL), dried (MgSO$_4$), filtered and evaporated yielding 960 mg (92%) of the desired product as a white solid.

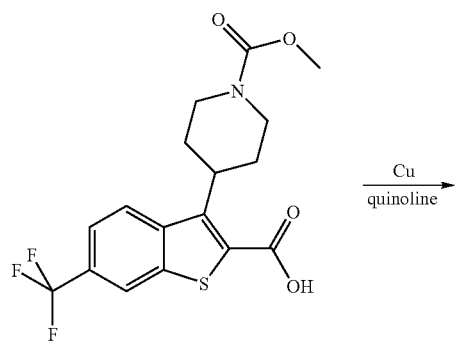

4-(6-Trifluoromethyl-benzo[b]thiophen-3-yl)-piperidine-1-carboxylic acid methyl ester. A mixture of 4-(2-carboxy-6-trifluoromethyl-benzo[b]thiophen-3-yl)-piperidine-1-carboxylic acid methyl ester (4.3 g, 11.1 mmol) and copper (705 mg, 11.1 mmol) in quinoline (28 mL) was heated at 200° C. for 45 minutes. Upon cooling to room temperature the mixture was diluted with EtOAc (50 mL) and filtered. The filtrate was washed with 5% HCl (2×20 mL), water (20 mL) and brine (20 mL), dried (MgSO$_4$), filtered and evaporated. The residue was separated via chromatography (30% EtOAc in heptane) yielding 3.14 g (82%) of the desired product as a white solid.

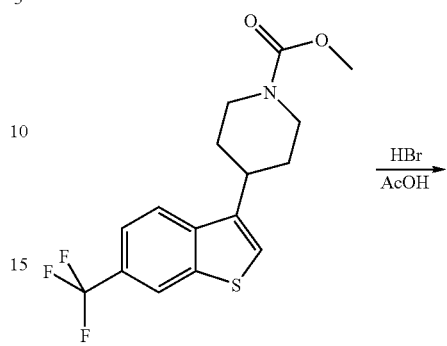

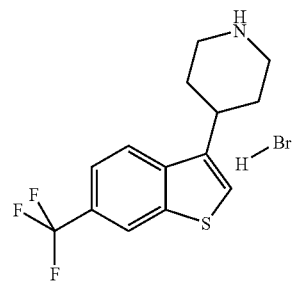

4-(6-Trifluoromethyl-benzo[b]thiophen-3-yl)-piperidine hydrobromide. A mixture of 4-(6-trifluoromethyl-benzo[b]thiophen-3-yl)-piperidine-1-carboxylic acid methyl ester (3.1 g, 9.0 mmol) in HBr (45 mL, 30% in acetic acid) was stirred at room temperature for 20 hours wher the volatiles were removed in vacuo. The residue was washed with EtOAc and the product was collected by filtration yielding 3.09 g (94%) of the desired product as a white solid.

Example 45

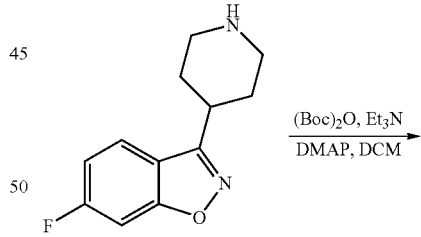

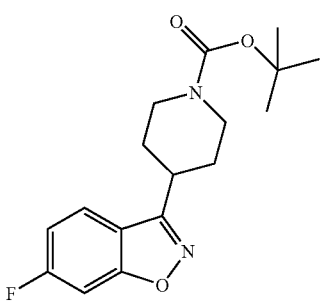

4-(6-Fluoro-benzo[d]isoxazol-3-yl)-piperidine-1-carboxylic acid tert-butyl ester (MDL 811778). To a stirred suspension of 4-(6-fluoro-benzo[d]isoxazol-3-yl)-piperidine (1.00 g, 454 mmol) in dry dichloromethane (10.0 mL) was added triethylamine (0.95 mL, 6.82 mmoles), 4-dimethylaminopyridine (55 mg, 0.454 mmoles) and di-tert-butyl dicarbonate (1.98 g, 9.09 mmoles). Gas spontaneously evolved for several minutes upon the addition of di-tert-butyl dicarbonate. The resulting solution was stirred at room temperature for 1 hour when the solution was diluted with $CH_2Cl_2$ (50 mL) and washed with water (10 mL), 10% $HCl_{aq}$ (10 mL), water (10 mL), saturated $NaHCO_3$ (10 mL), water (10 mL) and brine (10 mL) and dried ($MgSO_4$), filtered and evaporated. The residue was recrystallized from diethyl ether yielding 1.31 g (90%) as a white, crystalline solid, mp 117-188° C. Analysis calculated for $C_{17}H_{21}N_2FO_3$: 63.74%C, 6.61%H, 8.74%N. Found: 63.66%C, 6.64%H, 8.73%N.

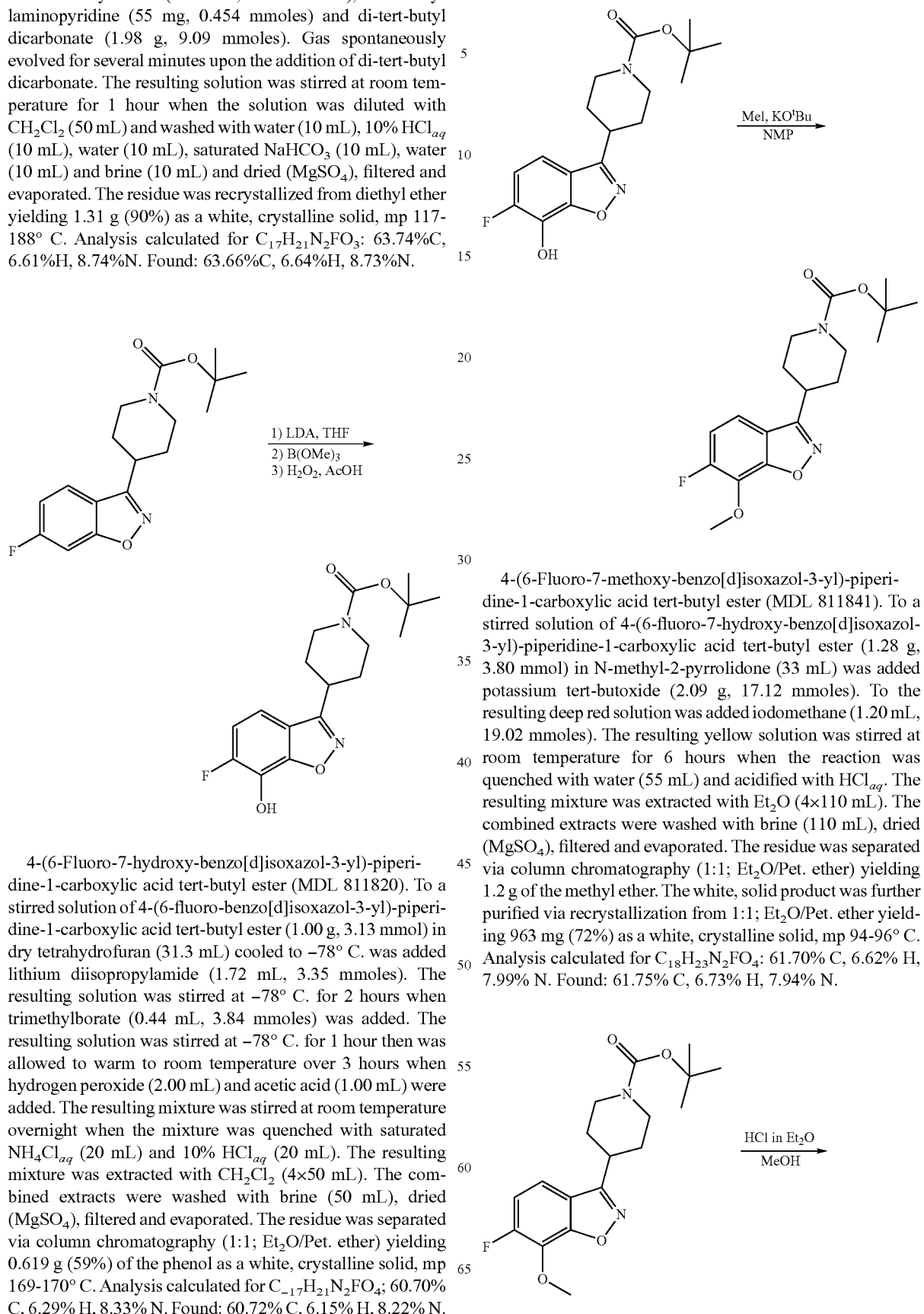

4-(6-Fluoro-7-hydroxy-benzo[d]isoxazol-3-yl)-piperidine-1-carboxylic acid tert-butyl ester (MDL 811820). To a stirred solution of 4-(6-fluoro-benzo[d]isoxazol-3-yl)-piperidine-1-carboxylic acid tert-butyl ester (1.00 g, 3.13 mmol) in dry tetrahydrofuran (31.3 mL) cooled to −78° C. was added lithium diisopropylamide (1.72 mL, 3.35 mmoles). The resulting solution was stirred at −78° C. for 2 hours when trimethylborate (0.44 mL, 3.84 mmoles) was added. The resulting solution was stirred at −78° C. for 1 hour then was allowed to warm to room temperature over 3 hours when hydrogen peroxide (2.00 mL) and acetic acid (1.00 mL) were added. The resulting mixture was stirred at room temperature overnight when the mixture was quenched with saturated $NH_4Cl_{aq}$ (20 mL) and 10% $HCl_{aq}$ (20 mL). The resulting mixture was extracted with $CH_2Cl_2$ (4×50 mL). The combined extracts were washed with brine (50 mL), dried ($MgSO_4$), filtered and evaporated. The residue was separated via column chromatography (1:1; $Et_2O$/Pet. ether) yielding 0.619 g (59%) of the phenol as a white, crystalline solid, mp 169-170° C. Analysis calculated for $C_{-17}H_{21}N_2FO_4$; 60.70% C, 6.29% H, 8.33% N. Found: 60.72% C, 6.15% H, 8.22% N.

4-(6-Fluoro-7-methoxy-benzo[d]isoxazol-3-yl)-piperidine-1-carboxylic acid tert-butyl ester (MDL 811841). To a stirred solution of 4-(6-fluoro-7-hydroxy-benzo[d]isoxazol-3-yl)-piperidine-1-carboxylic acid tert-butyl ester (1.28 g, 3.80 mmol) in N-methyl-2-pyrrolidone (33 mL) was added potassium tert-butoxide (2.09 g, 17.12 mmoles). To the resulting deep red solution was added iodomethane (1.20 mL, 19.02 mmoles). The resulting yellow solution was stirred at room temperature for 6 hours when the reaction was quenched with water (55 mL) and acidified with $HCl_{aq}$. The resulting mixture was extracted with $Et_2O$ (4×110 mL). The combined extracts were washed with brine (110 mL), dried ($MgSO_4$), filtered and evaporated. The residue was separated via column chromatography (1:1; $Et_2O$/Pet. ether) yielding 1.2 g of the methyl ether. The white, solid product was further purified via recrystallization from 1:1; $Et_2O$/Pet. ether yielding 963 mg (72%) as a white, crystalline solid, mp 94-96° C. Analysis calculated for $C_{18}H_{23}N_2FO_4$: 61.70% C, 6.62% H, 7.99% N. Found: 61.75% C, 6.73% H, 7.94% N.

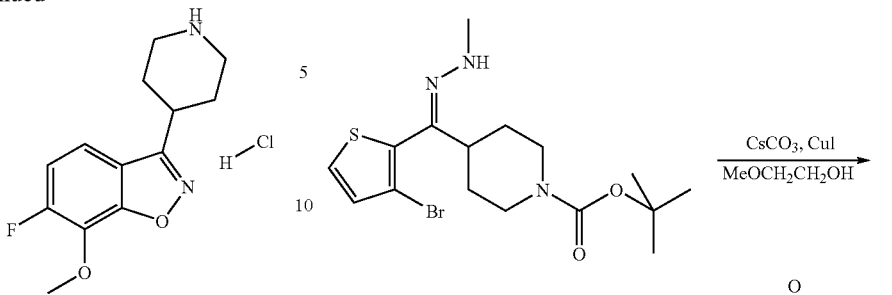

6-Fluoro-7-methoxy-3-piperidin-4-yl-benzo[d]isoxazole hydrochloride (MDL 811998). To a stirred solution of 4-(6-fluoro-7-methoxy-benzo[d]isoxazol-3-yl)-piperidine-1-carboxylic acid tert-butyl ester (4.00 g, 11.43 mmol) in dry hydrochloric acid in diethyl ether (100 mL) was added methanol (7.62 mL). The resulting solution was stirred at room temperature for 5 hours when a white solid precipitate formed. The resulting suspension was filtered and the white solid was wash thoroughly with ether yielding 1.76 g of the desired product as a white solid. The mother liquor precipitated yielding an additional 0.94 g of product providing a total of 2.70 g (83%) of the desired product as a pure, white solid, mp 246-248° C.

Example 46

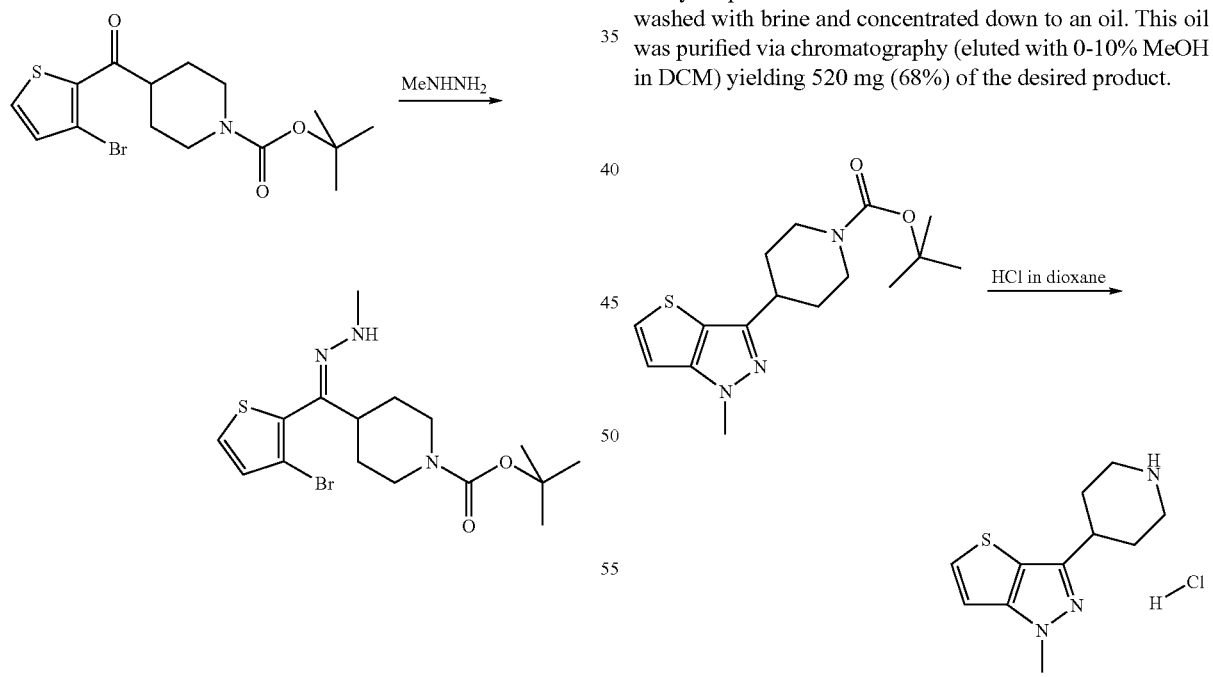

4-[(3-Bromo-thiophen-2-yl)-(methyl-hydrazono)-methyl]-piperidine-1-carboxylic acid tert-butyl ester. A mixture of 4-(thiophene-2-carbonyl)-piperidine-1-carboxylic acid tert-butyl ester (1.96 g, 5.2 mmol) in methylhydrazine (2 mL) was heated at 75° C. overnight. The excess methyl hydrazine was then removed with a vacuum pump. The residue was purified by chromatography (eluted with 0-8% of MeOH in DCM) yielding 0.95 g (45%) of the desired product.

4-(1-Methyl-1H-thieno[3,2-c]pyrazol-3-yl)-piperidine-1-carboxylic acid tert-butyl ester. 4-[(3-Bromo-thiophen-2-yl)-(methyl-hydrazono)-methyl]-piperidine-1-carboxylic acid tert-butyl ester (700 mg, 1.74 mmol) was mixed with CuI (20 mg), CsCO₃ (650 mg, 1.15 eq) in methoxyethanol (10 mL). The mixture was heated to 70 ° C. for 2 hr. then stirred overnight at room temperature. The solvent was stripped on rotary evaporator. The residue was extracted into EtOAc then washed with brine and concentrated down to an oil. This oil was purified via chromatography (eluted with 0-10% MeOH in DCM) yielding 520 mg (68%) of the desired product.

1-Methyl-3-piperidin-4-yl-1H-thieno[3,2-c]pyrazole hydrochloride (A002436287A). 4-(1-Methyl-1H-thieno[3,2-c]pyrazol-3-yl)-piperidine-1-carboxylic acid tert-butyl ester (520 mg, 1.6 mmol) was stirred at room temperature in a solution of HCl (5 mL, 4N HCl in dioxane) for 4 hours. The volatiles were removed in vacuo and the residue was triturated with ether (twice) to yield off white solids 304 mg (74%) as the desired hydrochloride salt.

Example 47

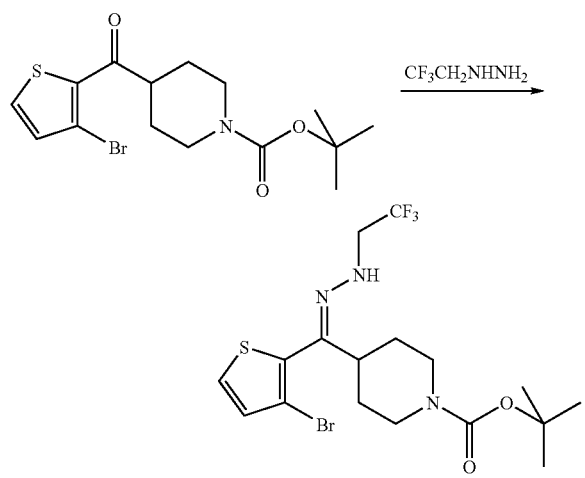

4-{(3-Bromo-thiophen-2-yl)-[(2,2,2-trifluoro-ethyl)-hydrazono]-methyl}-piperidine-1-carboxylic acid tert-butyl ester. To a mixture of 4-(thiophene-2-carbonyl)-piperidine-1-carboxylic acid tert-butyl ester (2.34 g, 6.24 mmol) in n-butanol (20 mL) was added trifluoroethylhydrazine (2.43 g, 12.4 mmol). The resulting mixture was heated at 110° C. overnight. The volatiles were then removed in vacuo. The residue was purified by chromatography (eluted with 0-10% MeOH in DCM) yielding 2.41 g (92%) of the desired product.

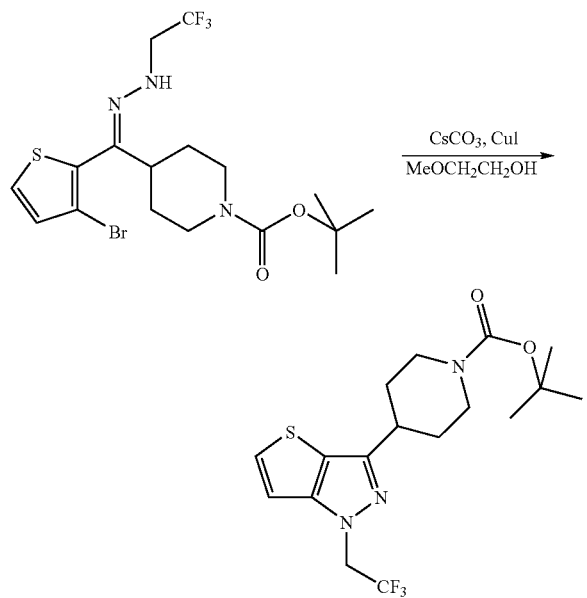

4-[1-(2,2,2-Trifluoro-ethyl)-1H-thieno[3,2-c]pyrazol-3-yl]-piperidine-1-carboxylic acid tert-butyl ester. 4-{(3-Bromo-thiophen-2-yl)-[(2,2,2-trifluoro-ethyl)-hydrazono]-methyl}-piperidine-1-carboxylic acid tert-butyl ester (2.34 g, 4.98 mmol) was mixed with CuI (50 mg), CsCO$_3$ (1.9 g, 1.2 eq) in methoxyethanol (25 mL). The mixture was heated to 75° C. for 1 hour. The mixture was then diluted with EtOAc and filtered. The filtrate was evaporated and the residue was purified via chromatography (eluted with 0-10% MeOH in DCM) yielding 2.03 g (>95%) of the desired product.

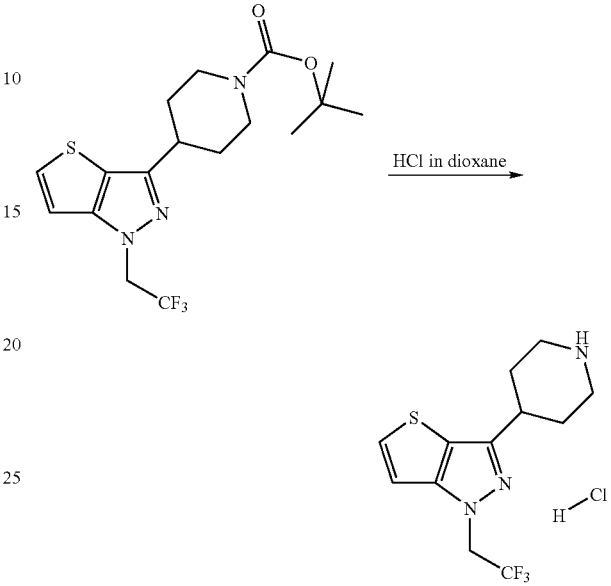

3-Piperidin-4-yl-1-(2,2,2-trifluoro-ethyl)-1H-thieno[3,2-c]pyrazole hydrochloride (833906). 4-[1-(2,2,2-Trifluoro-ethyl)-1H-thieno[3,2-c]pyrazol-3-yl]-piperidine-1-carboxylic acid tert-butyl ester (1.9 g, 4.87 mmol) was stirred at room temperature in a solution of HCl (6 mL, 4N HCl in dioxane) for 4 hours. The volatiles were removed in vacuo and the residue was triturated with ether (twice) to yield off white solids 2.1 g (74%) as the desired hydrochloride salt.

Example 48

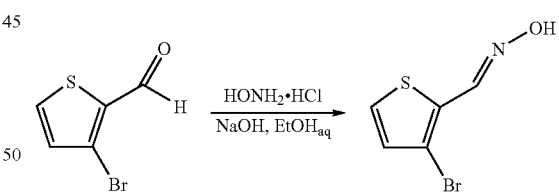

3-Bromo-thiophene-2-carbaldehyde oxime. 3-Bromothiophene-2-carbaldehyde (28.7 g, 0.15 mol) in ethanol (50 mL) was added in one portion to a solution of hydroxylamine hydrochloride (13.8 g, 0.2 mol), sodium hydroxide (8 g, 0.2 mol) in water (30 mL) and ethanol (100 mL). The mixture was stirred at 0° C. for 2 hours and was kept at 0° C. overnight when a precipitate formed. The mixture was diluted with cold water (600 ml) and the solid was collected by filtration yielding 20.5 g, (67%). The aqueous solution was further extracted with ethyl acetate. The organic solution was washed with brine, dried with magnesium sulfate, filtered and evaporated yielding 6.9 g of additional product as a light yellow solid. The total yield was 27.4 g (89%).

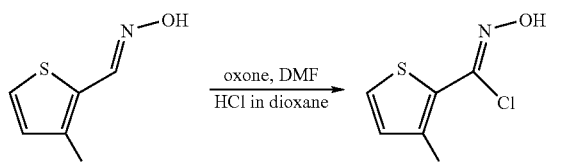

3-Bromo-thiophene-2-(chloro-carbaldehyde) oxime. To the solution of 3-bromo-thiophene-2-carbaldehyde oxime (10.8 g, 52.4 mmol), hydrogen chloride (14.5 mL, 4M in dioxane) in DMF (100 mL) was charged with oxone (16.9 g, 1.05 eqiv) in one portion at room temperature. The mixture was stirred at room temp overnight when the solution was poured in to water and extracted with ethyl acetate. The organic solution was washed with brine and dried over magnesium sulfate, filtered and evaporated to dryness to give a yellow solid (12.68 g, quantitative by weight) which was used in the next reaction without further purification.

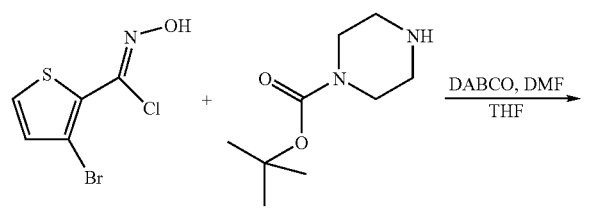

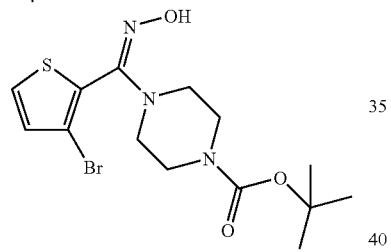

4-[(3-Bromo-thiophen-2-yl)-hydroxyimino-methyl]-piperazine)-1-carboxylic acid tert-butyl ester. A solution of 3-bromo-thiophene-2-(chloro-carbaldehyde) oxime (16.4 g, 68 mmol) in THF (70 mL) was added drop-wise to a solution of N-(t-butoxycarbonyl)piperazine (14 g, 1.1 equiv.), DABCO (9.5 g, 1.25 eqiv.) in DMF (100 mL) at 0° C. over 25 minutes. The mixture was stirred at 0° C. for 3.5 hours when the mixture was poured into water and was extracted with ethyl acetate. The organic layer was washed with brine and dried over magnesium sulfate, filtered and evaporated. The crude product (30.5 g) was purified via chromatography (eluted with 0-5% of MeOH in DCM) yielding 24.6 g (85%) of the desired product.

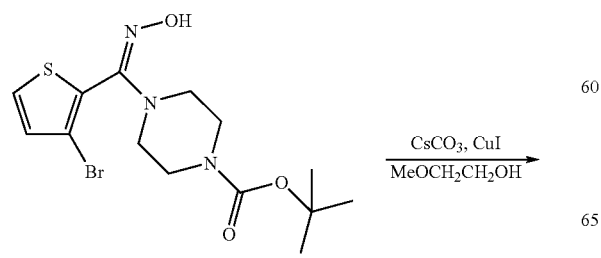

-continued

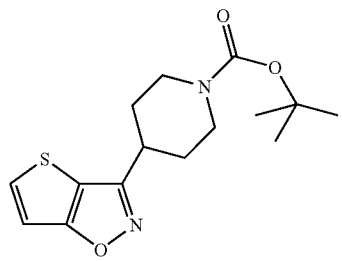

4-Thieno[2,3-d]isoxazol-3-yl-piperazine-1-carboxylic acid tert-butyl ester. A mixture of 4-[(3-bromo-thiophen-2-yl)-hydroxyimino-methyl]-piperazine)-1-carboxylic acid tert-butyl ester (10.3 g, 26.4 mmol), cesium carbonate (10.7 g, 32.7 mmol), copper iodide (500 mg) in methoxyethanol (200 mL) was stirred at room temperature overnight. The reaction mixture was diluted with ethyl acetate and washed with water. The aqueous solution was extracted three times with ethyl acetate. The combined organic layers (total 600 ml) were washed with brine, dried over magnesium sulfate, filtered and evaporated. The residue was purified via chromatography (120 gm of silica gel, eluted with 0-8% Methanol in dichloromethane) yielding 5.1 g (62%) of the desired product as light oil.

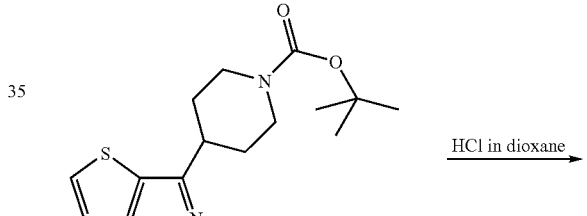

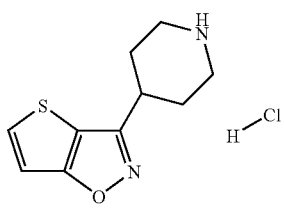

3-Piperazin-1-yl-thieno[2,3-d]isoxazole. 4-Thieno[2,3-d]isoxazol-3-yl-piperazine-1-carboxylic acid tert-butyl ester (5.0 g, 16.2 mmol) was stirred at room temperature in a solution of HCl (25 mL, 4N HCl in dioxane) for 4 hours. The volatiles were removed in vacuo and the residue was tritu-

Example 49

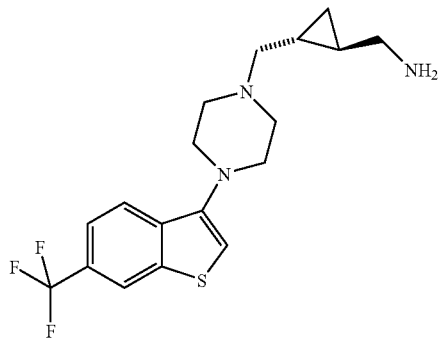

+

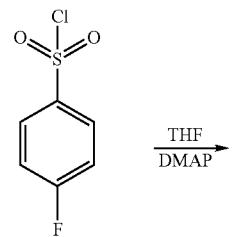

THF
DMAP
→

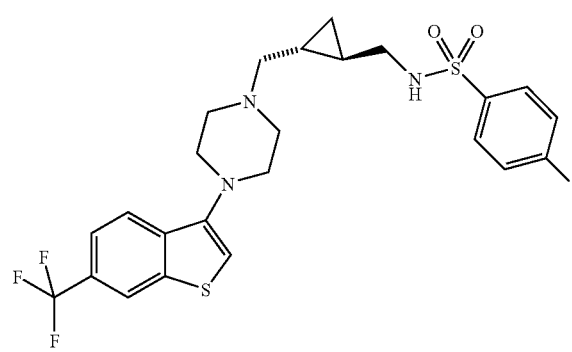

4-Fluoro-N-{2R-[4-(6-trifluoromethyl-benzo[b]thiophen-3-yl)-piperazin-1-ylmenthyl]-1R-cyclopropylmethyl}-benzenesulfonamide (MDL 831495). To a stirred solution of C-{(1R,2R )-2-[4-(6-Trifluoromethyl-benzo[b]thiophen-3-yl)-piperazin-1-ylmethyl]-cyclopropyl}methylamine (100 mg, 0.27 mmol) and DMAP (3 mg, 0.03 mmol) in THF (1.35 mL) was added 4-fluorobenzenesulfonyl chloride (53 mg, 0.27 mmol). The resulting solution was stirred at room temperature for 3 hours when the mixture was evaporated. The residue was separated via chromatography (gradient elution 5% to 30% MeOH in EtOAc) yielding 93 mg (65%) the desired product.

Example 50

Synthesis of (3-Imidazol-1-yl-propyl)-{(1R,2R)-2-[4-(6-trifluoromethyl-benzo[b]thiophen-3-yl)-piperazin-1-ylmethyl]-cyclopropylmethyl}-amine

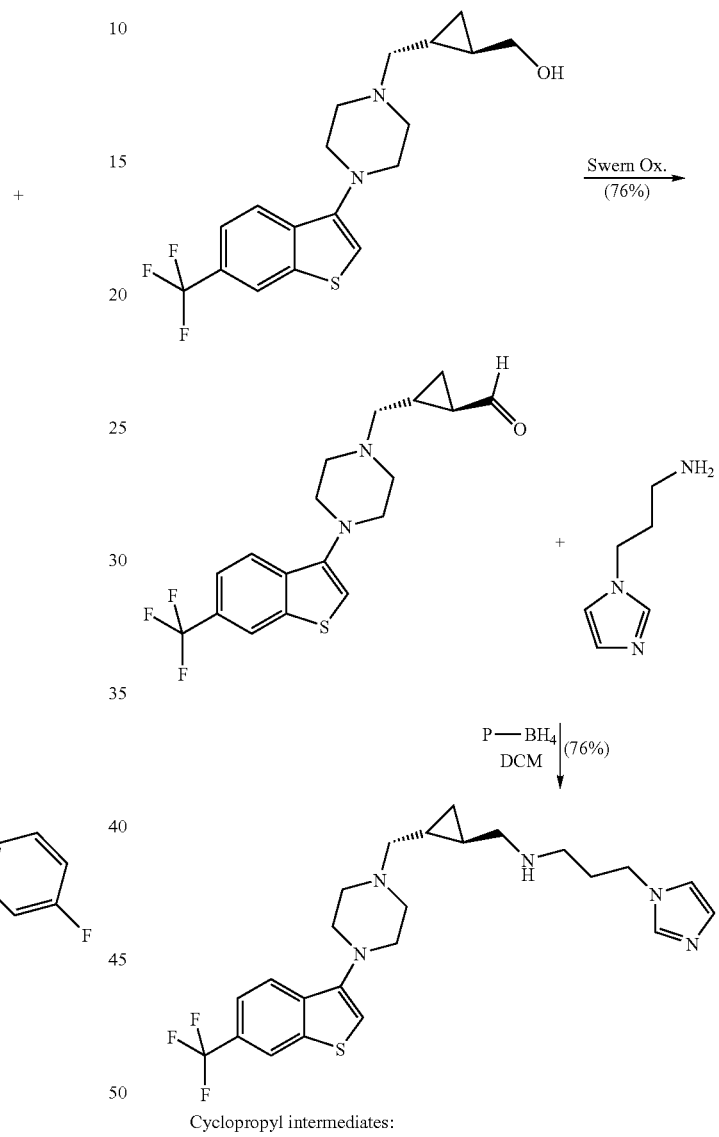

Cyclopropyl intermediates:

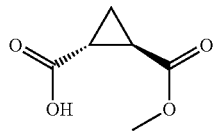

trans-Cyclopropane-1,2-dicarboxylic acid monomethyl ester

Suspend trans-cyclopropane-1,2-dicarboxylic acid dimethylester (59.8 g, 0.378 mol) is suspended in 1.0N phosphate buffer (1.5 L, pH=7) add pig liver esterase (2.25 mL, 7500 units), and monitor NaOH consumption with a pH meter to control the reaction. After 3 h the consumption of 189 mL of 2N NaOH indicates the complete hydrolysis of the diester to the monomethylester. Acidified the clear solution by the addition of 5N HCl to a pH=1. Separate the enzyme by addition of dichloromethane (500 mL) and diatomaceous earth (25 g). Stir for 5 min, and then filter the mixture. Saturate the filtrate with NaCl, and extract with ethyl acetate (5 times). Combine the extracts, dry (Na$_2$SO$_4$) and evaporate to obtain 50.8 g (93%) of solid, mp 46-47° C., m/z=145 (M+H)$^+$ (S,S)-(+)-Cyclopropane-1,2-dicarboxylic acid monomethyl ester Add trans-cyclopropane-1,2-dicarboxylic acid monomethyl ester, Example 3a, (19.46 g) in acetone to quinine (43.8 g) in one portion. Heat the reaction to reflux, and then add methylcyclohexane (150 mL). After crystallization (5 times) from acetone/methylcyclohexane, collect 6.2 g of the diastereomeric salt ($\alpha_D$: +173, c: 7.3 CHCl$_3$)

(R,R)-(−)-Cyclopropane-1,2-dicarboxylic acid monomethyl ester

Concentrate the filtrate from 3b above and treat the residue with 1N KHSO$_4$ solution to yield 12.0 g of the crude (R,R) enatiomer. Dissolve this material in acetone and add 1 equivalent of quinidine in one portion. Heat the reaction to reflux, and then add methylcyclohexane. After crystallization overnight, collect 10.3 g of the diastereomeric salt ($\alpha_D$: −235, c: 8.5 CHCl$_3$)

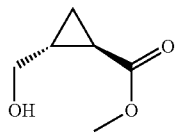

4a: trans-2-Hydroxymethyl-cyclopropanecarboxylic acid methyl ester

Add borane-methyl sulfide complex (177 mL, 0.354 mol), slowly, by means of a dropping funnel, to a stirring solution of trans-cyclopropane-1,2-dicarboxylic acid monomethyl, ester (Example 3a) (25.5 g, 0.177 mol), trimethyl borate (60.3 mL, 0.531 mol) and tetrahydrofuran (150 mL) at 0° C. After complete addition, allow the reaction to come to ambient temperature and stir for 2 h more. Pour the reaction mixture into a stirring solution of 50% aqueous sodium chloride solution (1.5 L)-concentrated HCl (10 mL). Extract the mixture with ethyl acetate (EtOAc) (3 times), combine the extracts, dry (Na$_2$SO$_4$) and concentrate the solvent to obtain a colorless oil: 22.6 g.

(S,S)-(+)-2-Hydroxymethyl-cyclopropanecarboxylic acid methyl ester

Follow the procedure of Example 4a, and substitute (S,S)-(+)-cyclopropane-1,2-dicarboxylic acid monomethyl ester (Example 3b) therein to obtain the title compound, $\alpha_D$: +54, c: 1.5 CHCl$_3$ (Tetrahedron Asymmetry Vol. 6, No. 3, pp. 683-684, 1995)

(R,R)-(−)-2-Hydroxymethyl-cyclopropanecarboxylic acid methyl ester

Follow the procedure of Example 4a, and substitute (R,R)-(−)-cyclopropane-1,2-dicarboxylic acid monomethyl ester (Example 3c) therein to obtain the title compound ($\alpha_D$: −78.6, c: 4.3 CHCl$_3$)

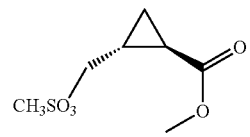

trans-2-Methanesulfonyloxymethyl-cyclopropanecarboxylic acid methyl ester

Add, dropwise, triethylamine (7.74 mL, 56 mmol) and 4-dimethylaminopyridine (0.013 g, 0.106 mmol) in dichloromethane (30 mL) to a stirred solution of trans-2-hydroxymethyl-cyclopropanecarboxylic acid methyl ester (Example 4a) (2.4 g, 18.64 mmol), at 0-5° C. After 0.5 h, pour the reaction mixture into water and extract the mixture with dichloromethane (3 times). Wash the combined extracts with 1N KHSO$_4$, dry (Na$_2$SO$_4$) and concentrate to yield 4.29 g of a pale yellow oil, which solidifies when stored at 0° C., m/z=209 (M+H)$^+$ (S,S)-(+)-2-Methanesulfonyloxymethyl-cyclopropanecarboxylic acid methyl ester Follow the procedure of Example 5a, and substitute (S,S)-(+)-2-hydroxymethyl-cyclopropanecarboxylic acid methyl ester (Example 4b) therein to obtain the title compound ($\alpha_D$: +75, c: 4.7 CHCl$_3$)

(R,R)-(−)-2-Methanesulfonyloxymethyl-cyclopropanecarboxylic acid methyl ester

Follow the procedure of Example 5a, and substitute (R,R)-(−)-2-hydroxymethyl-cyclopropanecarboxylic acid methyl ester (Example 4c) therein to obtain the title compound ($\alpha_D$: −74.4, c: 5.9 CHCl$_3$).

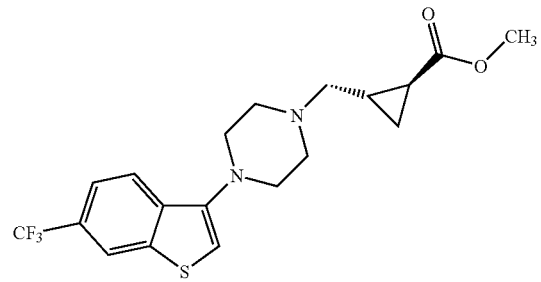

trans-2-[4-(6-Trifluoromethyl-benzo[b]thiophen-3-yl)-piperazin-1-ylmethyl]-cyclopropanecarboxylic acid methyl ester Heat at reflux for 16 h, a mixture of 1-(6-trifluoromethyl-benzo[b]thiophen-3-yl)-piperazine, free base of Example 2b, (23.0 g, 71.3 mmol), trans-2-methanesulfonyloxymethyl-cyclopropanecarboxylic acid methyl ester (Example 5a) (15.3 g, 73.5 mmol), and triethylamine (40 mL, 288 mmol) in acetonitrile (600 mL). Concentrate the reaction mixture under reduced pressure and dilute the resultant oil with EtOAc (30 mL). Filter the resulting precipitate (unreacted starting piperazine) away and purify the filtrate by column chromatography over silica gel (EtOAc/heptane/MeOH/triethylamine, 20:20:1). Concentration of the appropriate fractions gives 18.0 g of colorless oil, m/z=413 (M+H)$^+$.

(S,S)-(+)-2-[4-(6-Trifluoromethyl-benzo[b]thiophen-3-yl)-piperazin-1-ylmethyl]-cyclopropanecarboxylic acid methyl ester Follow the procedure of Example 6a, and substitute (S,S)-(+)-2-methanesulfonyloxymethyl-cyclopropanecarboxylic acid methyl ester (Example 5b) therein to obtain the title compound ($\alpha_D$: +48, c: 2.8 EtOH).

(R,R)-(-)-2-[4-(6-Trifluoromethyl-benzo[b]thiophen-3-yl)-piperazin-1-ylmethyl]-cyclopropanecarboxylic acid methyl ester Follow the procedure of Example 5, and substitute (R,R)-(-)-2-methanesulfonyloxymethyl-cyclopropanecarboxylic acid methyl ester, Example 5c, therein, to obtain the title compound ($\alpha_D$: -49.3, c: 3.5 CHCl$_3$).

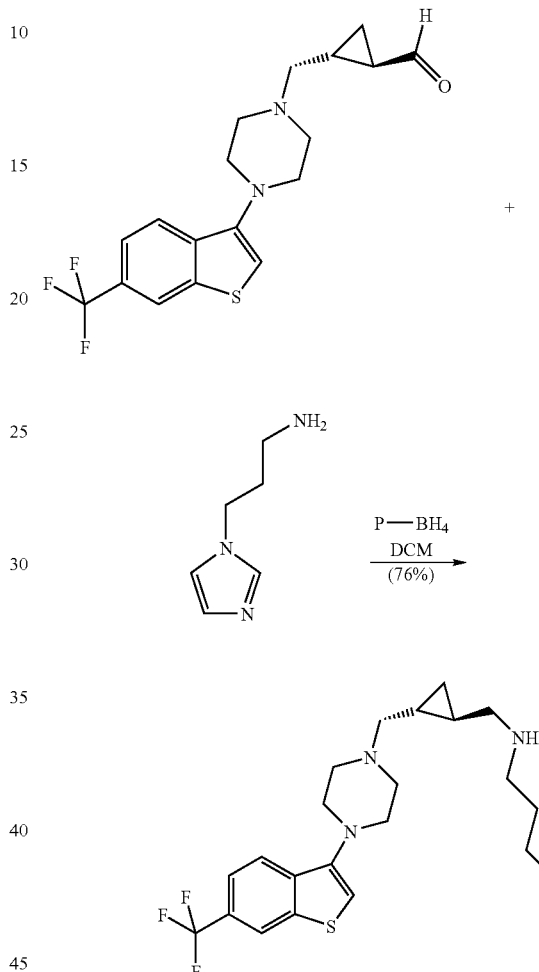

(1R,2R)-2-[4-(6-Trifluoromethyl-benzo[b]thiophen-3-yl)-piperazin-1-ylmethyl]-cyclopropanecarbaldehyde. A solution of oxalyl chloride (62 μl, 0.72 mmol) in anhydrous methylene chloride (10 ml) under N$_2$ was cooled to -78° C. while stirring. Dimethy sulfoxide (104 μl, 1.44 mmol) was then added followed by a solution of {(1R,2R)-2-[4-(6-Trifluoromethyl-benzo[b]thiophen-3-yl)-piperazin-1-ylmethyl]-cyclopropyl}-methanol (0.135 g, .36 mmol) in anhydrous methylene chloride (10 ml). Stirring was continued at -78° for 35 minutes and then triethyl amine (1.0 ml, .7.3 mmol) was added. This solution was stirred for 4 hours and then removed from the cold bath, filtered, concentrated and chromatagraphed on silica gel with methylene chloride/methanol (95:5). The resultant pure aldehyde, (1R,2R)-2-[4-(6-Trifluoromethyl-benzo[b]thiophen-3-yl)-piperazin-1-ylmethyl]-cyclopropanecarbaldehyde was verified by NMR and LC/MS, yielding 0.102 g, 76%.

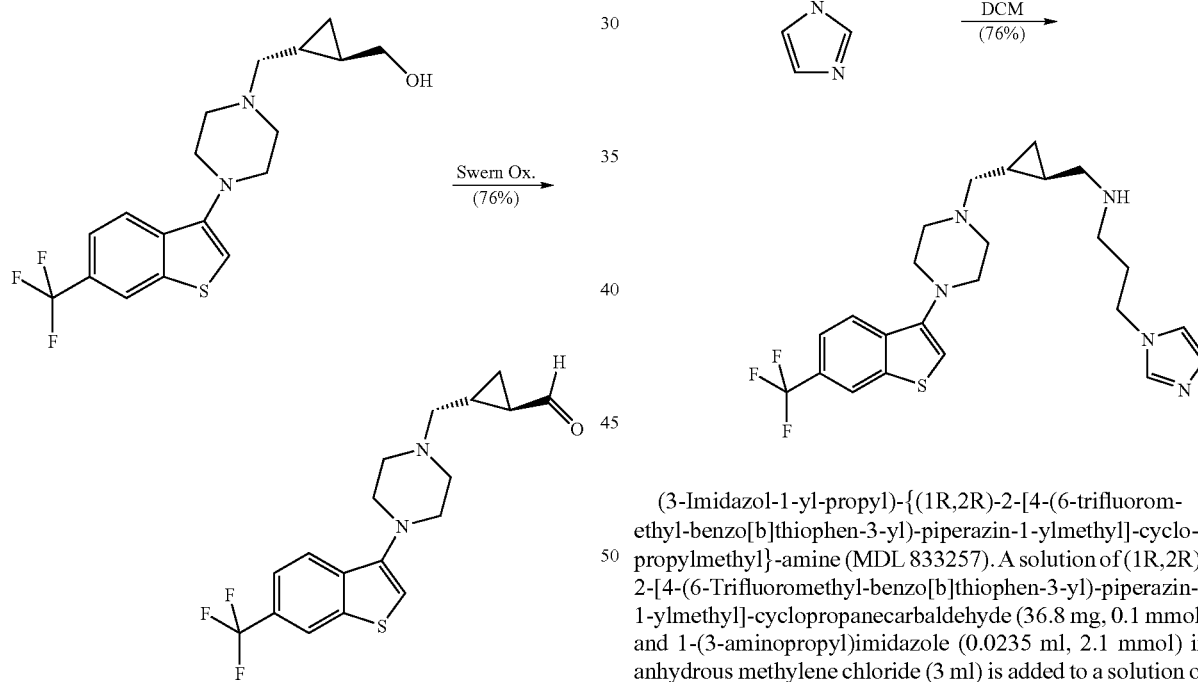

(3-Imidazol-1-yl-propyl)-{(1R,2R)-2-[4-(6-trifluoromethyl-benzo[b]thiophen-3-yl)-piperazin-1-ylmethyl]-cyclopropylmethyl}-amine (MDL 833257). A solution of (1R,2R)-2-[4-(6-Trifluoromethyl-benzo[b]thiophen-3-yl)-piperazin-1-ylmethyl]-cyclopropanecarbaldehyde (36.8 mg, 0.1 mmol) and 1-(3-aminopropyl)imidazole (0.0235 ml, 2.1 mmol) in anhydrous methylene chloride (3 ml) is added to a solution of polymer supported borohydride (0.863 g, 3 mmol) soaked in anhydrous methylene chloride (4 ml). This mixture was shook on an orbital shaker at room temperature overnight. The reaction was then quenched with water (2 ml) and products extracted with ethyl acetate (10 ml), then washed with brine, dried with sodium sulfate, and concentrated in vacuo. Silica gel chromatography eluted with methylene chloride/methanol (95:5) yielded the pure title compound, (3-Imidazol-1-yl-propyl)-{(1R,2R)-2-[4-(6-trifluoromethyl-benzo[b]thiophen-3-yl)-piperazin-1-ylmethyl]-cyclopropylmethyl}-amine as verified by NMR and LC/MS, yielding 36.2 mg, 76%.

Example 51

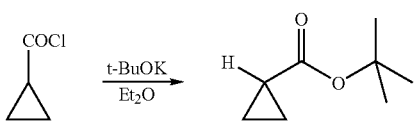

Cyclopropanecarboxylic acid tert-butyl ester. To a stirred suspension of 12.0 g (107.1 mmol) of potassium t-butoxide in 200 mL ether at 0° C. under nitrogen was added 13.4 g (128.6 mmol) of cyclopropanecarboxylic acid chloride over 5 min. After 30 min at 0° C. the mixture was stirred at ambient temperature for an additional 30 min. The reaction mixture was poured into aqueous saturated sodium bicarbonate and extracted with ether. The organic layer was dried and carefully concentrated to deliver 15.0 g (99%) of a yellow oil as the desired ester product.

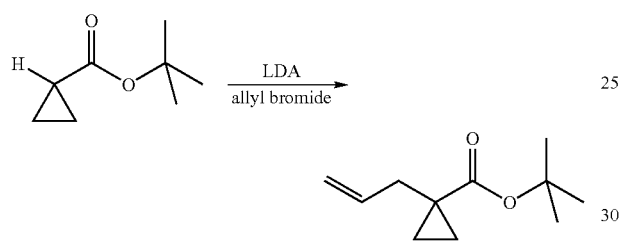

1-Allyl-cyclopropanecarboxylic acid tert-butyl ester. Lithium diisopropyl amide was generated from 7.5 g (58.1 mmol) diisopropyl amine and 23.2 mL of 2.5 M n-butyl lithium in 200 mL THF at 0° C. under nitrogen. After stirring for 30 minutes at 0° C. the solution was taken to −78° C. where 7.5 g (52.8 mmol) of cyclopropanecarboxylic acid tert-butyl ester in 30 mL of THF was added dropwise over 5 min. After 4 h 12.8 g (106 mmol) of allyl bromide in 30 mL THF was added drop-wise over 10 min. to the clear golden solution. The reaction was allowed to slowly warm to room temperature. After 19 hours the reaction was poured into aqueous saturated ammonium chloride solution, extracted with ether, dried and concentrated to deliver an oil which was purified via Kugelrohr distillation (approx. 20 mm Hg; 60-75° C. oven) to deliver 5.4 g (56%) of the desired product as a clear colorless oil.

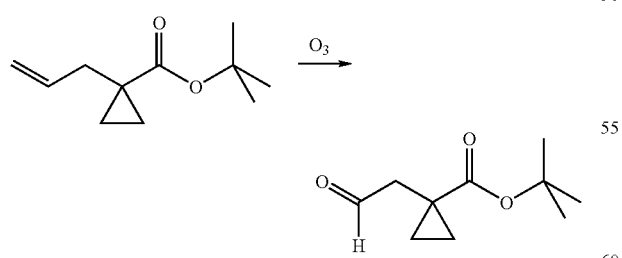

1-(2-Oxo-ethyl)-cyclopropanecarboxylic acid tert-butyl ester. A solution of 5.7 g (31.3 mmol) of 1-allyl-cyclopropanecarboxylic acid tert-butyl ester in 50 mL methanol and 50 mL dichloromethane under nitrogen was taken to −78° C. where ozone was bubbled in for 1 hour. Nitrogen was bubbled in until the familiar blue color dissipated. Three drops of pyridine followed by 2 mL of dimethyl sulfide were added and the cooling bath removed. After 2 hours the reaction was poured into aqueous saturated ammonium chloride solution, extracted with dichloromethane, dried and concentrated to deliver a quantitative yield of the desired aldehyde as an oil.

Example 52

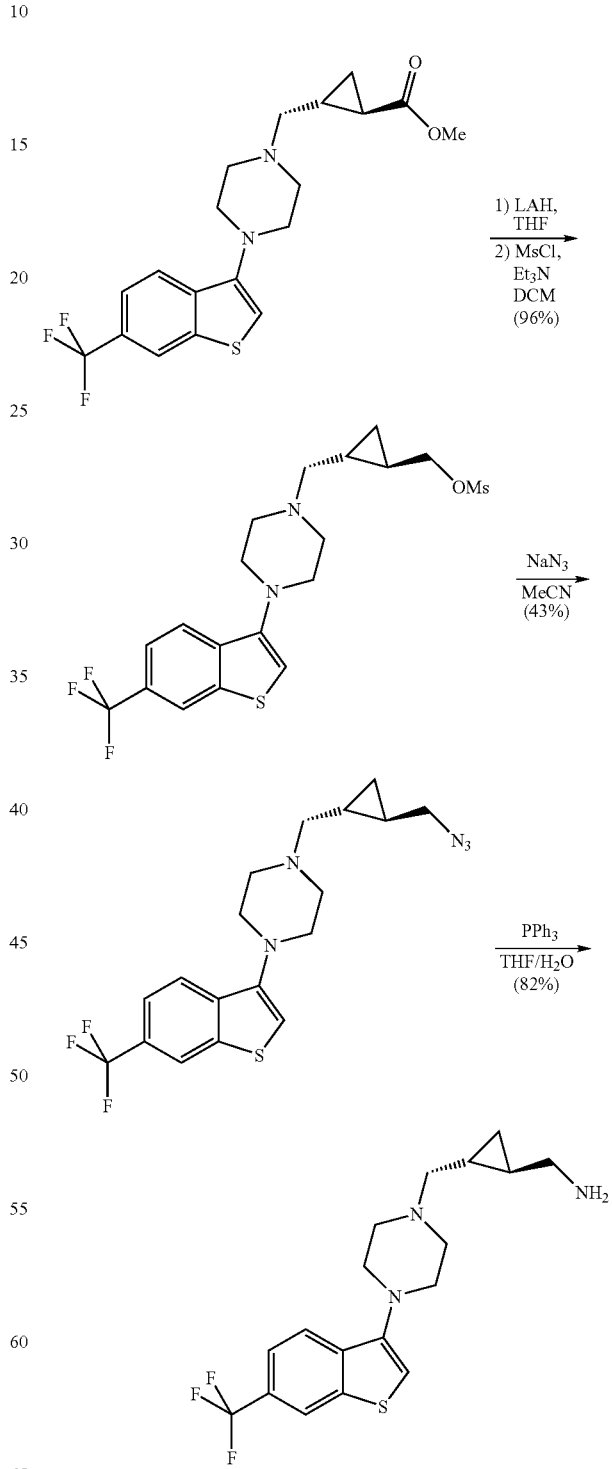

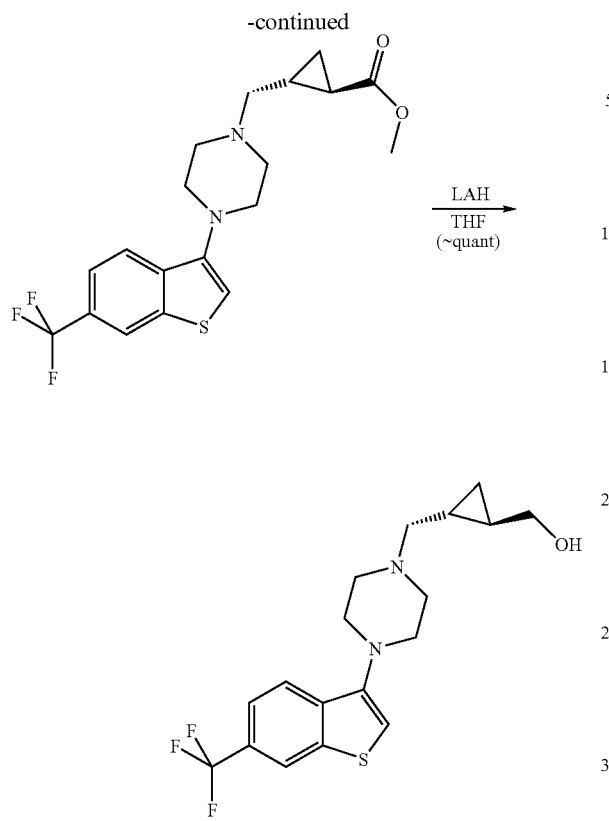

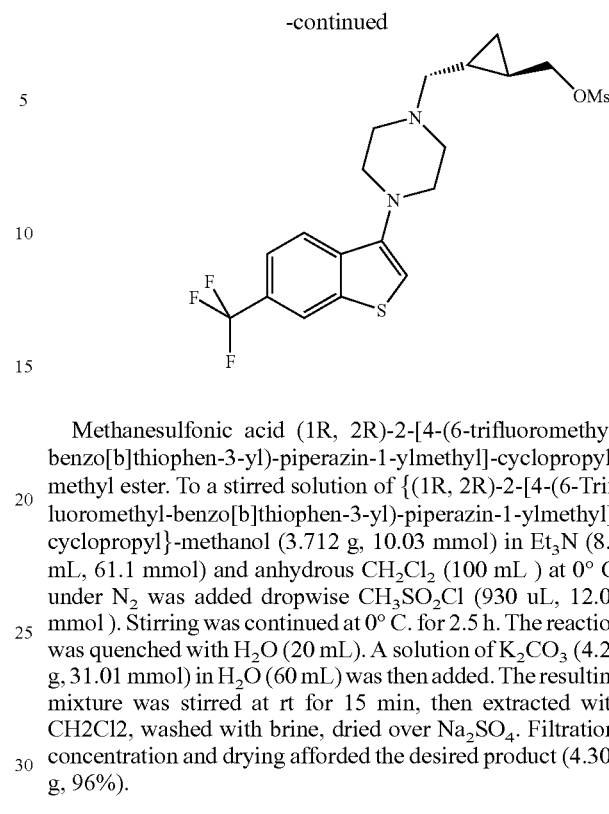

{(1R, 2R)-2-[4-(6-Trifluoromethyl-benzo[b]thiophen-3-yl)-piperazin-1-ylmethyl]-cyclopropyl}-methanol. To a stirred solution of 2R-[4-(6-trifluoromethyl-benzo[b]thiophen-3-yl)-piperazin-1-ylmethyl]-1R-cyclopropanecarboxylic acid methyl ester (5.0 g, 12.5 mmol) in THF (75 mL) cooled to 0° C. was added lithium aluminum hydride (18.75 mL, 18.75 mmol, 1.0 M in THF) drop-wise. The resulting mixture was stirred at 0° C. for 2 hours when water (1 mL), 2 N NaOH (1 mL) and water (3 mL) was added sequentially. The resulting mixture was diluted with DCM (90 mL) and filtered through a celite plug. The aluminum salts were thoroughly washed with DCM and the filtrate was dried (MgSO₄), filtered and evaporated yielding 4.6 g of the desired product.

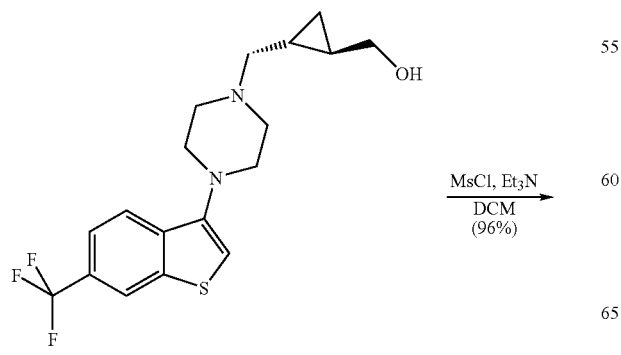

Methanesulfonic acid (1R, 2R)-2-[4-(6-trifluoromethyl-benzo[b]thiophen-3-yl)-piperazin-1-ylmethyl]-cyclopropyl-methyl ester. To a stirred solution of {(1R, 2R)-2-[4-(6-Trifluoromethyl-benzo[b]thiophen-3-yl)-piperazin-1-ylmethyl]-cyclopropyl}-methanol (3.712 g, 10.03 mmol) in Et₃N (8.5 mL, 61.1 mmol) and anhydrous CH₂Cl₂ (100 mL) at 0° C. under N₂ was added dropwise CH₃SO₂Cl (930 uL, 12.02 mmol). Stirring was continued at 0° C. for 2.5 h. The reaction was quenched with H₂O (20 mL). A solution of K₂CO₃ (4.28 g, 31.01 mmol) in H₂O (60 mL) was then added. The resulting mixture was stirred at rt for 15 min, then extracted with CH2Cl2, washed with brine, dried over Na₂SO₄. Filtration, concentration and drying afforded the desired product (4.301 g, 96%).

1-[(1R,2R)-2-Azidomethyl-cyclopropylmethyl]-4-(6-trifluoromethyl-benzo[b]thiophen-3-yl)-piperazine. A mixture of Methanesulfonic acid (1R, 2R)-2-[4-(6-trifluoromethyl-benzo[b]thiophen-3-yl)-piperazin-1-ylmethyl]-cyclopropyl-methyl ester (3.995 g, 8.92 mmol), NaN₃ (1.16 g, 17.85 mmol) and anhydrous CH₃CN (60 mL) was stirred at 47° C. under N₂ for 4 h, then an additional quantity of NaN₃ (580 mg, 8.92 mmol ) was added. Stirring was continued at 47° C. for a further 4 h. After cooling to rt, the mixture was filtered through Celite 545, washed with CH$_3$CN. The combined filtrate and washings were concentrated and then separated by Prep LC (heptane/EtOAc—70:30, 60:40, 50:50, 40:60, 30:70, 20:80, 100% EtOAc) to give the desired product (1.5 g, 43%).

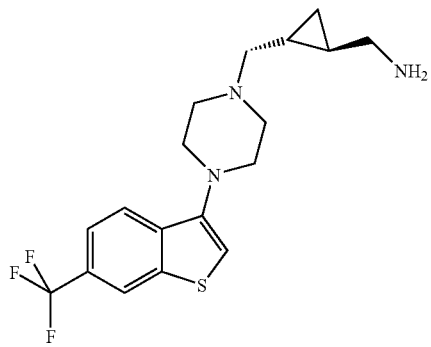

C{(1R,2R )-2-[4-(6-Trifluoromethyl-benzo[b]thiophen-3-yl)-piperazin-1-ylmethyl]-cyclopropyl}methylamine. A solution of 1-[(1R,2R)-2-Azidomethyl-cyclopropylmethyl]-4-(6-trifluoromethyl-benzo[b]thiophen-3-yl )-piperazine (1.495 g, 3.78 mmol), PPh$_3$ (3.97 g, 15.15 mmol) and H$_2$O (273 uL, 15.17 mmol) in THF (30 mL) was stirred at 40° C. under N$_2$ for 18 h, then at 55° C. for 23 h. After cooling to rt, the mixture was concentrated, and then flash chromatographed (100% EtOAc, then MeOH/CH$_2$Cl$_2$/Et$_3$N—60:40:10 ) to provide the desired product (1.14 g, 82%).

TABLE 2

| No. | R | n | | R$_2$ | Y | D$_3$K$_1$ (nM) |
|---|---|---|---|---|---|---|
| 811700 | benzothiophene-CF$_3$ | 2 | —(CH$_2$)$_4$—NHC(O)CH$_3$ | CH(CH$_3$)$_2$ | N | 42.1 |
| 811708 | benzothiophene-CF$_3$ | 2 | —(CH$_2$)$_4$—NHC(O)CH$_3$ | 2-thienyl | N | 5.77 |

TABLE 2-continued
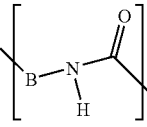
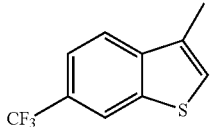
| No. | R | n | | R₂ | Y | D₃K₁ (nM) |
|---|---|---|---|---|---|---|
| 814238A | 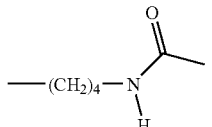 | 2 | —(CH₂)₄—NH—C(O)— | 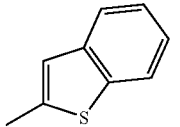 | N | 1.9 |
| 814854 | 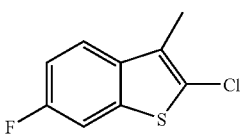 | 2 | —(CH₂)₄—NH—C(O)— | 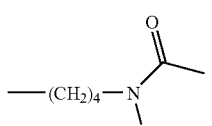 CF₃ | N | 35 |
| 815052 |  | 2 | —(CH₂)₄—NH—C(O)— | 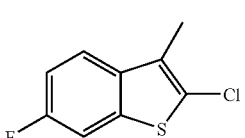 | N | 5.4 |
| 815053 | 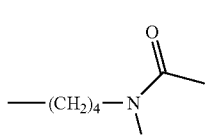 | 2 | —(CH₂)₄—NH—C(O)— | 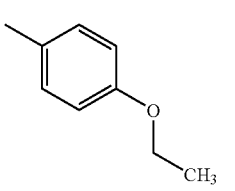 | N | 5.8 |
| 815054 | 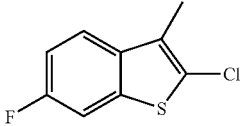 | 2 | —(CH₂)₄—NH—C(O)— | 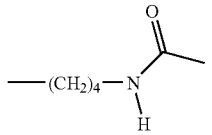 | N | 7.7 |
| 815055 | 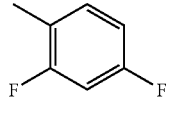 | 2 | —(CH₂)₄—NH—C(O)— | 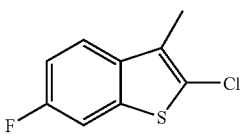 | N | 3.5 |
| 815056 | 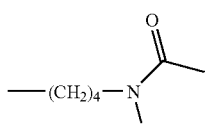 | 2 | —(CH₂)₄—NH—C(O)— |  | N | 9.6 |
| 815057 | 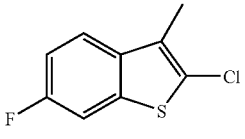 | 2 | —(CH₂)₄—NH—C(O)— | 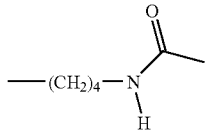 | N | 12.3 |

TABLE 2-continued
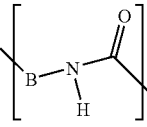
| No. | R | n | | R₂ | Y | D₃K₁ (nM) |
|---|---|---|---|---|---|---|
| 815058 | 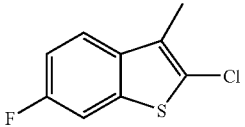 | 2 | 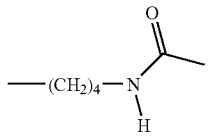 | 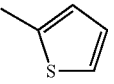 | N | 4.3 |
| 815059 | 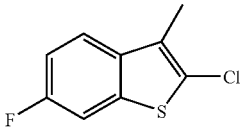 | 2 | 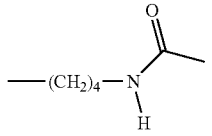 | 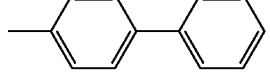 | N | 13.8 |
| 815060 | 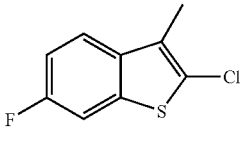 | 2 | 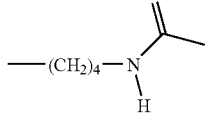 | 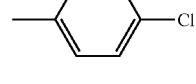 | N | 6.2 |
| 815061 | 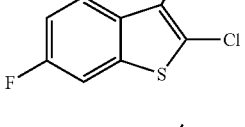 | 2 | 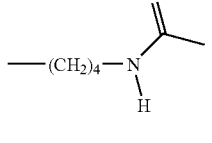 | 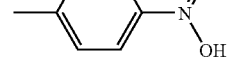 | N | 3.6 |
| 815062 | 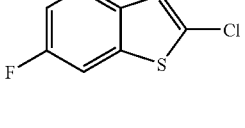 | 2 | 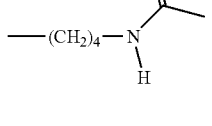 | 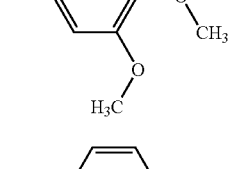 | N | 4.1 |
| 815063 | 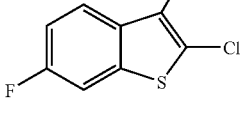 | 2 | 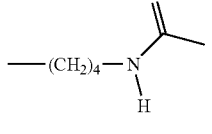 | 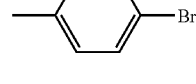 | N | 6.3 |
| 815064 | 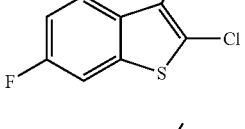 | 2 | 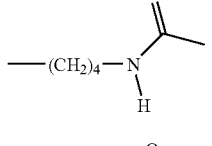 | 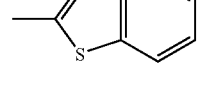 | N | 1.9 |
| 815065 | 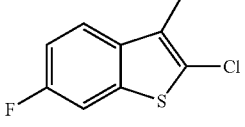 | 2 | 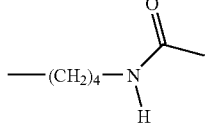 | 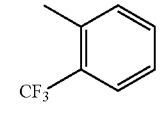 | N | 43.8 |

TABLE 2-continued

| No. | R | n | | $R_2$ | Y | $D_3K_1$ (nM) |
|---|---|---|---|---|---|---|
| 815066 | 3-methyl-2-chloro-6-fluorobenzothiophene | 2 | —(CH$_2$)$_4$—NHC(O)CH$_3$— | 2-methoxyphenyl | N | 28.7 |
| 815067 | 3-methyl-2-chloro-6-fluorobenzothiophene | 2 | —(CH$_2$)$_4$—NHC(O)CH$_3$— | 4-CF$_3$-phenyl | N | 20.1 |
| 815068 | 3-methyl-2-chloro-6-fluorobenzothiophene | 2 | —(CH$_2$)$_4$—NHC(O)CH$_3$— | 2-furyl | N | 4.9 |
| 815069 | 3-methyl-2-chloro-6-fluorobenzothiophene | 2 | —(CH$_2$)$_4$—NHC(O)CH$_3$— | 2,6-difluorophenyl | N | 15 |
| 815070 | 3-methyl-2-chloro-6-fluorobenzothiophene | 2 | —(CH$_2$)$_4$—NHC(O)CH$_3$— | 2-bromophenyl | N | 34.4 |
| 815071 | 3-methyl-2-chloro-6-fluorobenzothiophene | 2 | —(CH$_2$)$_4$—NHC(O)CH$_3$— | cyclopentyl | N | 7.2 |
| 826123 | 3-methyl-6-CF$_3$-benzothiophene | 2 | methyl-ethyl-cyclopropyl-CH$_2$NHC(O)— | 2-methylbenzothiophene | N | 20 |

TABLE 2-continued
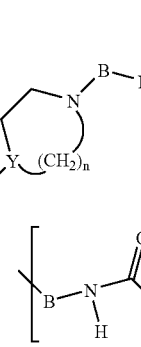
| No. | R | n | [structure] | R₂ | Y | D₃K₁ (nM) |
|---|---|---|---|---|---|---|
| 826124 | 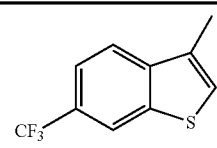 | 2 | 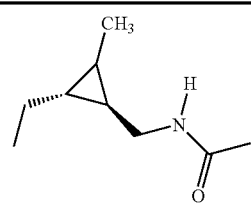 | 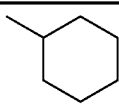 | N | 83 |
| 826125 | 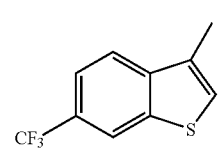 | 2 | 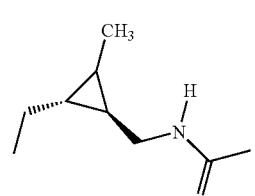 | 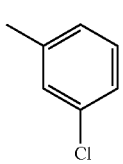 | N | 56 |
| 826126 | 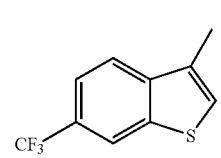 | 2 | 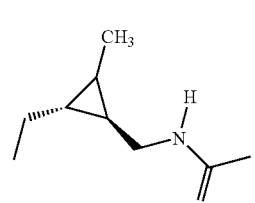 | 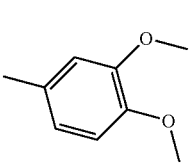 | N | 28 |
| 826127 | 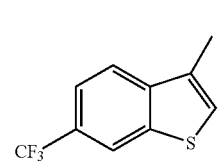 | 2 | 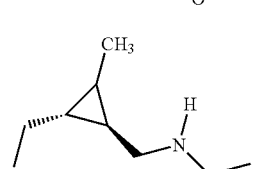 | 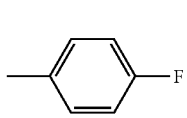 | N | 31 |
| 826128 | 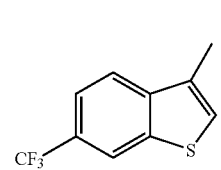 | 2 | 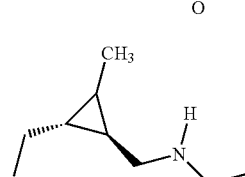 | 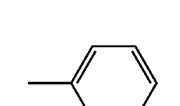 | N | 46 |
| 826129 | 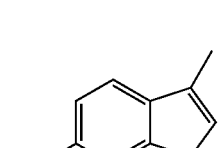 | 2 | 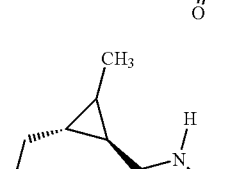 | 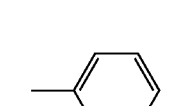 | N | 89 |

TABLE 2-continued
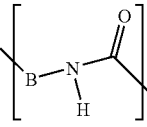
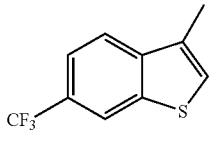
| No. | R | n | | R₂ | Y | D₃K₁ (nM) |
|---|---|---|---|---|---|---|
| 826131 | 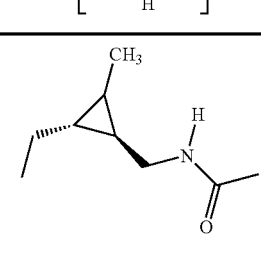 | 2 | 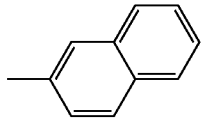 | 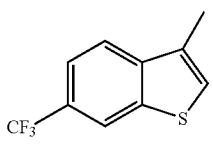 | N | 40.2 |
| 826132 | 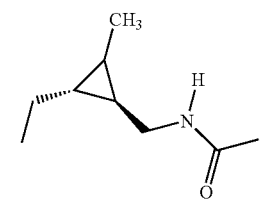 | 2 | 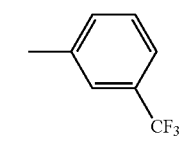 | 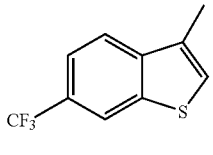 | N | 174 |
| 826269 | 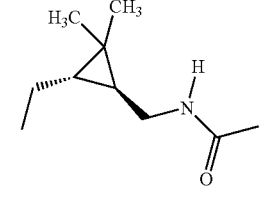 | 2 | 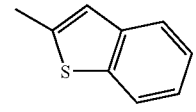 | 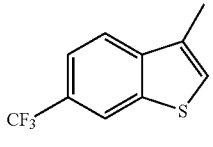 | N | 54 |
| 826270 | 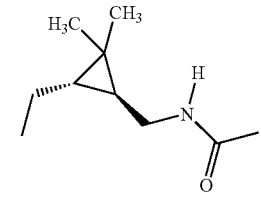 | 2 | 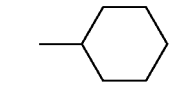 | 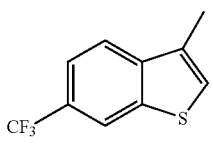 | N | 163 |
| 826272 | 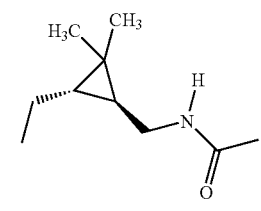 | 2 | 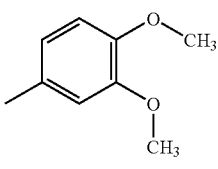 | 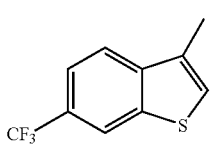 | N | 62 |
| 826273 | 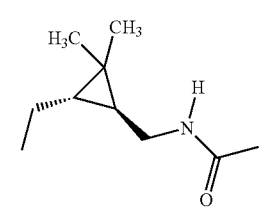 | 2 | 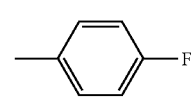 | | N | 51 |

TABLE 2-continued
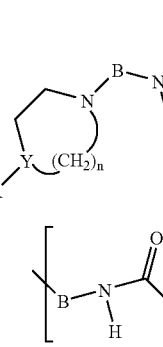
| No. | R | n | | R₂ | Y | D₃K₁ (nM) |
|---|---|---|---|---|---|---|
| 826274 | 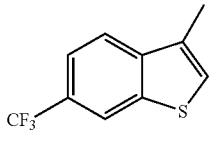 | 2 | 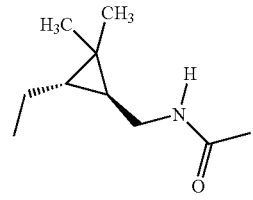 | 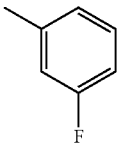 | N | 67 |
| 826275 | 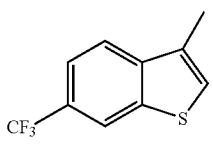 | 2 | 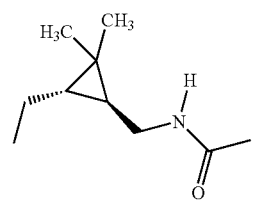 | 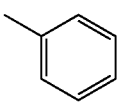 | N | 92 |
| 826276 | 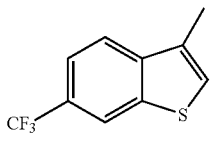 | 2 | 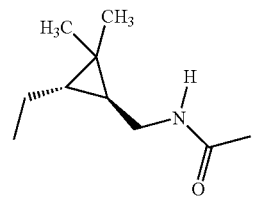 | 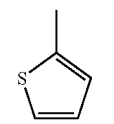 | N | 58 |
| 826277 | 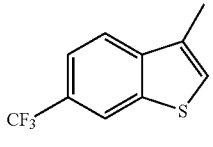 | 2 | 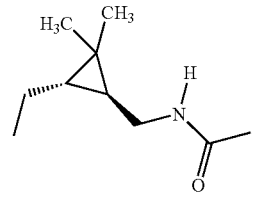 | 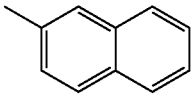 | N | 20.3 |
| 826278 | 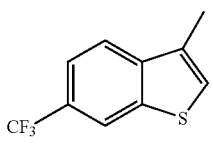 | 2 | 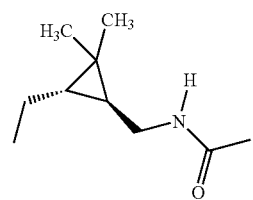 | 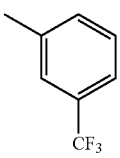 | N | 87 |
| 826279 | 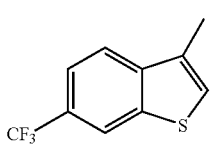 | 2 | 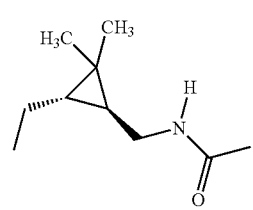 | 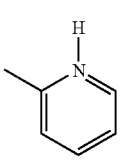 | N | 147 |

TABLE 2-continued
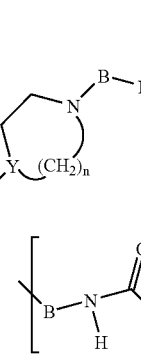
| No. | R | n | | R2 | Y | D3K1 (nM) |
|---|---|---|---|---|---|---|
| 826280 | 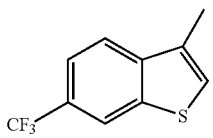 | 2 | 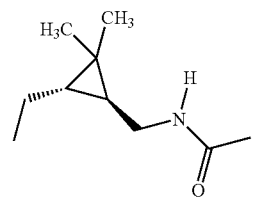 | 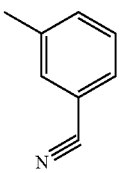 | N | 116 |
| 826281 | 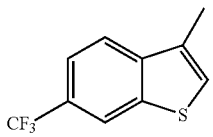 | 2 | 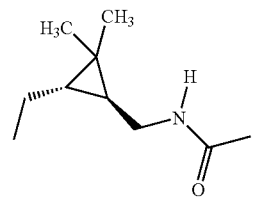 | 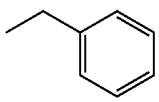 | N | 73.2 |
| 826282 | 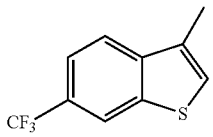 | 2 | 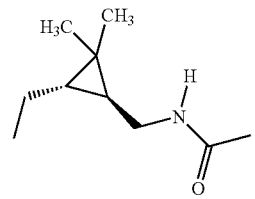 | 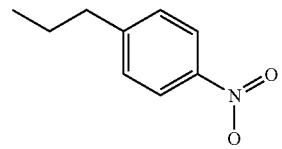 | N | 51 |
| 826283 | 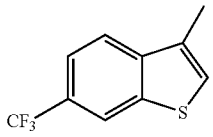 | 2 | 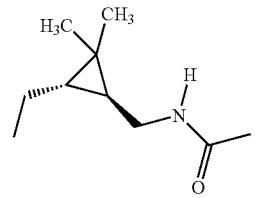 | 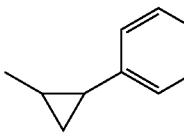 | N | 6.8 |
| 826284 | 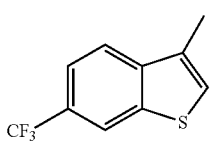 | 2 | 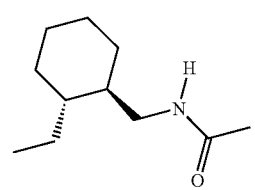 | 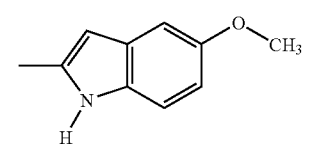 | N | 77 |
| 826285 | 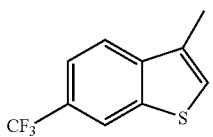 | 2 | 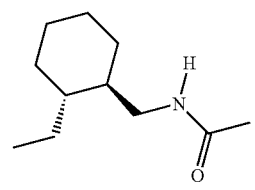 | 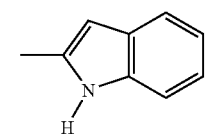 | N | 170 |

TABLE 2-continued
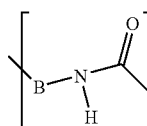
| No. | R | n | | $R_2$ | Y | $D_3K_1$ (nM) |
|---|---|---|---|---|---|---|
| 826287 | 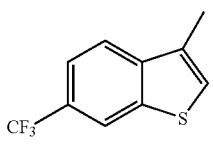 | 2 | 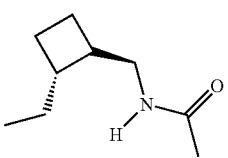 | 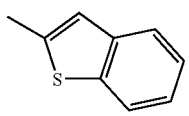 | N | 43 |
| 826288 | 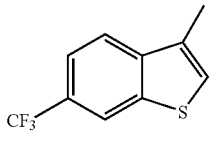 | 2 | 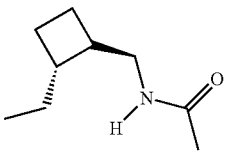 | 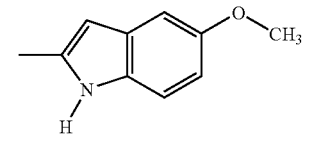 | N | 71 |
| 826289 | 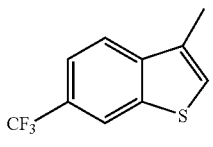 | 2 | 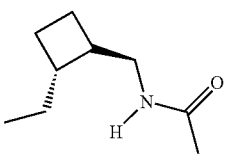 | 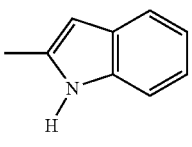 | N | 49 |
| 826290 | 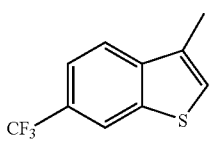 | 2 | 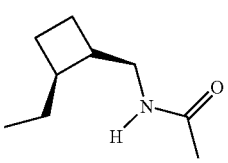 | 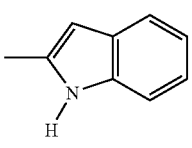 | N | 72 |
| 826291 | 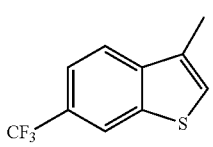 | 2 | 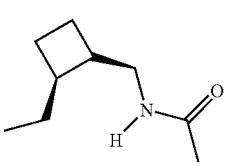 | 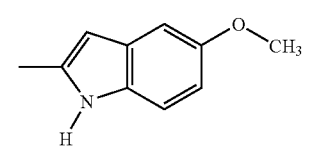 | N | 37 |
| 826292 | 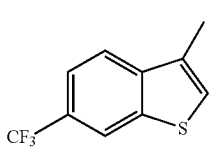 | 2 | 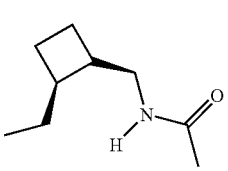 | 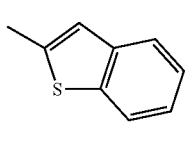 | N | 200 |
| 826293 | 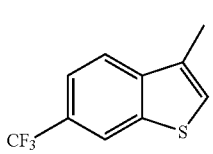 | 2 | 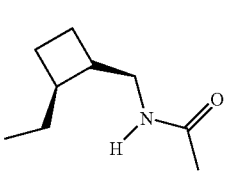 | 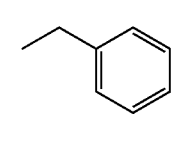 | N | 240 |

TABLE 2-continued

| No. | R | n | | R₂ | Y | D₃K₁ (nM) |
|---|---|---|---|---|---|---|
| 826332 | 3-methyl-6-(trifluoromethyl)benzothiophene | 2 | -CH₂-CH=CH-CH₂-NHC(O)- | 3-methylthiophene | N | 20 |
| 826333 | 3-methyl-6-(trifluoromethyl)benzothiophene | 2 | -CH₂-CH=CH-CH₂-NHC(O)- | cyclobutyl | N | 24 |
| 826334 | 3-methyl-6-(trifluoromethyl)benzothiophene | 2 | -CH₂-CH=CH-CH₂-NHC(O)- | cyclopentyl | N | 21 |
| 826335 | 3-methyl-6-(trifluoromethyl)benzothiophene | 2 | -CH₂-CH=CH-CH₂-NHC(O)- | 2-pyridyl | N | 42 |
| 826336 | 3-methyl-6-(trifluoromethyl)benzothiophene | 2 | -CH₂-CH=CH-CH₂-NHC(O)- | 3-pyridyl | N | 41 |
| 826337 | 3-methyl-6-(trifluoromethyl)benzothiophene | 2 | -CH₂-CH=CH-CH₂-NHC(O)- | phenyl | N | 29 |
| 826338 | 3-methyl-6-(trifluoromethyl)benzothiophene | 2 | -CH₂-CH=CH-CH₂-NHC(O)- | 3,5-difluorophenyl | N | 93 |
| 826339 | 3-methyl-6-(trifluoromethyl)benzothiophene | 2 | -CH₂-CH=CH-CH₂-NHC(O)- | cyclohexyl | N | 24 |

TABLE 2-continued
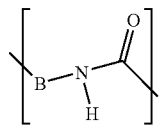
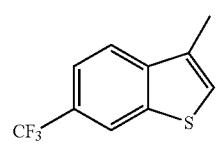
| No. | R | n | | R$_2$ | Y | D$_3$K$_i$ (nM) |
|---|---|---|---|---|---|---|
| 826340 | 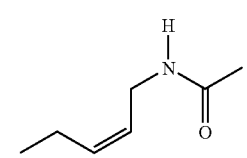 | 2 | 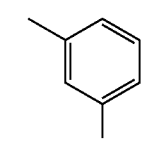 | 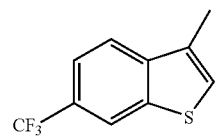 | N | 73 |
| 826341 | 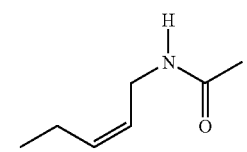 | 2 | 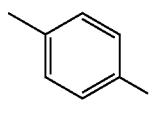 | 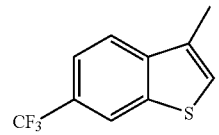 | N | 11 |
| 826342 | 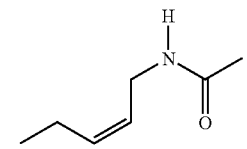 | 2 | 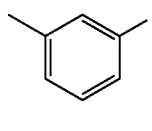 | 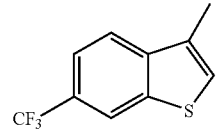 | N | 47 |
| 826343 | 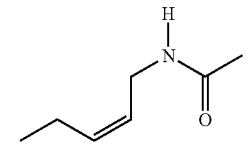 | 2 | 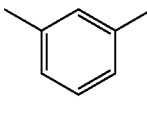 | 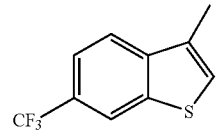 | N | 53 |
| 826344 | 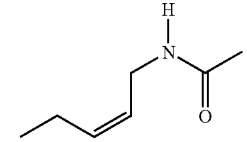 | 2 | 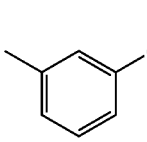 | 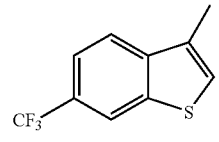 | N | 29 |
| 826345 | 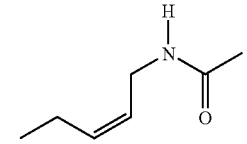 | 2 | 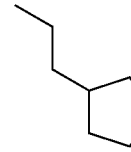 | 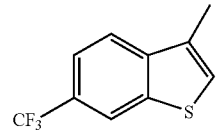 | N | 77 |
| 826346 | 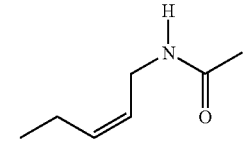 | 2 | 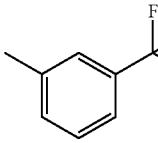 |  | N | 170 |

TABLE 2-continued

| No. | R | n | | R₂ | Y | D₃K₁ (nM) |
|---|---|---|---|---|---|---|
| 826347 | 3-methyl-6-CF₃-benzothiophene | 2 | CH₂CH=CHCH₂CH₂NHC(O)– | phenoxy | N | 67 |
| 826348 | 3-methyl-6-CF₃-benzothiophene | 2 | CH₂CH=CHCH₂CH₂NHC(O)– | 4-(trifluoromethoxy)phenyl | N | 61 |
| 826349 | 3-methyl-6-CF₃-benzothiophene | 2 | CH₂CH=CHCH₂CH₂NHC(O)– | benzyloxyethyl | N | 180 |
| 827709 | 3-methyl-6-CF₃-benzothiophene | 2 | CH₂CH=CHCH₂CH₂NHC(O)– | 2-methylbenzothiophene | N | 28 |
| 827710 | 3-methyl-6-CF₃-benzothiophene | 2 | CH₃CH₂CH=CHCH₂NHC(O)– | 3-methylthiophene | N | 31 |
| 827711 | 3-methyl-6-CF₃-benzothiophene | 2 | CH₂CH=CHCH₂CH₂NHC(O)– | cyclobutyl | N | 230 |
| 827712 | 3-methyl-6-CF₃-benzothiophene | 2 | CH₃CH₂CH=CHCH₂NHC(O)– | cyclopentyl | N | 66 |
| 827713 | 3-methyl-6-CF₃-benzothiophene | 2 | CH₃CH₂CH=CHCH₂NHC(O)– | 2-methylpyridine | N | 65 |

TABLE 2-continued
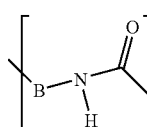
| No. | R | n | | R₂ | Y | D₃K₁ (nM) |
|---|---|---|---|---|---|---|
| 827714 | 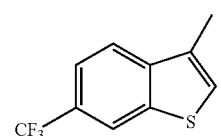 | 2 | 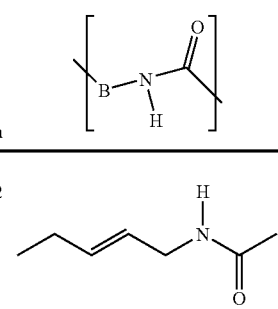 | 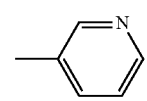 | N | 43 |
| 827715 | 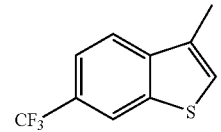 | 2 | 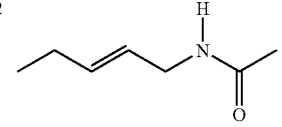 | 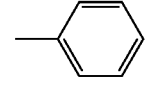 | N | 24 |
| 827716 | 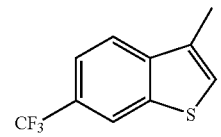 | 2 | 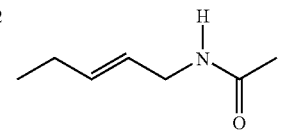 | 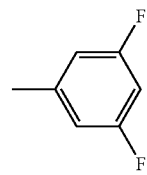 | N | 98 |
| 827717 | 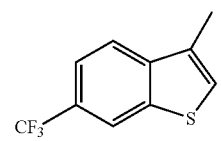 | 2 | 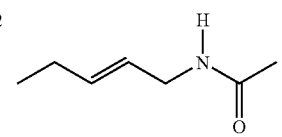 | 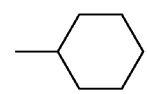 | N | 9.5 |
| 827718 | 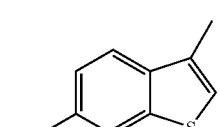 | 2 | 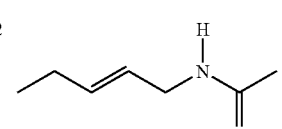 | 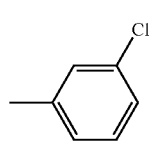 | N | 150 |
| 827719 | 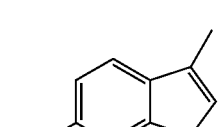 | 2 | 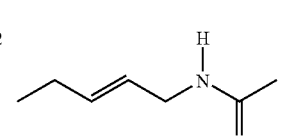 | 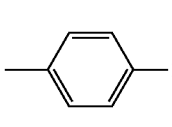 | N | 51 |
| 827720 | 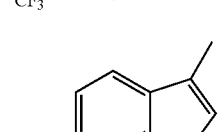 | 2 | 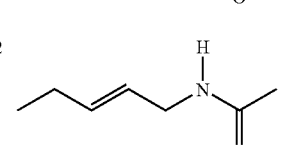 | 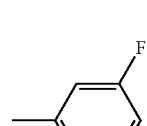 | N | 86 |
| 827721 | 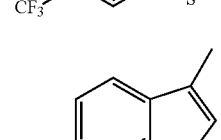 | 2 | 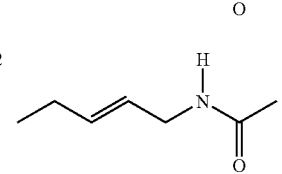 | 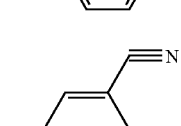 | N | 91 |

TABLE 2-continued
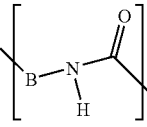
| No. | R | n | | R₂ | Y | D₃K₁ (nM) |
|---|---|---|---|---|---|---|
| 827722 | 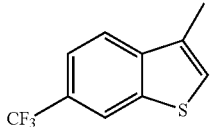 | 2 | 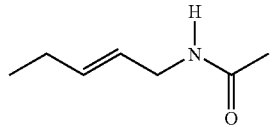 | 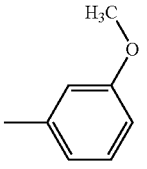 | N | 59 |
| 827724 | 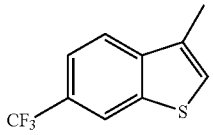 | 2 | 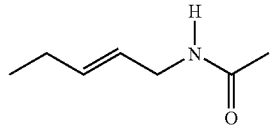 | 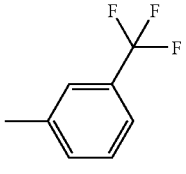 | N | 120 |
| 827725 | 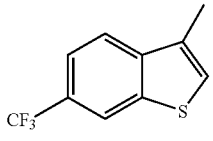 | 2 | 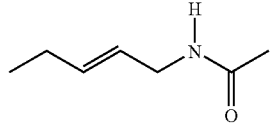 | 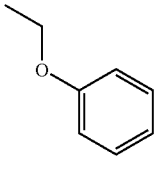 | N | 120 |
| 827726 | 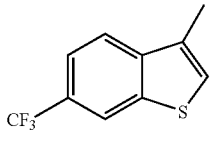 | 2 | 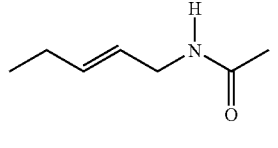 | 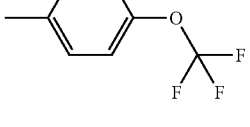 | N | 92 |
| 827728 | 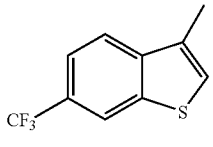 | 2 | 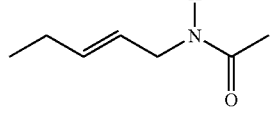 | 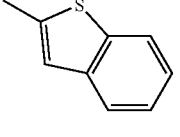 | N | 16 |
| 81708A | 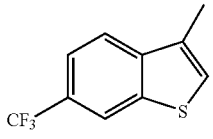 | 2 | 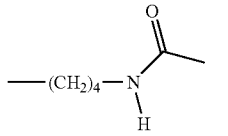 |  | N | 4.5 |
| 815541 | 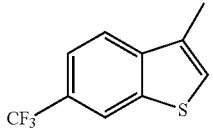 | 2 | 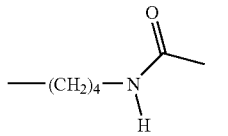 | 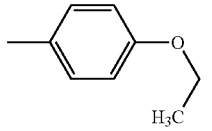 | N | 12 |
| 815542 | 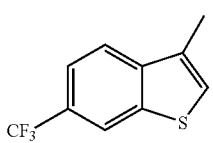 | 2 | 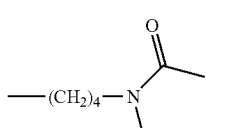 | 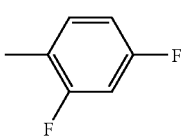 | N | 5.6 |

TABLE 2-continued
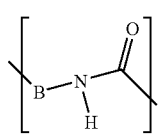
| No. | R | n | | R₂ | Y | D₃K₁ (nM) |
|---|---|---|---|---|---|---|
| 815543 | 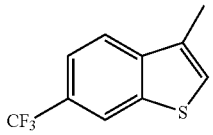 | 2 | 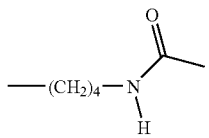 | 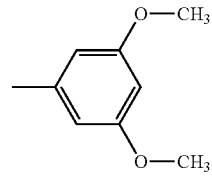 | N | 32 |
| 815544 | 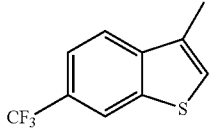 | 2 | 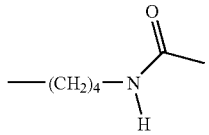 | 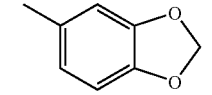 | N | 1.7 |
| 815545 | 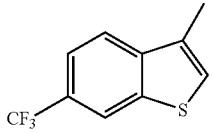 | 2 | 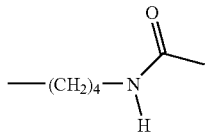 | 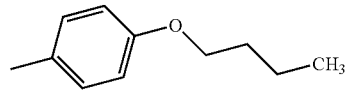 | N | 38.6 |
| 815546 | 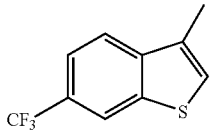 | 2 | 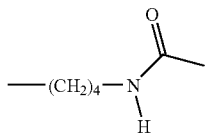 | 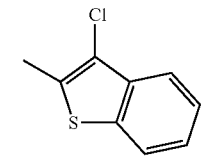 | N | 49 |
| 815547 | 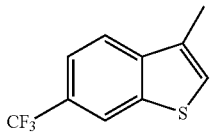 | 2 | 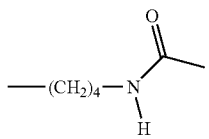 | 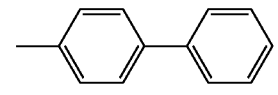 | N | 4.4 |
| 815548 | 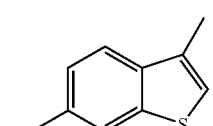 | 2 | 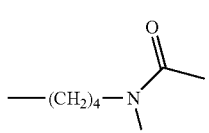 | 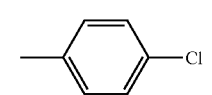 | N | 1.6 |
| 815549 | 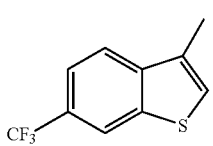 | 2 | 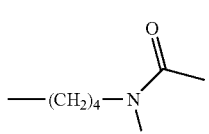 | 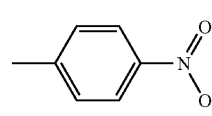 | N | 2.1 |

TABLE 2-continued

| No. | R | n | | R₂ | Y | D₃K₁ (nM) |
|---|---|---|---|---|---|---|
| 815550 | 3-methyl-6-CF₃-benzothiophene | 2 | —(CH₂)₄—NHC(O)CH₂— | 3,4-dimethoxyphenyl | N | 6.9 |
| 815551 | 3-methyl-6-CF₃-benzothiophene | 2 | —(CH₂)₄—NHC(O)CH₂— | 4-bromophenyl | N | 4.3 |
| 815552 | 3-methyl-6-CF₃-benzothiophene | 2 | —(CH₂)₄—NHC(O)CH₂— | 4-(pentyloxy)phenyl | N | 140 |
| 815553 | 3-methyl-6-CF₃-benzothiophene | 2 | —(CH₂)₄—NHC(O)CH₂— | 2-(trifluoromethyl)phenyl | N | 41 |
| 815554 | 3-methyl-6-CF₃-benzothiophene | 2 | —(CH₂)₄—NHC(O)CH₂— | 2-methoxyphenyl | N | 9.7 |
| 815555 | 3-methyl-6-CF₃-benzothiophene | 2 | —(CH₂)₄—NHC(O)CH₂— | 4-(trifluoromethyl)phenyl | N | 7 |
| 815556 | 3-methyl-6-CF₃-benzothiophene | 2 | —(CH₂)₄—NHC(O)CH₂— | 2-furyl | N | 6.4 |

TABLE 2-continued
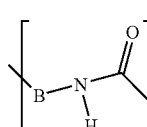
| No. | R | n | | R₂ | Y | D₃K₁ (nM) |
|---|---|---|---|---|---|---|
| 815557 | 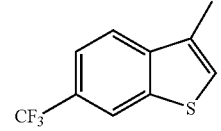 | 2 | —(CH₂)₄—NH—C(O)CH₃ | 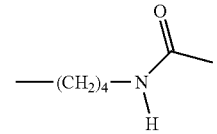 | N | 8.7 |
| 815558 | 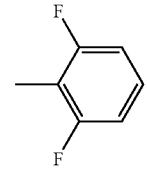 | 2 | —(CH₂)₄—NH—C(O)CH₃ | 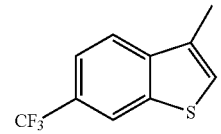 | N | 23 |
| 815559 | 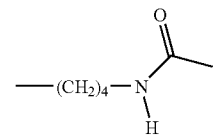 | 2 | —(CH₂)₄—NH—C(O)CH₃ | 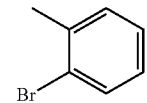 | N | 13.5 |
| 815560 | 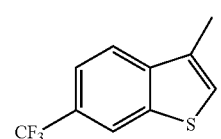 | 2 | —(CH₂)₄—NH—C(O)CH₃ | 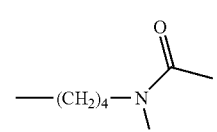 | N | 22 |
| 815561 | 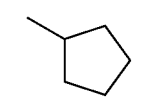 | 2 | —(CH₂)₄—NH—C(O)CH₃ | 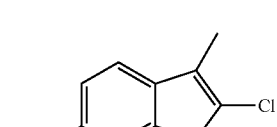 | N | 41 |
| 815563 | 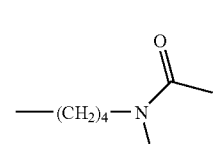 | 2 | —(CH₂)₄—NH—C(O)CH₃ | 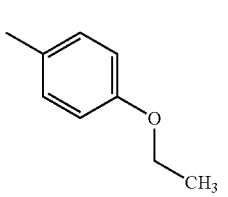 | N | 21 |
| 815564 | 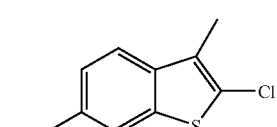 | 2 | —(CH₂)₄—NH—C(O)CH₃ | 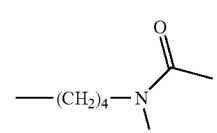 | N | 159 |

TABLE 2-continued

| No. | R | n | [structure] | R$_2$ | Y | D$_3$K$_1$ (nM) |
|---|---|---|---|---|---|---|
| 815566 | 2-chloro-3-methyl-6-trifluoromethyl-benzothiophene | 2 | —(CH$_2$)$_4$—NHC(O)— | 2-methylthiophene | N | 32 |
| 815568 | 2-chloro-3-methyl-6-trifluoromethyl-benzothiophene | 2 | —(CH$_2$)$_4$—NHC(O)— | 4-chlorophenyl | N | 30 |
| 815569 | 2-chloro-3-methyl-6-trifluoromethyl-benzothiophene | 2 | —(CH$_2$)$_4$—NHC(O)— | 4-nitrophenyl | N | 13 |
| 815570 | 2-chloro-3-methyl-6-trifluoromethyl-benzothiophene | 2 | —(CH$_2$)$_4$—NHC(O)— | 3,4-dimethoxyphenyl | N | 30 |
| 815571 | 2-chloro-3-methyl-6-trifluoromethyl-benzothiophene | 2 | —(CH$_2$)$_4$—NHC(O)— | 4-bromophenyl | N | 34.2 |
| 815573 | 2-chloro-3-methyl-6-trifluoromethyl-benzothiophene | 2 | —(CH$_2$)$_4$—NHC(O)— | 2-(trifluoromethyl)phenyl | N | 35 |
| 815574 | 2-chloro-3-methyl-6-trifluoromethyl-benzothiophene | 2 | —(CH$_2$)$_4$—NHC(O)— | 2-methoxyphenyl | N | 53 |
| 815575 | 2-chloro-3-methyl-6-trifluoromethyl-benzothiophene | 2 | —(CH$_2$)$_4$—NHC(O)— | 4-(trifluoromethyl)phenyl | N | 50 |

TABLE 2-continued
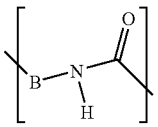
| No. | R | n | | R2 | Y | D3K1 (nM) |
|---|---|---|---|---|---|---|
| 815576 | 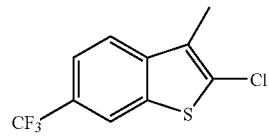 | 2 | —(CH2)4—NH— 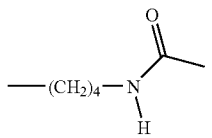 | 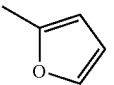 | N | 63 |
| 815577 | 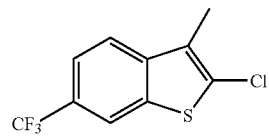 | 2 | —(CH2)4—NH— 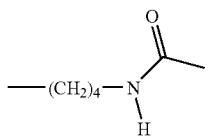 | 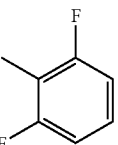 | N | 95 |
| 815578 | 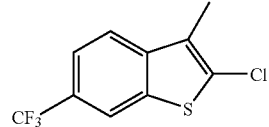 | 2 | —(CH2)4—NH— 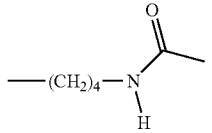 | 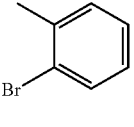 | N | 117 |
| 815579 | 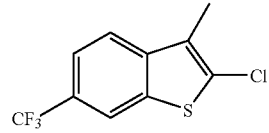 | 2 | —(CH2)4—NH— 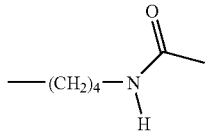 | 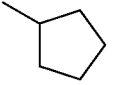 | N | 104 |
| 815665 | 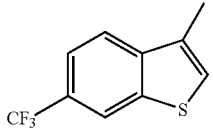 | 2 | 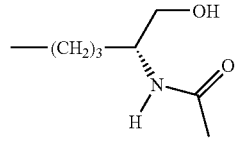 | 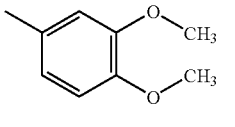 | N | 163 |
| 815667 | 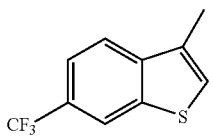 | 2 | 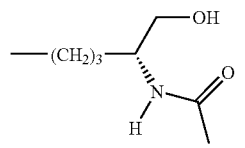 | 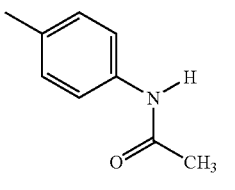 | N | 203 |
| 815668 | 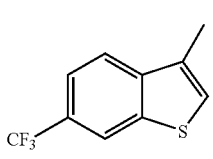 | 2 | 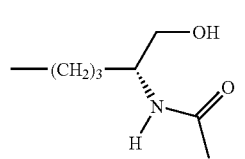 | 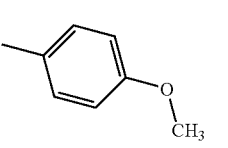 | N | 150 |

TABLE 2-continued
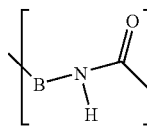
| No. | R | n | | R₂ | Y | D₃K₁ (nM) |
|---|---|---|---|---|---|---|
| 815670 | 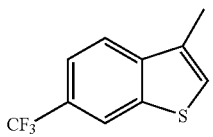 | 2 | 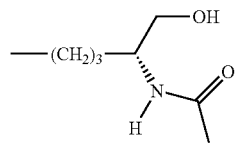 | 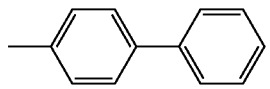 | N | 192 |
| 815671 | 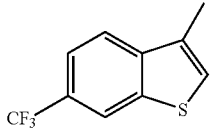 | 2 | 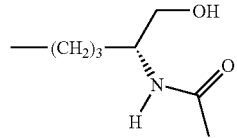 | 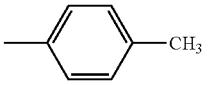 | N | 309 |
| 815674 | 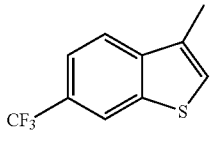 | 2 | 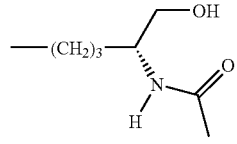 | 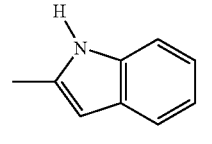 | N | 314 |
| 815676 | 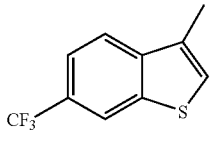 | 2 | 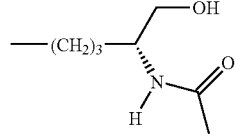 | 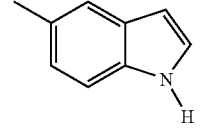 | N | 224 |
| 815677 | 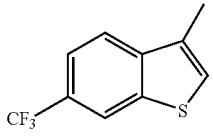 | 2 | 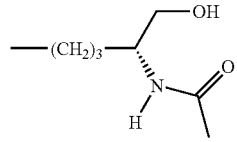 | 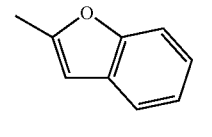 | N | 297 |
| 815679 | 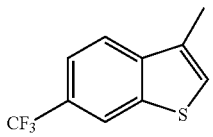 | 2 | 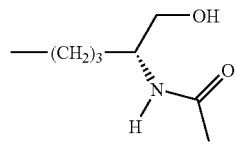 | 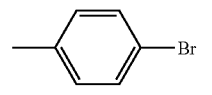 | N | 129 |
| 815680 | 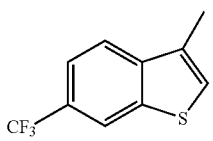 | 2 | 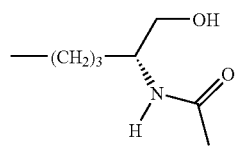 | 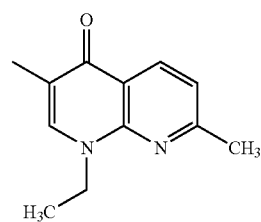 | N | 197 |

TABLE 2-continued

| No. | R | n | | R₂ | Y | D₃K₁ (nM) |
|---|---|---|---|---|---|---|
| 815681 | 3-methyl-6-CF₃-benzothiophene | 2 | —(CH₂)₃—CH(CH₂OH)—NH—C(O)CH₃ | 3-methyl-2-(methylthio)pyridine | N | 261 |
| 815683 | 3-methyl-6-CF₃-benzothiophene | 2 | —(CH₂)₃—CH(CH₂OH)—NH—C(O)CH₃ | 1,3-dimethylindene | N | 293 |
| 815684 | 3-methyl-6-CF₃-benzothiophene | 2 | —(CH₂)₃—CH(CH₂OH)—NH—C(O)CH₃ | 2-methylbenzothiophene | N | 208 |
| 815685 | 3-methyl-6-CF₃-benzothiophene | 2 | —(CH₂)₃—CH(CH₂OH)—NH—C(O)CH₃ | 3-methylthioxanthone-S,S-dioxide | N | 186 |
| 815686 | 3-methyl-6-CF₃-benzothiophene | 2 | —(CH₂)₃—CH(CH₂OH)—NH—C(O)CH₃ | 2-methyl-6-chlorobenzothiophene | N | 275 |
| 815688 | 3-methyl-6-CF₃-benzothiophene | 2 | —(CH₂)₃—CH(CH₂OH)—NH—C(O)CH₃ | 2-methyl-6-CF₃-phenyl | N | 190 |
| 815689 | 3-methyl-6-CF₃-benzothiophene | 2 | —(CH₂)₃—CH(CH₂OH)—NH—C(O)CH₃ | 5-methyl-2,3-dimethoxyphenyl | N | 225 |

TABLE 2-continued
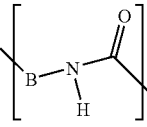
| No. | R | n | | R₂ | Y | D₃K₁ (nM) |
|---|---|---|---|---|---|---|
| 815690 | 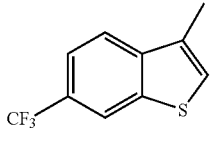 | 2 | 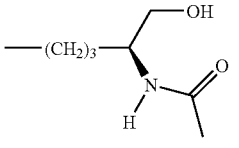 | 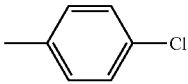 | N | 245 |
| 815691 | 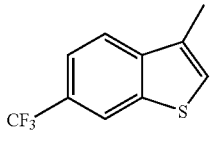 | 2 | 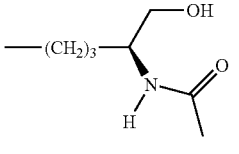 | 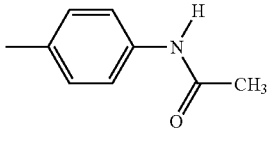 | N | 241 |
| 815692 | 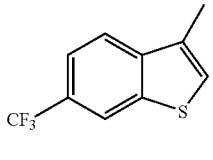 | 2 | 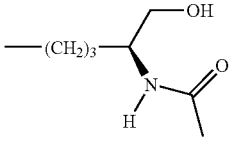 | 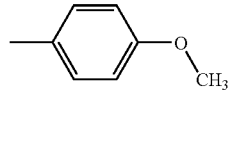 | N | 191 |
| 815694 | 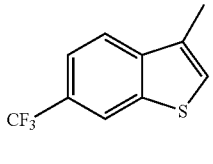 | 2 | 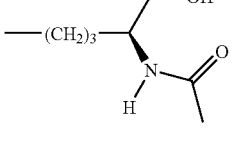 | 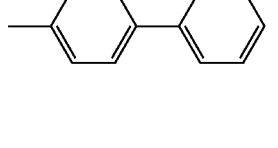 | N | 197 |
| 815695 | 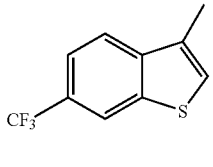 | 2 | 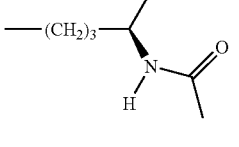 | 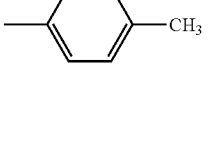 | N | 198 |
| 815696 | 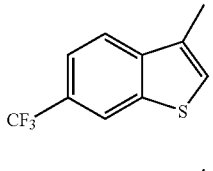 | 2 | 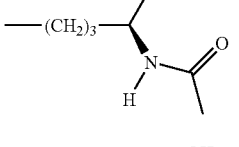 | 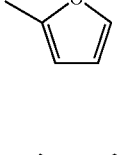 | N | 871 |
| 815697 | 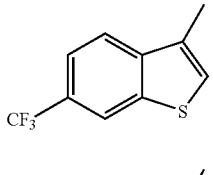 | 2 | 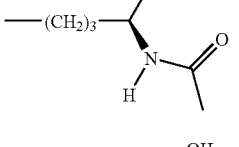 | 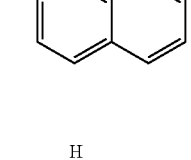 | N | 294 |
| 815698 | 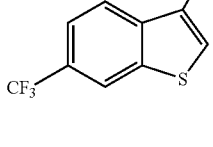 | 2 | 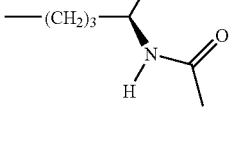 | 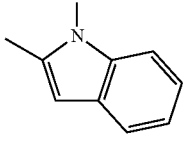 | N | 329 |

TABLE 2-continued
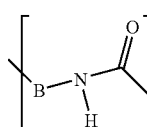
| No. | R | n | | R₂ | Y | D₃K₁ (nM) |
|---|---|---|---|---|---|---|
| 815700 | 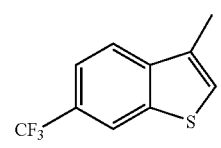 | 2 | 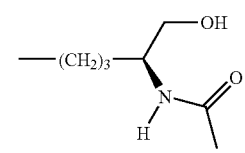 | 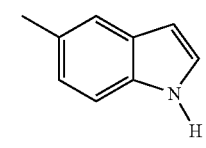 | N | 128 |
| 815702 | 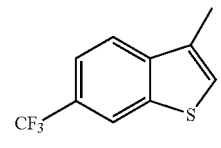 | 2 | 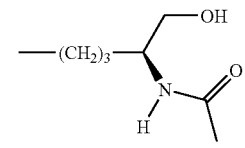 | 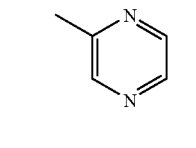 | N | 439 |
| 815704 | 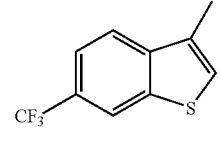 | 2 | 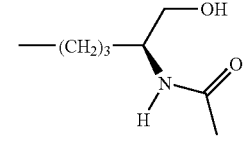 | 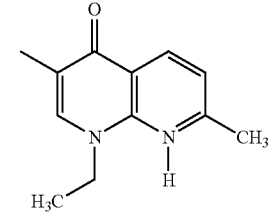 | N | 137 |
| 815708 | 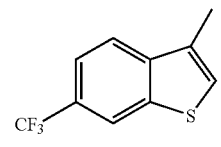 | 2 | 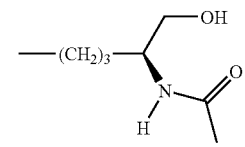 | 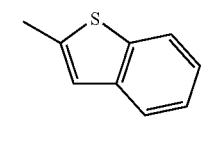 | N | 180 |
| 815709 | 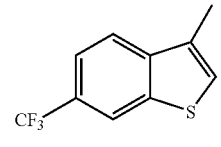 | 2 | 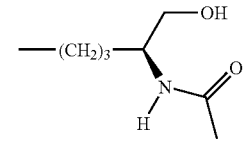 | 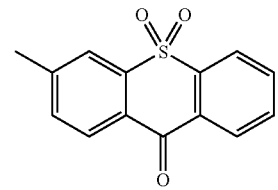 | N | 124 |
| 815710 | 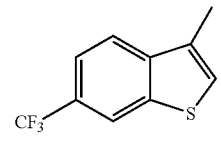 | 2 | 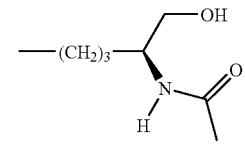 | 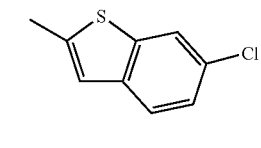 | N | 210 |
| 816315 | 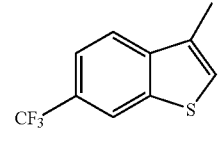 | 2 | 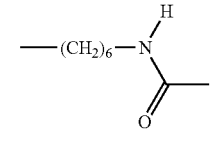 | 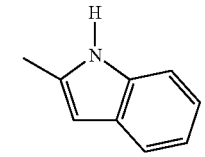 | N | 3.7 |

TABLE 2-continued
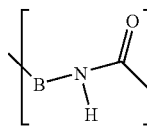
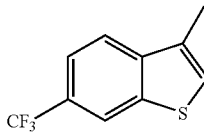
| No. | R | n | | R₂ | Y | D₃K₁ (nM) |
|---|---|---|---|---|---|---|
| 826738 | 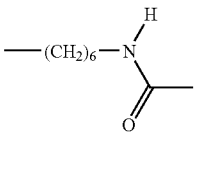 | 2 |  | 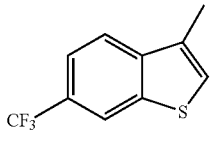 | N | 6.1 |
| 826739 | 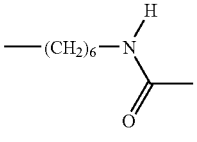 | 2 | 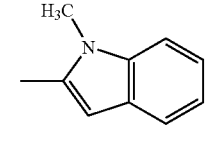 | 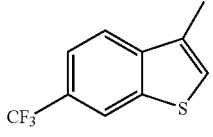 | N | 2.1 |
| 826740 | 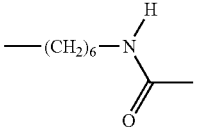 | 2 | 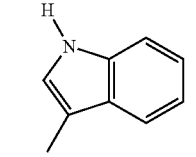 | 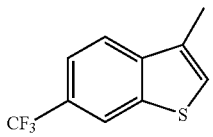 | N | 44 |
| 826741 | 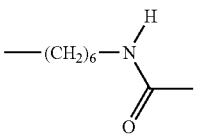 | 2 | 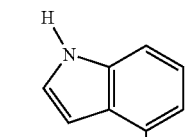 | 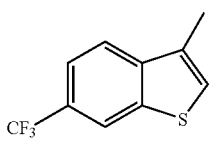 | N | 9.8 |
| 816316 | 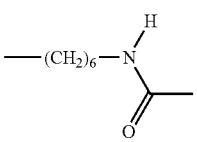 | 2 | 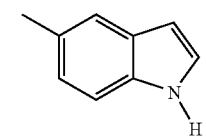 | 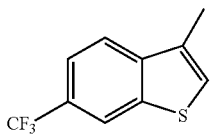 | N | 2.7 |
| 826742 | 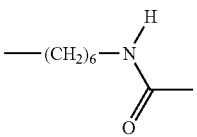 | 2 | 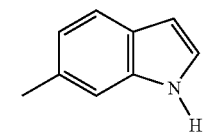 | 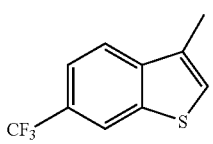 | N | 1.7 |
| 826743 | 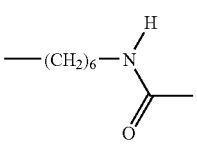 | 2 | 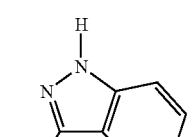 | | N | 15 |

TABLE 2-continued
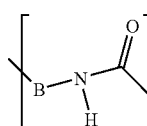
| No. | R | n | | R₂ | Y | D₃K₁ (nM) |
|---|---|---|---|---|---|---|
| 826744 | 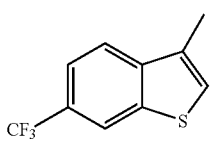 | 2 | 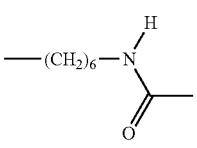 | 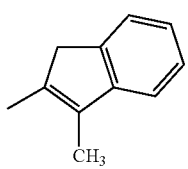 | N | 4 |
| 826745 | 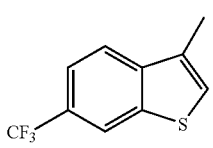 | 2 | 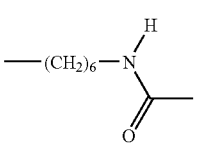 | 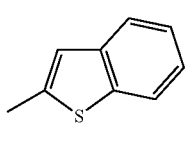 | N | 8.8 |
| 826746 | 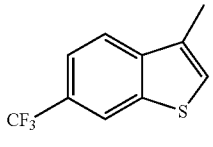 | 2 | 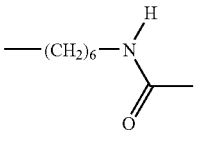 | 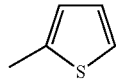 | N | 0.8 |
| 826747 | 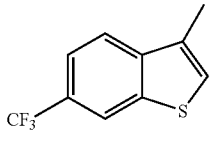 | 2 | 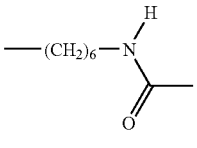 | 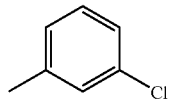 | N | 0.12 |
| 826748 | 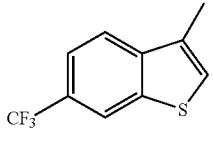 | 2 | 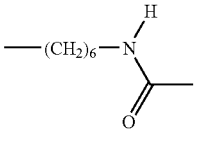 | 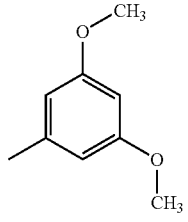 | N | 4.9 |
| 826749 | 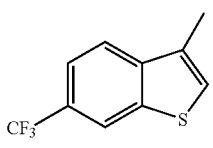 | 2 | 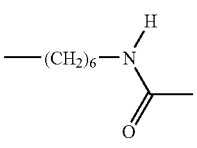 | 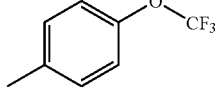 | N | 8.7 |
| 826750 | 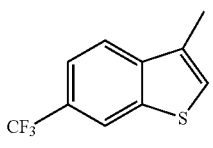 | 2 | 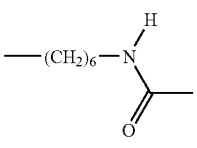 | 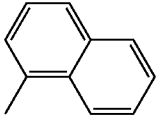 | N | 3.2 |

TABLE 2-continued
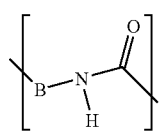
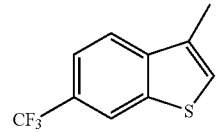
| No. | R | n | [B-N-C(=O)] group | R₂ | Y | D₃K₁ (nM) |
|---|---|---|---|---|---|---|
| 826751 | 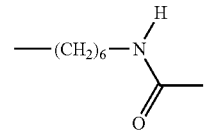 | 2 | —(CH₂)₆—NHC(O)— | 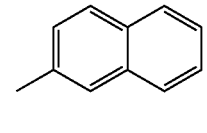 | N | 2.8 |
| 826752 | 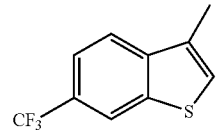 | 2 | —(CH₂)₆—NHC(O)— | 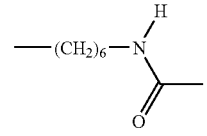 | N | 14 |
| 826753 | 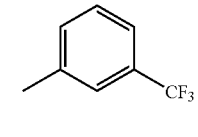 | 2 | —(CH₂)₆—NHC(O)— | 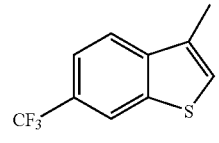 | N | 4.4 |
| 827730 | 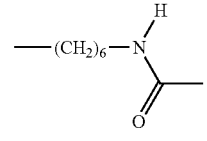 | 2 | —(CH₂)₆—NHC(O)— | 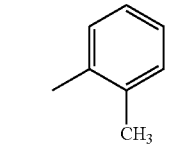 | N | 2.7 |
| 826754 | 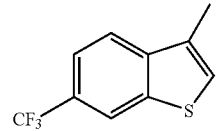 | 2 | —(CH₂)₆—NHC(O)— | 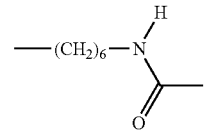 | N | 3.2 |
| 826764 | 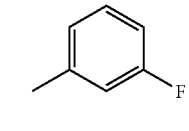 | 2 | —(CH₂)₅—NHC(O)— | 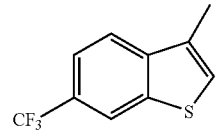 | N | 7.8 |
| 826765 | 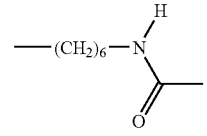 | 2 | —(CH₂)₅—NHC(O)— | 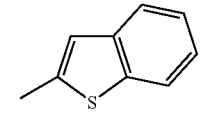 | N | 23 |

TABLE 2-continued
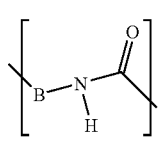
| No. | R | n | | R2 | Y | D3K1 (nM) |
|---|---|---|---|---|---|---|
| 826766 | 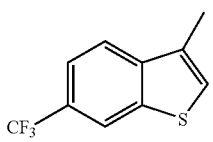 | 2 | 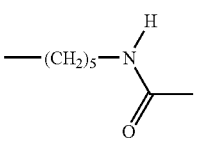 | 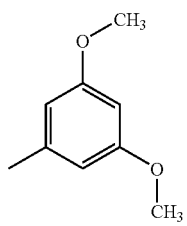 | N | 11 |
| 826767 | 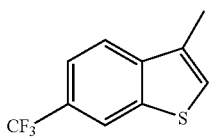 | 2 | 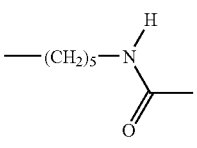 | 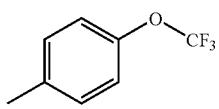 | N | 14 |
| 826768 | 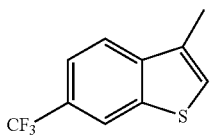 | 2 | 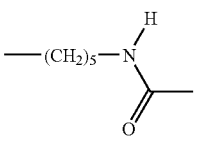 | 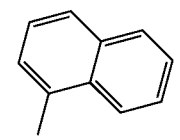 | N | 23 |
| 826769 | 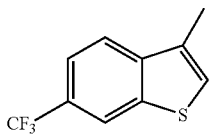 | 2 | 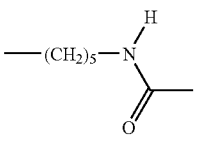 | 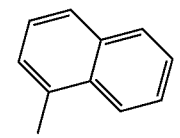 | N | 7 |
| 826770 | 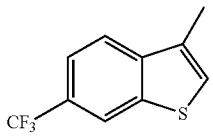 | 2 | 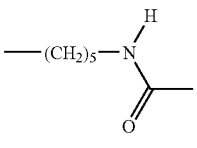 | 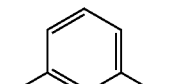 | N | 14 |
| 826771 | 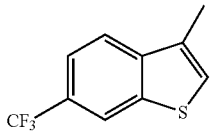 | 2 | 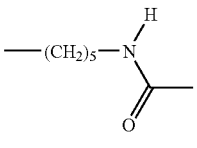 | 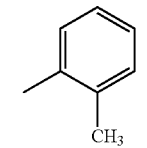 | N | 6.7 |
| 826772 | 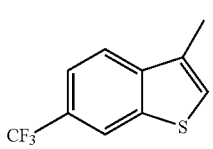 | 2 | 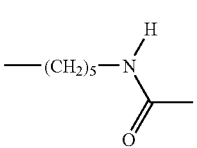 | 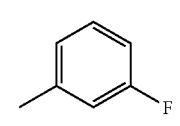 | N | 7.8 |

TABLE 2-continued
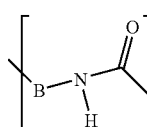
| No. | R | n | | R2 | Y | D3K1 (nM) |
|---|---|---|---|---|---|---|
| 826773 | 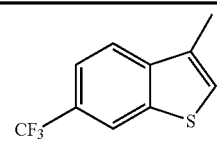 | 2 | 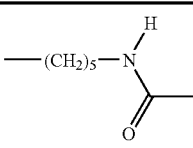 | 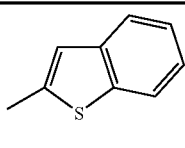 | N | 11 |
| 826794 | 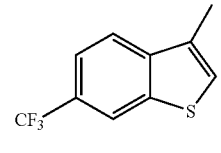 | 2 | 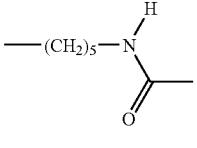 | 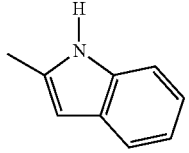 | N | 11.1 |
| 826795 | 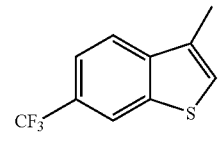 | 2 | 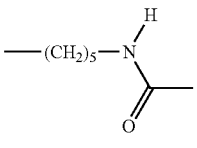 | 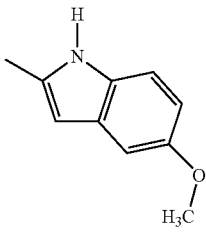 | N | 13.9 |
| 826796 | 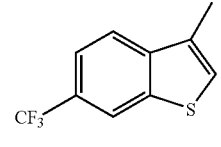 | 2 | 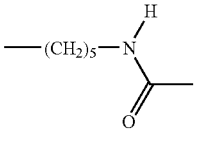 | 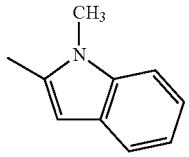 | N | 14.9 |
| 826797 | 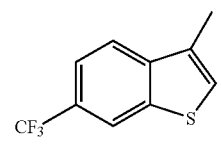 | 2 | 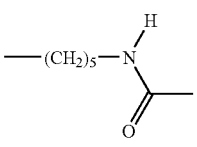 | 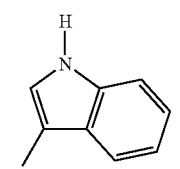 | N | 36.4 |
| 826798 | 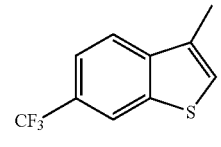 | 2 | 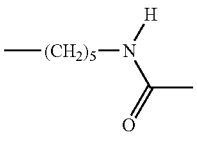 | 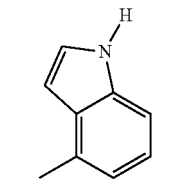 | N | 6.44 |
| 826799 | 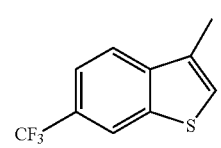 | 2 | 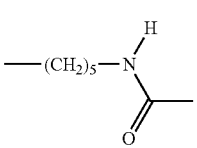 | 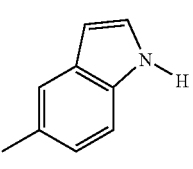 | N | 6.48 |

TABLE 2-continued
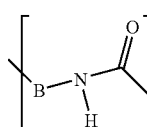
| No. | R | n | | R₂ | Y | D₃K₁ (nM) |
|---|---|---|---|---|---|---|
| 826800 | 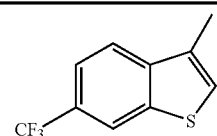 | 2 | 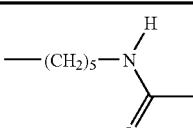 | 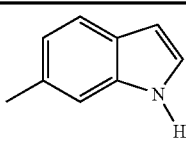 | N | 27.2 |
| 826801 | 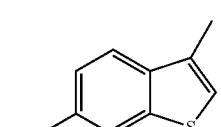 | 2 | 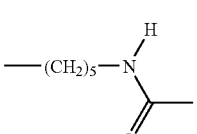 | 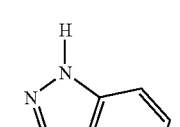 | N | 49.8 |
| 826802 | 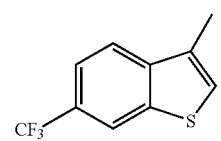 | 2 | 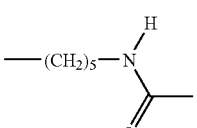 | 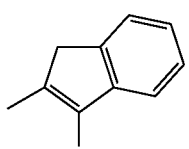 | N | 16.9 |
| 826803 | 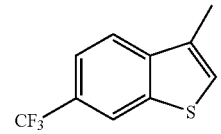 | 2 | 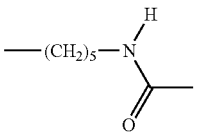 | 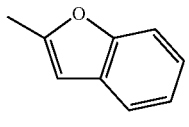 | N | 16.9 |
| 815870 | 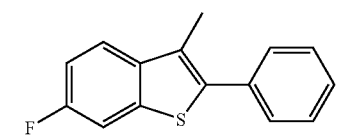 | 2 | 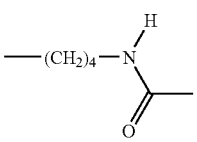 | 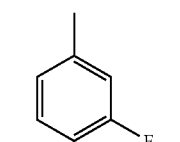 | N | 28.4 |
| 815871 | 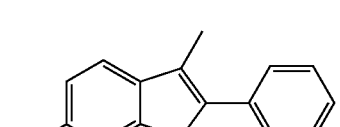 | 2 | 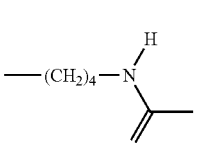 | 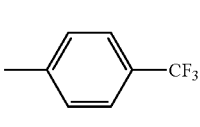 | N | 796 |
| 815872 | 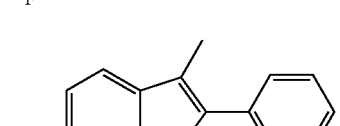 | 2 | 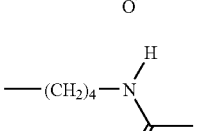 | 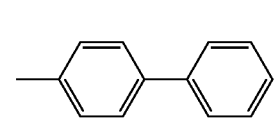 | N | 567 |
| 815873 | 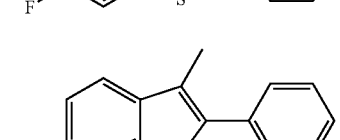 | 2 | 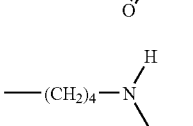 | 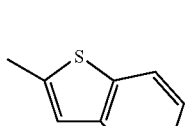 | N | 263 |

TABLE 2-continued
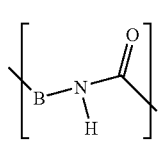
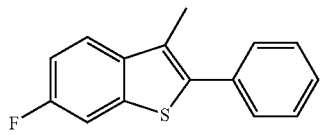
| No. | R | n | | R₂ | Y | D₃K₁ (nM) |
|---|---|---|---|---|---|---|
| 815874 | 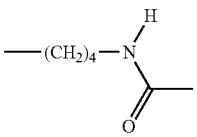 | 2 | 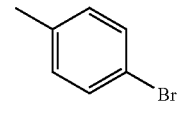 | 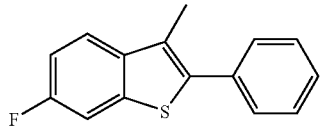 | N | 282 |
| 815878 | 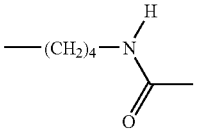 | 2 | 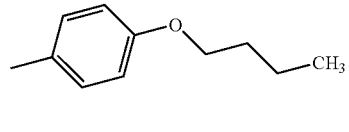 | 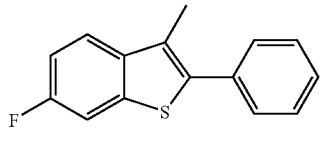 | N | 326 |
| 815879 | 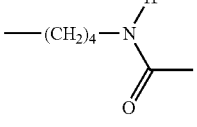 | 2 | 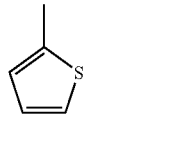 | 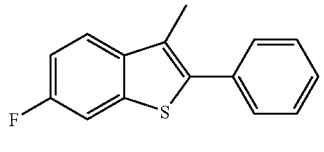 | N | 292 |
| 815880 | 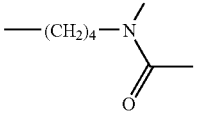 | 2 | 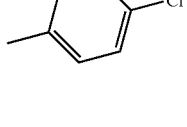 | 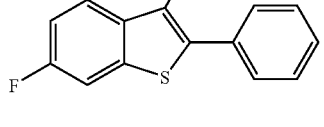 | N | 837 |
| 815883 | 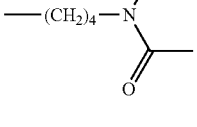 | 2 | 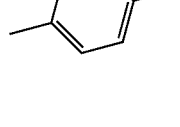 | 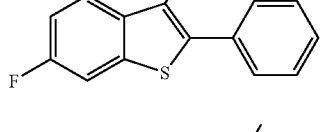 | N | 339 |
| 815884 | 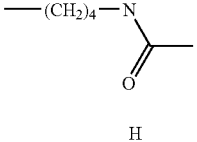 | 2 | 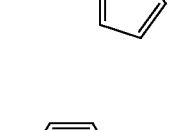 | 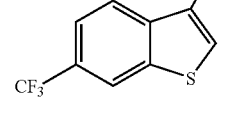 | N | 296 |
| 827734 | 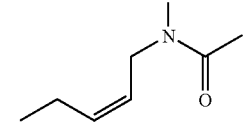 | 2 | 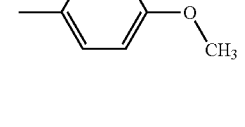 | 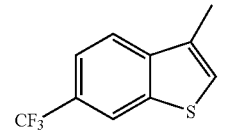 | N | 37.3 |
| 827735 | 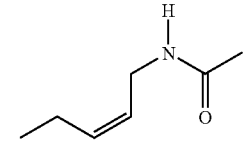 | 2 | 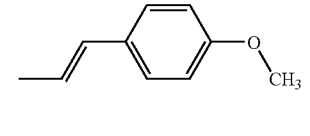 | | N | 24.4 |

TABLE 2-continued

| No. | R | n | | R₂ | Y | D₃K₁ (nM) |
|---|---|---|---|---|---|---|
| 827736 | 3-methyl-6-(trifluoromethyl)benzothiophene | 2 | pent-2-enyl-NH-C(O)- | 1-methyl-1-phenylcyclopropyl | N | 173 |
| 827737 | 3-methyl-6-(trifluoromethyl)benzothiophene | 2 | pent-2-enyl-NH-C(O)- | 3-ethyl-2,2-dimethyl-1-acetylcyclobutyl | N | 108 |
| 827738 | 3-methyl-6-(trifluoromethyl)benzothiophene | 2 | pent-2-enyl-NH-C(O)- | 4-methoxyphenyl | N | 22.6 |
| 827739 | 3-methyl-6-(trifluoromethyl)benzothiophene | 2 | pent-2-enyl-NH-C(O)- | 4-methoxystyryl | N | 22.4 |
| 827740 | 3-methyl-6-(trifluoromethyl)benzothiophene | 2 | pent-2-enyl-NH-C(O)- | 1-phenylcyclopropyl | N | 397 |
| 827741 | 3-methyl-6-(trifluoromethyl)benzothiophene | 2 | pent-2-enyl-NH-C(O)- | 3-ethyl-2,2-dimethyl-1-acetylcyclobutyl | N | 246 |
| 827742 | 3-methyl-6-(trifluoromethyl)benzothiophene | 2 | pent-2-enyl-NH-C(O)- | 2-methyl-1H-indol-3-yl | N | 21.3 |

TABLE 2-continued
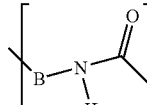
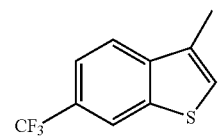
| No. | R | n | (CH₂)ₙ | R₂ | Y | D₃K₁ (nM) |
|---|---|---|---|---|---|---|
| 827743 | 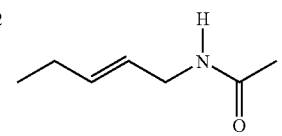 | 2 | 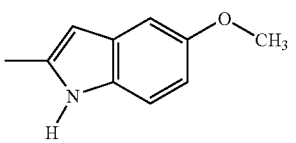 | 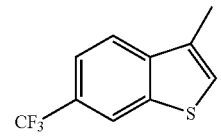 | N | 22.4 |
| 827744 | 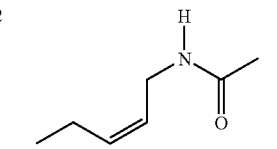 | 2 | 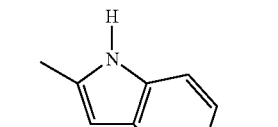 | 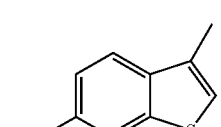 | N | 18.3 |
| 827745 | 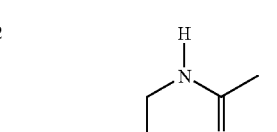 | 2 | 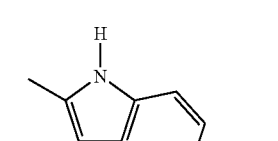 | 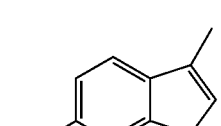 | N | 10 |
| 815541A HCl Salt HMR 2554 | 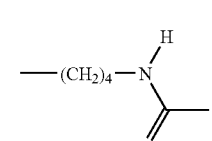 | 2 | 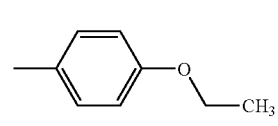 | 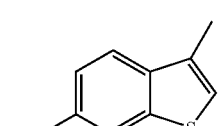 | N | 3.45 |
| 815547A HCl Salt | 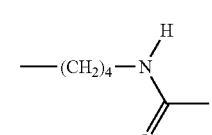 | 2 | 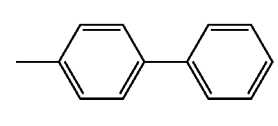 | 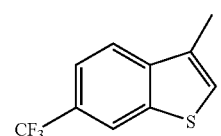 | N | 3.43 |
| 816692 | 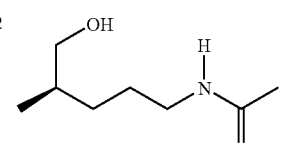 | 2 | 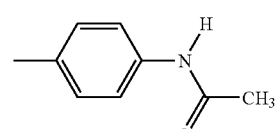 | 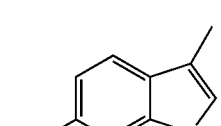 | N | 474 |
| 816693 | 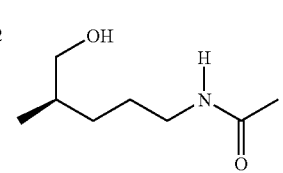 | 2 | 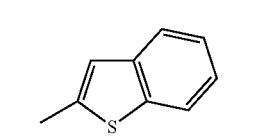 | | N | 355 |

TABLE 2-continued
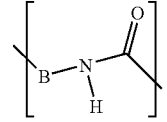
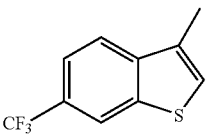
| No. | R | n | | R2 | Y | D3K1 (nM) |
|---|---|---|---|---|---|---|
| 816701 | 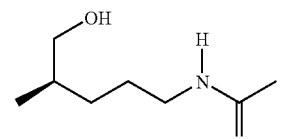 | 2 | 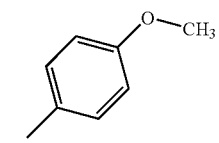 | 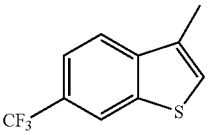 | N | 109 |
| 816704 | 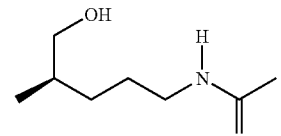 | 2 | 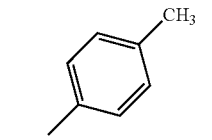 | 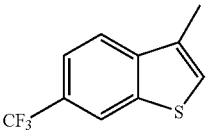 | N | 353 |
| 816706 | 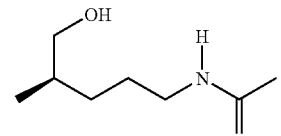 | 2 | 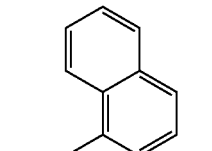 | 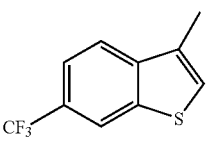 | N | 464 |
| 816707 | 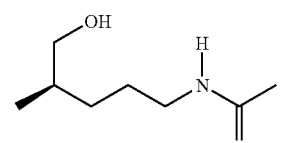 | 2 | 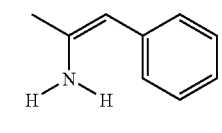 | 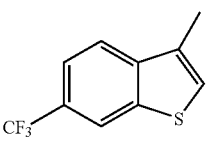 | N | 351 |
| 816710 | 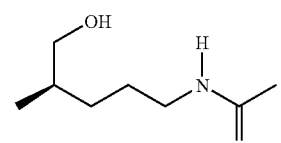 | 2 | 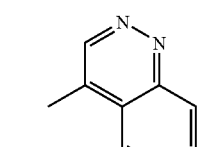 | 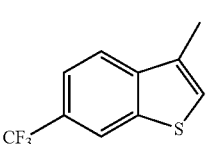 | N | 406 |
| 816711 | 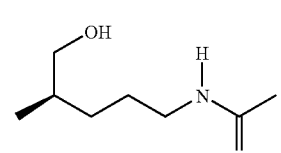 | 2 | 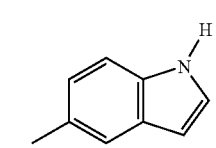 | 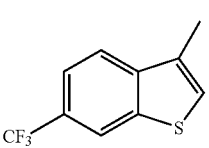 | N | 547 |
| 816713 | 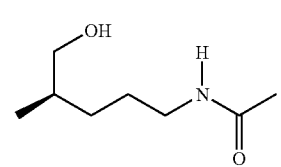 | 2 | 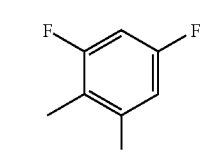 | | N | 191 |

TABLE 2-continued
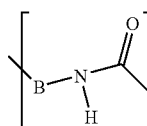
| No. | R | n | | R₂ | Y | D₃K₁ (nM) |
|---|---|---|---|---|---|---|
| 816715 | 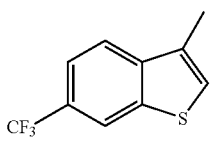 | 2 | 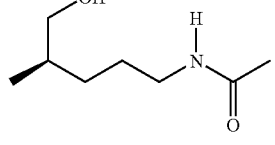 | 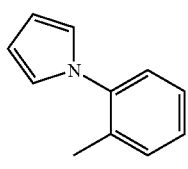 | N | 243 |
| 816716 | 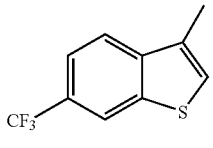 | 2 | 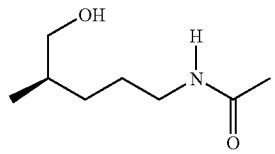 | 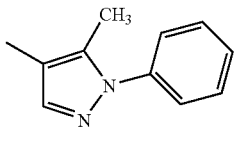 | N | 837 |
| 816719 | 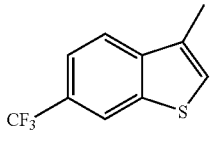 | 2 | 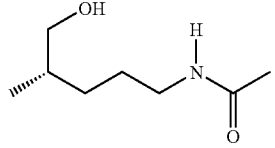 | 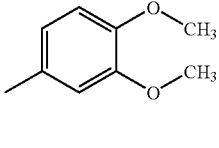 | N | 479 |
| 816720 | 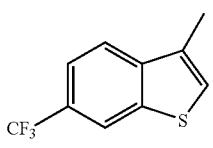 | 2 | 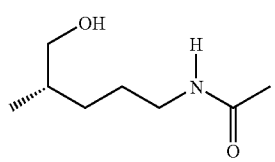 | 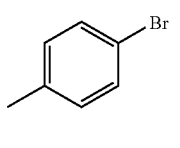 | N | 264 |
| 816721 | 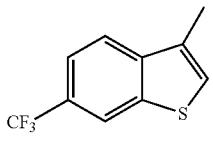 | 2 | 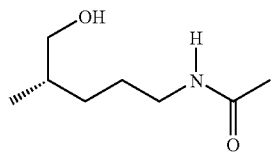 | 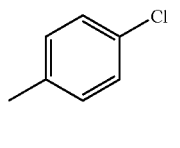 | N | 238 |
| 816722 | 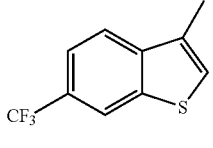 | 2 | 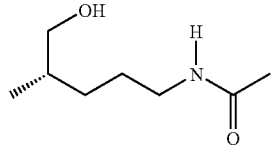 | 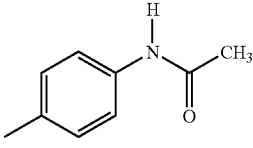 | N | 173 |
| 816723 | 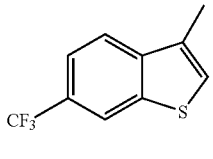 | 2 | 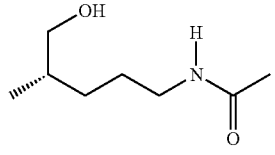 | 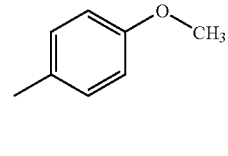 | N | 160 |

TABLE 2-continued
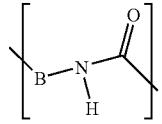
| No. | R | n | | R2 | Y | D3K1 (nM) |
|---|---|---|---|---|---|---|
| 816725 | 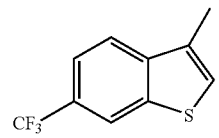 | 2 | 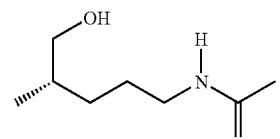 | 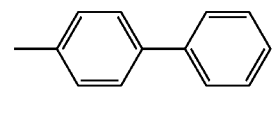 | N | 559 |
| 816726 | 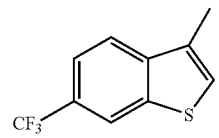 | 2 | 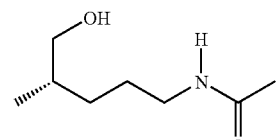 | 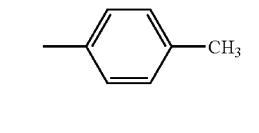 | N | 349 |
| 816727 | 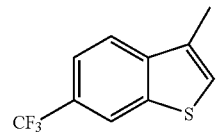 | 2 | 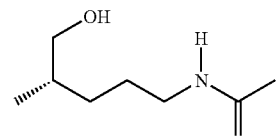 | 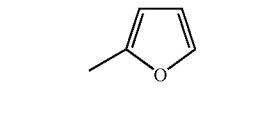 | N | 492 |
| 816728 | 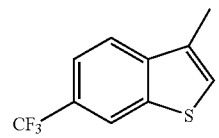 | 2 | 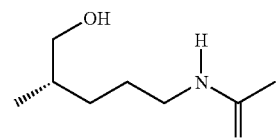 | 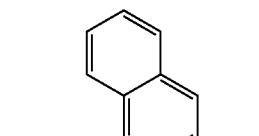 | N | 222 |
| 816729 | 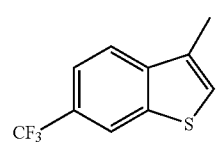 | 2 | 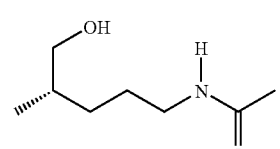 | 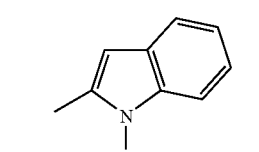 | N | 175 |
| 816730 | 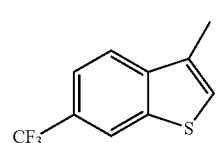 | 2 | 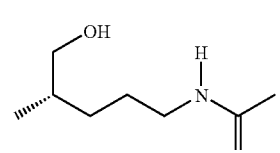 | 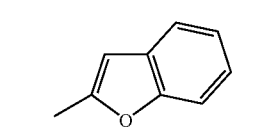 | N | 230 |
| 816733 | 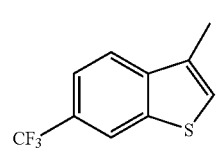 | 2 | 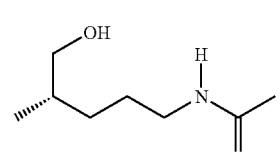 | 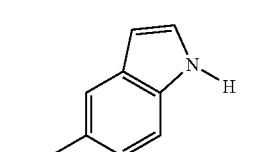 | N | 318 |

TABLE 2-continued
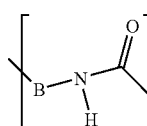
| No. | R | n | | R₂ | Y | D₃K₁ (nM) |
|---|---|---|---|---|---|---|
| 816736 | 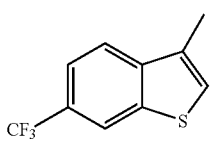 | 2 | 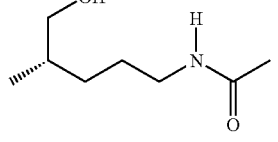 | 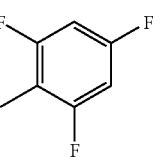 | N | 436 |
| 816738 | 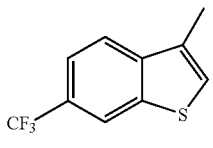 | 2 | 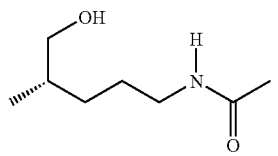 | 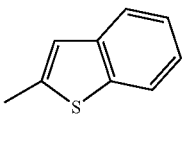 | N | 187 |
| 816741 | 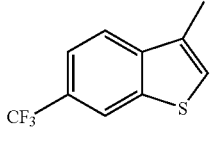 | 2 | 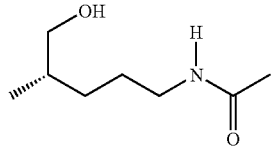 | 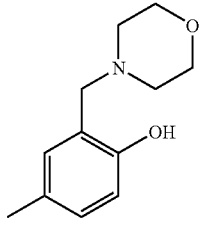 | N | 319 |
| 817147A HCl Hydrate | 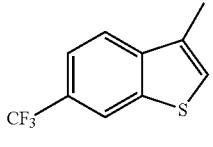 | 2 | —(CH₂)₄—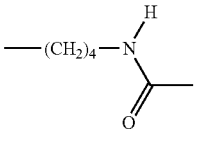 | 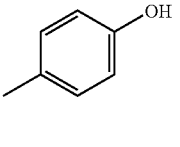 | N | 3.49 |
| 817140A HCl Salt | 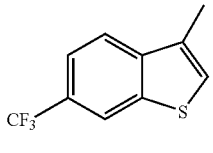 | 2 | —(CH₂)₄—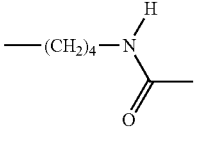 | 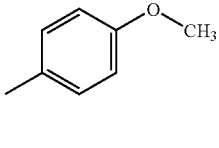 | N | 2.9 |
| 817386A | 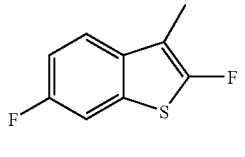 | 2 | —(CH₂)₄—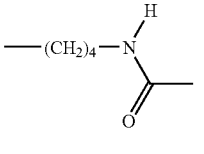 | 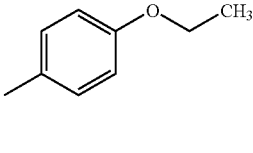 | N | 1.82 |
| 817402 | 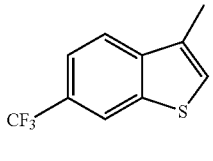 | 2 | 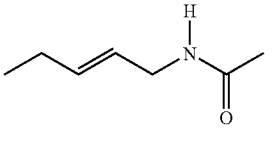 | 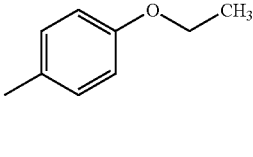 | N | 150 |

TABLE 2-continued

| No. | R | n | (CH₂)ₙ group | R₂ | Y | D₃K₁ (nM) |
|---|---|---|---|---|---|---|
| 817403 | 3-methyl-6-(trifluoromethyl)benzo[b]thiophene | 2 | pent-2-enyl-N-acetyl | 4-ethoxyphenyl | N | 110 |
| 817484 | 3-methyl-2-phenyl-6-(trifluoromethyl)benzo[b]thiophene | 2 | —(CH₂)₄—NH-acetyl | benzo[1,3]dioxol-5-yl | N | 157 |
| 817500 | 2,6-difluoro-3-methylbenzo[b]thiophene | 2 | —(CH₂)₄—NH-acetyl | 2-methylbenzo[b]thiophene | N | 0.581 |
| 817501 | 2,6-difluoro-3-methylbenzo[b]thiophene | 2 | —(CH₂)₄—NH-acetyl | 4-biphenyl | N | 0.5 |
| 817502 | 2,6-difluoro-3-methylbenzo[b]thiophene | 2 | —(CH₂)₄—NH-acetyl | 2,6-difluoro-3-methylphenyl | N | 3.23 |
| 817503 | 2,6-difluoro-3-methylbenzo[b]thiophene | 2 | —(CH₂)₄—NH-acetyl | 2-methylthiophene | N | 1.23 |
| 817504 | 2,6-difluoro-3-methylbenzo[b]thiophene | 2 | —(CH₂)₄—NH-acetyl | 4-chlorophenyl | N | 0.799 |
| 817505 HCl Salt | 2,6-difluoro-3-methylbenzo[b]thiophene | 2 | —(CH₂)₄—NH-acetyl | 2-methylbenzo[b]thiophene | N | 3.01 |

TABLE 2-continued

| No. | R | n | | R₂ | Y | D₃K₁ (nM) |
|---|---|---|---|---|---|---|
| 817506 | 3-methyl-2,6-difluorobenzothiophene | 2 | —(CH₂)₄—NH—C(=O)— | 4-CF₃-phenyl | N | 3.8 |
| 817507 | 3-methyl-2,6-difluorobenzothiophene | 2 | —(CH₂)₄—NH—C(=O)— | 4-Br-phenyl | N | 2.52 |
| 817508 | 3-methyl-2,6-difluorobenzothiophene | 2 | —(CH₂)₄—NH—C(=O)— | 4-OCH₃-phenyl | N | 0.826 |
| 817509 | 3-methyl-2,6-difluorobenzothiophene | 2 | —(CH₂)₄—NH—C(=O)— | 6-methylnaphthalen-2-yl | N | 0.958 |
| 818551 | 3-methyl-6-CF₃-benzothiophene | 2 | 2-ethyl-4-hydroxymethyl chain-NH-C(=O) | 4-(NHCOCH₃)-phenyl | N | 547 |
| 818552 | 3-methyl-6-CF₃-benzothiophene | 2 | 2-ethyl-4-hydroxymethyl chain-NH-C(=O) | 2-methylindol-1-yl | N | 76.6 |
| 818554 | 3-methyl-6-CF₃-benzothiophene | 2 | 2-ethyl-4-hydroxymethyl chain-NH-C(=O) | 4-OCH₃-phenyl | N | 267 |
| 818593ES | 3-methyl-6-CF₃-benzothiophene | 2 | 2-ethyl-4-hydroxymethyl chain-NH-C(=O) | 3-benzoylphenyl | N | 314 |

TABLE 2-continued
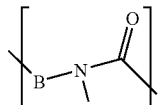
| No. | R | n | | R₂ | Y | D₃K₁ (nM) |
|---|---|---|---|---|---|---|
| 818597ES | 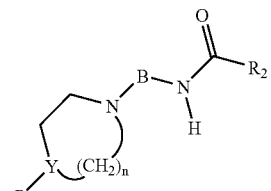 | 2 | 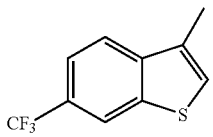 | 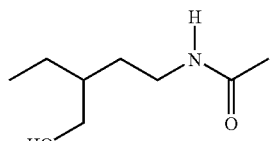 | N | 849 |
| 818601ES | 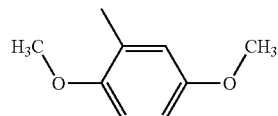 | 2 | 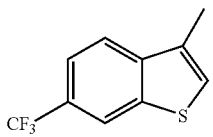 | 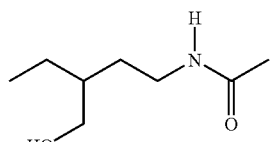 | N | 414 |
| 818608ES | 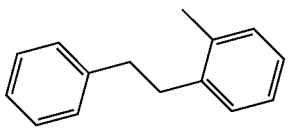 | 2 | 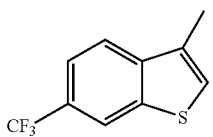 | 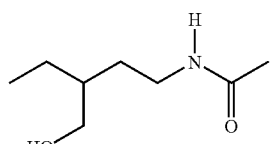 | N | 442 |
| 818610ES | 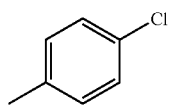 | 2 | 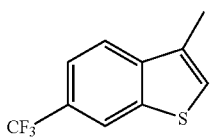 | 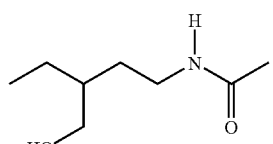 | N | 464 |
| 818612ES | 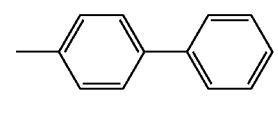 | 2 | 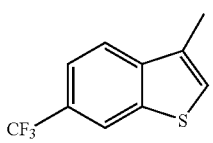 | 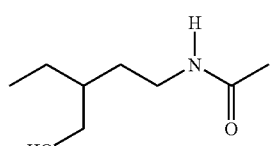 | N | 742 |
| 818619ES | 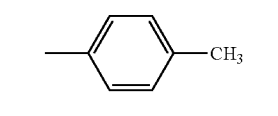 | 2 | 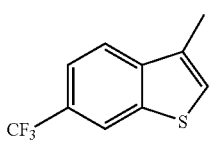 | 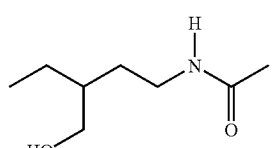 | N | 324 |
| 818620ES | 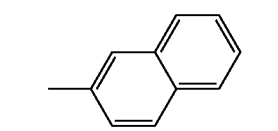 | 2 | 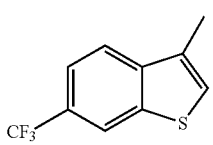 | 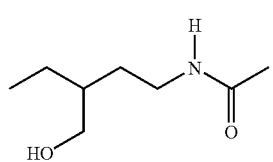 | N | 246 |

TABLE 2-continued
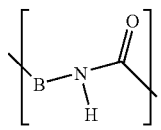
| No. | R | n | | $R_2$ | Y | $D_3K_1$ (nM) |
|---|---|---|---|---|---|---|
| 818634ES | 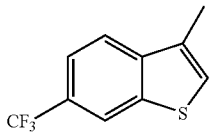 | 2 | 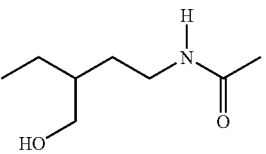 | 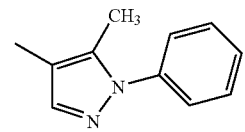 | N | 305 |
| 818900ES | 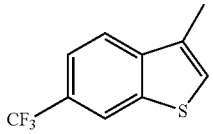 | 2 | 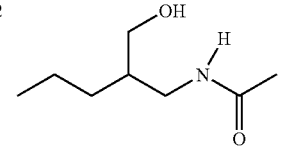 | 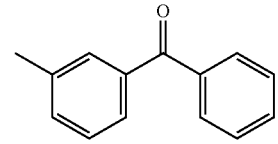 | N | 135 |
| 818901ES | 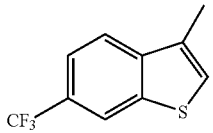 | 2 | 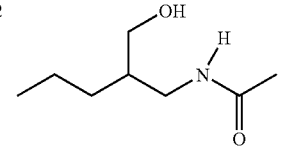 | 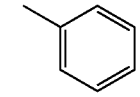 | N | 131 |
| 818902ES | 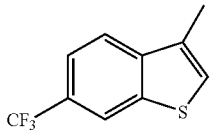 | 2 | 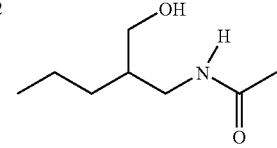 | 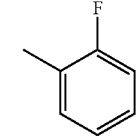 | N | 325 |
| 818903ES | 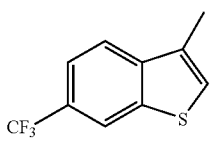 | 2 | 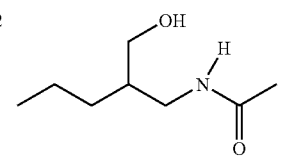 | 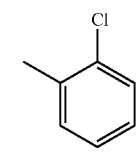 | N | 339 |
| 818905ES | 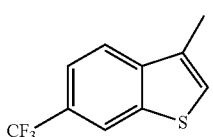 | 2 | 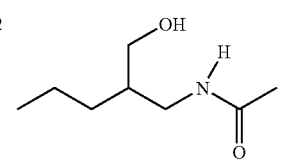 | 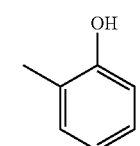 | N | 188 |
| 818907ES | 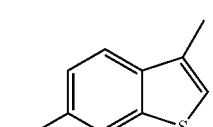 | 2 | 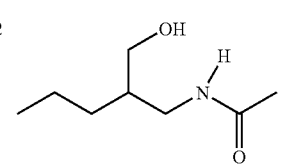 | 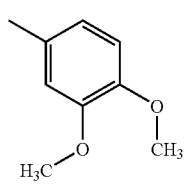 | N | 166 |

TABLE 2-continued
| No. | R | n | | R₂ | Y | D₃K₁ (nM) |
|---|---|---|---|---|---|---|
| 818910ES | 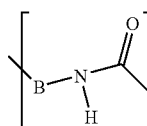 | 2 | 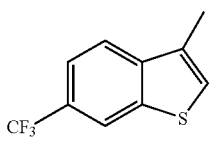 | 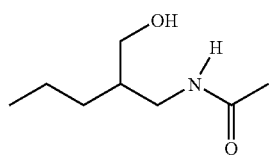 | N | 190 |
| 818913ES | 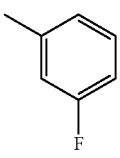 | 2 | 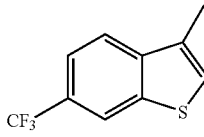 | 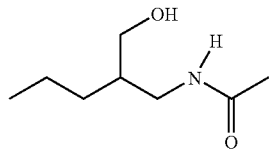 | N | 142 |
| 818914ES | 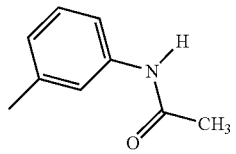 | 2 | 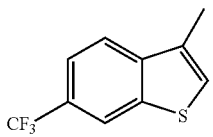 | 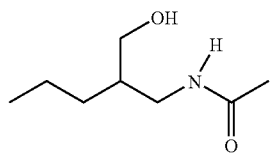 | N | 285 |
| 818915ES |  | 2 | 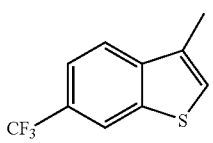 | 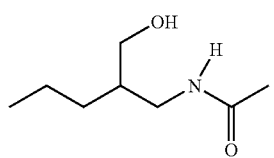 | N | 191 |
| 818916ES |  | 2 | 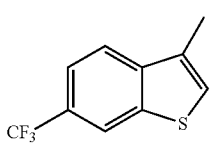 | 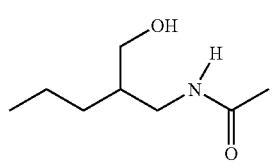 | N | 128 |
| 818917ES | 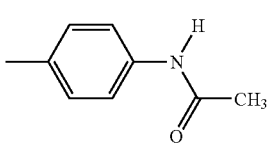 | 2 | 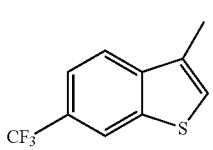 | 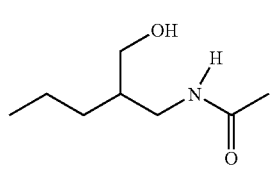 | N | 101 |
| 818918ES | 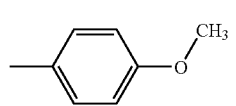 | 2 | 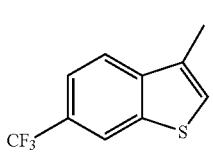 | 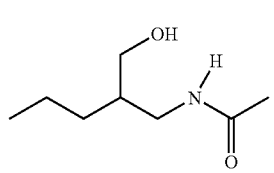 | N | 277 |

TABLE 2-continued
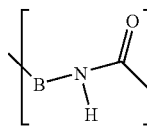
| No. | R | n | | R₂ | Y | D₃K₁ (nM) |
|---|---|---|---|---|---|---|
| 818919ES | 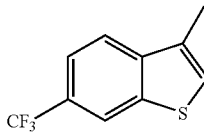 | 2 | 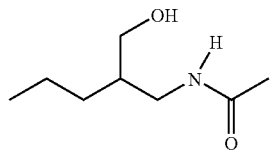 | 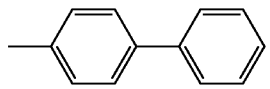 | N | 181 |
| 818921ES | 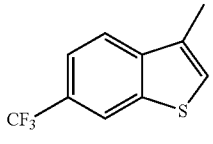 | 2 | 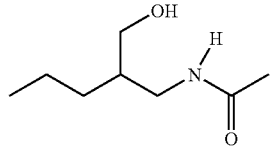 | 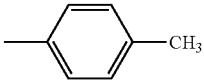 | N | 331 |
| 818923ES | 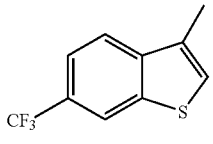 | 2 | 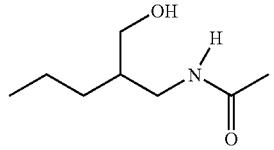 | 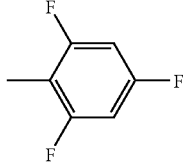 | N | 319 |
| 818924ES | 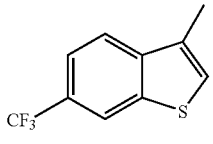 | 2 | 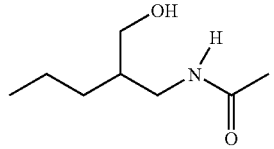 | 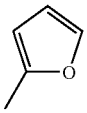 | N | 318 |
| 818925ES | 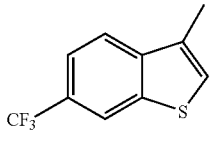 | 2 | 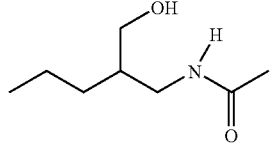 | 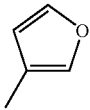 | N | 293 |
| 818926ES | 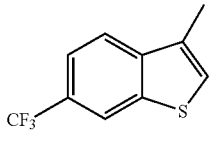 | 2 | 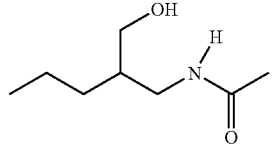 | 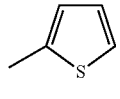 | N | 206 |
| 818927ES | 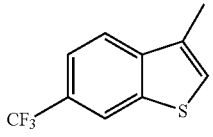 | 2 | 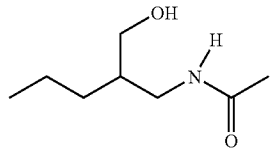 | 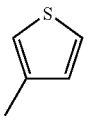 | N | 164 |

TABLE 2-continued
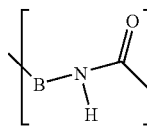
| No. | R | n | | R₂ | Y | D₃K₁ (nM) |
|---|---|---|---|---|---|---|
| 818928ES | 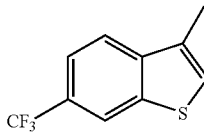 | 2 | 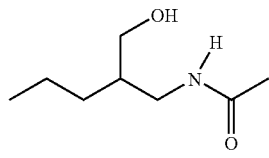 | 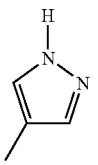 | N | 158 |
| 818929ES | 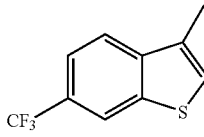 | 2 | 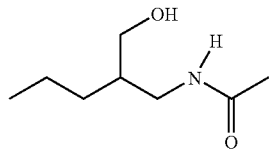 | 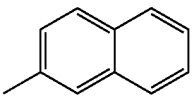 | N | 201 |
| 818930ES | 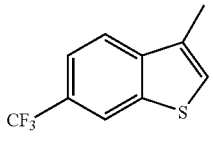 | 2 | 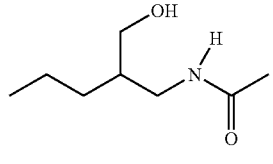 | 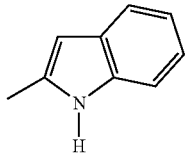 | N | 79.3 |
| 818931ES | 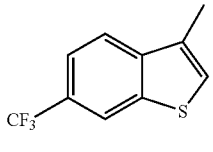 | 2 | 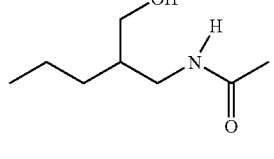 | 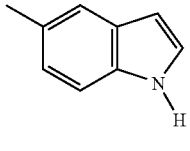 | N | 97.2 |
| 818932ES | 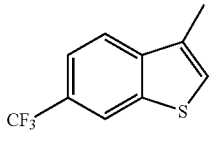 | 2 | 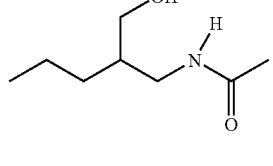 | 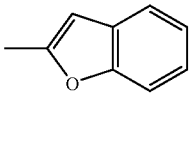 | N | 207 |
| 818934ES | 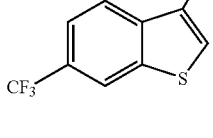 | 2 | 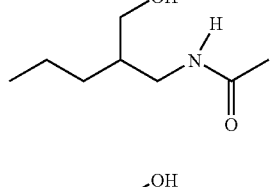 | 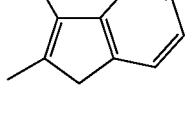 | N | 218 |
| 818935ES | 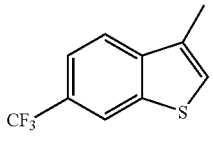 | 2 | 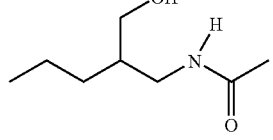 | 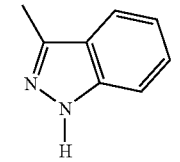 | N | 244 |

TABLE 2-continued
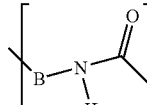
| No. | R | n | | R₂ | Y | D₃K₁ (nM) |
|---|---|---|---|---|---|---|
| 818937ES | 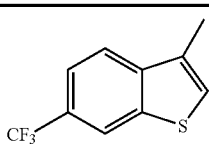 | 2 | 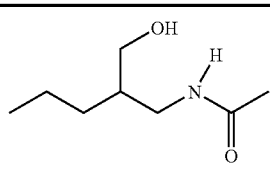 | 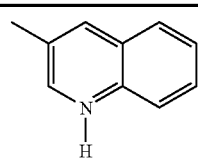 | N | 325 |
| 818938ES | 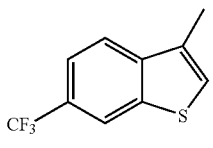 | 2 | 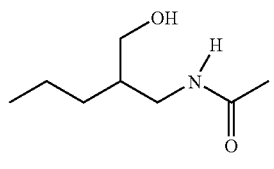 | 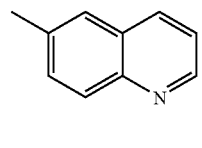 | N | 141 |
| 818940ES | 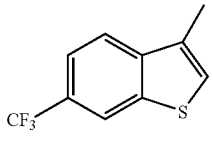 | 2 | 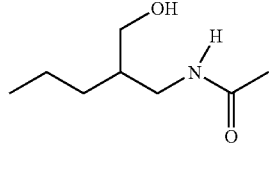 | 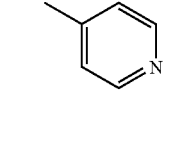 | N | 307 |
| 826699 | 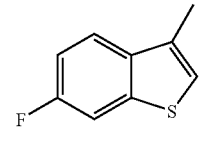 | 3 | 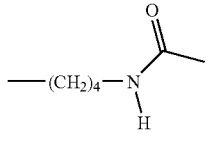 | 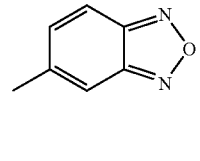 | N | 6.73 |
| 826762 | 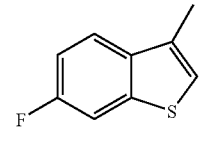 | 3 | 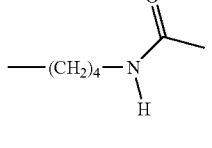 | 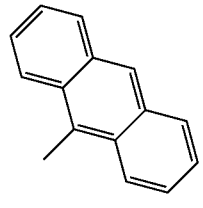 | N | 57 |
| 817276 | 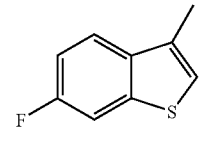 | 3 | 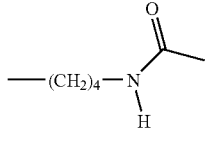 | 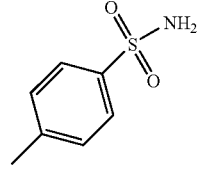 | N | 2.44 |
| 827120 | 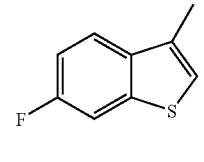 | 3 | 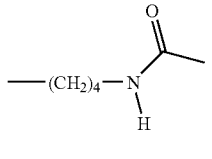 | 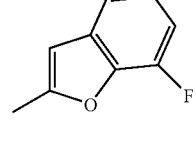 | N | 32.9 |

TABLE 2-continued
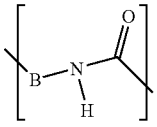
| No. | R | n | | R₂ | Y | D₃K₁ (nM) |
|---|---|---|---|---|---|---|
| 827121 | 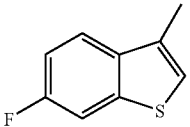 | 3 | 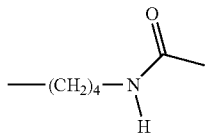 | 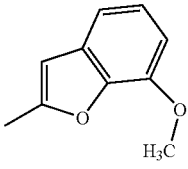 | N | 21.6 |
| 827122 | 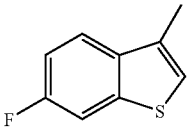 | 3 | 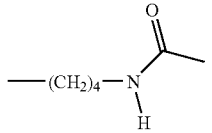 | 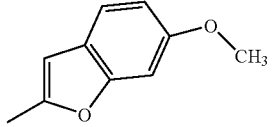 | N | 6.06 |
| 827123 | 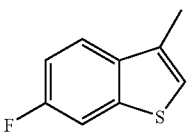 | 3 | 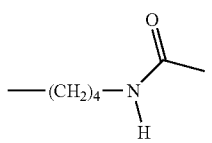 | 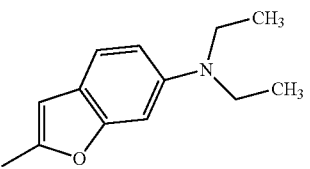 | N | 107 |
| 827124 | 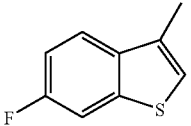 | 3 | 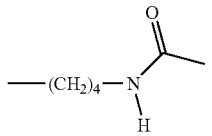 | 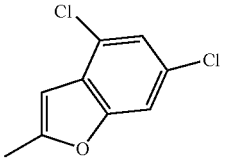 | N | 16.6 |
| 827125 | 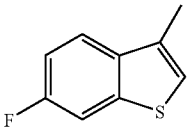 | 3 | 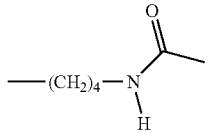 | 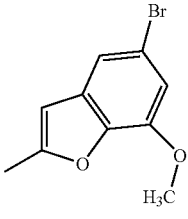 | N | 28.3 |
| 827126 | 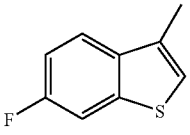 | 3 | 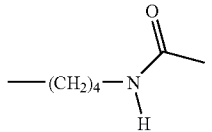 | 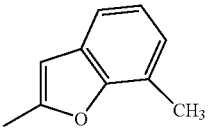 | N | 3.1 |

TABLE 2-continued
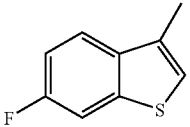
| No. | R | n | | R₂ | Y | D₃K₁ (nM) |
|---|---|---|---|---|---|---|
| 827127 | 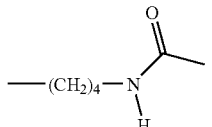 | 3 | 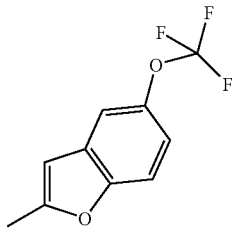 | 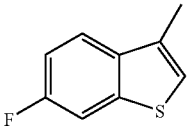 | N | 74.3 |
| 827128 | 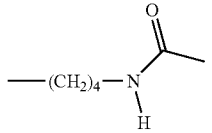 | 3 | 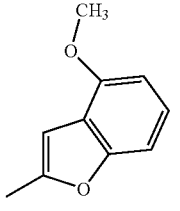 | 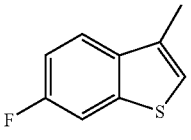 | N | 19.1 |
| 827129 | 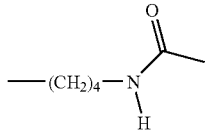 | 3 | 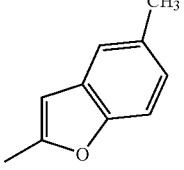 | 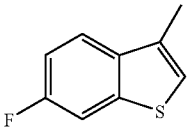 | N | 7.75 |
| 827130 | 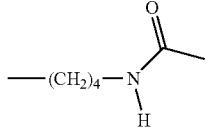 | 3 | 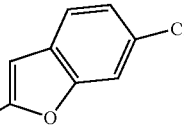 | 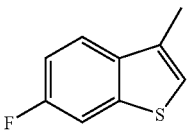 | N | 15.4 |
| 827131 | 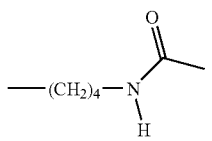 | 3 | 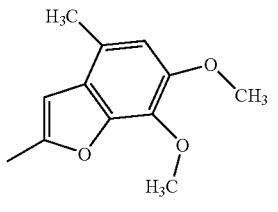 | 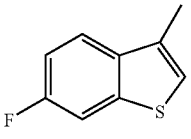 | N | 4.18 |
| 827132 | 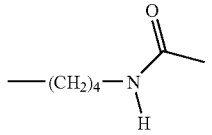 | 3 | 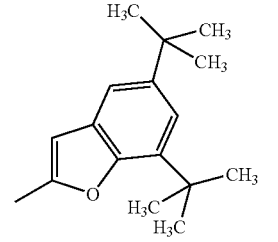 | | N | 129 |

TABLE 2-continued

| No. | R | n | [structure] | R₂ | Y | D₃K₁ (nM) |
|---|---|---|---|---|---|---|
| 827133 | 6-fluoro-3-methylbenzothiophene | 3 | —(CH₂)₄—NH—C(O)— | 2-methyl-7-ethoxybenzofuran | N | 12.6 |
| 827134 | 6-fluoro-3-methylbenzothiophene | 3 | —(CH₂)₃—NH—C(O)— | 2-thienyl | N | 62 |
| 827135 | 6-fluoro-3-methylbenzothiophene | 3 | —(CH₂)₃—NH—C(O)— | 3-chlorophenyl | N | 141 |
| 827136 | 6-fluoro-3-methylbenzothiophene | 3 | —(CH₂)₃—NH—C(O)— | 3,5-dimethoxyphenyl | N | 268 |
| 827138 | 6-fluoro-3-methylbenzothiophene | 3 | —(CH₂)₃—NH—C(O)— | 1-naphthyl | N | 166 |
| 827139 | 6-fluoro-3-methylbenzothiophene | 3 | —(CH₂)₃—NH—C(O)— | 2-naphthyl | N | 131 |
| 827141 | 6-fluoro-3-methylbenzothiophene | 3 | —(CH₂)₃—NH—C(O)— | 2-methoxyphenyl | N | 99 |

TABLE 2-continued
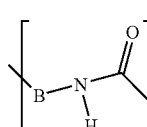
| No. | R | n | | R₂ | Y | D₃K₁ (nM) |
|---|---|---|---|---|---|---|
| 827142 | 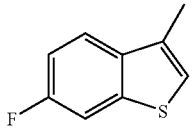 | 3 | 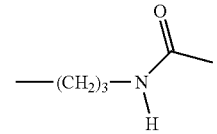 | 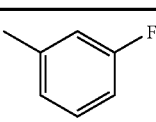 | N | 101 |
| 827143 | 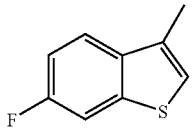 | 3 | 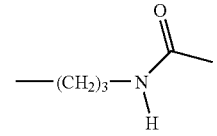 | 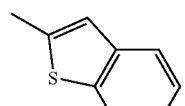 | N | 123 |
| 827159 | 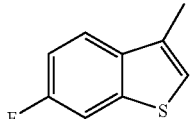 | 3 | 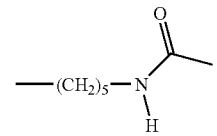 | 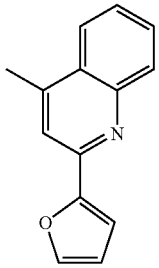 | N | 5.85 |
| 817258 | 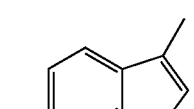 | 3 | 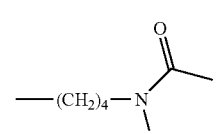 | 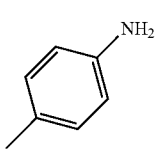 | N | 3.13 |
| 817259 | 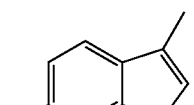 | 3 | 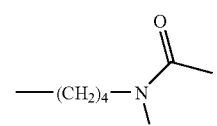 | 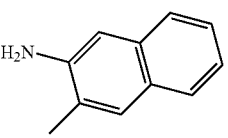 | N | 2.93 |
| 817262 | 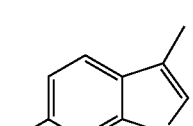 | 3 | 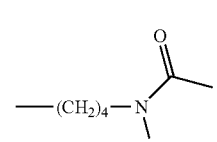 | 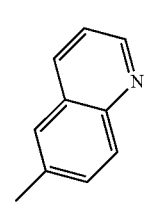 | N | 1.89 |
| 817264 | 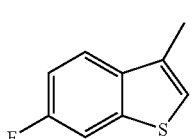 | 3 | 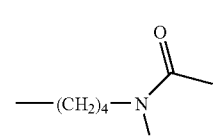 | 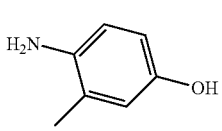 | N | 6.44 |

TABLE 2-continued
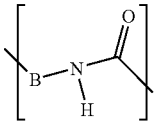
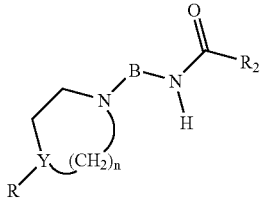
| No. | R | n | [structure] | R₂ | Y | D₃K₁ (nM) |
|---|---|---|---|---|---|---|
| 817265 | 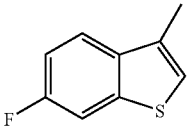 | 3 | —(CH₂)₄—NH—C(O)— 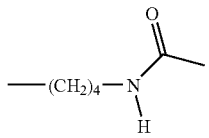 | 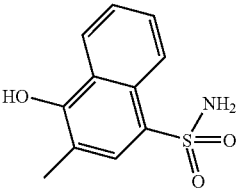 | N | 46 |
| 817266 | 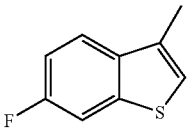 | 3 | —(CH₂)₄—NH—C(O)— | 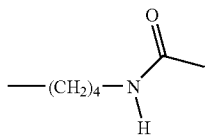 | N | 8.73 |
| 817267 | 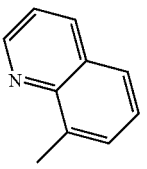 | 3 | —(CH₂)₄—NH—C(O)— | 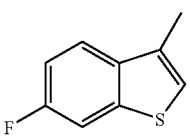 | N | 3.03 |
| 817268 | 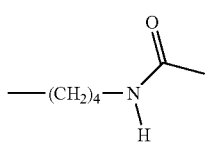 | 3 | —(CH₂)₄—NH—C(O)— | 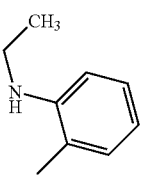 | N | 7.1 |
| 817269 | 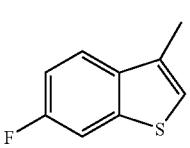 | 3 | —(CH₂)₄—NH—C(O)— | 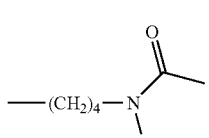 | N | 4.74 |
| 817263 | 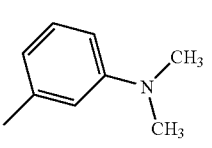 | 3 | —(CH₂)₄—NH—C(O)— | 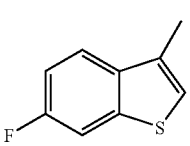 | N | 331 |

TABLE 2-continued
| No. | R | n | | R₂ | Y | D₃K₁ (nM) |
|---|---|---|---|---|---|---|
| 817271 | 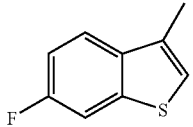 | 3 | 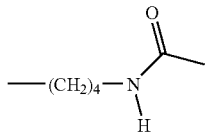 | 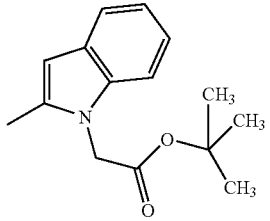 | N | 326 |
| 815674 | 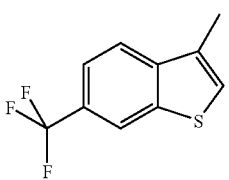 | 2 | 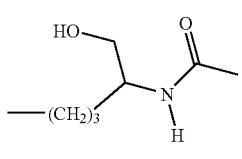 | 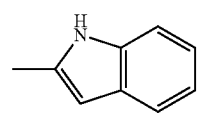 | N | 314 |
| 815676 | 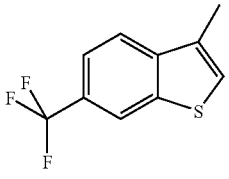 | 2 | 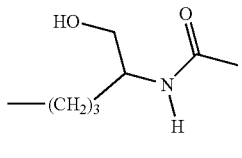 | 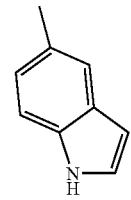 | N | 224 |
| 815677 | 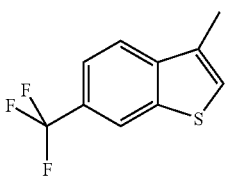 | 2 | 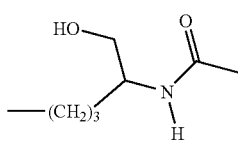 | 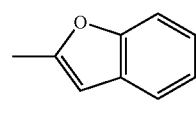 | N | 297 |
| 815679 | 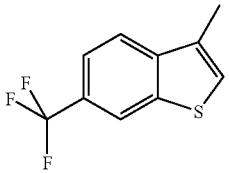 | 2 | 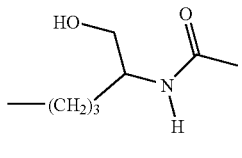 |  | N | 129 |
| 815680 | 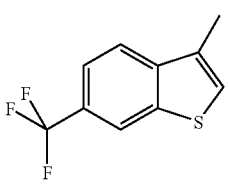 | 2 | 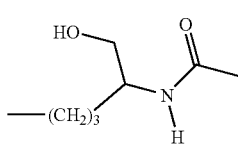 | 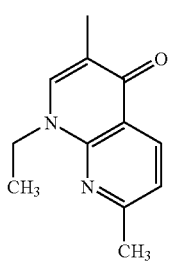 | N | 197 |

TABLE 2-continued
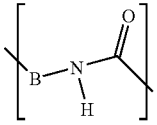
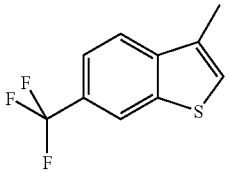
| No. | R | n | | R₂ | Y | D₃K₁ (nM) |
|---|---|---|---|---|---|---|
| 815681 | 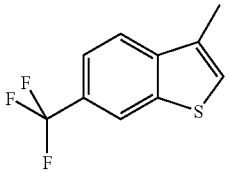 | 2 | 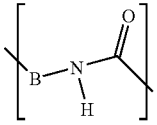 | 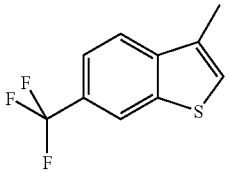 | N | 261 |
| 815683 | 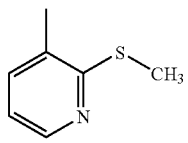 | 2 | 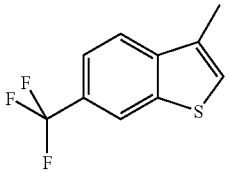 | 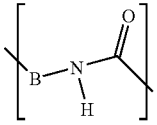 | N | 293 |
| 815684 | 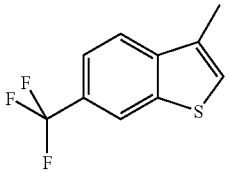 | 2 | 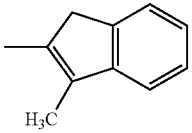 | 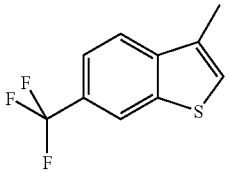 | N | 208 |
| 815685 | 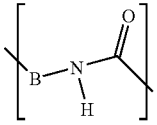 | 2 | 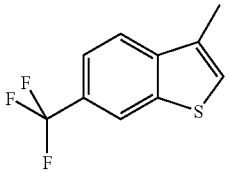 | 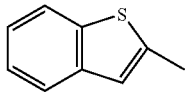 | N | 186 |
| 815686 | 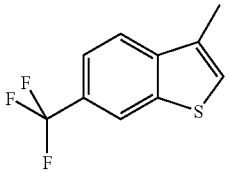 | 2 | 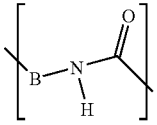 | 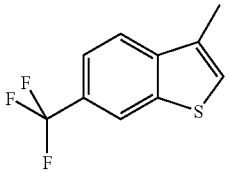 | N | 275 |
| 815688 | 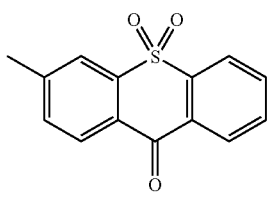 | 2 | 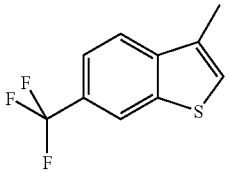 | 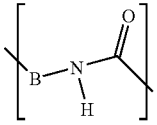 | N | 190 |

TABLE 2-continued

| No. | R | n | | R$_2$ | Y | D$_3$K$_1$ (nM) |
|---|---|---|---|---|---|---|
| 815689 | 3-methyl-6-trifluoromethyl-benzothiophene | 2 | HO-CH$_2$-CH(NHAc)-(CH$_2$)$_3$- | 3,4-dimethoxyphenyl | N | 225 |
| 815690 | 3-methyl-6-trifluoromethyl-benzothiophene | 2 | HO-CH$_2$-CH(NHAc)-(CH$_2$)$_3$- | 4-chlorophenyl | N | 245 |
| 815691 | 3-methyl-6-trifluoromethyl-benzothiophene | 2 | HO-CH$_2$-CH(NHAc)-(CH$_2$)$_3$- | 4-acetamidophenyl | N | 241 |
| 815692 | 3-methyl-6-trifluoromethyl-benzothiophene | 2 | HO-CH$_2$-CH(NHAc)-(CH$_2$)$_3$- | 4-methoxyphenyl | N | 191 |
| 815694 | 3-methyl-6-trifluoromethyl-benzothiophene | 2 | HO-CH$_2$-CH(NHAc)-(CH$_2$)$_3$- | 4-biphenyl | N | 197 |
| 815695 | 3-methyl-6-trifluoromethyl-benzothiophene | 2 | HO-CH$_2$-CH(NHAc)-(CH$_2$)$_3$- | 4-methylphenyl | N | 198 |

TABLE 2-continued
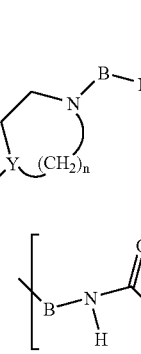
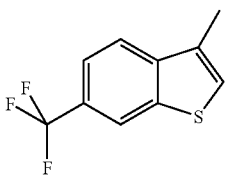
| No. | R | n | | R₂ | Y | D₃K₁ (nM) |
|---|---|---|---|---|---|---|
| 815696 | 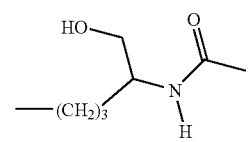 | 2 | 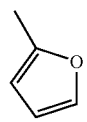 | 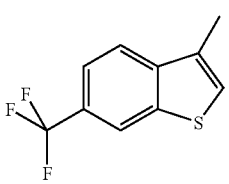 | N | 871 |
| 815697 | 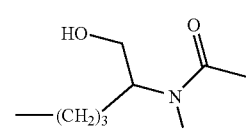 | 2 | 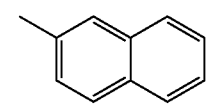 | 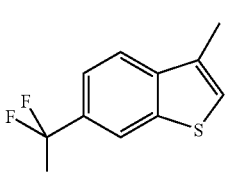 | N | 294 |
| 815698 | 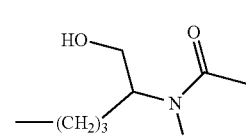 | 2 | 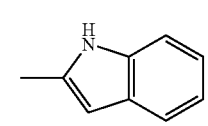 | 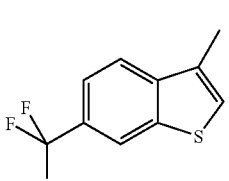 | N | 329 |
| 815700 | 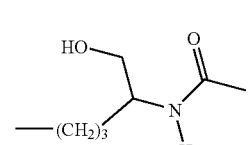 | 2 | 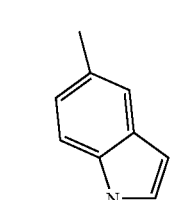 | 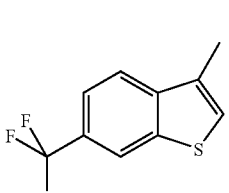 | N | 128 |
| 815702 | 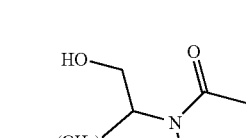 | 2 | 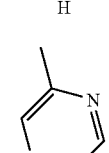 | 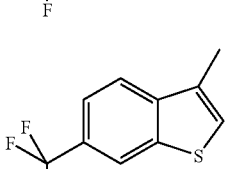 | N | 439 |
| 815704 | 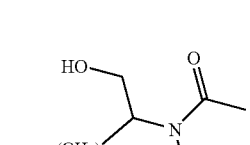 | 2 | 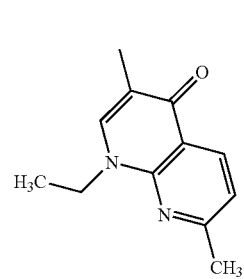 | | N | 137 |

TABLE 2-continued

| No. | R | n | | R₂ | Y | D₃K₁ (nM) |
|---|---|---|---|---|---|---|
| 815708 | 3-methyl-6-trifluoromethyl-benzothiophene | 2 | —(CH₂)₃—CH(CH₂OH)—NH—C(O)— | 2-methyl-benzothiophene | N | 180 |
| 815709 | 3-methyl-6-trifluoromethyl-benzothiophene | 2 | —(CH₂)₃—CH(CH₂OH)—NH—C(O)— | 3-methyl-thioxanthone-S,S-dioxide | N | 124 |
| 815710 | 3-methyl-6-trifluoromethyl-benzothiophene | 2 | —(CH₂)₃—CH(CH₂OH)—NH—C(O)— | 2-methyl-6-chloro-benzothiophene | N | 210 |
| 816315 | 3-methyl-6-trifluoromethyl-benzothiophene | 2 | —(CH₂)₆—NH—C(O)— | 2-methyl-1H-indole | N | 3.7 |
| 816316 | 3-methyl-6-trifluoromethyl-benzothiophene | 2 | —(CH₂)₆—NH—C(O)— | 5-methyl-1H-indole | N | 2.7 |
| 815870 | 3-methyl-2-phenyl-6-trifluoromethyl-benzothiophene | 2 | —(CH₂)₄—NH—C(O)— | 3-fluoro-methylphenyl | N | 28.4 |

TABLE 2-continued
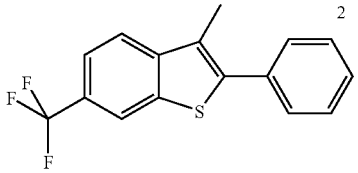
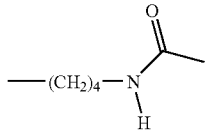
| No. | R | n | | R₂ | Y | D₃K₁ (nM) |
|---|---|---|---|---|---|---|
| 815871 | 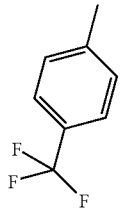 | 2 | 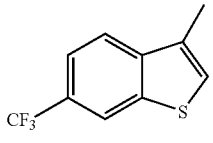 | 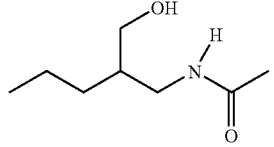 | N | 796 |
| 818943ES | 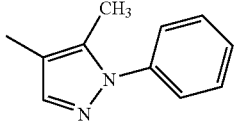 | 2 | 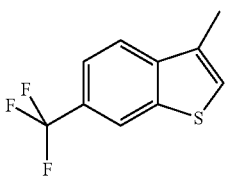 | 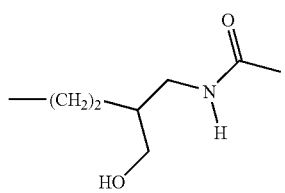 | N | 295 |
| 818912ES | 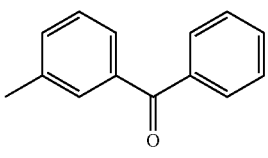 | 2 | 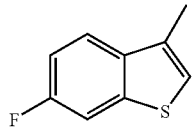 | 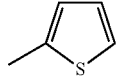 | N | 249 |
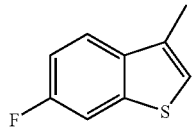
| CMPD NUM | R | n | B | R₂ | Y | D3K$_i$ |
|---|---|---|---|---|---|---|
| 822149 | 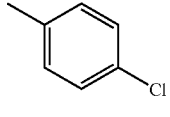 | 3 | —(CH₂)₄— | (2-thienyl) | N | 2.7 |
| 822150 | (6-fluorobenzothiophene) | 3 | —(CH₂)₄— | (4-chlorophenyl) | N | 6.3 |

-continued

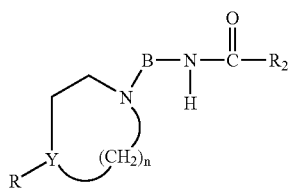

| CMPD NUM | R | n | B | R₂ | Y | D3K$_i$ |
|---|---|---|---|---|---|---|
| 82251 | 6-F-benzothiophen-3-yl | 3 | —(CH$_2$)$_4$— | 3,5-dimethoxyphenyl | N | 10.9 |
| 822152 | 6-F-benzothiophen-3-yl | 3 | —(CH$_2$)$_4$— | 4-OCF$_3$-phenyl | N | 4.5 |
| 822153 | 6-F-benzothiophen-3-yl | 3 | —(CH$_2$)$_4$— | naphthalen-1-yl | N | 6.1 |
| 822154 | 6-F-benzothiophen-3-yl | 3 | —(CH$_2$)$_4$— | 3-F-phenyl | N | 5.3 |
| 822155 | 6-F-benzothiophen-3-yl | 3 | —(CH$_2$)$_4$— | 3-CF$_3$-phenyl | N | 10.8 |
| 822156 | 6-F-benzothiophen-3-yl | 3 | —(CH$_2$)$_4$— | naphthalen-2-yl | N | 0.67 |
| 822223G maleate | 6-F-benzothiophen-3-yl | 3 | —(CH$_2$)$_4$— | naphthalen-2-yl | N | 2.45 |
| 822157 | 6-F-benzothiophen-3-yl | 3 | —(CH$_2$)$_4$— | 2-OCH$_3$-phenyl | N | 1.4 |

-continued

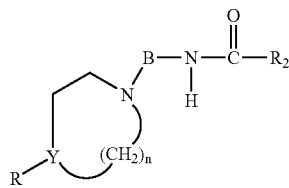

| CMPD NUM | R | n | B | R₂ | Y | D3K$_i$ |
|---|---|---|---|---|---|---|
| 822158 | 6-F-benzothiophen-3-yl | 3 | —(CH$_2$)$_4$— | 2-benzothienyl | N | 1.1 |
| 822224G maleate | 6-F-benzothiophen-3-yl | 3 | —(CH$_2$)$_4$— | 2-benzothienyl | N | 1.07 |
| 822195 | 6-F-benzothiophen-3-yl | 3 | —(CH$_2$)$_4$— | 2-F-phenyl | N | 4.7 |
| 822196 | 6-F-benzothiophen-3-yl | 3 | —(CH$_2$)$_4$— | 3,4-dimethoxyphenyl | N | 5 |
| 822197 | 6-F-benzothiophen-3-yl | 3 | —(CH$_2$)$_4$— | 3-methoxyphenyl | N | 6.5 |
| 822198 | 6-F-benzothiophen-3-yl | 3 | —(CH$_2$)$_4$— | 4-tert-butylphenyl | N | 10.5 |
| 822199 | 6-F-benzothiophen-3-yl | 3 | —(CH$_2$)$_4$— | 2-methylphenyl (with CH$_3$) | N | 3.8 |
| 822200 | 6-F-benzothiophen-3-yl | 3 | —(CH$_2$)$_4$— | 2-quinoxalinyl | N | 10.6 |
| 822201 | 6-F-benzothiophen-3-yl | 3 | —(CH$_2$)$_4$— | 2-Cl-3-pyridyl | N | 15 |

-continued

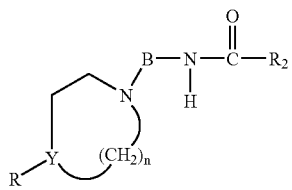

| CMPD NUM | R | n | B | R₂ | Y | D3K$_i$ |
|---|---|---|---|---|---|---|
| S977818 | 6-F-benzothiophen-3-yl | 3 | —(CH$_2$)$_4$ | 2-methyl-1H-indol-3-yl | N | 1.85 |
| S977819 | 6-F-benzothiophen-3-yl | 3 | —(CH$_2$)$_4$ | 2-methylbenzofuran-3-yl | N | 3.21 |
| 822226G maleate | 6-F-benzothiophen-3-yl | 3 | —(CH$_2$)$_4$ | 2-methylbenzofuran-3-yl | N | 0.82 |
| S977820 | 6-F-benzothiophen-3-yl | 3 | —(CH$_2$)$_4$ | 5-methoxy-2-methyl-1H-indol-3-yl | N | 1.05 |
| 822227G maleate | 6-F-benzothiophen-3-yl | 3 | —(CH$_2$)$_4$ | 5-methoxy-2-methyl-1H-indol-3-yl | N | 1.9 |
| S977821 | 6-F-benzothiophen-3-yl | 3 | —(CH$_2$)$_4$ | 1,2-dimethyl-1H-indol-3-yl | N | 1.65 |
| 822228G maleate | 6-F-benzothiophen-3-yl | 3 | —(CH$_2$)$_4$ | 1,2-dimethyl-1H-indol-3-yl | N | 1.78 |
| S977822 | 6-F-benzothiophen-3-yl | 3 | —(CH$_2$)$_4$ | 3-methyl-1H-indol-2-yl | N | 4.12 |

-continued

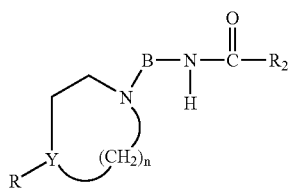

| CMPD NUM | R | n | B | R$_2$ | Y | D3K$_i$ |
|---|---|---|---|---|---|---|
| S977823 | 6-fluoro-3-methylbenzothiophene | 3 | —(CH$_2$)$_4$ | 4-methylindole | N | 3.96 |
| 822229G maleate | 6-fluoro-3-methylbenzothiophene | 3 | —(CH$_2$)$_4$ | 4-methylindole | N | 1.16 |
| S977824 | 6-fluoro-3-methylbenzothiophene | 3 | —(CH$_2$)$_4$ | 5-methylindole | N | 1.14 |
| S977825 | 6-fluoro-3-methylbenzothiophene | 3 | —(CH$_2$)$_4$ | 6-methylindole | N | 0.882 |
| 822230G maleate | 6-fluoro-3-methylbenzothiophene | 3 | —(CH$_2$)$_4$ | 6-methylindole | N | 0.725 |
| S977827 | 6-fluoro-3-methylbenzothiophene | 3 | —(CH$_2$)$_4$ | 1,2-dimethylindene | N | 0.987 |
| 822231G maleate | 6-fluoro-3-methylbenzothiophene | 3 | —(CH$_2$)$_4$ | 1,2-dimethylindene | N | 1.22 |
| S977828 | 6-fluoro-3-methylbenzothiophene | 3 | —(CH$_2$)$_4$ | 1,2-dimethylpyrrole | N | 6.97 |

-continued

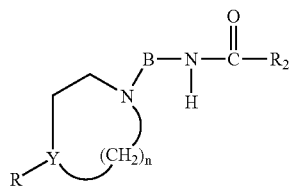

| CMPD NUM | R | n | B | R₂ | Y | D3$K_i$ |
|---|---|---|---|---|---|---|
| S977829 | 6-F-3-methylbenzothiophene | 3 | —(CH₂)₄ | 3-methylthiophene | N | 4.18 |
| S977830 | 6-F-3-methylbenzothiophene | 3 | —(CH₂)₄ | 5-methyl-1,3,4-triazole | N | 5.8 |
| S977831 | 6-F-3-methylbenzothiophene | 3 | —(CH₂)₄ | 6-methylbenzimidazole | N | 1.87 |
| S981833 | 6-F-3-methylbenzothiophene | 3 | —(CH₂)₄ | 4,5-dimethyl-2-phenyl-2H-1,2,3-triazole | N | 9 |
| S981834 | 6-F-3-methylbenzothiophene | 3 | —(CH₂)₄ | 3-methyl-2-phenoxypyridine | N | 1.1 |
| S981835 | 6-F-3-methylbenzothiophene | 3 | —(CH₂)₄ | 3-methyl-2-(4-methylphenylthio)pyridine | N | 1.2 |
| S981836 | 6-F-3-methylbenzothiophene | 3 | —(CH₂)₄ | 5-methylisoxazole | N | 46 |
| S981837 | 6-F-3-methylbenzothiophene | 3 | —(CH₂)₄ | 4,5-dimethyl-1,2,3-thiadiazole | N | 1.3 |

-continued

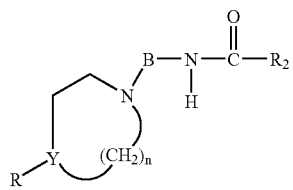

| CMPD NUM | R | n | B | R$_2$ | Y | D3K$_i$ |
|---|---|---|---|---|---|---|
| S981838 | 6-fluoro-3-methylbenzothiophene | 3 | —(CH$_2$)$_4$ | 3,5-bis(methylthio)-4-methylisothiazole | N | 6 |
| S981839 | 6-fluoro-3-methylbenzothiophene | 3 | —(CH$_2$)$_4$ | 2-methyl-3-methyl-5-phenylfuran | N | 1.4 |
| S981840 | 6-fluoro-3-methylbenzothiophene | 3 | —(CH$_2$)$_4$ | 2-methyl-3-methyl-5-(4-chlorophenyl)furan | N | 3.4 |
| S981842 | 6-fluoro-3-methylbenzothiophene | 3 | —(CH$_2$)$_4$ | 4'-methyl-2-fluorobiphenyl | N | 2.2 |
| S981843 | 6-fluoro-3-methylbenzothiophene | 3 | —(CH$_2$)$_4$ | 2-furyl | N | 0.066 |
| S981844 | 6-fluoro-3-methylbenzothiophene | 3 | —(CH$_2$)$_4$ | 3,5-bis(trifluoromethyl)phenyl | N | 39 |
| S981845 | 6-fluoro-3-methylbenzothiophene | 3 | —(CH$_2$)$_4$ | 4-methoxyphenyl | N | 1.01 |
| S981846 | 6-fluoro-3-methylbenzothiophene | 3 | —(CH$_2$)$_4$ | 4-fluorophenyl | N | 26.9 |

-continued

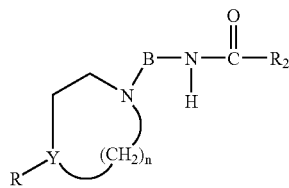

| CMPD NUM | R | n | B | R₂ | Y | D3$K_i$ |
|---|---|---|---|---|---|---|
| S9818147 | 6-fluoro-3-methylbenzothiophene | 3 | —(CH₂)₄ | 4-CF₃-phenyl | N | 30.8 |
| S981848 | 6-fluoro-3-methylbenzothiophene | 3 | —(CH₂)₄ | 3,5-dichlorophenyl | N | 8.3 |
| S981849 | 6-fluoro-3-methylbenzothiophene | 3 | —(CH₂)₄ | 3,5-difluorophenyl | N | 5.03 |
| S981850 | 6-fluoro-3-methylbenzothiophene | 3 | —(CH₂)₄ | (E)-propenylphenyl | N | 0.489 |
| S981851 | 6-fluoro-3-methylbenzothiophene | 3 | —(CH₂)₄ | 2-iodophenyl-methyl | N | 2.72 |
| S982506 | 6-fluoro-3-methylbenzothiophene | 3 | —(CH₂)₄ | 2-methylphenyl-ethyl | N | 3.4 |
| S982507 | 6-fluoro-3-methylbenzothiophene | 3 | —(CH₂)₄ | 2-methylphenyl-ethyl | N | 18 |
| S982508 | 6-fluoro-3-methylbenzothiophene | 3 | —(CH₂)₄ | 4-CF₃-phenyl-ethyl | N | 40.9 |
| S982509 | 6-fluoro-3-methylbenzothiophene | 3 | —(CH₂)₄ | 4-chlorophenyl-ethyl | N | 12.8 |

-continued
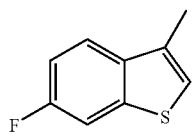
| CMPD NUM | R | n | B | R₂ | Y | D3K$_i$ |
|---|---|---|---|---|---|---|
| S982510 | 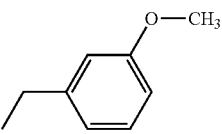 | 3 | —(CH$_2$)$_4$ | 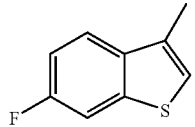 | N | 5.9 |
| S982511 | 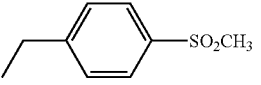 | 3 | —(CH$_2$)$_4$ | 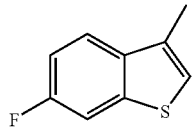 | N | 12 |
| S982512 | 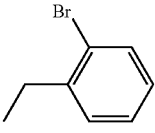 | 3 | —(CH$_2$)$_4$ | 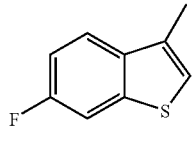 | N | 5.8 |
| S982513 | 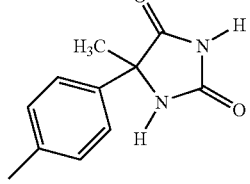 | 3 | —(CH$_2$)$_4$ | 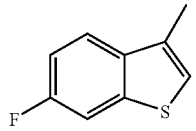 | N | 0.132 |
| S982514 | 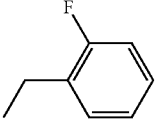 | 3 | —(CH$_2$)$_4$ | 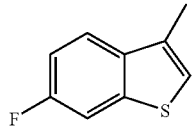 | N | 0.59 |
| S982535 | 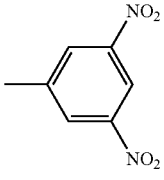 | 3 | —(CH$_2$)$_4$ | 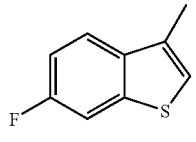 | N | 5.3 |
| S982536 | 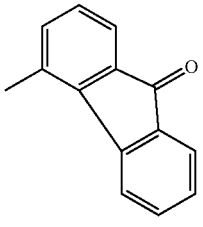 | 3 | —(CH$_2$)$_4$ |  | N | 1.4 |

-continued
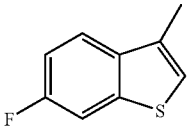
| CMPD NUM | R | n | B | R$_2$ | Y | D3K$_i$ |
|---|---|---|---|---|---|---|
| S982538 | 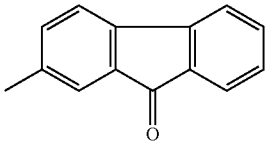 | 3 | —(CH$_2$)$_4$ | 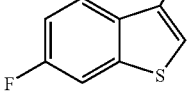 | N | 0.51 |
| S982539 | 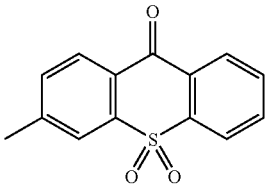 | 3 | —(CH$_2$)$_4$ | 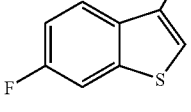 | N | 0.8 |
| 817270 | 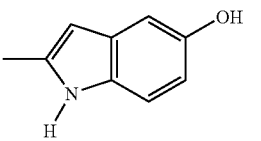 | 3 | —(CH$_2$)$_4$ | 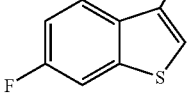 | N | 0.448 |
| S982540 | 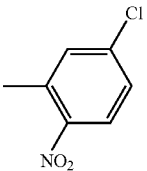 | 3 | —(CH$_2$)$_4$ | 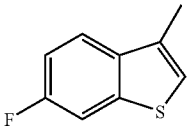 | N | 1.2 |
| S982542 | 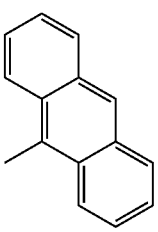 | 3 | —(CH$_2$)$_5$ | 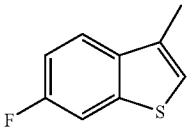 | N | 57 |
| S984485 | 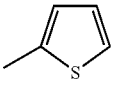 | 3 | —(CH$_2$)$_5$ | 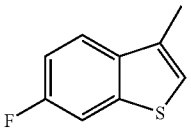 | N | 31.6 |
| S984486 | 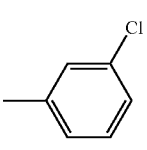 | 3 | —(CH$_2$)$_5$ |  | N | 31.5 |

-continued

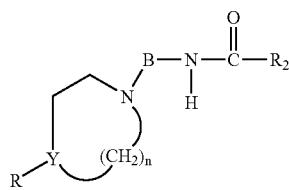

| CMPD NUM | R | n | B | R$_2$ | Y | D3K$_i$ |
|---|---|---|---|---|---|---|
| S984487 | 6-fluoro-3-methylbenzothiophene | 3 | —(CH$_2$)$_5$— | 3,5-dimethoxy-phenyl (with methyl) | N | 31.8 |
| S9894488 | 6-fluoro-3-methylbenzothiophene | 3 | —(CH$_2$)$_5$— | 4-(trifluoromethoxy)phenyl | N | 23.8 |
| S984489 | 6-fluoro-3-methylbenzothiophene | 3 | —(CH$_2$)$_5$— | 1-naphthyl | N | 41.5 |
| S984490 | 6-fluoro-3-methylbenzothiophene | 3 | —(CH$_2$)$_5$— | 2-naphthyl | N | 15.5 |
| S984491 | 6-fluoro-3-methylbenzothiophene | 3 | —(CH$_2$)$_5$— | 3-(trifluoromethyl)phenyl | N | 54 |
| S984492 | 6-fluoro-3-methylbenzothiophene | 3 | —(CH$_2$)$_5$— | 2-methoxyphenyl | N | 34.7 |
| S984493 | 6-fluoro-3-methylbenzothiophene | 3 | —(CH$_2$)$_5$— | 3-fluorophenyl | N | 25.9 |
| S984494 | 6-fluoro-3-methylbenzothiophene | 3 | —(CH$_2$)$_5$— | 2-benzothiophenyl | N | 11.6 |

-continued

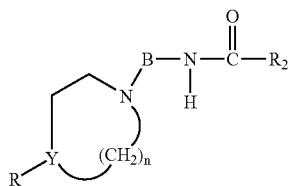

| CMPD NUM | R | n | B | R₂ | Y | D3K$_i$ |
|---|---|---|---|---|---|---|
| S984495 | 3-methyl-6-fluorobenzothiophene | 3 | —(CH$_2$)$_5$ | 7-methyl-1H-indole | N | 26.2 |
| S984496 | 3-methyl-6-fluorobenzothiophene | 3 | —(CH$_2$)$_5$ | methyl-SO$_2$CH$_3$ substituted dihydroisobenzothiophene | N | 8.44 |
| S984497 | 3-methyl-6-fluorobenzothiophene | 3 | —(CH$_2$)$_5$ | 5-methyl-2-(3-pyridyl)thiazole | N | 49.3 |
| S984498 | 3-methyl-6-fluorobenzothiophene | 3 | —(CH$_2$)$_5$ | 4-methyl-1,2,3-thiadiazole | N | 39.5 |
| S984499 | 3-methyl-6-fluorobenzothiophene | 3 | —(CH$_2$)$_5$ | 2-methyl-3-(1H-pyrrol-1-yl)thiophene | N | 28.5 |
| S984501 | 3-methyl-6-fluorobenzothiophene | 3 | —(CH$_2$)$_5$ | 5-methyl-2-(2-pyridyl)thiophene | N | 15.8 |
| S984502 | 3-methyl-6-fluorobenzothiophene | 3 | —(CH$_2$)$_5$ | 2-methylthieno[3,2-b]thiophene | N | 6.41 |
| S984503 | 3-methyl-6-fluorobenzothiophene | 3 | —(CH$_2$)$_5$ | 1,3-dimethyl-5-methylthieno[2,3-c]pyrazole | N | 10.2 |

-continued
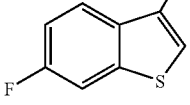
| CMPD NUM | R | n | B | R$_2$ | Y | D3K$_i$ |
|---|---|---|---|---|---|---|
| S984504 | 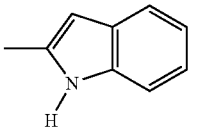 | 3 | —(CH$_2$)$_5$ | 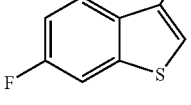 | N | 17.1 |
| S984505 | 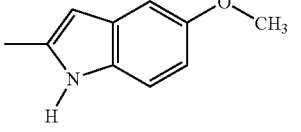 | 3 | —(CH$_2$)$_5$ | 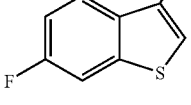 | N | 13 |
| S984506 | 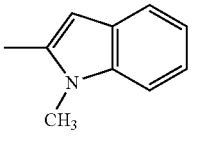 | 3 | —(CH$_2$)$_5$ | 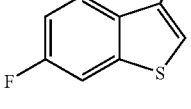 | N | 33.4 |
| S984507 | 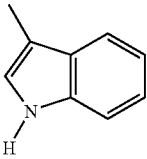 | 3 | —(CH$_2$)$_5$ | 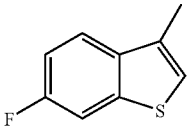 | N | 62 |
| S984508 | 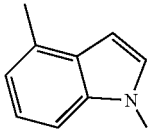 | 3 | —(CH$_2$)$_5$ | 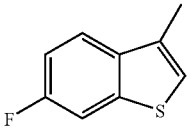 | N | 34.8 |
| S984509 | 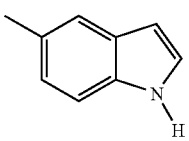 | 3 | —(CH$_2$)$_5$ | 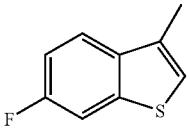 | N | 11.9 |
| S984510 | 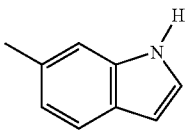 | 3 | —(CH$_2$)$_5$ | 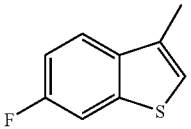 | N | 10.1 |
| S984511 | 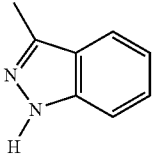 | 3 | —(CH$_2$)$_5$ | | N | 25.4 |

-continued

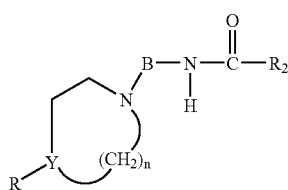

| CMPD NUM | R | n | B | R$_2$ | Y | D3K$_i$ |
|---|---|---|---|---|---|---|
| S984512 | 3-methyl-6-fluoro-benzothiophene | 3 | —(CH$_2$)$_5$— | 1,2-dimethyl-indene | N | 11.7 |
| S984513 | 3-methyl-6-trifluoromethyl-benzothiophene | 3 | —(CH$_2$)$_4$— | 2-methyl-benzofuran | N | 19 |
| S980627 | 3-methyl-6-trifluoromethyl-benzothiophene | 3 | —(CH$_2$)$_4$— | 2-methyl-thiophene | N | 40 |
| S980628 | 3-methyl-6-trifluoromethyl-benzothiophene | 3 | —(CH$_2$)$_4$— | 3-chloro-phenyl | N | 110 |
| S980630 | 3-methyl-6-trifluoromethyl-benzothiophene | 3 | —(CH$_2$)$_4$— | 3,5-dimethoxy-phenyl | N | 160 |
| S980630 | 3-methyl-6-trifluoromethyl-benzothiophene | 3 | —(CH$_2$)$_4$— | 4-OCF$_3$-phenyl | N | 120 |
| S980631 | 3-methyl-6-trifluoromethyl-benzothiophene | 3 | —(CH$_2$)$_4$— | 1-naphthyl | N | 100 |
| S980632 | 3-methyl-6-trifluoromethyl-benzothiophene | 3 | —(CH$_2$)$_4$— | 2-naphthyl | N | 23 |

-continued

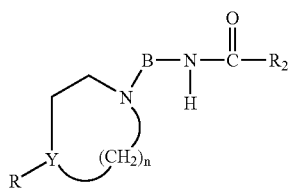

| CMPD NUM | R | n | B | R₂ | Y | D3$K_i$ |
|---|---|---|---|---|---|---|
| S980633 | 6-(trifluoromethyl)benzothiophen-3-yl | 3 | —(CH₂)₄ | 3-(trifluoromethyl)phenyl | N | 230 |
| S980634 | 6-(trifluoromethyl)benzothiophen-3-yl | 3 | —(CH₂)₄ | 2-methoxyphenyl | N | 14 |
| S980635 | 6-(trifluoromethyl)benzothiophen-3-yl | 3 | —(CH₂)₄ | 3-fluorophenyl | N | 71 |
| S980636 | 6-(trifluoromethyl)benzothiophen-3-yl | 3 | —(CH₂)₄ | benzothiophen-2-yl | N | 18 |
| S980637 | 6-(trifluoromethyl)benzothiophen-3-yl | 3 | —(CH₂)₄ | 4-fluorophenyl | N | 43 |
| S980638 | 6-(trifluoromethyl)benzothiophen-3-yl | 3 | —(CH₂)₄ | 3,4-dimethoxyphenyl | N | 39 |
| S980639 | 6-(trifluoromethyl)benzothiophen-3-yl | 3 | —(CH₂)₄ | 2-methylphenyl | N | 40 |
| S980640 | 6-(trifluoromethyl)benzothiophen-3-yl | 3 | —(CH₂)₄ | 3-methoxyphenyl | N | 43 |

-continued

[Structure: B-N(H)-C(=O)-R₂ with a ring containing N-(CH₂)₂-Y(R)-(CH₂)ₙ-B]

| CMPD NUM | R | n | B | R₂ | Y | D3K$_i$ |
|---|---|---|---|---|---|---|
| S980641 | 6-CF₃-benzothiophen-3-yl | 3 | —(CH₂)₄ | 4-biphenyl | N | 29 |
| S980642 | 6-CF₃-benzothiophen-3-yl | 3 | —(CH₂)₄ | 4-tert-butylphenyl | N | 69 |
| S980643 | 6-CF₃-benzothiophen-3-yl | 3 | —(CH₂)₄ | quinoxalin-2-yl | N | 96 |
| S980644 | 6-CF₃-benzothiophen-3-yl | 3 | —(CH₂)₄ | 4-CF₃-phenyl | N | 570 |
| S980645 | 6-CF₃-benzothiophen-3-yl | 3 | —(CH₂)₄ | pyridin-4-yl | N | 44 |
| S980646 | 6-CF₃-benzothiophen-3-yl | 3 | —(CH₂)₄ | 2-chloropyridin-3-yl | N | 110 |
| S980647 | 6-CF₃-benzothiophen-3-yl | 3 | —(CH₂)₄ | 6-methoxy-2-methyl-1H-indol-3-yl | N | 17 |
| S980648 | 6-CF₃-benzothiophen-3-yl | 3 | —(CH₂)₄ | 1,2-dimethyl-indol-3-yl | N | 35 |
| S980649 | 6-CF₃-benzothiophen-3-yl | 3 | —(CH₂)₄ | 1H-indol-3-yl | N | 54 |

-continued

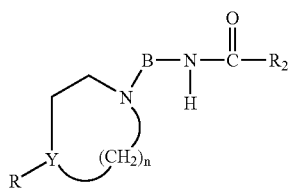

| CMPD NUM | R | n | B | R₂ | Y | D3$K_i$ |
|---|---|---|---|---|---|---|
| S980650 | 3-methyl-6-(trifluoromethyl)benzothiophene | 3 | —(CH₂)₄ | 4-methyl-1H-indole | N | 43 |
| S980651 | 3-methyl-6-(trifluoromethyl)benzothiophene | 3 | —(CH₂)₄ | 5-methyl-1H-indole | N | 54 |
| S980652 | 3-methyl-6-(trifluoromethyl)benzothiophene | 3 | —(CH₂)₄ | 6-methyl-1H-indole | N | 16.8 |
| S980653 | 3-methyl-6-(trifluoromethyl)benzothiophene | 3 | —(CH₂)₄ | 3-methyl-1H-indazole | N | 61 |
| S980655 | 3-methyl-6-(trifluoromethyl)benzothiophene | 3 | —(CH₂)₄ | 1,2-dimethyl-1H-pyrrole | N | 40 |
| S980656 | 3-methyl-6-(trifluoromethyl)benzothiophene | 3 | —(CH₂)₄ | 3-methylthiophene | N | 28 |
| S980657 | 3-methyl-6-(trifluoromethyl)benzothiophene | 3 | —(CH₂)₄ | 4,5-dimethyl-2-phenyl-2H-1,2,3-triazole | N | 175 |
| S980659 | 3-methyl-6-(trifluoromethyl)benzothiophene | 3 | —(CH₂)₄ | 4-methyl-2-(p-tolylthio)pyridine | N | 110 |

-continued

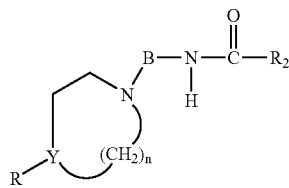

| CMPD NUM | R | n | B | R₂ | Y | D3$K_i$ |
|---|---|---|---|---|---|---|
| S980660 | 3-methyl-6-(trifluoromethyl)benzothiophene | 3 | —(CH$_2$)$_4$ | 4-methyl-5-methyl-1,2,3-thiadiazole | N | 43.8 |
| S980661 | 3-methyl-6-(trifluoromethyl)benzothiophene | 3 | —(CH$_2$)$_4$ | 3,5-bis(methylthio)-4-methylisothiazole | N | 151 |
| S980662 | 3-methyl-6-(trifluoromethyl)benzothiophene | 3 | —(CH$_2$)$_4$ | 2-methyl-3-methyl-5-phenylfuran | N | 48 |
| S980663 | 3-methyl-6-(trifluoromethyl)benzothiophene | 3 | —(CH$_2$)$_4$ | 2-methyl-3-methyl-5-(4-chlorophenyl)furan | N | 96 |
| S980664 | 3-methyl-6-(trifluoromethyl)benzothiophene | 3 | —(CH$_2$)$_4$ | 5-methylbenzo[c][1,2,5]oxadiazole | N | 6.1 |
| S908665 | 3-methyl-6-(trifluoromethyl)benzothiophene | 3 | —(CH$_2$)$_4$ | 4'-methyl-2-fluorobiphenyl | N | 20.3 |
| 815147 | 3-methylthieno[3,2-d]isoxazole | 2 | —(CH$_2$)$_4$ | 2-methylbenzothiophene | CH | 371 |
| 815151 | 3-methylthieno[3,2-d]isoxazole | 2 | —(CH$_2$)$_4$ | 4-chlorophenyl | CH | 136 |

-continued
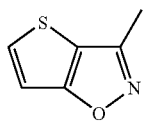
| CMPD NUM | R | n | B | R₂ | Y | D3$K_i$ |
|---|---|---|---|---|---|---|
| 815152 | 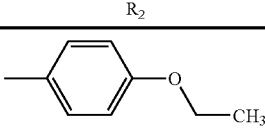 | 2 | —(CH₂)₄ | 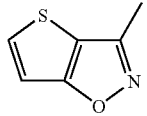 | CH | 158 |
| 81514 | 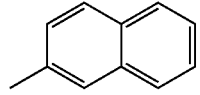 | 2 | —(CH₂)₄ | 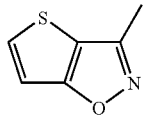 | CH | 191 |
| 816196 | 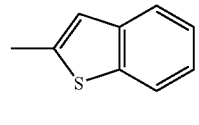 | 2 | —(CH₂)₅ | 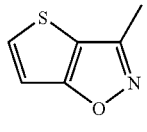 | CH | 161 |
| 816197 | 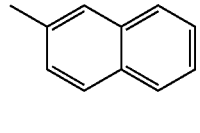 | 2 | —(CH₂)₅ | 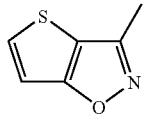 | CH | 116 |
| 816198 | 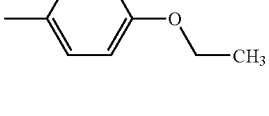 | 2 | —(CH₂)₅ | 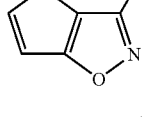 | CH | 110 |
| 816199 | 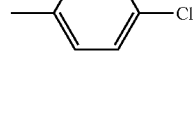 | 2 | —(CH₂)₅ | 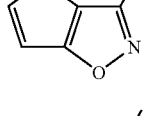 | CH | 157 |
| 816202 | 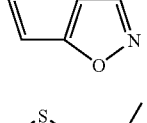 | 2 | —(CH₂)₅ | —(CH₂)₅CH₃ | CH | 326 |
| 816203 | 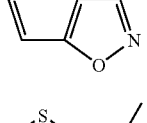 | 2 | —(CH₂)₅ | —(CH₂)₆=CH₂ | CH | 94.1 |
| 816204 | 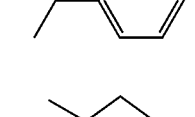 | 2 | —(CH₂)₅ | 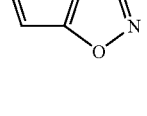 | CH | 218 |
| 816205 | 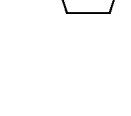 | 2 | —(CH₂)₅ |  | CH | 455 |

-continued

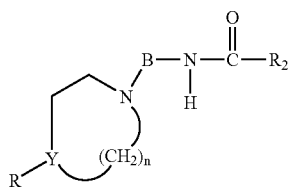

| CMPD NUM | R | n | B | R₂ | Y | D3K$_i$ |
|---|---|---|---|---|---|---|
| 816206 | 3-methylthieno[3,2-d]isoxazole | 2 | —(CH$_2$)$_5$ | 2-ethylbenzothiophene | CH | 505 |
| 816207 | 3-methylthieno[3,2-d]isoxazole | 2 | —(CH$_2$)$_5$ | 2-nitrotolyl | CH | 182 |
| 816208 | 3-methylthieno[3,2-d]isoxazole | 2 | —(CH$_2$)$_5$ | biphenyl | CH | 84.9 |
| 816211 | 3-methylthieno[3,2-d]isoxazole | 2 | —(CH$_2$)$_5$ | 2-(trifluoromethyl)phenyl | CH | 224 |
| 816212 | 3-methylthieno[3,2-d]isoxazole | 2 | —(CH$_2$)$_5$ | phenyl | CH | 570 |
| 816214 | 3-methylthieno[3,2-d]isoxazole | 2 | —(CH$_2$)$_5$ | 3-chlorophenyl | CH | 264 |
| 816215 | 3-methylthieno[3,2-d]isoxazole | 2 | —(CH$_2$)$_5$ | 3,4-dimethoxyphenyl | CH | 272 |
| 816217 | 3-methylthieno[3,2-d]isoxazole | 2 | —(CH$_2$)$_5$ | 4-fluorophenyl | CH | 364 |
| 816218 | 3-methylthieno[3,2-d]isoxazole | 2 | —(CH$_2$)$_5$ | 4-butylphenyl | CH | 316 |

-continued
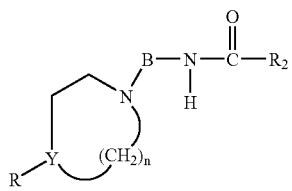
| CMPD NUM | R | n | B | R₂ | Y | D3K$_i$ |
|---|---|---|---|---|---|---|
| 816219 | 3-methylthieno[3,2-d]isoxazole | 2 | —(CH₂)₅— | 4-(CH₂)₅CH₃-phenyl | CH | 132 |
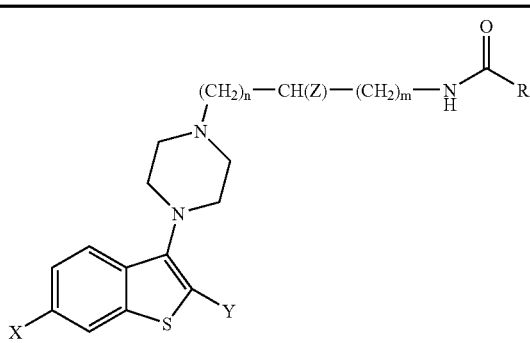
| MDL # | D3 Ki (nM) | Chirality | X | Y | Z | n | m | R |
|---|---|---|---|---|---|---|---|---|
| 815665 | 163 | R | CF₃ | H | CH₂OH | 3 | 0 | 3,4-dimethoxyphenyl |
| 815667 | 203 | R | CF₃ | H | CH₂OH | 3 | 0 | 4-(N-acetylamino)phenyl |
| 815668 | 150 | R | CF₃ | H | CH₂OH | 3 | 0 | 4-methoxyphenyl |
| 815670 | 192 | R | CF₃ | H | CH₂OH | 3 | 0 | 4-biphenyl |
| 815671 | 309 | R | CF₃ | H | CH₂OH | 3 | 0 | 4-methylphenyl |
| 815674 | 314 | R | CF₃ | H | CH₂OH | 3 | 0 | 2-methylindole |

-continued
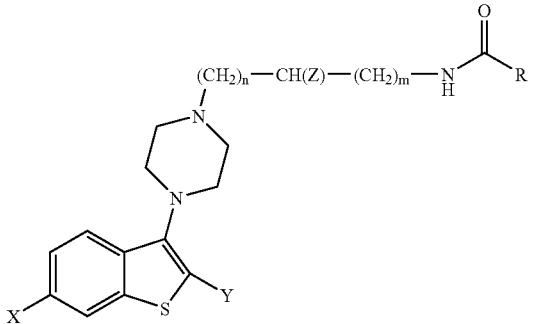
| MDL # | D3 Ki (nM) | Chirality | X | Y | Z | n | m | R |
|---|---|---|---|---|---|---|---|---|
| 815676 | 224 | R | CF₃ | H | CH₂OH | 3 | 0 | 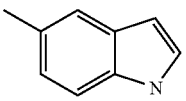 |
| 815677 | 297 | R | CF₃ | H | CH₂OH | 3 | 0 | 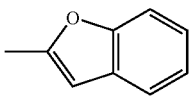 |
| 815679 | 129 | R | CF₃ | H | CH₂OH | 3 | 0 | 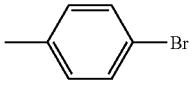 |
| 815680 | 197 | R | CF₃ | H | CH₂OH | 3 | 0 | 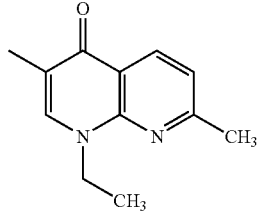 |
| 815681 | 261 | R | CF₃ | H | CH₂OH | 3 | 0 | 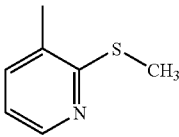 |
| 815683 | 293 | R | CF₃ | H | CH₂OH | 3 | 0 | 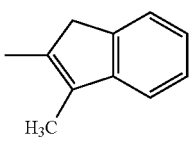 |
| 815684 | 208 | R | CF₃ | H | CH₂OH | 3 | 0 | 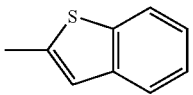 |
| 815685 | 186 | R | CF₃ | H | CH₂OH | 3 | 0 | 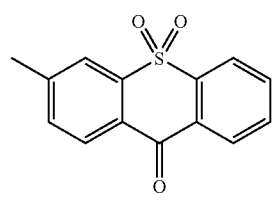 |

-continued
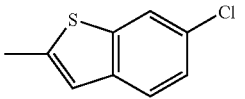
| MDL # | D3 Ki (nM) | Chirality | X | Y | Z | n | m | R |
|---|---|---|---|---|---|---|---|---|
| 815686 | 275 | R | CF$_3$ | H | CH$_2$OH | 3 | 0 | 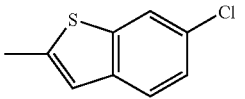 6-chlorobenzothiophen-2-yl |
| 815688 | 190 | S | CF$_3$ | H | CH$_2$OH | 3 | 0 | 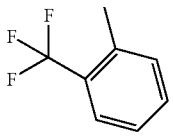 2-(trifluoromethyl)phenyl |
| 815689 | 225 | S | CF$_3$ | H | CH$_2$OH | 3 | 0 | 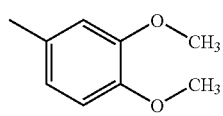 3,4-dimethoxyphenyl |
| 815690 | 245 | S | CF$_3$ | H | CH$_2$OH | 3 | 0 |  4-chlorophenyl |
| 815691 | 241 | S | CF$_3$ | H | CH$_2$OH | 3 | 0 | 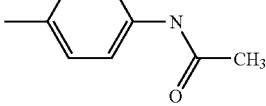 4-acetamidophenyl |
| 815692 | 191 | S | CF$_3$ | H | CH$_2$OH | 3 | 0 | 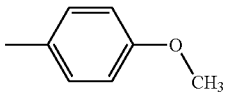 4-methoxyphenyl |
| 815694 | 197 | S | CF$_3$ | H | CH$_2$OH | 3 | 0 | 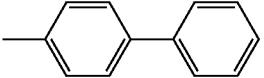 biphenyl-4-yl |
| 815695 | 198 | S | CF$_3$ | H | CH$_2$OH | 3 | 0 | 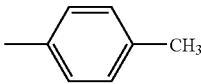 4-methylphenyl |
| 815696 | 871 | S | CF$_3$ | H | CH$_2$OH | 3 | 0 | 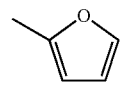 furan-2-yl |
| 815697 | 294 | S | CF$_3$ | H | CH$_2$OH | 3 | 0 | 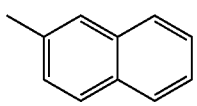 naphthalen-2-yl |

-continued
| MDL # | D3 Ki (nM) | Chirality | X | Y | Z | n | m | R |
|---|---|---|---|---|---|---|---|---|
| 815698 | 329 | S | CF$_3$ | H | CH$_2$OH | 3 | 0 |  |
| 815700 | 128 | S | CF$_3$ | H | CH$_2$OH | 3 | 0 | 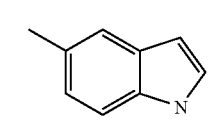 |
| 815702 | 439 | S | CF$_3$ | H | CH$_2$OH | 3 | 0 | 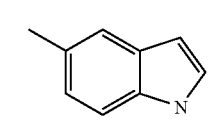 |
| 815704 | 137 | S | CF$_3$ | H | CH$_2$OH | 3 | 0 | 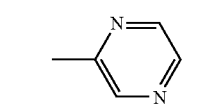 |
| 815708 | 180 | S | CF$_3$ | H | CH$_2$OH | 3 | 0 | 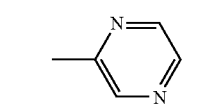 |
| 815709 | 124 | S | CF$_3$ | H | CH$_2$OH | 3 | 0 | 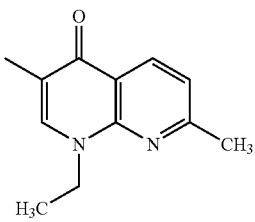 |
| 815710 | 210 | S | CF$_3$ | H | CH$_2$OH | 3 | 0 | 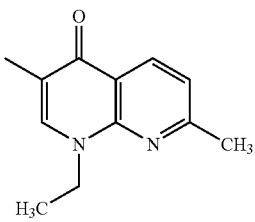 |
| 815710 | 210 | S | CF$_3$ | H | CH$_2$OH | 3 | 0 | 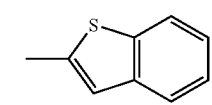 |
| 815870 | 28.4 | | F | Ph | H | 3 | 0 | 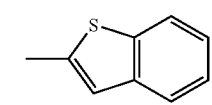 |

-continued
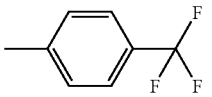
| MDL # | D3 Ki (nM) | Chirality | X | Y | Z | n | m | R |
|---|---|---|---|---|---|---|---|---|
| 815871 | 796 | | F | Ph | H | 3 | 0 | 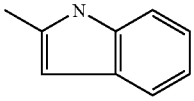 |
| 816315 | 3.7 | | CF₃ | H | H | 5 | 0 | 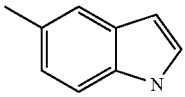 |
| 816316 | 2.7 | | CF₃ | H | H | 5 | 0 | 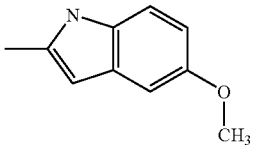 |
| 826738 | 6.1 | | CF₃ | H | H | 5 | 0 | 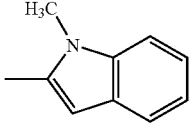 |
| 826739 | 2.1 | | CF₃ | H | H | 5 | 0 | 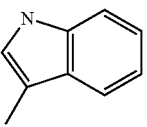 |
| 826740 | 44 | | CF₃ | H | H | 5 | 0 | 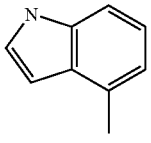 |
| 826741 | 9.8 | | CF₃ | H | H | 5 | 0 | 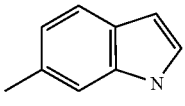 |
| 826742 | 1.7 | | CF₃ | H | H | 5 | 0 | 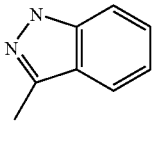 |
| 826743 | 15 | | CF₃ | H | H | 5 | 0 | |

-continued
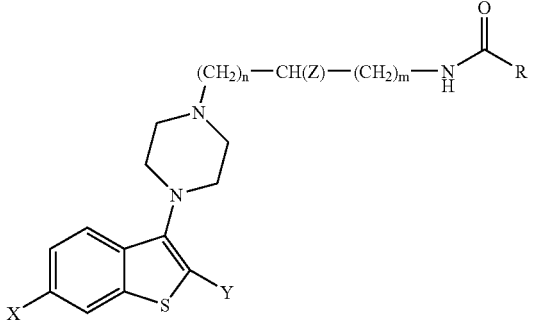
| MDL # | D3 Ki (nM) | Chirality | X | Y | Z | n | m | R |
|---|---|---|---|---|---|---|---|---|
| 826744 | 4 | | CF$_3$ | H | H | 5 | 0 | 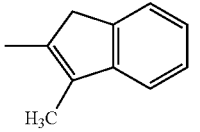 |
| 826745 | 8.8 | | CF$_3$ | H | H | 5 | 0 | 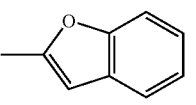 |
| 826746 | 0.8 | | CF$_3$ | H | H | 5 | 0 | 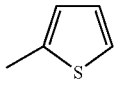 |
| 826747 | 0.12 | | CF$_3$ | H | H | 5 | 0 | 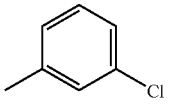 |
| 826748 | 4.9 | | CF$_3$ | H | H | 5 | 0 | 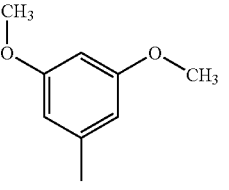 |
| 826749 | 8.7 | | CF$_3$ | H | H | 5 | 0 | 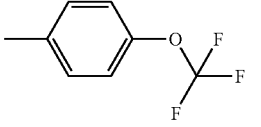 |
| 826750 | 3.2 | | CF$_3$ | H | H | 5 | 0 | 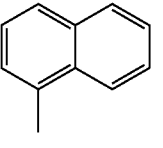 |
| 826751 | 2.8 | | CF$_3$ | H | H | 5 | 0 | 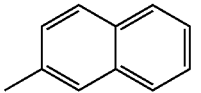 |
| 826752 | 14 | | CF$_3$ | H | H | 5 | 0 | 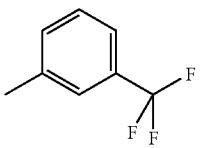 |

-continued
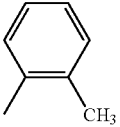
| MDL # | D3 Ki (nM) | Chirality | X | Y | Z | n | m | R |
|---|---|---|---|---|---|---|---|---|
| 826753 | 4.4 | | CF$_3$ | H | H | 5 | 0 | 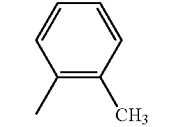 |
| 826754 | 3.2 | | CF$_3$ | H | H | 5 | 0 | 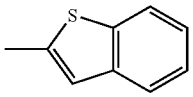 |
| 826764 | 7.8 | | CF$_3$ | H | H | 4 | 0 | 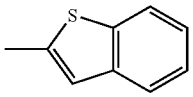 |
| 826765 | 23 | | CF$_3$ | H | H | 4 | 0 | 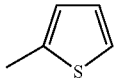 |
| 826766 | 11 | | CF$_3$ | H | H | 4 | 0 | 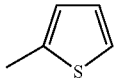 |
| 826767 | 14 | | CF$_3$ | H | H | 4 | 0 | 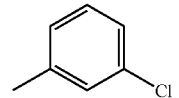 |
| 826768 | 23 | | CF$_3$ | H | H | 4 | 0 | 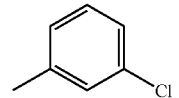 |
| 826769 | 7 | | CF$_3$ | H | H | 4 | 0 | 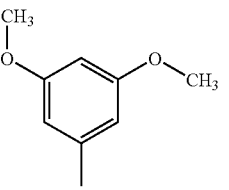 |
| 826770 | 14 | | CF$_3$ | H | H | 4 | 0 | 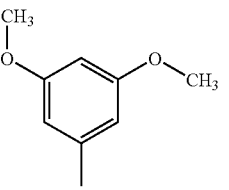 |

-continued

| MDL # | D3 Ki (nM) | Chirality | X | Y | Z | n | m | R |
|---|---|---|---|---|---|---|---|---|
| 826771 | 6.7 | | CF₃ | H | H | 4 | 0 | 2,3-dimethylphenyl |
| 826772 | 7.8 | | CF₃ | H | H | 4 | 0 | 3-fluorophenyl |
| 826773 | 11 | | CF₃ | H | H | 4 | 0 | benzothiophen-2-yl |
| 826774 | 8.25 | | F | H | H | 4 | 0 | thiophen-2-yl |
| 826775 | 6.24 | | F | H | H | 4 | 0 | 3-chlorophenyl |
| 826776 | 1.27 | | F | H | H | 4 | 0 | 3,5-dimethoxyphenyl |
| 826777 | 4.56 | | F | H | H | 4 | 0 | 4-trifluoromethoxyphenyl |
| 826778 | 2.75 | | F | H | H | 4 | 0 | naphthalen-1-yl |
| 826779 | 0.984 | | F | H | H | 4 | 0 | naphthalen-2-yl |

-continued
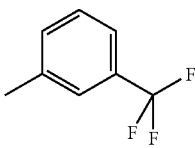
| MDL # | D3 Ki (nM) | Chirality | X | Y | Z | n | m | R |
|---|---|---|---|---|---|---|---|---|
| 826780 | 4.46 | | F | H | H | 4 | 0 | 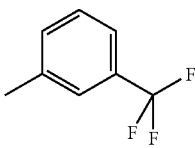 |
| 826781 | 9.94 | | F | H | H | 4 | 0 | 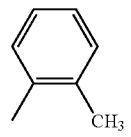 |
| 826782 | 4.55 | | F | H | H | 4 | 0 | 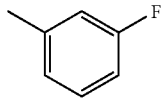 |
| 826783 | 2.7 | | F | H | H | 4 | 0 | 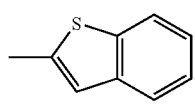 |
| 826784 | 3.28 | | F | H | H | 4 | 0 | 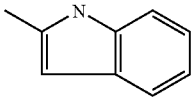 |
| 826785 | 1.43 | | F | H | H | 4 | 0 | 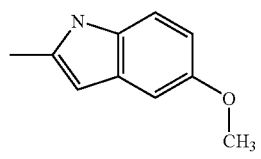 |
| 826786 | 1.09 | | F | H | H | 4 | 0 | 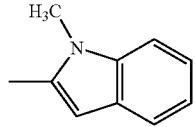 |
| 826787 | 1.19 | | F | H | H | 4 | 0 | 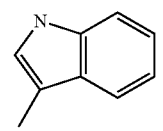 |
| 826790 | 5.66 | | F | H | H | 4 | 0 | 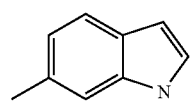 |

-continued
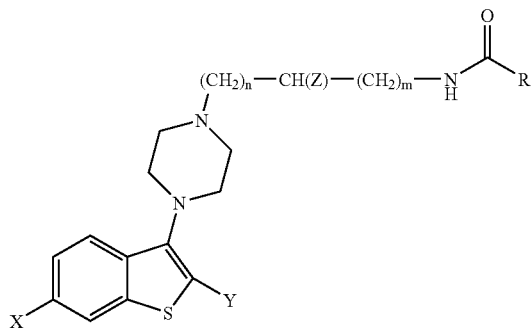
| MDL # | D3 Ki (nM) | Chirality | X | Y | Z | n | m | R |
|---|---|---|---|---|---|---|---|---|
| 826791 | 11.9 | | F | H | H | 4 | 0 | 3-methyl-indazol-yl |
| 826792 | 3.91 | | F | H | H | 4 | 0 | 2,3-dimethyl-indenyl |
| 826793 | 3.7 | | F | H | H | 4 | 0 | 2-methyl-benzofuranyl |
| 826794 | 11.1 | | CF$_3$ | H | H | 4 | 0 | 2-methyl-indolyl |
| 826795 | 13.9 | | CF$_3$ | H | H | 4 | 0 | 2-methyl-5-methoxy-indolyl |
| 826796 | 14.9 | | CF$_3$ | H | H | 4 | 0 | 1,2-dimethyl-indolyl |
| 826797 | 36.4 | | CF$_3$ | H | H | 4 | 0 | 3-methyl-indolyl |
| 826798 | 6.44 | | CF$_3$ | H | H | 4 | 0 | 4-methyl-indolyl |
| 826799 | 6.48 | | CF$_3$ | H | H | 4 | 0 | 5-methyl-indolyl |

-continued
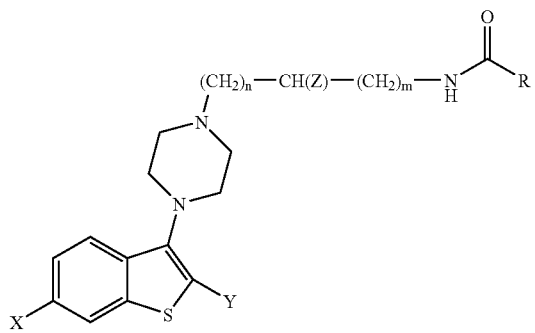
| MDL # | D3 Ki (nM) | Chirality | X | Y | Z | n | m | R |
|---|---|---|---|---|---|---|---|---|
| 826800 | 27.2 | | CF$_3$ | H | H | 4 | 0 | 6-methyl-1H-indole |
| 826801 | 49.8 | | CF$_3$ | H | H | 4 | 0 | 3-methyl-1H-indazole |
| 826802 | 16.9 | | CF$_3$ | H | H | 4 | 0 | 2,3-dimethyl-1H-indene |
| 826803 | 16.9 | | CF$_3$ | H | H | 4 | 0 | 2-methylbenzofuran |
| 827730 | 2.7 | | CF$_3$ | H | H | 5 | 0 | 3-fluorophenyl |
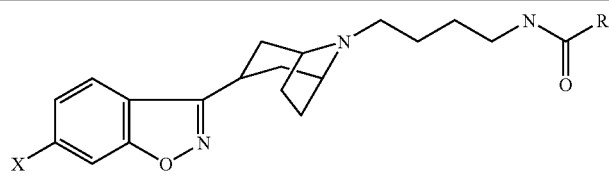
| MDL # | D3 Ki (nM) | X | R |
|---|---|---|---|
| 816323 | 832 | F | 2-methylthiophene |
| 816325 | 58.3 | F | 4-butoxyphenyl |

-continued
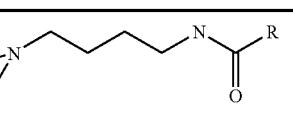
| MDL # | D3 Ki (nM) | X | R |
|---|---|---|---|
| 816326 | 223 | F | 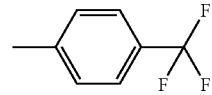 |
| 816327 | 392 | F | 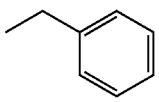 |
| 816329 | 356 | F | 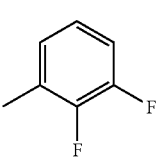 |
| 816330 | 186 | F | 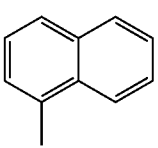 |
| 816331 | 44.2 | F | 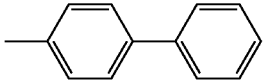 |
| 816332 | 588 | F | 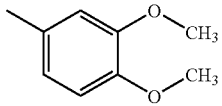 |
| 816333 | 474 | F |  |
| 816334 | 64.6 | F | 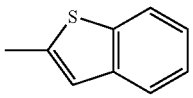 |
| 816335 | 268 | F |  |
| 816338 | 692 | F | 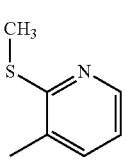 |
| 816340 | 427 | F | 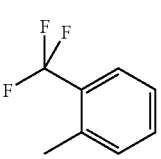 |

-continued
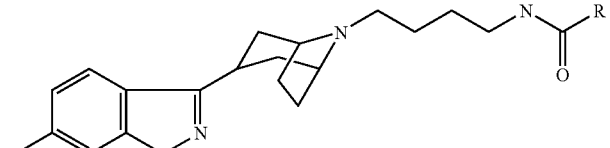
| MDL # | D3 Ki (nM) | X | R |
|---|---|---|---|
| 816341 | 50.9 | F | 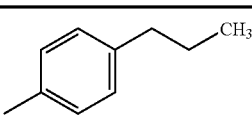 |
| 816343 | 344 | F | 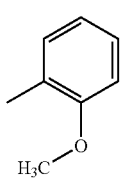 |
| 816344 | 378 | F |  |
| 816345 | 95.6 | F | 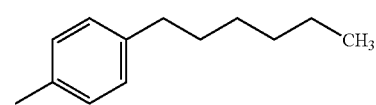 |
| 816519 | 305 | H | 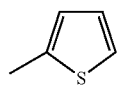 |
| 816520 | 292 | H | 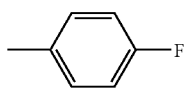 |
| 816521 | 328 | H | 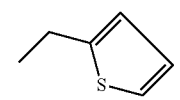 |
| 816522 | 240 | H | 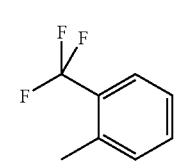 |
| 816523 | 165 | H |  |
| 816524 | 357 | H | 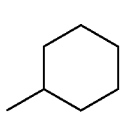 |
| 816525 | 148 | H | 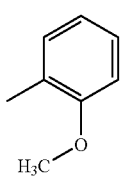 |

-continued
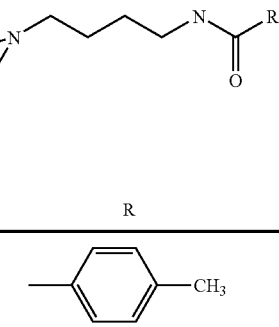
| MDL # | D3 Ki (nM) | X | R |
|---|---|---|---|
| 816526 | 375 | H | 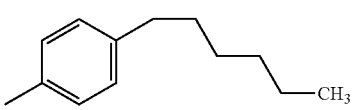 |
| 816527 | 64.8 | H | 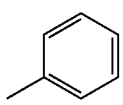 |
| 816528 | 299 | H | 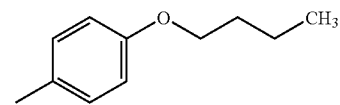 |
| 816529 | 42.5 | H | 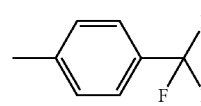 |
| 816530 | 110 | H | 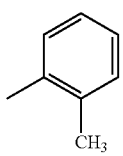 |
| 816531 | 299 | H | 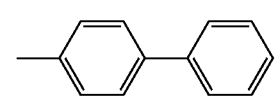 |
| 816532 | 56.8 | H | 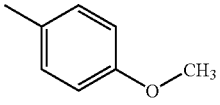 |
| 816534 | 149 | H | 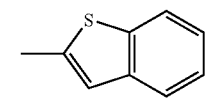 |
| 816535 | 66.4 | H | 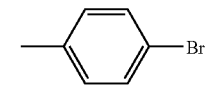 |
| 816536 | 140 | H | 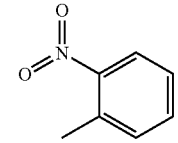 |
| 816537 | 411 | H | |

-continued
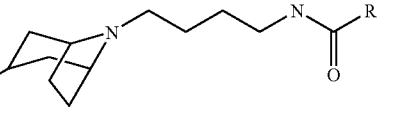
| MDL # | D3 Ki (nM) | X | R |
|---|---|---|---|
| 816538 | 178 | H | 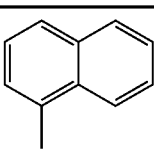 |
| 816540 | 225 | H | 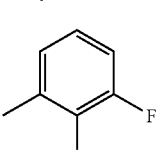 |
| 816541 | 511 | H | 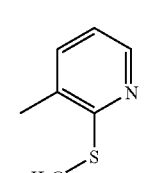 |
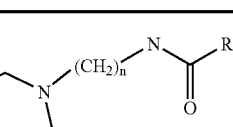
| MDL # | D3 Ki (nM) | n | R |
|---|---|---|---|
| 817258 | 3.13 | 4 | 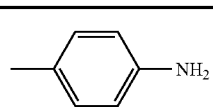 |
| 817259 | 2.93 | 4 | 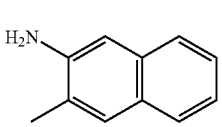 |
| 817262 | 1.89 | 4 | 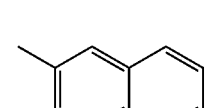 |
-continued
| MDL # | D3 Ki (nM) | n | R |
|---|---|---|---|
| 817263 | 331 | 4 | 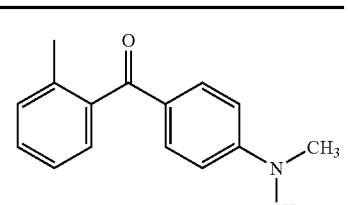 |
| 817264 | 6.44 | 4 | 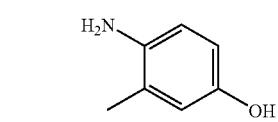 |

-continued
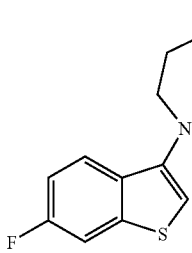
| MDL # | D3 Ki (nM) | n | R |
|---|---|---|---|
| 817265 | 46 | 4 | 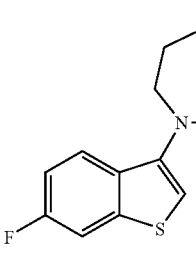 |
| 817266 | 8.73 | 4 | 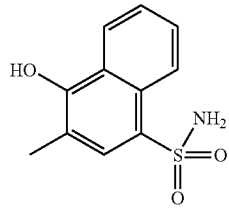 |
| 817267 | 3.03 | 4 | 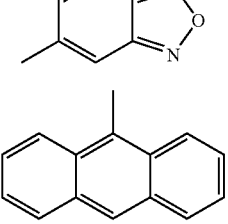 |
| 817268 | 7.1 | 4 | 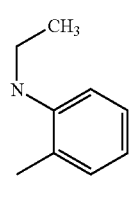 |
| 817269 | 4.74 | 4 | 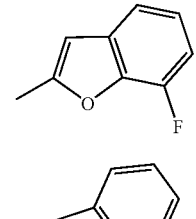 |
| 817271 | 326 | 4 | 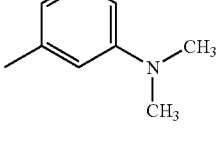 |
| 817276 | 2.44 | 4 | 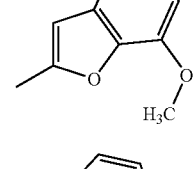 |
-continued
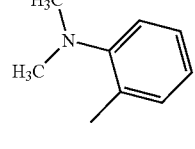
| MDL # | D3 Ki (nM) | n | R |
|---|---|---|---|
| 826699 | 6.73 | 4 | 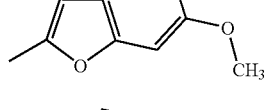 |
| 826762 | 57 | 4 | 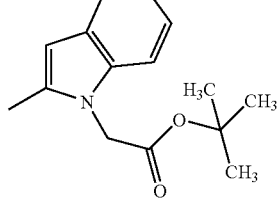 |
| 827120 | 32.9 | 4 | 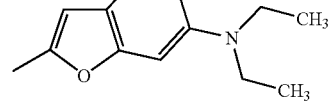 |
| 827121 | 21.6 | 4 | 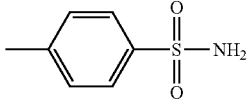 |
| 827122 | 6.06 | 4 | 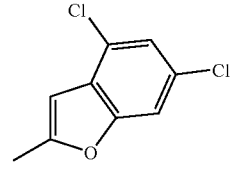 |
| 827123 | 107 | 4 | 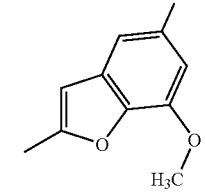 |
| 827124 | 16.6 | 4 |  |
| 827125 | 28.3 | 4 |  |

315
-continued
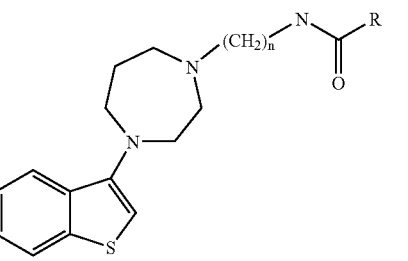
| MDL # | D3 Ki (nM) | n | R |
|---|---|---|---|
| 827126 | 3.1 | 4 | 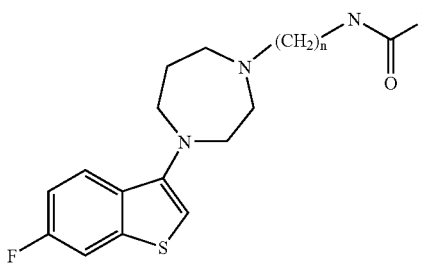 |
| 827127 | 74.3 | 4 | 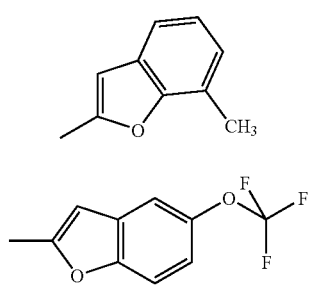 |
| 827128 | 19.1 | 4 | 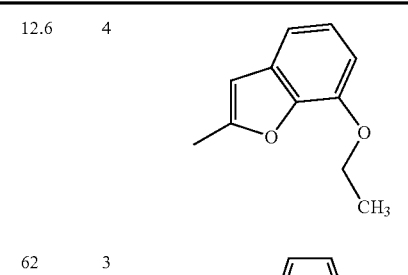 |
| 827129 | 7.75 | 4 | 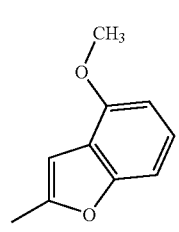 |
| 827130 | 15.4 | 4 | 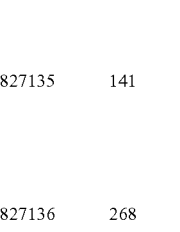 |
| 827131 | 4.18 | 4 | 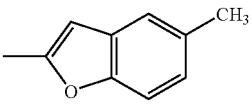 |
| 827132 | 129 | 4 |  |
316
-continued
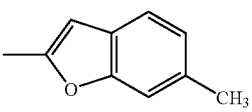
| MDL # | D3 Ki (nM) | n | R |
|---|---|---|---|
| 827133 | 12.6 | 4 | 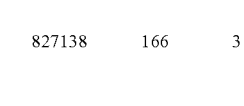 |
| 827134 | 62 | 3 | 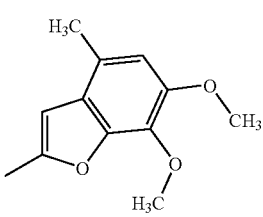 |
| 827135 | 141 | 3 | 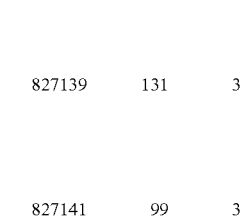 |
| 827136 | 268 | 3 | 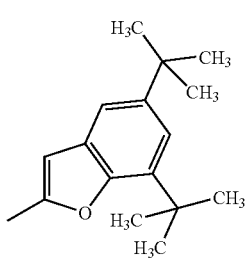 |
| 827138 | 166 | 3 | 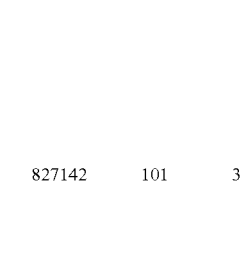 |
| 827139 | 131 | 3 | 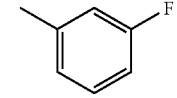 |
| 827141 | 99 | 3 | |
| 827142 | 101 | 3 | |

317
-continued
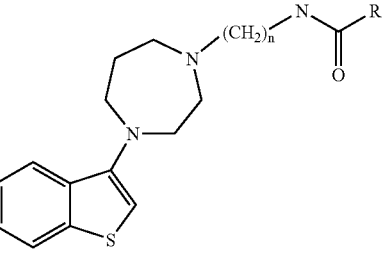
| MDL # | D3 Ki (nM) | n | R |
|---|---|---|---|
| 827143 | 123 | 3 | 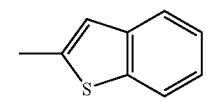 |
318
-continued
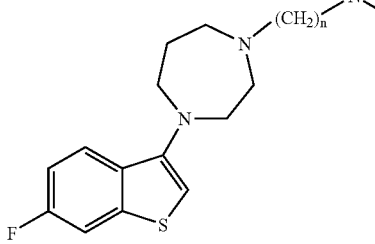
| MDL # | D3 Ki (nM) | n | R |
|---|---|---|---|
| 827159 | 5.85 | 5 | 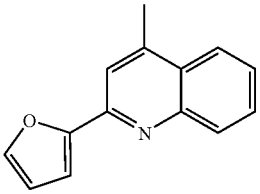 |
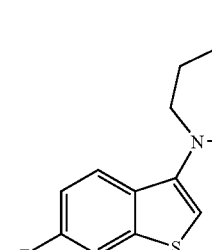
| MDL # | D3 Ki (nM) | Chirality | R1 | R2 |
|---|---|---|---|---|
| 830393 | 21.8 | Racemic | 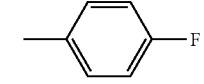 | Bn |
| 830394 | 10.7 | Racemic | 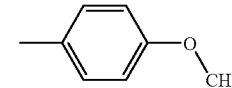 | Bn |
| 830395 | 27.6 | Racemic | 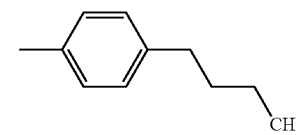 | Bn |
| 830396 | 16.5 | Racemic | 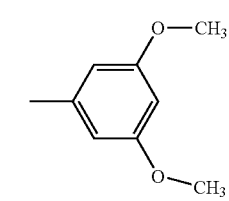 | Bn |
| 830397 | 55.4 | Racemic | 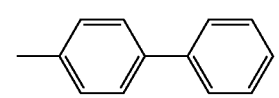 | Bn |

-continued
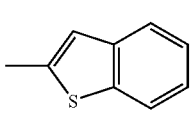
| MDL # | D3 Ki (nM) | Chirality | R1 | R2 |
|---|---|---|---|---|
| 830398 | 15.9 | Racemic | 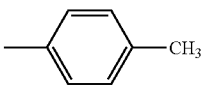 | Bn |
| 830403 | 59.9 | Racemic | 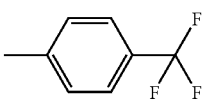 | H |
| 830404 | 51.9 | Racemic | 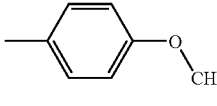 | H |
| 830405 | 1.65 | Racemic | 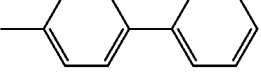 | H |
| 830406 | 27 | Racemic | 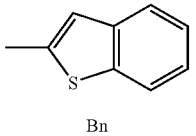 | H |
| 830407 | 10.4 | Racemic | 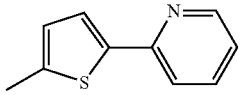 | H |
| 831203 | 3.21 | R,R | Bn | H |
| 831204 | 5.05 | S,S | Bn | H |
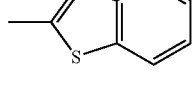
| MDL # | D3 Ki (nM) | R |
|---|---|---|
| 818320G | 11.2 |  |
-continued
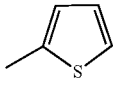
| MDL # | D3 Ki (nM) | R |
|---|---|---|
| 818321G | 78.7 | (2-methylbenzothiophene) |
| 826295 | 46 | (2-methylthiophene) |

-continued
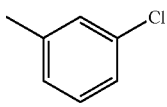
| MDL # | D3 Ki (nM) | R |
|---|---|---|
| 826296 | 106 | 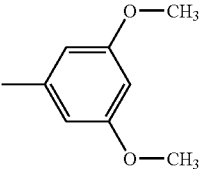 |
| 826297 | 31 | 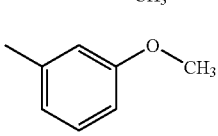 |
| 826298 | 59 | 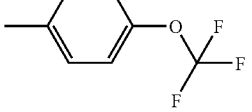 |
| 826299 | 95 | 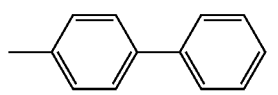 |
| 826300 | 36 | 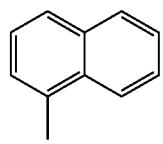 |
| 826301 | 94 | 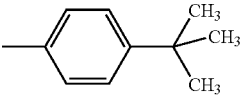 |
| 826302 | 16 | 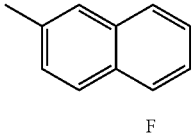 |
| 826303 | 64 | 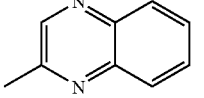 |
| 826304 | 84 | 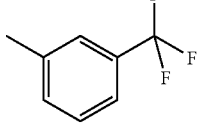 |
| 826305 | 30 | 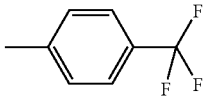 |
-continued
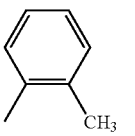
| MDL # | D3 Ki (nM) | R |
|---|---|---|
| 826306 | 89 | 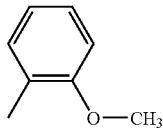 |
| 826307 | 47 | 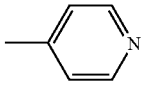 |
| 826308 | 206 | 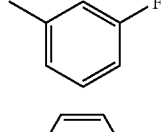 |
| 826309 | 63 | 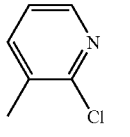 |
| 826310 | 203 | 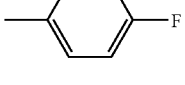 |
| 826311 | 74 | 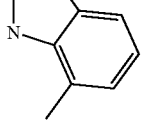 |
| 826312 | 29 | 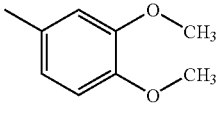 |
| 826313 | 134 | 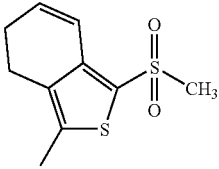 |
| 826314 | 46 | |
| 826315 | 31 | |

| 323 | | | 324 | | |
|---|---|---|---|---|---|
| -continued | | | -continued | | |
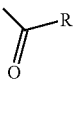
| MDL # | D3 Ki (nM) | R |
|---|---|---|
| 826316 | 32 | 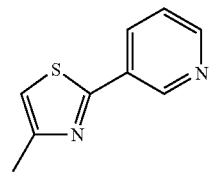 |
| 826317 | 48 | 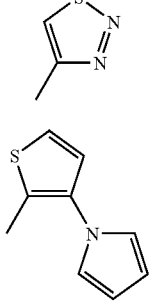 |
| 826318 | 90 | 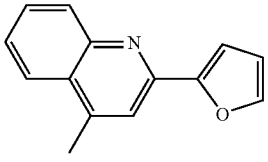 |
| 826319 | 273 | 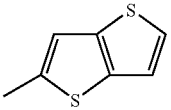 |
| 826320 | 75.3 | 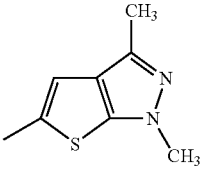 |
| 826321 | 41.3 | 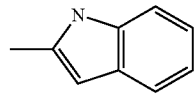 |
| 826322 | 296 | 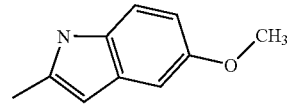 |
| 826323 | 67 | 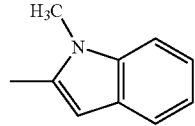 |
| 826324 | 120 | 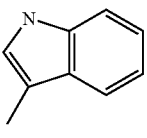 |
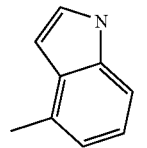
| MDL # | D3 Ki (nM) | R |
|---|---|---|
| 826325 | 54 | 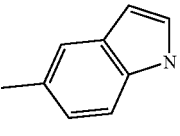 |
| 826326 | 71 | 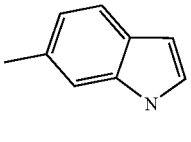 |
| 826327 | 20 | 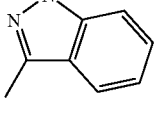 |
| 826328 | 28 | 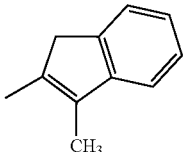 |
| 826329 | 14 | 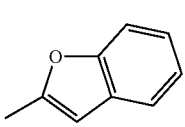 |
| 826330 | 16 | |
| 826331 | 51 | |

| MDL # | D3 Ki (nM) | n | Substitution | R |
|---|---|---|---|---|
| 822159 | 96.7 | 0 | m | 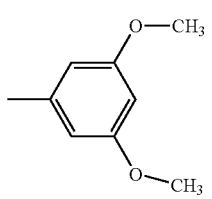 |
| 822161 | 163 | 0 | m | 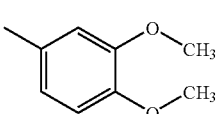 |
| 822162 | 380 | 0 | m | 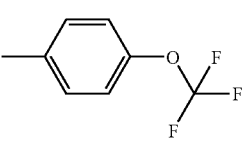 |
| 822164 | 167 | 0 | m | 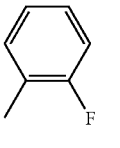 |
| 822180 | 26.5 | 0 | m | 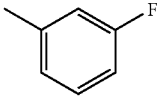 |
| 822181 | 332 | 0 | m | 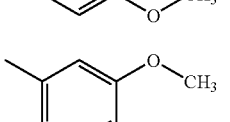 |
| 822183 | 154 | 0 | m | 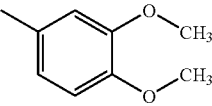 |
| 822184 | 271 | 0 | m | 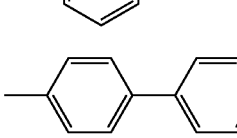 |
| 822185 | 50.7 | 0 | m | 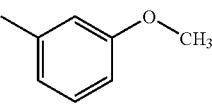 |
-continued
| MDL # | D3 Ki (nM) | n | Substitution | R |
|---|---|---|---|---|
| 822186 | 50.4 | 0 | m | 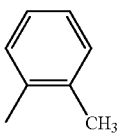 |
| 822188 | 140 | 1 | o | 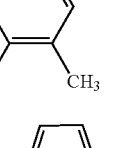 |
| 822207 | 221 | 0 | p | 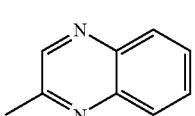 |
| 822208 | 183 | 0 | p | 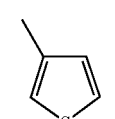 |
| 822209 | 360 | 0 | p | 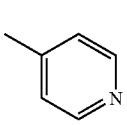 |
| 822210 | 39.5 | 0 | p | 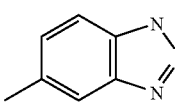 |
| 822212 | 162 | 0 | p | 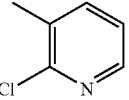 |
| 822213 | 63 | 0 | p | 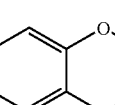 |
| 825654 | 245 | 0 | m | 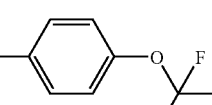 |
| 825656 | 33 | 0 | m | 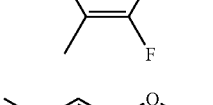 |

327
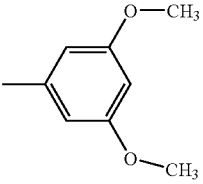
| MDL # | D3 Ki (nM) | R |
|---|---|---|
| 825837 | 190 | 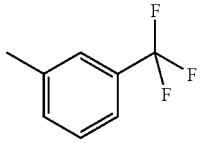 |
| 825841 | 146 | 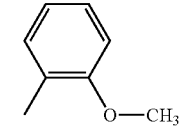 |
| 825842 | 532 | 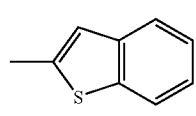 |
| 825844 | 601 |  |
| 825845 | 206 | 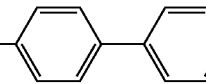 |
| 825848 | 250 | 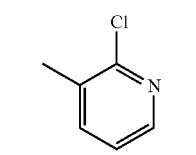 |
| 825853 | 237 | |
328
| MDL # | D3 Ki (nM) | X | R |
|---|---|---|---|
| 826929 | 217 | $CF_3$ | |
| 826930 | 74.7 | $CF_3$ | |
| 826931 | 219 | $CF_3$ | |
| 826932 | 384 | $CF_3$ | |
| 826933 | 276 | $CF_3$ | |
| 826934 | 227 | $CF_3$ | |
| 826935 | 268 | $CF_3$ | |
| 826936 | 96.1 | $CF_3$ | |
| 826937 | 253 | $CF_3$ | |
| 826938 | 175 | $CF_3$ | |

-continued
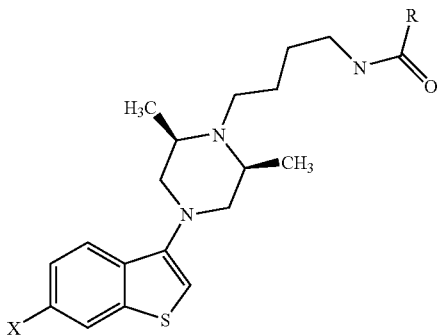
| MDL # | D3 Ki (nM) | X | R |
|---|---|---|---|
| 826939 | 19 | F | 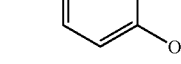 |
| 826940 | 49.2 | F | 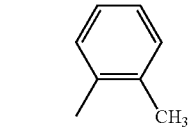 |
| 826941 | 36.3 | F | 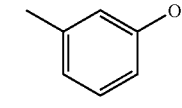 |
| 826942 | 57.4 | F |  |
| 826943 | 12.7 | F | 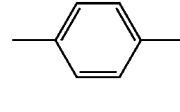 |
| 826944 | 128 | F | 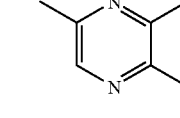 |
| 826945 | 133 | F | 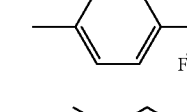 |
| 826946 | 35.9 | F | 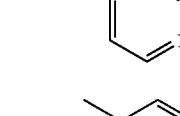 |
| 826947 | 47.6 | F | 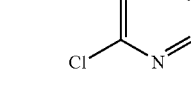 |
| 826948 | 154 | F | 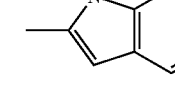 |
-continued
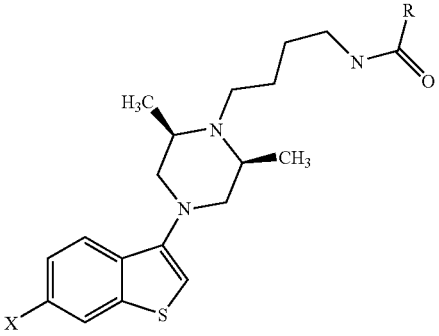
| MDL # | D3 Ki (nM) | X | R |
|---|---|---|---|
| 826949 | 91.5 | CF$_3$ | 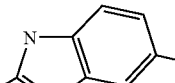 |
| 826950 | 81.2 | CF$_3$ | 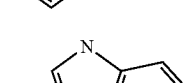 |
| 826951 | 41.3 | CF$_3$ | 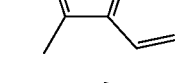 |
| 826952 | 164 | CF$_3$ | 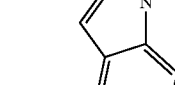 |
| 826953 | 222 | CF$_3$ | 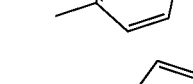 |
| 826954 | 39.4 | CF$_3$ | 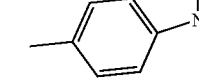 |
| 826955 | 70.5 | CF$_3$ | 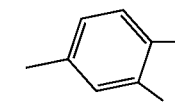 |
| 826956 | 190 | CF$_3$ | |
| 826957 | 153 | CF$_3$ | |

-continued

| MDL # | D3 Ki (nM) | X | R |
|---|---|---|---|
| 826958 | 148 | CF₃ | 2-benzofuranyl |
| 826959 | 28.6 | CF₃ | 2-indolyl |
| 826960 | 15.3 | F | 5-methoxy-2-indolyl |
| 826961 | 51.2 | F | 1-methyl-2-indolyl |
| 826962 | 79.8 | F | 3-indolyl |
| 826963 | 72.9 | F | 4-indolyl |
| 826964 | 32.2 | F | 5-indolyl |
| 826965 | 25.6 | F | 6-indolyl |
| 826966 | 77.1 | F | 3-indazolyl |

-continued

| MDL # | D3 Ki (nM) | X | R |
|---|---|---|---|
| 827036 | 51.2 | F | 2-benzofuranyl |
| 827037 | 106 | CF₃ | 2-thienyl |
| 827038 | 155 | CF₃ | 3-chlorophenyl |
| 827039 | 378 | CF₃ | 3,5-dimethoxyphenyl |
| 827040 | 165 | CF₃ | 4-trifluoromethoxyphenyl |
| 827041 | 357 | CF₃ | 1-naphthyl |
| 827042 | 112 | CF₃ | 2-naphthyl |
| 827043 | 322 | CF₃ | 3-trifluoromethylphenyl |
| 827044 | 186 | CF₃ | 3-fluorophenyl |

-continued
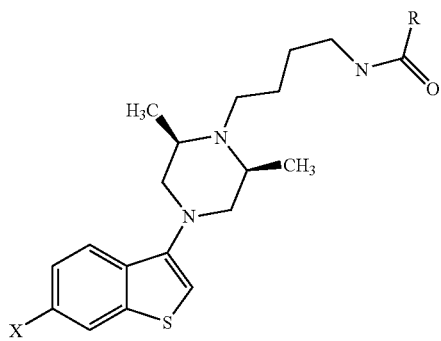
| MDL # | D3 Ki (nM) | X | R |
|---|---|---|---|
| 827045 | 97.8 | CF₃ | 2-benzothiophenyl |
| 827046 | 56.9 | CF₃ | 2-thienyl |
| 827047 | 65.1 | F | 3-chlorophenyl |
| 827048 | 317 | F | 3,5-dimethoxyphenyl |
| 827049 | 50.9 | F | 4-(trifluoromethoxy)phenyl |
| 827050 | 186 | F | 1-naphthyl |
-continued
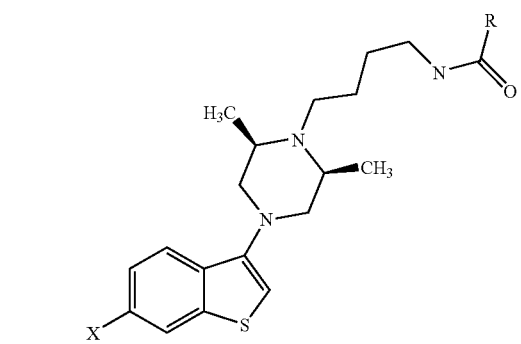
| MDL # | D3 Ki (nM) | X | R |
|---|---|---|---|
| 827051 | 29.5 | F | 2-naphthyl |
| 827052 | 153 | F | 3-(trifluoromethyl)phenyl |
| 827053 | 53.9 | F | 3-fluorophenyl |
| 827054 | 43.5 | F | 2-benzothiophenyl |
| 827255 | 53.7 | F | 3-methyl-1H-inden-2-yl |

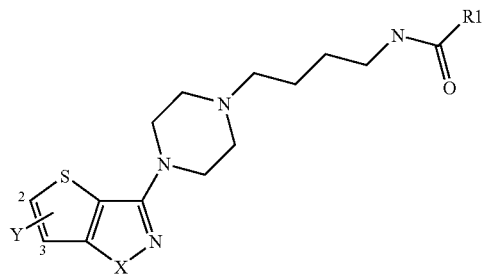
| MDL # | D3 Ki(nM) | X | Y | R1 | R2 |
|---|---|---|---|---|---|
| 825145 | 174 | N-R2 | H | 2-methoxyphenyl | 2'-methoxyacetophenone |
| 825146 | 188 | N-R2 | H | 2-methylphenyl | 2'-methylacetophenone |
| 825147 | 62.7 | N-R2 | H | 4-methylphenyl | 4'-methylacetophenone |
| 825148 | 36.4 | N-R2 | H | 4-fluorophenyl | 4'-fluoroacetophenone |
| 825149 | 164 | N-R2 | H | 4-trifluoromethylphenyl | 4'-trifluoromethylacetophenone |
| 825150 | 199 | N-R2 | H | 3,4-difluorophenyl | 3',4'-difluoroacetophenone |
| 825153 | 8.57 | N-R2 | H | 4-biphenyl | H |
| 825159 | 92.1 | N-R2 | H | 2-methoxyphenyl | H |

-continued
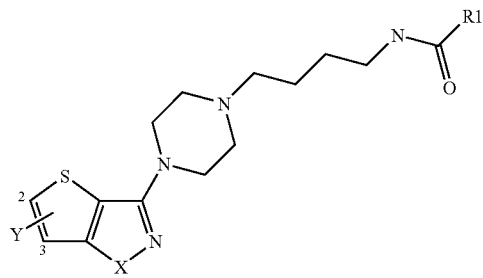
| MDL # | D3 Ki(nM) | X | Y | R1 | R2 |
|---|---|---|---|---|---|
| 825161 | 244 | N-R2 | H | 2-methylphenyl | H |
| 825162 | 114 | N-R2 | H | 4-fluorophenyl | H |
| 825163 | 221 | N-R2 | H | 3,4-difluorophenyl | H |
| 825164 | 10.4 | N-R2 | H | benzothiophen-2-yl | 2-acetylbenzothiophene |
| 829673 | 515 | O | H | 3-(trifluoromethyl)phenyl | |
| 829674 | 90.2 | O | H | 4-fluorophenyl | |
| 829675 | 38.9 | O | H | 4-chlorophenyl | |
| 829677 | 96.6 | O | H | 4-(trifluoromethyl)phenyl | |
| 829678 | 275 | O | H | 3,5-dichlorophenyl | |

-continued
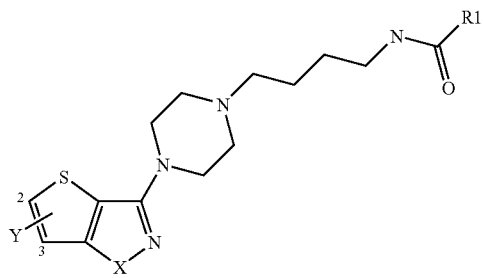
| MDL # | D3 Ki(nM) | X | Y | R1 | R2 |
|---|---|---|---|---|---|
| 829680 | 14.7 | O | H | biphenyl | |
| 829681 | 17.7 | O | H | benzothiophene | |
| 829682 | 18.9 | O | H | indole (2-yl) | |
| 829683 | 37.5 | O | H | 5-methylindole | |
| 829685 | 149 | O | H | 4-butylphenyl | |
| 829686 | 42.1 | O | H | 4-cyanophenyl | |
| 829687 | 50.3 | O | H | 2-thienyl | |
| 829688 | 673 | O | H | quinoxalinyl | |
| 829691 | 151 | O | H | 4-fluoro-3-(trifluoromethyl)phenyl | |
| 830748 | 63.8 | O | 3-CH$_3$ | —(CH$_2$)$_3$-Ph | |

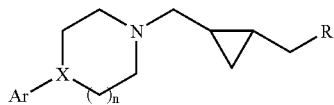

| MDL # | D3 Ki (nM) | Chirality | X | n | Ar | R |
|---|---|---|---|---|---|---|
| 830391 | 2.22 | Racemic | N | 2 | 6-fluorobenzothiophen-3-yl | N-Bn |
| 830388 | 22.5 | Racemic | N | 2 | 6-fluorobenzothiophen-3-yl | N-methyl-N,N-diallyl |
| 831205DA | 6.38 | Racemic | CH | 1 | thieno[3,2-d]isoxazol-3-yl | (1-methylpiperidin-4-yl)-thieno-isoxazole |
| 832296FH | 126 | Racemic | CH | 1 | thieno[3,2-d]isoxazol-3-yl | N-methyl-2-phenoxyethyl |
| 832297GW | 392.55 | Racemic | CH | 1 | thieno[3,2-d]isoxazol-3-yl | N-methyl-(4-methylpiperazin-1-yl)-3,4-dichlorobenzyl |
| 831876 | 12 | R, R | N | 1 | 2-methylphenyl | N-methyl-trans-4-ethylcyclohexyl |
| 831909 | 41.5 | Racemic | N | 1 | 6-(trifluoromethyl)benzothiophen-3-yl | N-methyl-4-methoxybenzyl |
| 832181 | 16 | Racemic | N | 1 | 6-(trifluoromethyl)benzothiophen-3-yl | N-methyl-3-(trifluoromethoxy)benzyl |

-continued

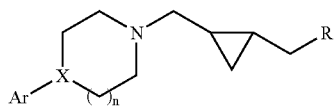

| | | | | | Ar group | R group |
|---|---|---|---|---|---|---|
| 832182 | 98 | Racemic | N | 1 | 3-methyl-6-(trifluoromethyl)benzo[b]thiophene | —N(CH₃)—CH₂—(4-isopropylphenyl) |
| 832209 | 13.47 | R, R | N | 1 | 3-methyl-6-(trifluoromethyl)benzo[b]thiophene | —N(CH₃)—(trans-4-methylcyclohexyl) |
| 832265 | 72.79 | R, R | N | 1 | 2,4-dimethylphenyl | —N(CH₃)—(trans-4-ethylcyclohexyl) |
| 832266 | 29.6 | R, R | N | 1 | 2,4-dimethylphenyl | —N(CH₃)—(trans-4-ethylcyclohexyl) |
| 832275 | 33.6 | R, R | CH | 1 | 3-methyl-7-(trifluoromethyl)benzo[d]isoxazole | —N(CH₃)—(trans-4-methylcyclohexyl) |
| 832276 | 30.31 | R, R | N | 1 | 3-methyl-6-(trifluoromethyl)benzo[b]thiophene | —N(CH₃)—CH₂CH₂—CH(CH₃)₂ |
| 832277 | 29.36 | R, R, (R, S) | N | 1 | 3-methyl-6-(trifluoromethyl)benzo[b]thiophene | —N—CH₂CH₂CH₂—(2-methylpiperidin-1-yl) |
| 832278 | 19 | R, R, (R, S) (R, S) | N | 1 | 3-methyl-6-(trifluoromethyl)benzo[b]thiophene | —N(CH₃)—(2-ethylcyclopentyl) |

-continued
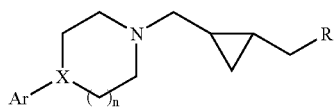
| | | | | | | |
|---|---|---|---|---|---|---|
| 832279 | 56.97 | R, R | N | 1 |  |  |
| 832280 | 19.2 | R, R | N | 1 |  | 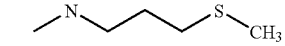 |
| 832281 | 5.59 | R, R | N | 1 |  |  |
| 832322 | 226.91 | R, R | N | 1 |  | —N—(CH$_2$)$_2$-Ph |
| 832329 | 150.60 | R, R | N | 1 |  |  |
| 832387 | 36.47 | R, R | N | 1 |  |  |
| 832388 | 71.9 | R, R | N | 1 |  |  |

-continued
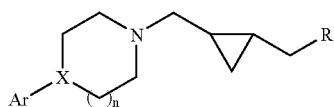
| | | | | | | |
|---|---|---|---|---|---|---|
| 832390FH | 21.8 | Racemic | N | 1 |  |  |
| 832568 | 46.21 | Racemic | N | 1 |  |  |
| 832609 | 39.6 | Racemic | N | 1 |  |  |
| 832644 | 97.51 | Racemic | N | 1 |  |  |
| 832659 | 28.32 | Racemic | N | 1 |  |  |
| 832783 | 47.55 | R, R | CH | 1 |  |  |
| 832817 | 36.46 | R, R | N | 1 |  |  |

-continued
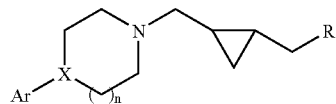
| MDL # | | | | | Structure | | D3 Ki (nM) |
|---|---|---|---|---|---|---|---|
| 833067 | 54.88 | R, R | N | 1 | 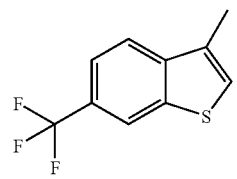 | 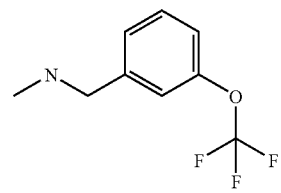 | |
| 833257 | 2.62 | R, R | N | 1 | 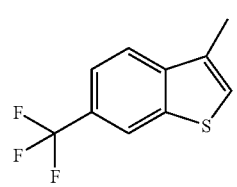 | 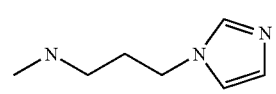 | |
| 833329 | 31.9 | R, R | CH | 1 | 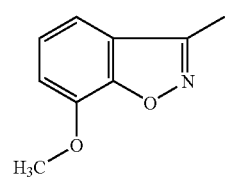 | 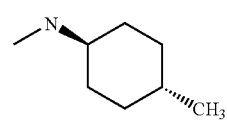 | |
| 833349 | 22.9 | R, R | N | 1 | 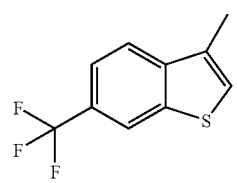 | 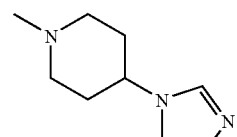 | |
| 833379 | 0.84 | R, R | N | 1 | 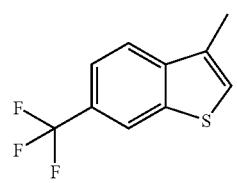 | 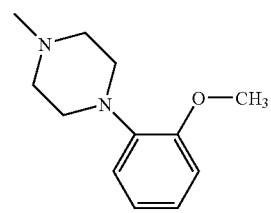 | |
| 833433 | 111.54 | R, R | CH | 1 | 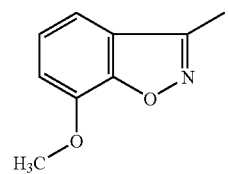 | 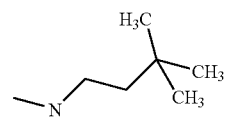 | |
| MDL # | Structure | D3 Ki (nM) |
|---|---|---|
| 832401 | 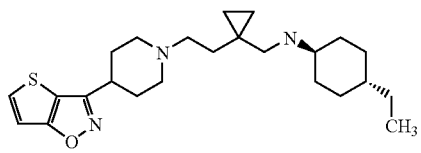 | 124 |

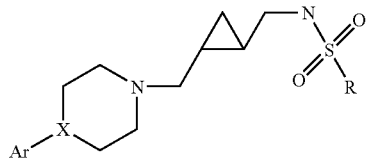

(All Compounds Racemic)

| MDL # | D3 Ki (nM) | X | Ar | R |
|---|---|---|---|---|
| 831363 | 36.3 | CH | 3-methylthieno[3,2-d]isoxazole | 4-F-phenyl |
| 831366 | 113 | CH | 3-methylthieno[3,2-d]isoxazole | —CH(CH₃)₂ |
| 831464 | 43.3 | CH | 3-methylthieno[3,2-d]isoxazole | 4-OMe-phenyl |
| 831511 | 50.6 | CH | 3-methylthieno[3,2-d]isoxazole | —CH(CH₂)₃—CH₃ |
| 831512 | 53.9 | CH | 3-methylthieno[3,2-d]isoxazole | 4-C(CH₃)₃-phenyl |
| 831513 | 65.5 | CH | 3-methylthieno[3,2-d]isoxazole | 4-OCF₃-phenyl |
| 831495 | 35.1 | N | 6-CF₃-benzothiophene | 4-F-phenyl |
| 831500 | 28.1 | N | 6-CF₃-benzothiophene | 4-OMe-phenyl |
| 831591 | 93.31 | N | 6-CF₃-benzothiophene | 4-C(CH₃)₃-phenyl |

-continued
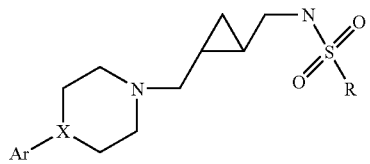
(All Compounds Racemic)
| MDL # | D3 Ki (nM) | X | Ar | R |
|---|---|---|---|---|
| 831592 | 195.38 | N | 6-trifluoromethyl-benzothiophen-3-yl | 4-OCF3-phenyl |
| 831636 | 186 | N | 6-trifluoromethyl-benzothiophen-3-yl | —(CH2)3—CH3 |
| 831910 | 277 | N | 6-trifluoromethyl-benzothiophen-3-yl | 2-(naphthalen-1-yl)ethyl |
-continued
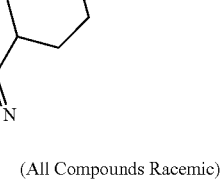
(All Compounds Racemic)
| MDL # | D3 Ki (nM) | R |
|---|---|---|
| 831671 | 96.4 | 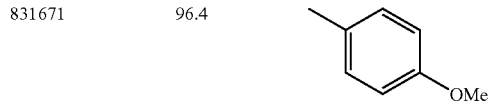 4-OMe-phenyl |
| 831696 | 29.3 | —(CH2)3—CH3 |
| 831697 | 8.35 | 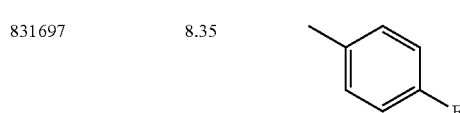 4-F-phenyl |
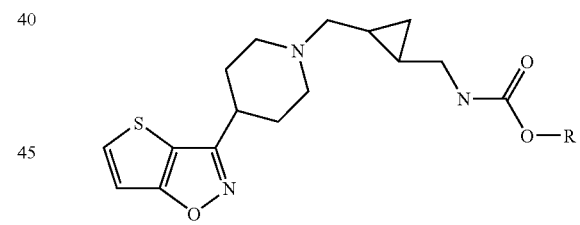
(All Compounds Racemic)
| MDL # | D3 Ki (nM) | R |
|---|---|---|
| 831698 | 29.4 |  4-CH3-phenyl |
| 831699 | 3.04 | Ph |

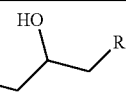

| MDL # | D3 Ki (nM) | R |
|---|---|---|
| 831939 | 90 | 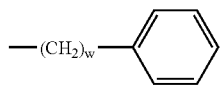 |
| 831940 | 356 | 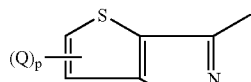 |
| 831941 | 161 | 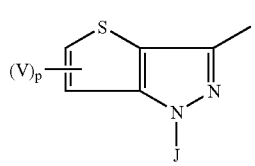 |
| 831943 | 264 | |
| 831944 | 38.5 | |
| 831945 | 700 | —N—(CH$_2$)$_2$-Ph |

We claim:

1. A compound of the formula (I):

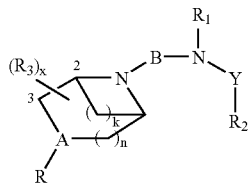

I wherein
Y is carbonyl, sulfonyl, or a bond;
A is N;
n is 1;
k is 0 and the bridging bonds are absent;
x is 0, 1 or 2;
each $R_3$ is independently hydrogen, $C_1$-$C_6$alkyl, or

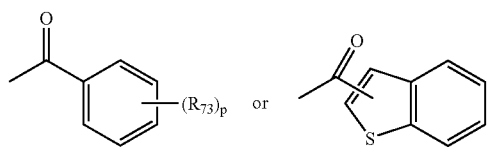

wherein w is 1, 2, or 3;
R is selected from the group consisting of (b) and (d):

b)

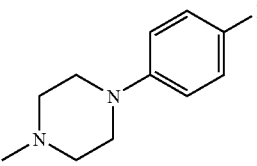

d)

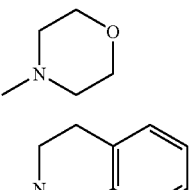

wherein
each Q, and V is independently hydrogen, $C_1$-$C_6$alkyl, $C_1$-$C_6$alkoxy, halogen, trifluoromethyl or —CH$_2$OC$_1$-C$_6$alkyl;
p is 0, 1 or 2;
J is hydrogen,

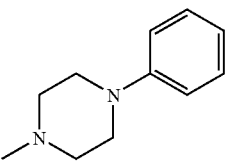

wherein each $R_{73}$ is independently hydrogen, $C_1$-$C_6$alkyl, halogen or trifluoromethyl and p is as hereinbefore defined;

—B— represents a group selected from groups (a) through (m):

(a) —(CH$_2$)$_z$— wherein z is 2, 3, 4, 5, 6 or 7;

(b)

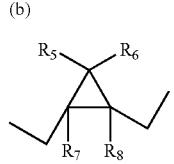

wherein
$R_5$ and $R_6$ are each independently hydrogen or $C_1$-$C_3$ linear alkyl;
$R_7$ and $R_8$ are each independently hydrogen or $C_1$-$C_3$linear alkyl with the proviso that when $R_7$ is $C_1$-$C_3$linear alkyl, $R_8$ cannot be $C_1$-$C_3$linear alkyl;

(c) 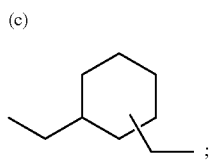

(d) 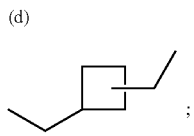

(e) 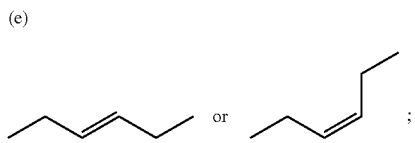

(f) 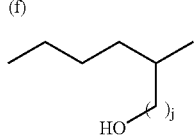

wherein j is 0 or 1;

(g) 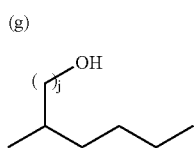

wherein j is defined as above;

(h) 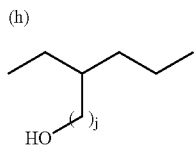

wherein j is defined as above;

(i) 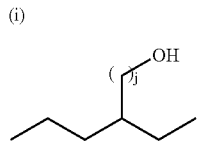

wherein j is defined as above;

(j) 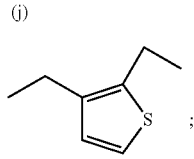

(k) 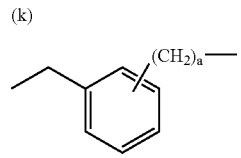

wherein a is 0 or 1;

(l) 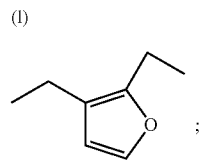

(m) 

$R_1$ is a) hydrogen;
  b) saturated or unsaturated $C_1$-$C_6$alkyl which is optionally mono- or di-substituted with hydroxy; or c) 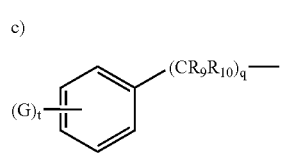

wherein
  each G is independently hydrogen, $C_1$-$C_6$alkyl, halogen or trifluoromethyl;
  each $R_9$ and $R_{10}$ is independently hydrogen or $C_1$-$C_3$alkyl;
  t is 0 or 1; and
  q is 0 or 1;

$R_2$ is a group selected from saturated or unsaturated $C_1$-$C_{10}$alkyl, trifluoromethyl or a group selected from (a)-(ss):

(a) 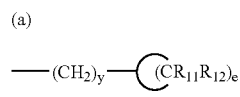

(b) 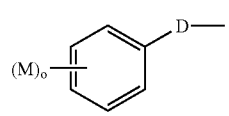

(c) 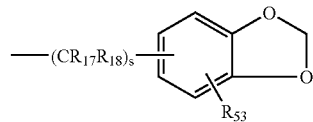

(d)
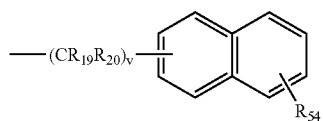
(e)
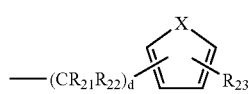
(f)
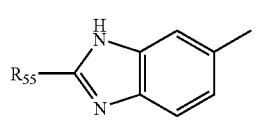
(g)
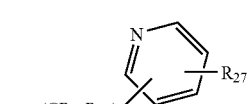
(h)
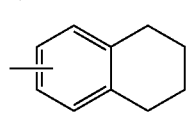
(i)
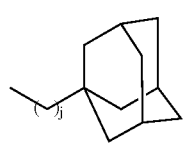
(j)
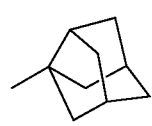
(k)
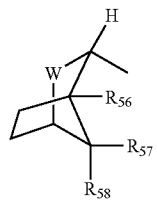
(l)
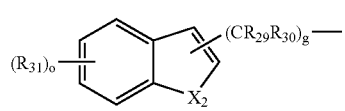
(m)
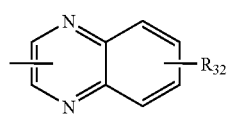
(n)
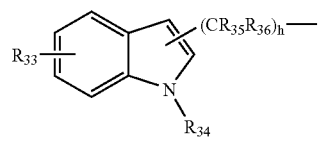
(o)
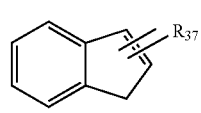
(p)
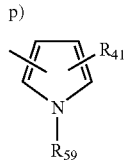
(q)
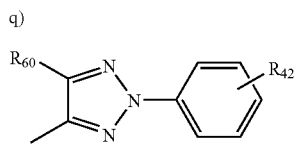
(s)
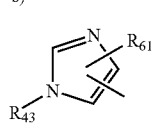
(t)
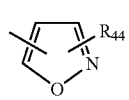
(u)
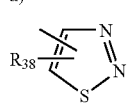
(v)
(w)
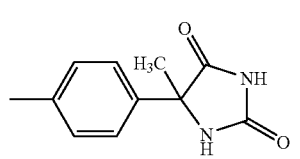
(x)
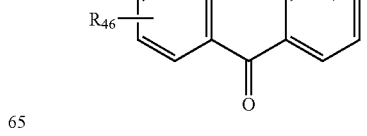

-continued
y)
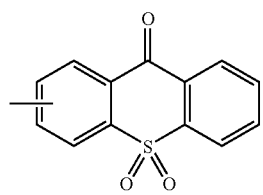
z)
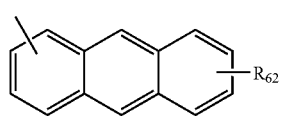
aa)
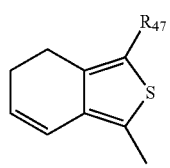
bb)
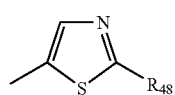
cc)
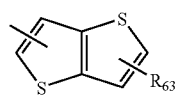
dd)
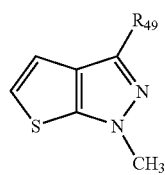
ee)
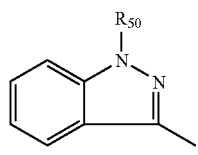
ff)
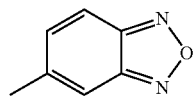
gg)
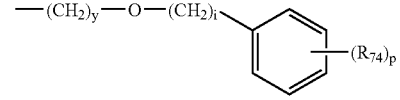
-continued
hh)
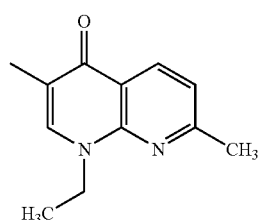
ii)
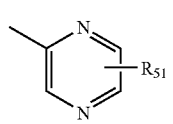
jj)
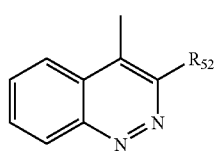
kk)
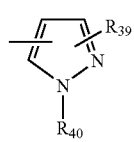
ll)
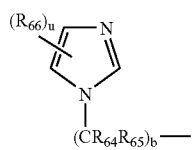
mm)
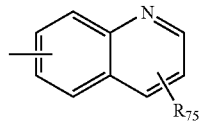
nn)
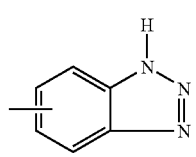
oo)
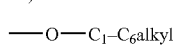
—O—$C_1$–$C_6$alkyl
pp)
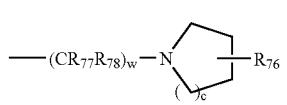
qq)
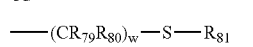

rr)

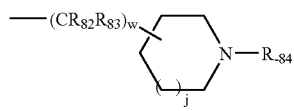

ss)

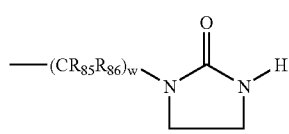

(14)

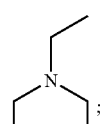

(15)

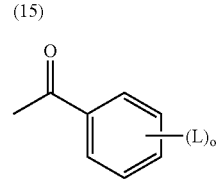

wherein e is 3, 4 or 5;

y is 0, 1, or 2;

each $R_{11}$ and $R_{12}$ is independently hydrogen or $C_1$-$C_3$ linear alkyl;

D is a group selected from (a) or (b):
(a) —$(CR_{13}R_{14})_u$—
wherein each $R_{13}$ and $R_{14}$ is independently hydrogen, halogen or $C_1$-$C_3$ linear alkyl; and
u is 0, 1, 2 or 3;
(b) —$CR_{15}$=$CR_{16}$—
wherein each $R_{15}$ and $R_{16}$ is independently hydrogen, $C_1$-$C_3$ linear alkyl or amino;

o is 0, 1 or 2;

M is a group selected from:
(1) hydrogen;
(2) $C_1$-$C_8$ alkyl;
(3) $C_1$-$C_6$ alkoxy;
(4) hydroxy;
(5) trifluoromethyl;
(6) trifluoromethoxy;
(7) —$NO_2$;
(8) —CN;
(9) —$SO_2CH_3$;
(10) halogen;

(11)

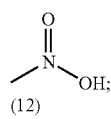

(12)

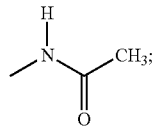

(13)

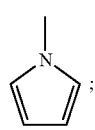

wherein each L is independently hydrogen or —$NR_{67}R_{68}$, wherein $R_{67}$ and $R_{68}$ are each independently hydrogen, $C_1$-$C_6$ alkyl or $C_1$-$C_6$ alkoxy and o is 0, 1 or 2 as hereinbefore defined;

(16)

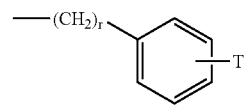

wherein T is hydrogen or halogen and r is 0, 1, or 2;

(17)

wherein $R_{69}$ and $R_{70}$ are each independently hydrogen or $C_1$-$C_6$ alkyl:

(18)

each $R_{17}$ and $R_{18}$ is independently hydrogen or $C_1$-$C_3$ alkyl;

s is 0, 1 or 2;

$R_{53}$ is hydrogen, halogen, hydroxy, $C_1$-$C_6$ alkyl, amino or $C_1$-$C_3$ alkoxy;

$R_{54}$ is hydrogen, halogen, hydroxy, $C_1$-$C_6$ alkyl, amino, —$SO_2NH_2$ or $C_1$-$C_3$ alkoxy;

each $R_{19}$ and $R_{20}$ is independently hydrogen or $C_1$-$C_3$ alkyl;

v is 0, 1 or 2;

X is O or S;

each $R_{21}$ and $R_{22}$ is independently hydrogen or $C_1$-$C_3$ alkyl;

d is 0, 1 or 2;

$R_{23}$ is a group selected from (a)-(h):
(a) hydrogen;
(b) $C_1$-$C_6$ alkyl;
(c) halogen;
(d) hydroxy;
(e) $C_1$-$C_3$ alkoxy; and (f)

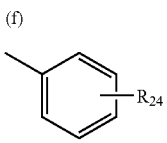

wherein R₂₄ is hydrogen or halogen;

(g)

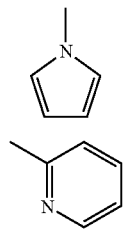

(h)

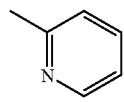

$R_{55}$ is hydrogen or $C_1$-$C_6$alkyl;
each $R_{25}$ and $R_{26}$ is independently hydrogen or $C_1$-$C_3$alkyl;
f is 0, 1 or 2;
$R_{27}$ is a group selected from (a)-(e):
 (a) hydrogen;
 (b) $C_1$-$C_6$alkyl;
 (c) halogen;
 (d) —$SCH_3$; and (e)

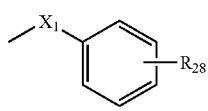

wherein $X_1$ is O or S and $R_{28}$ is hydrogen or $C_1$-$C_6$alkyl;
j is 0 or 1 as hereinbefore defined;
each $R_{56}$, $R_{57}$ and $R_{58}$ is independently hydrogen or $C_1$-$C_6$alkyl;
W is $CH_2$, $CH_2OH$ or C=O;
each $R_{29}$ and $R_{30}$ is independently hydrogen or $C_1$-$C_3$alkyl;
g is 0 or 1;
$X_2$ is O or S;
each $R_{31}$ is independently hydrogen, halogen, $C_1$-$C_6$alkyl, trifluoromethyl, trifluoromethoxy; $C_1$-$C_6$alkoxy, or —$NR_{71}R_{72}$ wherein $R_{71}$ and $R_{72}$ are each independently hydrogen or $C_1$-$C_6$alkyl;
o is 0, 1 or 2 as hereinbefore defined;
$R_{32}$ is hydrogen, halogen or $C_1$-$C_6$alkyl;
$R_{33}$ is hydrogen, halogen, hydroxy, $C_1$-$C_6$alkyl or $C_1$-$C_3$alkoxy;
$R_{34}$ is hydrogen, $C_1$-$C_6$alkyl or —$CH_2CO_2C_1$-$C_6$alkyl;
each $R_{35}$ and $R_{36}$ is hydrogen or $C_1$-$C_3$ linear alkyl;
h is 0 or 1;
$R_{37}$ is hydrogen or $C_1$-$C_6$alkyl;
$R_{41}$ is hydrogen, $C_1$-$C_6$alkyl, benzyl, acyl, tosyl, pyridyl or phenyl wherein said phenyl is optionally mono- or di-substituted with substituents independently selected from halogen, hydroxy, $C_1$-$C_6$alkyl, $C_1$-$C_6$alkoxy and $C_1$-$C_6$acyl;
$R_{59}$ and $R_{60}$ are hydrogen, methyl or phenyl which is optionally mono- or di-substituted with substituents independently selected from halogen, hydroxy, $C_1$-$C_6$alkyl, $C_1$-$C_6$alkoxy and $C_1$-$C_6$acyl;
$R_{42}$ is hydrogen, $C_1$-$C_6$alkyl, $C_1$-$C_6$alkoxy, halogen, trifluoromethyl or phenoxy;
$R_{43}$ is hydrogen, $C_1$-$C_6$alkyl or benzyl;
$R_{61}$ is hydrogen or $C_1$-$C_6$alkyl;
$R_{44}$ is hydrogen, hydroxy, $C_1$-$C_6$alkyl, phenyl or acyl;
$R_{38}$ is hydrogen, methyl or phenyl which is optionally mono- or di-substituted with substituents independently selected from halogen, hydroxy, $C_1$-$C_6$alkyl, $C_1$-$C_6$alkoxy and $C_1$-$C_6$acyl;
$R_{45}$ is hydrogen, $C_1$-$C_6$alkyl, S—$C_1$-$C_6$alkyl, halogen or phenyl which is optionally mono- or di-substituted with substituents independently selected from halogen, hydroxy, $C_1$-$C_6$alkyl, $C_1$-$C_6$alkoxy and $C_1$-$C_6$acyl;
$R_{46}$ is hydrogen or halogen;
$R_{62}$ is hydrogen, halogen or $C_1$-$C_6$alkyl;
$R_{47}$ is SMe, SOMe or $SO_2Me$;
$R_{48}$ is hydrogen, $C_1$-$C_6$alkyl, trifluoromethyl, pyridyl, thiophenyl or phenyl which is optionally mono- or di-substituted with substituents independently selected from halogen, hydroxy, $C_1$-$C_6$alkyl, $C_1$-$C_6$alkoxy and $C_1$-$C_6$acyl;
$R_{63}$ is hydrogen or $C_1$-$C_6$alkyl;
$R_{49}$ is methyl, trifluoromethyl, phenyl or —$CH_2SPh$;
$R_{50}$ is hydrogen, methyl, acyl or benzyl;
i is 0 or 1;
y is 0, 1 or 2 as hereinbefore defined;
p is 0, 1 or 2 as hereinbefore defined;
each $R_{74}$ is independently hydrogen, $C_1$-$C_6$alkyl, $C_1$-$C_6$alkoxy or halogen;
$R_{51}$ is hydrogen, hydroxy, methyl, methoxy, chlorine or —$SC_1$-$C_6$alkyl;
$R_{52}$ is hydrogen, phenyl or thiophene;
$R_{39}$ is hydrogen or $C_1$-$C_6$alkyl;
$R_{40}$ is hydrogen, $C_1$-$C_6$alkyl, phenyl or benzyl;
b is 1, 2, 3 or 4;
each $R_{64}$ and $R_{65}$ is independently hydrogen or $C_1$-$C_3$alkyl;
u is 0, 1, 2, or 3 as hereinbefore defined;
each $R_{66}$ is independently hydrogen, $C_1$-$C_6$alkyl, halogen or phenyl which is optionally mono- or di-substituted with halogen, $C_1$-$C_6$alkyl or trifluoromethyl;
$R_{75}$ is hydrogen, halogen, $C_1$-$C_6$alkyl or furanyl;
c is 1 or 2;
w is 1, 2 or 3 as hereinbefore defined;
$R_{76}$ is hydrogen or $C_1$-$C_6$alkyl;
each $R_{77}$ and $R_{78}$ is independently hydrogen or $C_1$-$C_3$alkyl;
each $R_{79}$ and $R_{80}$ is independently hydrogen or $C_1$-$C_3$alkyl;
$R_{81}$ is $C_1$-$C_6$alkyl or phenyl optionally substituted with halogen;
each $R_{82}$ and $R_{83}$ is independently hydrogen or $C_1$-$C_3$alkyl;
$R_{84}$ is hydrogen or $C_1$-$C_6$alkyl;
j is 0 or 1 as hereinbefore defined; and
each $R_{85}$ and $R_{86}$ is independently hydrogen or $C_1$-$C_3$alkyl and wherein a hydroxyl group or an amino group can be acylated with ($C_4$-$C_{18}$)alkanoyl group or a ($C_4$-$C_{18}$)alkoxycarbonyl group.

2. A pharmaceutical composition comprising an effective amount of a compound of claim 1 with a pharmaceutically-acceptable carrier or diluent.

3. A depot pharmaceutical composition, which comprises a pharmaceutically acceptable carrier and a therapeutically effective amount of a compound of claim 1, wherein the compound contains an acylated hydroxy group, or an acylated amino group.

4. A compound according to claim 1 wherein R is group (b).

5. A compound according to claim 1 wherein R is group (d).

* * * * *